US008017127B2

(12) United States Patent
Birkett

(10) Patent No.: US 8,017,127 B2
(45) **Date of Patent: *Sep. 13, 2011**

(54) INFLUENZA IMMUNOGEN AND VACCINE

(75) Inventor: Ashley J. Birkett, Boston, MA (US)

(73) Assignee: Apovia, Inc., San Diego, CA (US)

( * ) Notice: Subject to any disclaimer, the term of this patent is extended or adjusted under 35 U.S.C. 154(b) by 817 days.

This patent is subject to a terminal disclaimer.

(21) Appl. No.: 11/509,382

(22) Filed: Aug. 24, 2006

(65) Prior Publication Data

US 2007/0036826 A1 Feb. 15, 2007

Related U.S. Application Data

(60) Division of application No. 10/787,734, filed on Feb. 26, 2004, now Pat. No. 7,361,352, which is a continuation-in-part of application No. 10/732,862, filed on Dec. 10, 2003.

(51) Int. Cl.
*A61K 39/29* (2006.01)
*A61K 39/00* (2006.01)

(52) U.S. Cl. ............... 424/189.1; 424/184.1; 424/185.1; 435/69.1; 435/69.7; 536/23.1

(58) Field of Classification Search ............... 424/204.1, 424/130.1, 184.1, 185.1, 189.1; 435/69.1, 435/69.7; 536/23.1
See application file for complete search history.

(56) References Cited

U.S. PATENT DOCUMENTS

| | | | | |
|---|---|---|---|---|
| 4,539,205 | A | 9/1985 | Goodman et al. | 514/45 |
| 4,643,992 | A | 2/1987 | Goodman et al. | 514/45 |
| 4,767,842 | A | 8/1988 | Stevens | 530/324 |
| 4,818,527 | A | 4/1989 | Thornton et al. | 424/88 |
| 4,882,145 | A | 11/1989 | Thornton et al. | 424/88 |
| 4,977,092 | A | 12/1990 | Bitter | 435/320 |
| 4,987,237 | A | 1/1991 | Myers et al. | 549/222 |
| 5,011,828 | A | 4/1991 | Goodman et al. | 514/45 |
| 5,023,179 | A | 6/1991 | Lam et al. | 435/172.3 |
| 5,057,540 | A | 10/1991 | Kensil et al. | 514/25 |
| 5,093,318 | A | 3/1992 | Goodman et al. | 514/45 |
| 5,110,732 | A | 5/1992 | Benfey et al. | 435/172.3 |
| 5,143,726 | A | 9/1992 | Thornton et al. | 424/88 |
| 5,297,441 | A | 3/1994 | Smith et al. | 73/860 |
| 5,387,744 | A | 2/1995 | Curtiss, III et al. | 424/235.1 |
| 5,478,726 | A | 12/1995 | Shinnick et al. | 435/724 |
| 5,618,988 | A | 4/1997 | Hauptmann et al. | 800/205 |
| 5,656,472 | A | 8/1997 | Ausich et al. | 435/193 |
| 5,679,880 | A | 10/1997 | Curtiss, III et al. | 800/205 |
| 5,709,879 | A | 1/1998 | Barchfeld et al. | 424/450 |
| 5,888,799 | A | 3/1999 | Curtiss, III | 435/252.3 |
| 5,977,081 | A | 11/1999 | Marciani | |
| 5,990,085 | A | 11/1999 | Ireland et al. | 514/12 |
| 6,024,961 | A | 2/2000 | Curtiss, III et al. | 424/200 |
| 6,080,725 | A | 6/2000 | Marciani | |
| 6,086,901 | A | 7/2000 | O'Hagan et al. | 424/283.1 |
| 6,231,864 | B1 | 5/2001 | Birkett | 424/189.1 |
| 7,361,352 | B2 * | 4/2008 | Birkett et al. | 424/189.1 |
| 2006/0246092 | A1 * | 11/2006 | Neirynck et al. | 424/209.1 |

FOREIGN PATENT DOCUMENTS

| | | | |
|---|---|---|---|
| EP | 399 843 | B1 | 11/1990 |
| EP | 421635 | B1 | 4/1991 |
| EP | 671 948 | B1 | 9/1995 |
| EP | 671948 | B1 | 9/1995 |
| EP | 689 454 | B1 | 1/1996 |
| EP | 689454 | B1 | 1/1996 |
| GB | 2122204 | A | 1/1984 |
| WO | WO 91/13922 | | 9/1991 |
| WO | WO 95/17210 | | 6/1995 |
| WO | WO 96/02555 | | 2/1996 |
| WO | WO 96/33739 | | 10/1996 |
| WO | WO 99/07839 | | 2/1999 |
| WO | WO 99/12565 | | 3/1999 |
| WO | WO 99/40934 | | 8/1999 |
| WO | WO 99/52549 | | 10/1999 |
| WO | WO99/52549 | | 10/1999 |
| WO | WO 00/32625 | | 6/2000 |
| WO | WO 01/27281 | | 4/2001 |
| WO | WO 01/41759 | | 6/2001 |
| WO | WO 01/98333 | | 12/2001 |
| WO | WO 02/13765 | | 2/2002 |
| WO | WO 02/13765 | A2 | 2/2002 |
| WO | WO 02/14478 | | 2/2002 |

OTHER PUBLICATIONS

U.S. Appl. No. 09/930,915, filed Jul. 24, 2003, Ashley J. Birkett.
Gianfrani er al., (2000) *Hum. Immunol.*, 61(5):438-352.
Brett et al., (1991) *J. Immunol.*, 147(3):984-991.
He et al. (Nov. 2000) *Clin. Diagn. Lab. Immunol.*, 7(6):899-903.
Benfey et al., "Regulated Genes in Transgenic Plants", *Science* (Apr. 1989) 244:174-181. Birkett et al., "A Modified Hepatitis B Virus Core Particle Containing Multiple Epitopes of the *Plasmodium falciparum* Circumsporozoite Protein Provides a Highly Immunogenic Malaria Vacccine in Preclinical Analyses in Rodent and Primate Hosts", *Infection and Immunity* (Dec. 2002) 70(12):6860-6870.
Black, et al., "Antibody Response to the M2 Protein of Influenza A Virus Expressed in Insect Cells", *J. of General Virol.* (1993) 74:143-146.
Colucci et al., "Identification of a Major Hepatitis B Core Antigen (HBcAg) Determinant by Using Synthetic Peptides and Monoclonal Antibodies", *J. of Immunology* (Dec. 1988) 141:4376-4380.
Cregg et al., "*Pichia pastoris* as a Host System for Transformation", *Molecular and Cellular Biology* (Dec. 1985) 5(12): 3376-3385.
Cregg et al., "High-Level Expression and Efficient Assembly of Hepatitis B Surface Antigen in the BMethylotrophic Yeast, *Pichia pastoris", Bio/Technology* (May 1987) 5:479-485.

(Continued)

*Primary Examiner* — Chih-Min Kam
(74) *Attorney, Agent, or Firm* — Husch Blackwell

(57) ABSTRACT

A chimeric, carboxy-terminal truncated hepatitis B virus nucleocapsid (HBc) protein is disclosed that contains an immunogen for inducing the production of antibodies to the influenza M2 protein. An immunogenic influenza sequence in two to four copies is preferably expressed at or near the N-terminus or in the HBc immunogenic loop sequence. The HBc chimer preferably contains an influenza-specific T cell epitope and is preferably engineered for both enhanced stability of self-assembled particles and enhanced yield of those chimeric particles. Methods of making and using the chimers are also disclosed.

37 Claims, 15 Drawing Sheets

OTHER PUBLICATIONS

Deikman et al., "Interaction of a DNA Binding Factor with the 5'-Flanking Region of an Ethylene-Responsive Fruit Ripening Gene from Tomato", *EMBO J.* (1988) 7(11):3315-3320.

Deikman et al, "Organization of Ripening and Ethylene Regulatory Regions in a Fruit-Specific Promoter from Tomato", *Plant Physiol.* (1992) 100:2013-2017.

Delpeyroux et al., "A Poliovirus Neutralization Epitope Expressed on Hybrid Hepatitis B Surface Antigen Particles", *Science* (Jul. 1986) 233:472-475.

Dirita et al., "Deletion Analysis of the Mannopine Synthase Gene Promoter in Sunflower Crown Gall Tumors and *Agrobacterium tumefaciens", Mol. Gen. Genet.* (1987) 207:233-241.

Engelhard et al., "The Insect Tracheal System: A Conduit for the Systemic Spread of *Autographa Californica* M Nuclear Polyhedrosis Virus", *Proc. Natl. Acad Sci.*, USA (Apr. 1994) 91:3224-3227.

Galibert et al., "Nucleotide sequence of the hepatitis B virus genome (subtype ayw) cloned in *E. coli", Nature* (Oct. 1979) 281:646-650.

Galibert et al., "Nucleotide sequence of a Cloned Woodchuck Hepatitis Virus Genome: Comparison with the Hepatitis B Virus Sequence", *J. Virol.* (Jan. 1982) 41(1):51-65.

Graham et al., "A New Technique for the Assay of Infectivity of Human Adenovirus 5 DNA", *Virol.* (1973) 52:456-467.

"IUPAC-IUB Commission on Biochemical Nomenclature A One-Letter Notation for Amino Acid Sequences[1-3] Tentative Rules", *J. Biol. Chem.* (Jul. 1968) 243(13):3557-3559.

Jegerlehner et al., "A Molecular assembly system that renders antigens of choice highly repetitive for induction B cell responses", Vaccine 20 (2002) 3104-3112.

Jegerlehner et al., "Influenza A Vaccine based on the Extracellular Domain of M2: Weak Protection Mediated via Antibody-Dependent NK Cell Activity", *The Journal of Immunology*, 2004, 172: 5598-5605.

Keller et al., "Specific Expression of a Novel Cell Wall Hydroxyproline-Rich Glycoprotein Gene in Lateral root Initiation", *Genes & Development* (1989) 3:1639-1646.

Lamb et al., "In Vitro Influenza Virus-Specific Antibody Production in Man: Antigen-Specific and HLA-Restricted Induction of Helper Activity Mediated by Cloned Human T Lymphocytes", *J. of Immunology* (Oct. 1982) 129(4):1465-1470.

Tacket et al., "Safety and Immunogenicity in Humans of an Attenuated *Salmonella typhi* Vaccine Vector Strain Expressing Plasmid-Encoded Hepatitis B Antigens Stabilized by the Asd-Balanced Lethal Vector System", *Infect. & Immun.* (Aug. 1997) 65(8):3381-3385.

Treanor et al., "Passively Transferred Monoclonal Antibody to the M2 Protein Inhibits Influenza A Virus Replication in Mice", *J. Virol.* (Mar. 1990) 64(3):1375-1377.

Tsuda et al., "Application of the Human Hepatitis B Virus Core Antigen from Transgenic Tobacco Plants for Serological Diagnosis", *Vox Sang* (1998) 74:148-155.

Twell et al., "The 5'-Flanking DNA of a Patatin Gene Directs Tuber Specific Expression of a Chimaeric Gene in Potato", *Plant Mol. Biol.* (Mar. 1987) 9:365-375.

Valenzuela et al., "Purification of the Recombinant Hepatitis B core Antigen, and Its Potential Use for the Diagnosis of Hepatitis B Virus Infection", *Biotecnologia Aplicada* (2002) 19(3):136-142.

Vodkin et al., "cA Lectin Gene Insertion has the Structural Features of a Transposable Element", *Cell* (1983) 34:1023-1031.

Wasenauer et al., "Relevance of Cysteine Residues for Biosynthesis and Antigenicity of Human Hepatitis B Virus e Protein", *J. Virol.* (Mar. 1993) 67(3):1315-1321.

Wenzler et al., "Analysis of a Chimeric Class-I Patatin-GUS Gene in Transgenic Potato Plants: High-Level Expression in Tubers and Sucrose-Inducible Expression in Cultured Leaf and Stem Explants", *Plant Mol. Biol.* (1989) 12:41-50.

Yamamoto et al., "Characterization of *cis*-Acting Sequences Regulating Root-Specific Gene Expression in Tobacco", *The Plant Cell* (Apr. 1991) 3:371-382.

Yang et al., "Maize Sucrose Synthase-1 Promoter Directs Phloem Cell-Specific Expression of *Gus* Gene in Transgenic Tobacco Plants", *Proc. Natl. Acad Sci. USA* (Jun. 1990) 87:4144-4148.

Youvan et al., "Light-harvesting II (B800-B850 Complex) Structural Genes from *Rhodopseudomonas capsulata", Proc. Natl. Acad Sci. USA* (Jan. 1985) 82:58-62.

Zebedee et al., "Influenza A Virus $M_2$ Protein: Monoclonal Antibody Restriction of Virus Growth and Detection of $M_2$ in Virions", *J. Virol.* (1988) 62(8):2762-2772.

Zheng et al., "The Structure of Hepadnaviral Core Antigens", *J. Biol. Chem.* (1992) 267(13):9422-9429.

Gallina et al. (1989) *J. Virol.*, 63:4645-4652.

Inada, et al. (1989) *Virus Res.*, 14:27-48.

Maassen et al., (1994) *Arch. Virol.*, 135:131-142 .

Schodel et al., (1994) *J.Exp.Med.*, 180:1037-1046.

Schodel et al. (1994) *Infect. Immunol.*, 62:1669-1676.

Kratz et al., (1999) *Proc. Natl. Acad. Sci.*, U.S.A., 96:1915-1920.

Ulrich et al. *Adv. Virus Res.*, 50: 141-182 (1998) Academic Press.

Neirynck et al., (Oct. 1999) *Nature Med.*, 5(10):1157-1163.

Schodel et al. (Jan. 15, 1993) *J. Biol. Chem.*, 268(2):1332-1337.

Wasenauer et al. (Mar. 1993) *J. Virol.*, 67(3):1315-1322.

Nassal et al. (Jul. 1993) *J. Virol.*, 67(7):4307-4315.

Galibert et al. (1983) *Nature*, 281:646-650.

Ono et al. (1983) *Nucleic Acids Res.*, 11(6): 1747-1757.

Valenzuela et al., *Animal Virus Genetics*, Field et al. eds., Academic Press, New York (1980)pp. 57-70.

Pasek et al., "Hepatitis B virus genes and their expression in *E. coli", Nature* (Dec. 1979) 282:575-579.

Galibert et al. (1982) *J. Virol.*, 41:51-65.

Seeger et al. (1984) *J. Virol.*,51:367-375.

"IUPAC-IUB Commission on Biochemical Nomenclature A One-Letter Notation for Amino Acid Sequences[1-3] Tentative Rules", *J. Biol. Chem.* (Jul. 1968) 243(13):3557-3559.

Karpenko et al., *Amino Acids* (2000) 18:329-337.

Koschel et al. (Mar. 1999), *J. Virol.*, 73(3):2153-2160.

Schodel et al., "Hybrid Hepatitis-B Virus Core/Pre-S Particles Expressed In Live Attenuated *Salmonellae* for Oral Immunization", *Vaccines* (1991) 91, Cold Spring Harbor Laboratory, New York, pp. 319-325.

Schodel et al., *Behring Inst. Mitt.*, 1997(98): p. 114-119.

Schodel et al., "Recombinant HBV Core Particles Carrying Immunodominant B-Cell Epitopes of the HBV Pre-S2 Region", *Vaccines* (1990) 90, Cold Spring Harbor Laboratory, New York, pp. 193-198.

Poszkowski et al. (1989) *EMBO J.*, 3:2719.

Odell et al. *Nature* (1985), 313:810.

Chua et al. *Science* (1989), 244:174-181.

Nestle et al (2001) *Nature Medicine* 7, 761-765.

Birkett et al., "Development of a Vaccine to Prevent Falciparum Malaria Infection"—Poster presented by J. Haron at the Center for Advanced Technology and Medicine (CABM) Symposium, Rutgers University Medical Center on Oct. 13-14, 1999.

Birnbaum et al., "Hepatitis B Virus Nucleocapsid Assembly: Primary Structure Requirements in the Core Protein", *J. Virol.* (1990) 64:3319-3330.

Bottcher et al., "Determination of the fold of the core protein of hepatitis B virus by electron cryomicroscopy", *Nature* (1997) 386:88-91.

Clarke et al., "Expression and Immunological Analysis of Hepatitis-B Core Fusion Particles Carrying Internal Heterologous Sequences", *Vaccines* (1991) 91, Cold Spring Harbor Laboratory, New York, pp. 313-318.

Conway et al., "Visualization of a 4-helix bundle in the hepatitis B virus capsid by cryo-electron microscopy", *Nature* (1997) 386:91-94.
Isaguliants et al., "Immunogenic Combinations of HIV-1 B- and Heterologous T-cell Epitopes", *Immunol. Ltr*. (1994) 42:173-178.
Kruger et al., "Chimeric Virus-Like Particles as Vaccines", *Biol. Chem*. (Mar. 1999) 380:275-276.
Metzger et al., "Proline-138 is essential for the assembly of hepatitis B virus core protein", *J. Gen. Viol*. (1998) 79:587-590.
Milich et al., "The Nucleocapsid of Hepatitis B Virus is Both a T-Cell-Independent and a T-Cell-Dependent Antigen", *Science* (1986) 234(4782):1398-1401.
Palenzuela et al., "Purification of the Recombinant Hepatitis B core Antigen, and Its Potential Use for the Diagnosis of Hepatitis B Virus Infection", *Biotecnologia Aplicada* (2002) 19(3):136-142.
Pumpens et al., Hepatitis B Virus Core Particles as Epitope Carriers:, *Intervirology* (1995) 38:63-74.
Schodel et al., "Hybrid Hepatitis B Virus Core Antigen as a Vaccine Carrier Moiety: I. Presentation of Foreign Epitopes", *J. Biotechnol*. (1996) 44:91-96.
Seifer et al., "Assembly and Antigenicity of Hepatitis B Virus Core Particles", *Intervirology* (1995) 38:47-62.
Stoute et al., "A Preliminary Evaluation of a Recombinant Circumsporozoite Protein Vaccine Against *Plasmodium falciparum* Malaria", *N. Engl. J. Med*. (1997) 336(2):86-91.
Wynne et al., "The Crystal Structure of the Human Hepatitis B Virus Capsid", *Mol. Cell* (Jun. 1999) 3:771-780.
Zoltnick et al., "Localization of the C terminus of the assembly domain of hepatitis B virus capsid protein: Implications for morphogenesis and organization of encapsidated RNA", *Proc. Natl. Acad. Sci*., USA (1997) 94:9556-9561.
Lazdina et al., "Priming of Cytotoxic T Cell Responses to Exogenous Hepatitis B Virus Core Antigen is B Cell Dependent", *J. of General Virol*. (2003) 84:139-146.
Lindstrom et al., "Expression of Soybean Lectin Gene Deletions in Tobacco", *Developmental Genetics* (1990) 11:160-167.
Londono et al., "Immunisation of Mice Using *Salmonella typhimurium* Expressing Human Papillomavirus Type 16 E7 Epitopes Inserted into Hepatitis B Virus Core Antigen", *Vaccine* (1996) 14(6):545-552.
Luckow, "*Insect Cell Expression Technology*" Chapter 7 in *Protein Engineering: Principle and Practice*, J.L. Cleland et al. eds., Wiley-Liss, Inc. (1996) pp. 183-218.
Luckow et al., "Efficient Generation of Infectious Recombinant Baculoviruses by Site-Specific Transposon-Mediated Insertion of Foreign Genes into a Baculovirus Genome Propagated in *Escherichia coli", J. Virol*. (Aug. 1993) 67(8):4566-4579.
Matteucci et al., "Synthesis of Deoxyoligonucleotides on a Polymer Support", *J. Am. Chem. Soc*. (1981) 103:3185-3191.
Milich et al., "Conversion of Poorly Immunogenic Malaria Repeat Sequences into a Highly Immunogenic Vaccine Candidate", *Vaccine* (2002) 20:771-788.
Nardelli-Haefliger et al., "Oral and Rectal Immunization of Adult Female Volunteers with a Recombinant Attenuated *Salmonella typhi* Vaccine Strain", *Infect. and Immun*. (Dec. 1996) 64(12):5219-5224.
Nassal et al., "An Intramolecular Disulfide Bridge between Cys-7 and Cys61 Determines the Structure of the Secretory Core Gene Product (e Antigen) of Hepatitis B Virus", *J. Virol*. (Jul. 1993) 67(7):4307-4315.
Odell et al., "Identification of DNA Sequences Required for Activity of the Cauliflower Mosaic Virus 35S Promoter", *Nature* (Feb. 1985) 313:810-812.
Ono et al, "The complete nucleotide sequences of the cloned hepatitis B virus DNA; subtype adr and adw", *Nucleic Acids Res*. (1983) 11(6):1747-1757.
Pasek et al., "Hepatitis B virus genes and their expression in *E. coli", Nature* (Dec. 1979) 282:575-579.
Paszkowski et al., "Direct Gene Transfer to Plants", *EMBO J*. (1984) 3(12)2717-2722.
Rogers et al., "Improved Vectors for Plant Transformation: Expression Cassette Vectors and New Selectable Markers", *Meth. in Enzymol*. (1987) 153:253-277.
Salfeld et al., "Antigenic Determinants and Functional Domains in Core Antigen and e Antigen from Hepatitis B Vitus", *J. Virol*. (Feb. 1989) 63(2):798-808.
Sallberg et al., "A Malaria Vaccine Candidate Based on a Hepatitis B Virus Core Platform", *Intervirology* (2002) 45:350-361.
Scherle et al., "Functional Analysis of Influenza-Specific Helper T Cell Clones in Vivo", *J. Exp. Med* (Oct. 1986) 164:1114-1128.
Schodel et al., "Recombinant HBV Core Particles Carrying Immunodominant B-Cell Epitopes of the HBV Pre-S2 Region", *Vaccines* (1990) 90, Cold Spring Harbor Laboratory, New York, pp. 193-198.
Schodel et al., "Hybrid Hepatitis-B Virus Core/Pre-S Particles Expressed in Live Attenuated *Salmonellae* for Oral Immunization", *Vaccines* (1991) 91, Cold Spring Harbor Laboratory, New York, pp. 319-325.
Schodel et al., "The Position of Heterologous Epitopes Inserted in Hepatitis B Virus Core Particles Determines Their Immunogenicity", *J. Virol*. (Jan. 1992) 66(1):106-114.
Schodel et al., "Structure of Hepatitis B Virus Core and e-Antigen", *J. Biological Chemistry* (1993) 268(2):1332-1337.
Seeger et al., "Nucleotide Sequence of an Infectious Molecularly Cloned Genome of Ground Squirrel Hepatitis Virus", *J. Virol*. (Aug. 1984) 51(2):367-375.
Stahl, et al., "Hepatitis B Virus Core Antigen: Synthesis in *Eschericia coli* and Application in Diagnosis", *Proc. Natl. Acad. Sci. USA* (Mar. 1982) 79:1606-1610.
Valenzuela et al., *Animal Virus Genetics*, Field et al. eds., Academic Press, New York (1980)pp. 57-70.
Jameson et. al., Human Cytotoxic T-lymphocyte Repertoire to Influenza A. Viruses. J. Virol, 1998. 72(11): p. 8682-9.
Gianfrani, C., et al. Human memory CTL response specific for influenza. A virus is broad and multispecific. Hum Immunol, 2000. 61 (5): p. 438-52.
Saito et al., (2001) *Vaccine*, 20(1-2):125-33.
Poszkowski et al. (1989) *EMBO J*., 3:2717.
Chua et al. (1989) *Science*, 244:174-181.
Southern et al. (1982) *J. Mol. Appl. Genet*., 1:327.
Fromm et al. (1985) *Proc. Natl. Acad. Sci. USA*, 82:5824-5828.
Ravetch et al., (1991) *Annu. Rev. Immunol*., 9:457-492.
Liu et al., "N-terminus of M2 protein could induce antibodies with inhibitory activity against influenza virus replication" FEMS Immunology and Medical Microbiology 35 (2003) 141-146.
Frace et al., "Modified M2 proteins produce heterotypic immunity against influenza A virus" Vaccine 17 (1999) 2237-2244.
Jegerlehner et al., "A molecular assembly system that renders antigens of choice highly repetitive for induction of protective B cell responses." Vaccine 20 (2002) 3104-3112.
Jegerlehner et al., "Influenza A Vaccine Based on the Extracellular Domain of M2: Weak Protection Mediated via Antibody-Dependent NK Cell Activity." The Journal of Immunology 172, 5598-5605 (2004).

* cited by examiner

FIG. 1A

```
Ground Squirrel   mylfhlclvf acvpcptvqa sklclgwlwd

                  1
  HBc AYW         mdidpykefg atvellsflp sdffpsvrdl ldtasalyre
  HBc ADW         mdidpykefg atvellsflp sdffpsvrdl ldtasalyre
  HBc ADW2        mdidpykefg atvellsflp sdffpsvrdl ldtasalyre
  HBc ADYW        mdidpykefg atvellsflp sdffpsvrdl ldtaaalyrd
  Woodchuck       mdidpykefg ssyqllnflp ldffpdlnal vdtatalyee
  Ground Squirrel mdidpykefg ssyqllnflp ldffpdlnal vdtaaalyee

                  41
  HBc AYW         alespehcsp hhtalrqail cwgelmtlat wvgvnledpa
  HBc ADW         alespehcsp hhtalrqail cwgelmtlat wvgnnlqdpa
  HBc ADW2        alespehcsp hhtalrqail cwgelmtlat wvgnnledpa
  HBc ADYW        alespehcsp hhtalrqail cwgdlmtlat wvgtnledpa
  Woodchuck       eltgrehcsp hhtairqalv cwdeltklia wmssnitseq
  Ground Squirrel eltgrehcsp hhtairqalv cweeltrlit wmsentteev
```

FIG. 1B

| | 81 | | | |
|---|---|---|---|---|
| HBc AYW | srdlvvsyvn | tnmglkfrql | lwfhiscltf | gretvieylv |
| HBc ADW | srdlvvnyvn | tnmglkirql | lwfhiscltf | gretvleylv |
| HBc ADW2 | srdlvvnyvn | tnvglkirql | lwfhiscltf | gretvleylv |
| HBc ADYW | srdlvvsyvn | tnvglkfrql | lwfhiscltf | gretvleylv |
| Woodchuck | vrtiivnhvn | dtwglkvrqs | lwfhlscltf | gqhtvqeflv |
| Ground Squirrel | rriivdhvnn | twglkvrqtl | wfhlscltfg | qhtvqeflvs |

| | 121 | | | |
|---|---|---|---|---|
| HBc AYW | sfgvwirtpp | ayrppnapil | stlpettvvr | rrgrsprrrt |
| HBc ADW | sfgvwirtpp | ayrppnapil | stlpettvvr | rrdrgrsprr |
| HBc ADW2 | sfgvwirtpp | ayrppnapil | stlpettvvr | rrdrgrsprr |
| HBc ADYW | sfgvwirtpp | ayrppnapil | stlpettvvr | rrgrsprrrt |
| Woodchuck | sfgvwirtpa | pyrppnapil | stlpehtvir | rrggarasrs |
| Ground Squirrel | fgvwirtpap | yrppnapils | tlpehtvirr | rggsraarsp |

| | 161 | | |
|---|---|---|---|
| HBc AYW | psprrrrsqs | prrrrsqsre | sqc |
| HBc ADW | rtpsprrrrs | qsprrrrsqs | resqc |
| HBc ADW2 | rtpsprrrps | qsprrrrsqs | resqc |
| HBc ADYW | psprrrrsqs | prrrrsqsre | sqc |
| Woodchuck | prrrtpsprr | rrsqsprrrr | sqc |
| Ground Squirrel | rrrtpsprrr | rsqsprrrrs | qspasnc |

FIG. 2

HindIII pKK223-3

TTCACACAGGAAACAGAATTCCCGGGGATCCGTCGACCTGCAGCCAAG
CTT

SEQ ID NO:7 pKK223-3N TTCACATAAGGAGGAAAAAAccatggGATCCG--
-----------AAGCTT

NcoI

SEQ ID NO:8

Fig. 11
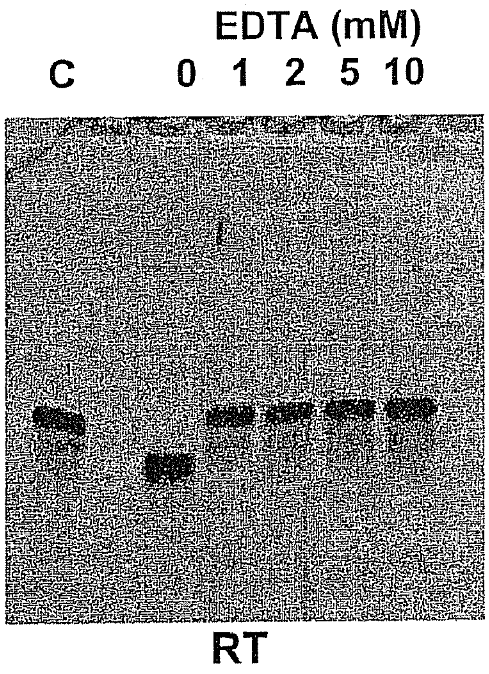
Fig. 11A
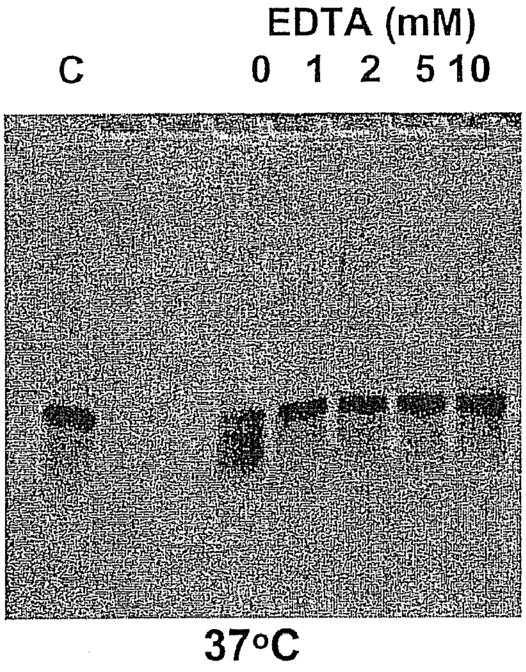
Fig. 11B

Fig. 13
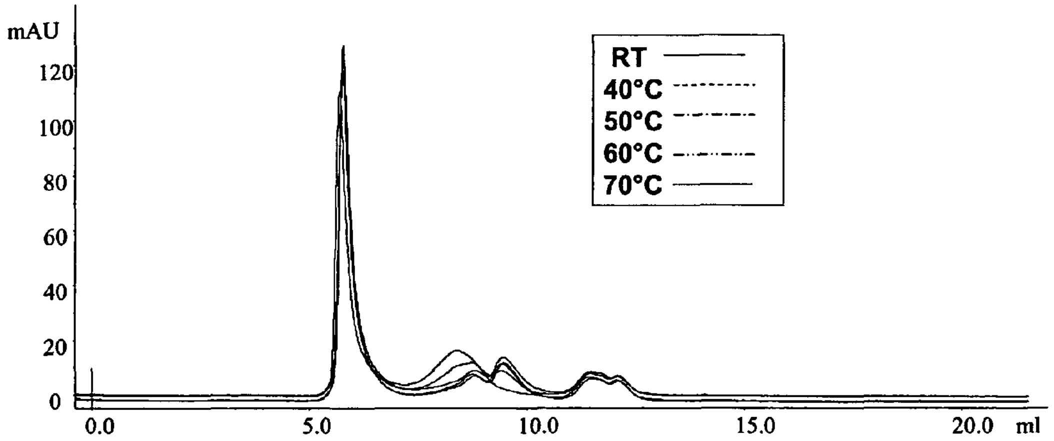
Fig. 13A
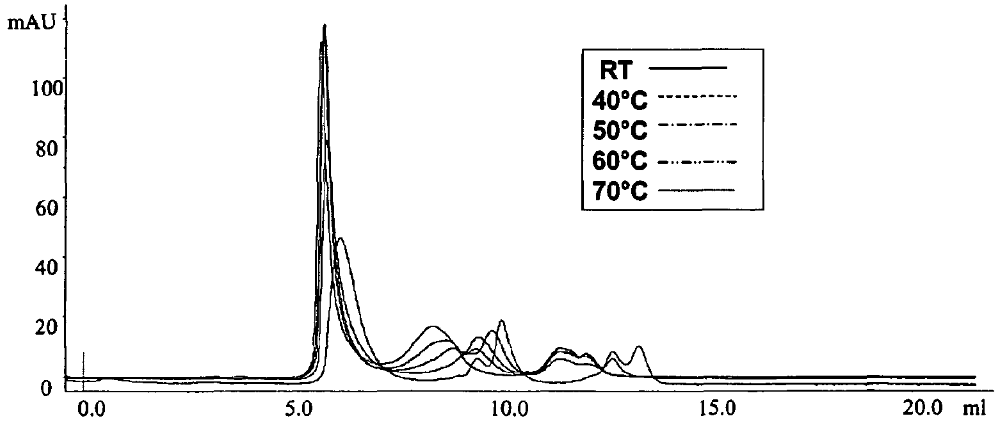
Fig. 13B

INFLUENZA IMMUNOGEN AND VACCINE

CROSS-REFERENCE TO RELATED APPLICATION

This application is a division of U.S. application Ser. No. 10/787,734, filed Feb. 26, 2004, now U.S. Pat. No. 7,361,352, which is a continuation-in-part of U.S. application Ser. No. 10/732,862, filed Dec. 10, 2003, which claims priority to PCT/US03/05196, filed Feb. 21, 2003, which is a continuation-in-part of U.S. application Ser. No. 10/274,616, filed Oct. 21, 2002, now abandoned, which is a continuation-in-part of U.S. application Ser. No. 10/082,014, filed Feb. 21, 2002, now abandoned, which claims priority to U.S. application Ser. No. 10/080,299, filed Feb. 21, 2002, now abandoned, which claims priority to U.S. application Ser. No. 09/930,915, filed Aug. 15, 2001.

TECHNICAL FIELD

The present invention relates to the intersection of the fields of immunology and protein engineering, and particularly to an immunogen and vaccine useful in prevention of influenza infection by influenza A virus.

BACKGROUND OF THE INVENTION

The family hepadnaviridae are enveloped DNA-containing animal viruses that can cause hepatitis B in humans (HBV). The hepadnavirus family includes hepatitis B viruses of other mammals, e.g., woodchuck (WHV), and ground squirrel (GSHV), and avian viruses found in ducks (DHV) and herons (HeHV). Hepatitis B virus (HBV) used herein refers to a member of the family hepadnaviridae that infects mammals, as compared to a virus that infects an avian host, unless the discussion refers to a specific example of a non-mammalian virus.

The nucleocapsid or core of the mammalian hepatitis B virus (HBV or hepadnavirus) contains a sequence of 183 or 185 amino acid residues, depending on viral subtype, whereas the duck virus capsid contains 262 amino acid residues. Hepatitis B core protein monomers of the several hepadnaviridae self-assemble in infected cells into stable aggregates known as hepatitis B core protein particles (HBc particles). Two three-dimensional structures are reported for C-terminally truncated HBc particles. A first that comprises a minor population contains 90 copies of the HBc subunit protein as dimers or 180 individual monomeric proteins, and a second, major population that contains 120 copies of the HBc subunit protein as dimers or 240 individual monomeric proteins. These particles are referred to as T=4 or T=3 particles, respectively, wherein "T" is the triangulation number. These HBc particles of the human-infecting virus (human virus) are about are about 30 or 34 nm in diameter, respectively. Pumpens et al. (1995) *Intervirology,* 38:63-74; and Metzger et al. (1998) *J. Gen. Viol.,* 79:587-590.

Conway et al., (1997) *Nature,* 386:91-94, describe the structure of human HBc particles at 9 Angstrom resolution, as determined from cryo-electron micrographs. Bottcher et al. (1997), *Nature,* 386:88-91, describe the polypeptide folding for the human HBc monomers, and provide an approximate numbering scheme for the amino acid residues at which alpha-helical regions and their linking loop regions form. Zheng et al., (1992) *J. Biol. Chem.,* 267(13): 9422-9429 report that core particle formation is not dependent upon the arginine-rich C-terminal domain, the binding of nucleic acids or the formation of disulfide bonds based on their study of mutant proteins lacking one or more cysteines and others' work with C-terminal-truncated proteins [Birnbaum et al., (1990) *J. Virol.* 64, 3319-3330]. The low resolution structure of HBc particles reported by Conway et al., (1997) and Bottcher et al., (1997) has been confirmed by a 3.3 Å resolution crystal structure of the T=4 particles reported by Wynne at al., (1999) *Mol. Cell,* 3(6):70-80.

The hepatitis B nucleocapsid or viral core protein (HBc) has been disclosed as an immunogenic carrier moiety that stimulates the T cell response of an immunized host animal. See, for example, U.S. Pat. Nos. 4,818,527, 4,882,145 and 5,143,726. A particularly useful application of this carrier is its ability to present foreign or heterologous B cell epitopes at the site of the immunodominant loop that is present at about residue positions 70-90, and more usually recited as about positions 75 through 85 from the amino-terminus (N-terminus) of the protein. Clarke et al. (1991) F. Brown et al. eds., *Vaccines* 91, Cold Spring Harbor Laboratory, Cold Spring Harbor, N.Y., pp. 313-318.

During viral replication, HBV nucleocapsids associate with the viral RNA pre-genome, the viral reverse transcriptase (Pol), and the terminal protein (derived from Pol) to form replication competent cores. The association between the nucleocapsid and the viral RNA pre-genome is mediated by an arginine-rich domain at the carboxyl-terminus (C-terminus). When expressed in heterologous expression systems, such as *E. coli* where viral RNA pre-genome is absent, the protamine-like C-terminus; i.e., residues at positions 150 through 183, can bind *E. coli* RNA. Zhang et al. (1992) *JBC,* 267(13) 9422-29.

HBcAg is a particulate protein derived from the hepatitis B virus that has been proposed as a carrier for heterologous epitopes. The relative immunogenicity of HBsAg (HBs) has been compared with HBcAg (HBc), and the ability of each to evoke immune responses in different genetic backgrounds [Milich et al., *Science,* (1986) 234(4782): p. 1398-1401]. These data emphasize the higher immunogenicity of HBc relative to HBs, and the universal responsiveness to HBc, irrespective of genetic background.

For example, HBc is more than 300 times more immunogenic than HBs in BALB/c mice; and, although both B10.S and B10.M mice are non-responders to HBs, every strain tested is responsive to HBc. These results re-emphasize the suitability of HBc as a vaccine carrier and specifically, its superiority over HBs, hence the selection of HBc as opposed to HBs to carry heterologous epitopes. These facets of HBc are thought to be important in influenza vaccine development, because they address issues of genetic restriction and inadequate antibody titers.

Another advantage of the HBc carrier is the fact that may not require complex adjuvants for efficacy. This is due to the high inherent immunogenicity of the particle. A comparison of the immunogenicity of HBc-*P. berghei* particles showed that alum, which is approved for human use, was more effective than either IFA or CFA [Schodel et al., *J. Exp. Med.,* (1994) 180(3): p. 1037-46]. The importance of this observation is highlighted by toxicity problems associated with newer, more complex adjuvants as was recently noted in clinical trials of SKB's candidate malaria vaccine [Stoute et al., *N. Engl. J. Med.,* *[*1997] 336(2): p. 86-91].

In an application as a vaccine carrier moiety, it may be preferable that the HBV nucleocapsids not bind nucleic acid derived from the host. Birnbaum et al. (1990) *J. Virol.,* 64:3319-3330 showed that the protamine-like C-terminal domain of HBV nucleocapsids could be deleted without interfering with the protein's ability to assemble into virus-like particles. It is thus reported that proteins truncated to about position 144; i.e., containing the HBc sequence from position one through about 144, can self-assemble, whereas deletions beyond residue 139 abrogate capsid assembly [Birnbaum et al., (1990) *J. Virl.,* 64:3319-30].

Zlotnick et al., (1997) *Proc. Natl. Acad. Sci., USA,* 94:9556-9561 studied the assembly of full length and truncated HBc proteins in to particles. In addition to discussing full length molecules, those authors reported the preparation of a truncated protein that contained the HBc sequence from position 1 through 149 in which the cysteines at positions 48, 61 and 107 were each replaced by alanines and in which a cysteine residue was added at the C-terminus (position 150). That C-terminal mercaptan was used for linkage to a gold atom cluster for labeling in electron microscopy.

More recently, Metzger et al. (1998) *J. Gen. Viol.,* 79:587-590 reported that the proline at position 138 (Pro-138 or P138) of the human viral sequence is required for particle formation. Those authors also reported that assembly capability of particles truncated at the carboxy-terminus to lengths of 142 and 140 residues was affected, with assembly capability being completely lost with truncations resulting in lengths of 139 and 137 residues.

Several groups have shown that truncated particles exhibit reduced stability relative to standard hepatitis B core particles [Gallina et al. (1989) *J. Virol.,* 63:4645-4652; Inada, et al. (1989) *Virus Res.,* 14:27-48], evident by variability in particle sizes and the presence of particle fragments in purified preparations [Maassen et al., (1994) *Arch. Virol.,* 135:131-142]. Thus, prior to the report of Metzger et al., above, Pumpens et al., (1995) *Intervirology,* 38:63-74 summarized the literature reports by stating that the carboxy-terminal border for HBc sequences required for self-assembly was located between amino acid residues 139 and 144, and that the first two or three amino-terminal residues could be replaced by other sequences, but elimination of four or eleven amino-terminal residues resulted in the complete disappearance of chimeric protein in transformed *E. coli* cells.

Recombinantly-produced hybrid HBc particles bearing internal insertions (referred to in the art as HBc chimeric particles or HBc chimers) containing various inserted polypeptide sequences have been prepared by heterologous expression in a wide variety of organisms, including *E. coli, B. subtilis, Vaccinia, Salmonella typhimurium, Saccharomyces cerevisiae*. See, for example Pumpens et al. (1995) *Intervirology,* 38:63-74, and the citations therein that note the work of several research groups. Native HBc particles have also been produced in plants (Tsuda et al., 1998) *Vox Sang,* 74(3):148-155.

Such HBc chimers often appear to have a less ordered structure, when analyzed by electron microscopy, compared to particles that lack heterologous epitopes [Schodel et al., (1994) *J. Exp. Med.,* 180:1037-1046]. In some cases the insertion of heterologous epitopes into C-terminally truncated HBc particles has such a dramatic destabilizing affect that hybrid particles cannot be recovered following heterologous expression [Schodel et al. (1994) *Infect. Immunol.,* 62:1669-1676]. Thus, many chimeric HBc particles are so unstable that they fall apart during purification to such an extent that they are unrecoverable or they show very poor stability characteristics, making them problematic for vaccine development.

The above Pumpens et al. (1995) *Intervirology,* 38:63-74 report lists particle-forming chimers in which the inserted polypeptide sequence is at the N-terminus, the C-terminus and between the termini. Insert lengths reported in that article are 24 to 50 residues at the N-terminus, 7 to 43 residues internally, and 11 to 741 residues at the C-terminus.

Kratz et al., (1999) *Proc. Natl. Acad. Sci., U.S.A.,* 96:1915-1920 recently described the *E. coli* expression of chimeric HBc particles comprised of a truncated HBc sequence internally fused to the 238-residue green fluorescent protein (GFP). This chimer contained the inserted GFP sequence flanked by a pair of glycine-rich flexible linker arms replacing amino acid residues 79 and 80 of HBc. Those particles were said to effectively elicit antibodies against native GFP in rabbits as host animals.

U.S. Pat. No. 5,990,085 describes two fusion proteins formed from an antigenic bovine inhibin peptide fused into (i) the immunogenic loop between residues 78 and 79 and (ii) after residue 144 of carboxy-terminal truncated HBc. Expressed fusion proteins were said to induce the production of anti-inhibin antibodies when administered in a host animal. The titers thirty days after immunization reported in that patent are relatively low, being 1:3000-15,000 for the fusion protein with the loop insertion and 1:100-125 for the insertion after residue 144.

U.S. Pat. No. 6,231,864 teaches the preparation and use of a strategically modified hepatitis B core protein that is linked to a hapten. The modified core protein contains an insert of one to about 40 residues in length that contains a chemically-reactive amino acid residue to which the hapten is pendently linked.

Recently published WO 01/27281 teaches that the immune response to HBc can be changed from a Th1 response to a Th2 response by the presence or absence, respectively, of the C-terminal cysteine-containing sequence of the native molecule. That disclosure also opines that disulfide formation by C-terminal cysteines could help to stabilize the particles. The presence of several residues of the native HBc sequence immediately upstream of the C-terminal cysteine was said to be preferred, but not required. One such alternative that might be used to replace a truncated C-terminal HBc sequence was said to include a C-terminal cysteine and an optional sequence that defines an epitope from other than HBc.

Published PCT application WO 01/98333 teaches the deletion of one or more of the four arginine repeats present at the C-terminus of native HBc, while maintaining the C-terminal cysteine residue. That application also teaches that the deleted region can be replaced by an epitope from a protein other than HBc so that the HBc portion of the molecule so formed acts as a carrier for the added epitope.

Published PCT applications corresponding to WO 02/13765 A2 and WO 02/14478 A2 teach that stabilization of C-terminally truncated HBc particles can be achieved through the use of one or more added cysteine residues in the chimer proteins from which the particles are assembled. Those added cysteine residues are taught to be at or near the C-terminus of the chimeric protein.

A structural feature whereby the stability of full-length HBc particles could be retained, while abrogating the nucleic acid binding ability of full-length HBc particles, would be highly beneficial in vaccine development using the hepadnaviral nucleocapsid delivery system. Indeed, Ulrich et al. in their recent review of the use of HBc chimers as carriers for foreign epitopes [*Adv. Virus Res.,* 50: 141-182 (1998) Academic Press] note three potential problems to be solved for use of those chimers in human vaccines. A first potential problem is the inadvertent transfer of nucleic acids in a chimer vaccine to an immunized host. A second potential problem is interference from preexisting immunity to HBc. A third possible problem relates to the requirement of reproducible preparation of intact chimer particles that can also withstand long-term storage.

The above four published PCT applications appear to contain teachings that can be used to overcome over come the potential problems disclosed by Ulrich et al. As disclosed hereinafter, the present invention provides another HBc chimer that provides unexpectedly high titers of antibodies against influenza, and in one aspect also provides a solution to the problems of HBc chimer stability as well as the substantial absence of nucleic acid binding ability of the construct. In addition, a contemplated recombinant chimer exhibits reduced antigenicity toward preexisting anti-HBc antibodies.

The above particle instability findings related to N-terminal truncated HBc chimer molecules notwithstanding, Neirynck et al., (October 1999) *Nature Med.,* 5(10):1157-1163 reported that particle formation occurred on *E. coli* expression of a HBc chimer that contained the N-terminal 24-residue portion of the influenza M2 protein (M2e), including the initiating methionine, fused at residue 5 to full length HBc.

Bachmann and co-workers [Jegerlehner et al., (2002) *Vaccine,* 20:3104-3112] compared a fusion construct substantially identical to that of Neirynck et al. above, with a coupled construct similar to that disclosed in U.S. Pat. No. 6,231,864 in which the external 23-residues (after in vivo removal of the methionine residue) of the M2 protein of influenza A was coupled via a linker to a lysine residue engineered into the loop in a C-terminally truncated HBc (1-149) that also had the cysteine residues at positions 48 and 107 replaced by serine residues. Their results indicated an increase in anti-M2 titers and enhanced survival (6/6 vs. 0/3) for the coupled construct over the N-terminal fusion protein.

The previously discussed use of hybrid HBc proteins with truncated C-termini for vaccine applications offers several advantages over their full-length counterparts, including enhanced expression levels and lack of bound *E. coli* RNA. However, C-terminally truncated particles engineered to display heterologous epitopes are often unstable, resulting in particles that either fail to associate into stable particulate structures following expression, or that readily dissociate into non-particulate structures during and/or following purification. Such a lack of stability is exhibited by particles comprised of chimeric HBc molecules that are C-terminally truncated to HBc position 149 and also contain the above residues 2-24 of the influenza A M2 protein.

Others have reported that in wild type hepadnaviral core antigens a cysteine residue upstream of the HBcAg start codon is directly involved in the prevention of particle formation [Schodel et al. (Jan. 15, 1993) *J. Biol. Chem.,* 268(2): 1332-1337; Wasenauer et al. (March 1993) *J. Virol.,* 67(3): 1315-1322; and Nassal et al. (July 1993) *J. Virol.,* 67(7):4307-4315]. All three groups reported that in wild type HBeAg, the cysteine residue at position −7 of the pre-core sequence, which is present when the core gene is translated from an upstream initiator methionine at position −30, is responsible for preventing particle formation and therefore facilitating the transition from particulate HBcAg to secreted, non-particulate HBeAg.

Based upon the above three publications, one would expect the inclusion of one or more cysteine residues at a position prior to the initiator methionine of HBc; i.e., at a residue position of less than one relative to the N-terminus of the sequence of SEQ ID NO:1, to actually destabilize C-terminal truncated hybrid particles rather than stabilize them. As will be seen from the discussion that follows, the present invention provides results that are contrary to those expectations.

BRIEF SUMMARY OF THE INVENTION

The present invention contemplates an hepadna virus-based immunogen for inducing antibodies to the extracellular domain of the influenza A M2 protein (M2e), and an inoculum and a vaccine comprising that immunogen dispersed in a physiologically tolerable diluent. Hereinafter, the designations "M2" and "M2e" are used interchangeably. A contemplated immunogen is a self-assembled particle comprised of recombinant hepatitis B virus core (HBc) chimer protein molecules. Each of those molecules has a length of about 150 to about 375 amino acid residues, includes a sequence of 6 to about 24 residues of SEQ ID NO: 9 and contains four peptide-linked amino acid residue sequence domains from the N-terminus that are denominated Domains I, II, III and IV.

The first domain, Domain I, comprises about 75 to about 160 amino acid residues. The sequence of this Domain includes at least the sequence of the residues of position 4 through about position 75 of HBc. One to three cysteine residues are also present at a position in the chimer molecule of about one to −55, preferably to about −30 and more preferably to about −20, relative to the N-terminus of HBc of SEQ ID NO:1 [N-terminal cysteine residue(s)]. The N-terminal cysteine residues are present within a sequence other than that of the pre-core sequence of HBc. A cysteine residue of Domain I can also be present in the two to four sequences of about 6 to about 24 residues of an influenza A M2 polypeptide $X_1X_2X_3X_4X_5X_6X_7X_8TX_{10}X_{11}X_{12}X_{13}X_{14}X_{15}X_{16}X_{17}X_{18}X_{19}X_{20}X_{21}$-$X_{22}X_{23}X_{24}$ of SEQ ID NO:9 such as a preferred polypeptide $X_1X_2X_3X_4X_5X_6X_7X_8$-TPIRNE-$X_{15}X_{16}X_{17}X_{18}X_{19}X_{20}X_{21}X_{22}X_{23}X_{24}$ of SEQ ID NO:10 that are peptide-bonded to or within about 15 residues of the N-terminus of the HBc sequence, and whose subscripted X residues are defined hereinafter, as well as one or more or HBc residues 1-4.

The second domain, Domain II, comprises about zero to about 60 amino acid residues peptide-bonded to about residue 75 of Domain I of which (i) zero to all ten residues in the sequence of HBc positions 76 through 85 are present peptide-bonded to (ii) an optional sequence of about 6 to about 48 residues that constitute one or more repeats of the above influenza A M2 polypeptide of SEQ ID NO:9.

The third domain, Domain III, is an HBc sequence from about position 86 through about position 135 peptide-bonded to about residue 85.

The fourth domain, Domain IV, comprises (i) the residues of positions 136 through 140 plus up to nine residues of an HBc amino acid residue sequence from position 141 through 149 peptide-bonded to the residue of about position 135 of Domain III, (ii) zero to three cysteine residues, (iii) fewer than four arginine or lysine residues, or mixtures thereof adjacent to each other, and (iv) up to about 100 amino acid residues in a sequence heterologous to HBc from position 164 to the C-terminus, and preferably a sequence heterologous to HBc from position 156 to the C-terminus.

A contemplated chimer molecule (i) contains no more than 10 percent conservatively substituted amino acid residues in the HBc sequence, (ii) self-assembles into particles that are substantially free of binding to nucleic acids on expression in a host cell, and those particles are more stable on formation than are particles formed from an otherwise identical HBc chimer that lacks said N-terminal cysteine residue(s) or in which an N-terminal cysteine residue present in the chimer molecule is replaced by another residue.

It is preferred that the HBc sequence of Domain I include the residues of position 4 through position 75 alone plus at least an N-terminal cysteine residue. It is further preferred that a contemplated immunogen contain one cysteine residue within Domain IV alone or in an amino acid residue sequence heterologous to that of HBc from position 164 to the C-terminus. It is particularly preferred that that heterologous sequence comprise a T cell epitope of influenza A.

Another embodiment comprises an inoculum or vaccine that comprises an above HBc chimer particle that is dissolved or dispersed in a pharmaceutically acceptable diluent composition that typically also contains water. When administered in an immunogenic effective amount to an animal such as a mammal or bird, an inoculum induces antibodies that immunoreact specifically with the chimer particle. The antibodies so induced also immunoreact specifically with (bind to) the N-terminal portion of the M2 protein.

The present invention has several benefits and advantages.

A particular benefit of the invention is that its use as a vaccine provides extraordinary antibody titers against influenza A.

An advantage of the invention is that those very high antibody titers have been produced with the aid of an adjuvant approved for use in humans.

Another benefit of the invention is that the recombinant immunogen can be prepared easily and in large quantities using well-known cell culture techniques to grow transformed host cells.

Another advantage of the invention is that the immunogen is easily prepared using well-known recombinant techniques.

Yet another benefit of the invention is that a preferred immunogen exhibits greater stability at elevated temperatures than to other HBc chimers.

Yet another advantage of the invention is that a contemplated immunogen is substantially free of nucleic acids.

Still further benefits and advantages will be apparent to the worker of ordinary skill from the disclosure that follows.

BRIEF DESCRIPTION OF THE DRAWINGS

In the drawings forming a portion of this disclosure:

FIG. 1, shown in two panels as FIG. 1A and FIG. 1B, provides an alignment of six published sequences for mammalian HBc proteins from six viruses. The first (SEQ ID NO:1), human viral sequence is of the ayw subtype and was published in Galibert et al. (1983) *Nature,* 281:646-650; the second human viral sequence (SEQ ID NO:2), of the adw subtype, was published by Ono et al. (1983) *Nucleic Acids Res.,* 11(6): 1747-1757; the third human viral sequence (SEQ ID NO:3), is of the adw2 subtype and was published by Valenzuela et al., *Animal Virus Genetics*, Field et al. eds., Academic Press, New York (1980) pages 57-70; the fourth human viral sequence (SEQ ID NO:4), is of the adyw subtype that was published by Pasek et al. (1979) *Nature,* 282:575-579; the fifth sequence (SEQ ID NO:5), is that of the woodchuck virus that was published by Galibert et al. (1982) *J. Virol.,* 41:51-65; and the sixth mammalian sequence, (SEQ ID NO:6), is that of the ground squirrel that was published by Seeger et al. (1984) *J. Virol.,* 51:367-375.

FIG. 2 shows the modifications made to commercial plasmid vector pKK223-3 in the preparation of plasmid vector pKK223-3N used herein for preparation of recombinant HBc chimers. The modified sequence (SEQ ID NO:7) is shown below the sequence of the commercially available vector (SEQ ID NO:8). The bases of the added NcoI site are shown in lower case letters and the added bases are shown with double underlines, whereas the deleted bases are shown as dashes. The two restriction sites present in this segment of the sequence (NcoI and HindIII) are indicated.

FIG. 11 in two panels shows photographs of SDS-PAGE analysis of CV-1818 particles that contain three serially linked copies of the M2e polypeptide after a stability study using 0, 1, 2, 5 and 10 mM EDTA in the 20 mM sodium phosphate, pH 7.2, particle storage buffer as shown over each column at room temperature (RT; FIG. 11A) and 37° C. (FIG. 11B), and illustrates the absence of cleavage with addition of EDTA (1-10 mM). The control (C) was a sample of the same particles retrieved from freezer storage just prior to use.

FIG. 13 in two panels shows a series of superimposed SEC graphs showing analysis of heat-treated (3 hours) particles shortly after that treatment (FIG. 13A) and thereafter upon maintenance for one week at room temperature (FIG. 13B).

DEFINITIONS

Figure 3:
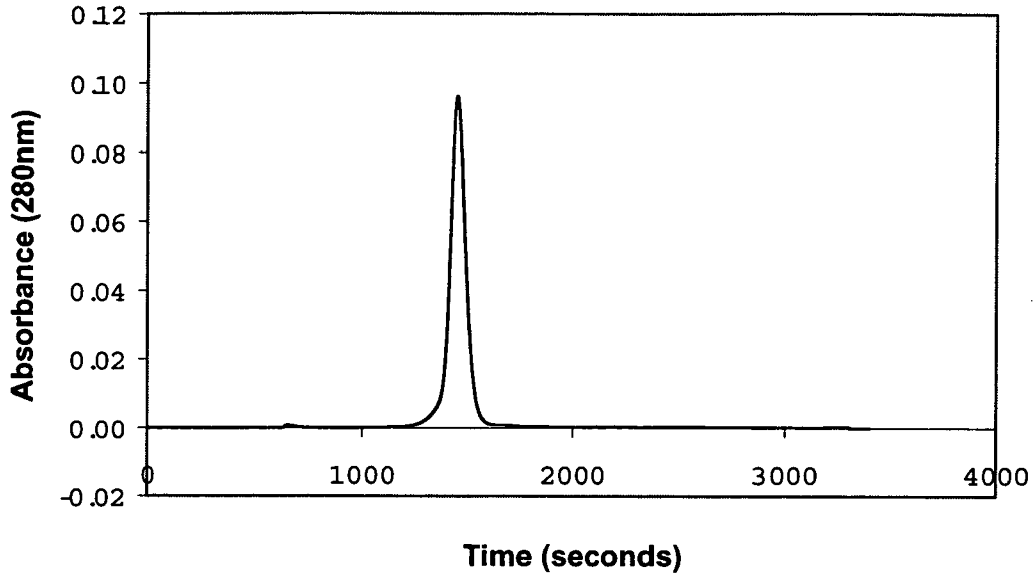
FIG. 3 is an analytical size exclusion chromatography elution profile for ICC-1603 particles in which absorbance at 280 nm is shown on the ordinate and time in seconds is shown on the abscissa.

Numerals utilized in conjunction with HBc chimers indicate the position in the HBc ayw amino acid residue sequence of SEQ ID NO:1 at which one or more residues has been added to or deleted from the sequence, regardless of whether additions or deletions to the amino acid residue sequence are present. Thus, HBc149 indicates that the chimer ends at residue 149, whereas HBc149+C150 indicates that that same chimer contains a cysteine residue at HBc position 150 relative to the sequence numbers of SEQ ID NO:1.

The term "antibody" refers to a molecule that is a member of a family of glycosylated proteins called immunoglobulins, which can specifically bind to an antigen.

The word "antigen" has been used historically to designate an entity that is bound by an antibody or receptor, and also to designate the entity that induces the production of the antibody. More current usage limits the meaning of antigen to that entity bound by an antibody or receptor, whereas the word "immunogen" is used for the entity that induces antibody production or binds to the receptor. Where an entity discussed herein is both immunogenic and antigenic, reference to it as either an immunogen or antigen is typically made according to its intended utility.

"Antigenic determinant" refers to the actual structural portion of the antigen that is immunologically bound by an antibody combining site or T-cell receptor. The term is also used interchangeably with "epitope".

The word "conjugate" as used herein refers to a hapten operatively linked to a carrier protein, as through an amino acid residue side chain.

The term "conservative substitution" as used herein denotes that one amino acid residue has been replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like.

The term "corresponds" in its various grammatical forms as used in relation to peptide sequences means the peptide sequence described plus or minus up to three amino acid residues at either or both of the amino- and carboxy-termini and containing only conservative substitutions in particular amino acid residues along the polypeptide sequence.

The term "Domain" is used herein to mean a portion of a recombinant HBc chimer molecule that is identified by (i) residue position numbering relative to the position numbers of HBcAg subtype ayw as reported by Galibert et al., (1979) *Nature,* 281:646-650 (SEQ ID NO:1). The polypeptide portions of at least chimer Domains I, II and III are believed to exist in a similar tertiary form to the corresponding sequences of naturally occurring HBcAg.

As used herein, the term "fusion protein" designates a polypeptide that contains at least two amino acid residue sequences not normally found linked together in nature that are operatively linked together end-to-end (head-to-tail) by a peptide bond between their respective carboxy- and amino-terminal amino acid residues. The fusion proteins of the present invention are HBc chimer molecules that induce the production of antibodies that immunoreact with a polypeptide that corresponds in amino acid residue sequence to the polypeptide portion of the fusion protein.

The phrase "hepatitis B" as used here refers in its broadest context to any member of the family of mammalian hepadnaviridae, as discussed before.

The words "polypeptide" and "peptide" are used interchangeably throughout the specification and designate a linear series of amino acid residues connected one to the other by peptide bonds between the alpha-amino and carboxy groups of adjacent amino acids. Polypeptides can be a variety of lengths, either in their neutral (uncharged) forms or in forms that are salts. It is well understood in the art that amino acid residue sequences contain acidic and basic groups, and that the particular ionization state exhibited by the peptide is dependent on the pH value of the surrounding medium when the peptide is in solution, or that of the medium from which it was obtained if the peptide is in solid form. Thus, "polypeptide" or its equivalent terms is intended to include the appropriate amino acid residue sequence referenced. A peptide or polypeptide is always shown herein from left to right and in the direction from amino-terminus (N-terminus) to carboxy-terminus (C-terminus).

The term "residue" is used interchangeably with the phrase amino acid residue. All amino acid residues identified herein are in the natural or L-configuration. In keeping with standard polypeptide nomenclature, [*J. Biol. Chem.,* 243, 3557-59 (1969)], abbreviations for amino acid residues are as shown in the following Table of Correspondence.

TABLE OF CORRESPONDENCE

| 1-Letter | 3-Letter | AMINO ACID |
|---|---|---|
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| Z | Glx | L-glutamic acid or L-glutamine |
| W | Trp | L-tryptophan |
| R | Arg | L-arginine |
| D | Asp | L-aspartic acid |
| N | Asn | L-asparagine |
| B | Asx | L-aspartic acid or L-asparagine |
| C | Cys | L-cysteine |

DETAILED DESCRIPTION OF THE INVENTION

The present invention contemplates an immunogen and a vaccine or inoculum comprising that immunogen against the influenza A virus. A contemplated immunogen is a particle comprised of recombinant hepatitis B virus core (HBc) protein chimer molecules with a length of about 150 to about 375 and preferably about 150 to 235 amino acid residues that contains four peptide-linked amino acid residue sequence domains from the N-terminus that are denominated Domains I, II, III and IV. One to three cysteine residues are present at or near the N-terminus of the chimer and two to four polypeptides containing 6 to about 24 residues of the influenza A M2 extracellular domain (or M2e) polypeptide of SEQ ID NO:9 such as that of SEQ ID NO:10, as defined hereinbelow, are present peptide-bonded (fused) to the chimer molecule.

It is to be noted that the M2e sequences of human, avian and swine influenza A viruses are very similar. Thus, residues 1-9 of the human and avian viruses are identical, as are residues 1-7 and 9-10 of the human and swine viruses. All three viruses share the positions of the two cysteines (17 and 19) and have identical residues at positions 22-24. Even though the other positions can contain different residues at the other positions of M2e, the residues of the human sequence have been found present in different isolates such that the human sequence represents a consensus sequence for all three viruses.

In a contemplated immunogenic chime particle, (a) Domain I comprises about 75 to about 160 amino acid residues whose sequence includes at least the sequence of the residues of position 4 through about position 75 of HBc. One to three cysteine residues is(are) also present at a position in the chimer molecule of about one to about −55, preferably to about −30 and more preferably to about −20, relative to the N-terminus of HBc of SEQ ID NO:1 [N-terminal cysteine residue(s)]. The N-terminal cysteine residues is(are) present within a sequence other than that of the pre-core sequence of HBc.

A cysteine residue of Domain I can also be present in an optionally, but preferably, present (i) two to four sequences of 6 to about 24 residues of an above-noted influenza A M2 polypeptide such as $X_1X_2X_3X_4X_5X_6X_7X_8TX_{10}X_{11}X_{12}X_{13}X_{14}X_{15}X_{16}X_{17}X_{18}X_{19}X_{20}X_{21}$-$X_{22}X_{23}X_{24}$ of SEQ ID NO:9 or a preferred polypeptide such as $X_1X_2X_3X_4X_5X_6X_7X_8$TPIRNE$X_{15}X_{16}X_{17}X_{18}X_{19}X_{20}$-$X_{21}X_{22}X_{23}X_{24}$ Of SEQ ID NO:10 that are peptide-bonded to or within about 15 residues of the N-terminus of the HBc sequence (See, Table 4), as well as (ii) one or more of HBc residues 1-4. In such an influenza A M2 polypeptide sequence, residues $X_1$ through $X_8$ are absent or present, and when present are the residues naturally present in the M2e protein sequence that are methionine, serine, leucine, leucine, threonine or proline, glutamic acid, valine, and glutamic acid or aspartic acid, respectively, with the proviso that when one subscripted X residue is present, any remaining subscripted X with a higher subscript number up to 8 is also present, $X_{10}$ is present and is proline, leucine or histidine, $X_{11}$ is present and is isoleucine or threonine, $X_{12}$ is present and is arginine or lysine, $X_{13}$ is present and is asparagine or serine, $X_{14}$ is present and is glutamic acid or glycine, residues $X_{15}$ and $X_{16}$ are present or absent, and when present are tryptophan and glycine or glutamic acid, respectively, residues $X_{17}$ and $X_{19}$ are present or absent, and when present are independently cysteine, serine, or alanine, residue $X_{18}$ is present or absent, and when present is arginine or lysine, and residues $X_{20}$ through $X_{24}$ are present or absent, and when present are the residues naturally present in the M2 protein sequence that are asparagine, glycine or serine, aspartic acid or glycine, serine, serine and aspartic acid respectively, with the proviso that when one subscripted X residue is present, any remaining subscripted X residue with a lower subscript number down to 15 is also present.

(b) Domain II comprises about zero to about 60 amino acid residues peptide-bonded to about residue 75. This sequence includes (i) zero to all 10 of the residues of a sequence of HBc from HBc position 76 through 85 peptide-bonded to (ii) an optional sequence of about 6 to about 48 residues that constitute one or more repeats of 6 to about 24 residues of an above influenza A M2 polypeptide of SEQ ID NO:9.

(c) Domain III is an HBc sequence from about position 86 through about position 135 that is peptide-bonded to about residue 85.

d) Domain IV comprises (i) the residues of positions 136 through 140 plus up to sixteen residues of an HBc amino acid residue sequence from position 141 through 156 peptide-bonded to the residue of position 135 of Domain III, (ii) zero to three cysteine residues, (iii) fewer than four arginine or lysine residues, or mixtures thereof adjacent to each other, and (iv) up to about 100 amino acid residues in a sequence heterologous to HBc from position 156 to the C-terminus. Thus, Domain IV contains at least the 5 residues of positions 136-140.

A contemplated chimer molecule (i) contains up to about 10 percent conservatively substituted amino acid residues in the HBc sequence, (ii) self-assembles into particles that are substantially free of binding to nucleic acids on expression in a host cell, and those particles are more stable on formation than are particles formed from an otherwise identical HBc chimer that lacks said N-terminal cysteine residue(s) or in which an N-terminal cysteine residue present in the chimer molecule is replaced by another residue.

A preferred chimer molecule contains a cysteine residue that is present at a position of about −50 to about +1 relative to the N-terminus of HBc as is illustrated in FIG. 1 and SEQ ID NO:1. The concept of a negative amino acid position is usually associated with a leader sequence such as the pre-core sequence of HBc. That concept is used similarly here in that one can simply align a given chimer molecule sequence with that of SEQ ID NO:1 to determine the position of the chimer that corresponds to that of the starting methionine residue of position +1 of HBc. Inasmuch as amino acid residue sequences are normally shown from left to right and in the direction from N-terminus to C-terminus, any aligned chimer molecule residue to the left of the position occupied by the HBc start methionine has a negative position. A contemplated cysteine residue can occur at a position about twenty residues to the left of the aligned start methionine of HBc to the position corresponding to that start methionine.

In examining the length of a contemplated HBc chimer, such a recombinant protein can have a length of about 150 to about 325 amino acid residues. Preferably, that length is about 150 to about 235 residues. More preferably, the length is about 170 to about 215 residues. These differences in length arise from changes in the length of Domains I, II and IV, and particularly the number of M2 polypeptides present and whether a C-terminal sequence heterologous to HBc is present.

HBc chimers having a Domain I that contains more than a deletion of the first three amino-terminal (N-terminal) residues have been reported to result in the complete disappearance of HBc chimer protein in *E. coli* cells. Pumpens et al., (1995) *Intervirology,* 38:63-74. On the other hand, a recent study in which an immunogenic 23-mer polypeptide from the influenza M2 protein was fused to the HBc N-terminal sequence reported that the resultant fusion protein formed particles when residues 1-4 of the native HBc sequence were replaced. Neirynck et al. (October 1999) *Nature Med.,* 5(10): 1157-1163 and patent application WO9907839. Thus, the art teaches that particles can form when an added amino acid sequence is present peptide-bonded the one of residues 1-5 of HBc, whereas particles do not form if no additional sequence is present and more than residues 1-3 are deleted from the N-terminus of HBc.

An N-terminal sequence peptide-bonded to one of the first five N-terminal residues of HBc can contain a sequence of up to about 40 residues that are heterologous to HBc; i.e., a portion of a pre-core sequence can be present in a contemplated chimer molecule. Exemplary sequences include an influenza A B cell or T cell epitopes such as are discussed hereinafter, a sequence of another (heterologous) protein such as β-galactosidase as can occur in fusion proteins as a result of the expression system used.

Domain I preferably has the sequence of residues of positions 2-, 3- or 4-through position 75 of HBc. Domain I also contains one to three, preferably one, added cysteine residue(s) and also preferably includes two to four sequences of about 6 to about 24 residues of the sequence of the extracellular region of the influenza A M2e protein peptide-bonded at the amino-terminus as discussed herein below. Domain I therefore typically contains a deletion of at least the methionine residue of position 1 of HBc and can include deletions of the residues at HBc positions 2, 3 and 4.

The one to three cysteine residues is(are) present at a position in the chimer molecule of about one to about −55, preferably to about −30 and more preferably to about −20, relative to the N-terminus of HBc of SEQ ID NO:1 [N-terminal cysteine residue(s)]. Thus, using the sequence of SEQ ID NO:1 as a reference point, the N-terminal cysteine residue(s) is located in the chimer molecule at a position that corresponds to the methionine at position 1 of SEQ ID NO:1 (FIG. 1), or at a position up to about 50 residues upstream from that position. Most preferably, an N-terminal cysteine is located at a position of about one to about minus 14 relative to position 1 of SEQ ID NO:1.

The one or more N-terminal cysteine residues are present within a sequence other than that of the pre-core sequence of HBc. As was noted previously, the HBeAg molecule contains the pre-core sequence that includes a cysteine residue. That molecule does not form particles, whereas particles are desired herein. Thus, although an N-terminal cysteine residue can be adjacent to a pre-core sequence, such a residue is not present within a pre-core sequence or a contemplated chimer molecule.

Domain I can have a length of about 160 residues. Preferably, Domain I has a length of about 95 to about 145 amino acid residues, and includes two to four, and preferably three influenza A M2 polypeptide epitope sequences of SEQ ID NO:9 such as a sequence of SEQ ID NO:10, that preferably includes the C-terminal 19 residues of the M2 polypeptide of SEQ ID NO:9.

Recent studies have indicated that the N-terminal residues upstream from the first glutamic acid residue (between residues $X_5$ and $X_6$ in the above sequence) are or can be cleaved during preparation and expression by one or more hitherto unknown proteases that are thought to include a serine protease [whose activity can be inhibited by phenylmethanesulfonyl fluoride (PMSF)] or a metalloprotease [whose activity can be inhibited by ethylenediaminetetra-acetic acid (EDTA)]. Thus, some preferred embodiments utilize one or more 19-mer or shorter M2 sequences whose N-terminal residue is the glutamic acid at $X_6$ in SEQ ID NO: 9.

More preferably, it has been found that the activity of the protease can be minimized and likely eliminated by heating a buffer solution of the chimer particles to a temperature of about 50° to about 70° C. for a time period of about 1.5 to about 3 hours. The effect of the protease can also be minimized or eliminated by maintaining the particles in an aqueous composition that also contains a protease-inhibiting amount of EDTA (e.g. about 1-10 mM) or a similar sequestrant. An exemplary group of other useful metalloprotease-inhibiting sequestrants (chelators) include 2,2'-bipyridyl, dimercaptopropanol, ethyleneglycol-bis-(2-aminoethyl)-N,N,N'N"-tetraacetic acid (EGTA), nitrilotriacetic acid (NTA), ortho-phenanthroline, salicylic acid, triethanolamine (TEA), bestatin, and phosphoramidon. The sequestrant and protease can be removed from the composition by passage of the otherwise purified particles over a size-exclusion or similar column followed by dialysis or similar treatment. The protease can also be dealt with by similar heating of a sequestrant-containing aqueous composition of the chimer particles.

Where two or three M2e sequences are peptide-bonded together and thereby joined serially, the cysteine residues present at one or both of positions 17 and 19 of a native M2 sequence can be absent and a contemplated N-terminal cysteine residue can be present between an added M2 sequence and the N-terminus of the HBc sequence. Preferably, a contemplated N-terminal cysteine is present in one or more of the M2 sequences at one or both of positions 17 and 19 of the native sequence. A cysteine can be present in each of two or three M2 sequences, in the N-terminal M2 sequence (at about position −52 or −54), in a middle sequence of three (at about position −30 or −32) or in the sequence joined to the HBc sequence (at about position −6 or −8). When two or three M2 sequences are present, it is preferred that one or two cysteines, preferably two cysteines, be present in the M2 sequence peptide bonded to the HBc sequence; i.e., the M2 sequence that is bonded directly to the HBc sequence or that is distal from the N-terminus of the molecule.

Domain II, which is peptide-bonded to about residue 75, contains about zero to about 60 amino acid residues. This Domain includes zero (none), and preferably at least 4 residues, and more preferably at least 8, through all 10 of the HBc sequence residues of about positions 76 through about position 85. Domain II also optionally includes a sequence of about 6 to about 48 residues that constitute one or more repeats of the before-mentioned influenza A M2 polypeptide of SEQ ID NO:9. The influenza A M2 polypeptide sequence, when present, is preferably peptide-bonded between HBc residues 78 and 79, and all of the HBc sequence from position 76 through 85 is present.

Preferred influenza A M2 polypeptide sequences for insertion into Domains I or II, or both, of a contemplated recombinant HBc chimer are enumerated in Table A, below. A sequence beginning with a methionine residue (M) is designed to be N-terminal sequence for insertion into the N-terminus of Domain I, whereas a sequence free of an N-terminal M residue is designed for insertion into Domain II.

TABLE A

Influenza A M2 Protein B Cell Epitopes

| Sequence | SEQ ID NO |
|---|---|
| SLLTEVETPIRNEWGCRCNGSSD | 11 |
| SLLTEVETPIRNEWGCRCNDSSD | 12 |
| SLLTEVETPIRNEWGARANDSSD | 13 |
| SLLTEVETPIRNEWGSRSNDSSD | 14 |
| SLLTEVETPIRNEWGSRCNDSSD | 15 |
| SLLTEVETPIRNEWGCRSNDSSD | 16 |
| SLLTEVETPIRNEWGCRANDSSD | 17 |
| SLLTEVETPIRNEWGARCNDSSD | 18 |
| MSLLTEVETPIRNEWGCRCNDSSD | 19 |
| MSLLTEVETPIRNEWGSRSNDSSD | 20 |
| MGISLLTEVETPIRNEWGCRCND-SSDELLGWLWGI | 21 |
| MSLLTEVETPIRNEWGARANDSSD | 22 |

TABLE A-continued

| Sequence | SEQ ID NO |
|---|---|
| **Influenza A M2 Protein B Cell Epitopes** | |
| MSLLTEVETPIRNEWGCRANDSSD | 23 |
| MSLLTEVETPIRNEWGARCNDSSD | 24 |
| MSLLTEVETPIRNEWGCRSNDSSD | 25 |
| MSLLTEVETPIRNEWGSRCNDSSD | 26 |
| SLLTEVETPIRNEWGSRSNDSSDSLL-TEVETPIRNEWGSRSNDSSD | 27 |
| SLLTEVETPIRNEWGSRSNDSSDSLL-TEVETPIRNEWGSRSNDSSDSLL-TEVETPIRNEWGCRCNDSSD | 28 |
| SLLTEVETPIRNEWGARANDSSDSLL-TEVETPIRNEWGCRCNDSSD | 29 |
| SLLTEVETPIRNEWGARANDSSDSLL-TEVETPIRNEWGARANDSSDSLL-TEVETPIRNEWGCRCNDSSD | 30 |
| EVETPIRNEWGSRCNDSSD | 31 |
| EVETPIRNEWGSRCNDSSDEVET-PIRNEWGSRCNDSSD | 32 |
| EVETPIRNEWGSRCNDSSDEVET-PIRNEWGSRCNDSSDEVE-TPIRNEWGCRCNDSSD | 33 |
| SLLTEVETPIRNEWGSRSNDSSDSLL-TEVETPIRNEWGSRSNDSSDSLL-TEVETPIRNEWGSRSNDSSDSLL-TEVETPIRNEWGCRCNDSSD | 130 |
| SLLTEVETPIRNEWGSRSNDSSDSLL-TEVETPIRNEWGSRSNDSSDSLL-TEVETPIRNEWGSRSNDSSDSLL-TEVETPIRNEWGSRSNDSSDSLL-TEVETPIRNEWGCRCNDSSD | 131 |
| $X_1X_2X_3X_4X_5X_6X_7X_8$TPIRNE$X_{15}X_{16}X_{17}$-$X_{18}X_{19}X_{20}X_{21}X_{22}X_{23}X_{24}$ | 10 |
| $X_1X_2X_3X_4X_5X_6X_7X_8$TPIRNE$X_{15}X_{16}X_{17}$-$X_{18}X_{19}X_{20}X_{21}X_{22}X_{23}X_{24}X_2$-$X_3X_4X_5X_6X_7X_8$TPIRNE$X_{15}X_{16}$-$X_{17}X_{18}X_{19}X_{20}X_{21}X_{22}X_{23}X_{24}$ | 34 |
| $X_1X_2X_3X_4X_5X_6X_7X_8$TPIRNE$X_{15}X_{16}X_{17}$-$X_{18}X_{19}X_{20}X_{21}X_{22}X_{23}X_{24}X_2$-$X_3X_4X_5X_6X_7X_8$TPIRNE$X_{15}X_{16}X_{17}$-$X_{18}X_{19}X_{20}X_{21}X_{22}X_{23}X_{24}X_2$-$X_3X_4X_5X_6X_7X_8$TPIRNE$X_{15}X_{16}X_{17}$-$X_{18}X_{19}X_{20}X_{21}X_{22}X_{23}X_{24}$ | 35 |
| $X_1X_2X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}$ | 9 |
| $X_1X_2X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}X_2$-$X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}$ | 36 |
| $X_1X_2X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}X_2$-$X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}X_2$-$X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}$ | 37 |
| $X_1X_2X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}X_2$-$X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}X_2$-$X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}X_2$-$X_3X_4X_5X_6X_7X_8TX_{10}X_{11}X_{12}X_{13}X_{14}X_{15}$-$X_{16}X_{17}X_{18}X_{19}X_{20}X_{21}X_{22}X_{23}X_{24}$ | 132 |
| SLLTEVETPTRNEWGCRCNDSSD | 134 |
| SLLTEVETPTRNGWGCRCNDSSD | 135 |
| SLLTEVETPIRNEWECRCNGSSD | 136 |
| SLLTEVETPTKNEWECRCNDSSD | 137 |
| SLLTEVETPTRNGWECKCSDSSD | 138 |
| SLLTEVDTLTRNGWGCRCSDSSD | 139 |
| SLLTEVETLTRNGWECKCRDSSD | 140 |
| **Influenza B Protein** | |
| NNATFNYTNVNPISHIR | 38 |

In the polypeptide of SEQ ID NO:9, residues $X_1$ through $X_8$ are absent or present, and when present are the residues naturally present in the M2 protein sequence that are methionine, serine, leucine, leucine, threonine or proline, glutamic acid, valine, and glutamic acid or aspartic acid, respectively, with the proviso that when one subscripted X residue is present, any remaining subscripted X with a higher subscript number up to 8 is also present, $X_{10}$ is present and is proline, leucine or histidine, $X_{11}$ is present and is isoleucine or threonine, $X_{12}$ is present and is arginine or lysine, $X_{13}$ is present and is asparagine or serine, $X_{14}$ is present and is glutamic acid or glycine, residues $X_{15}$ and $X_{16}$ are present or absent, and when present are tryptophan and glycine or glutamic acid, respectively, residues $X_{17}$ and $X_{19}$ are present or absent, and when present are independently cysteine, serine, or alanine, residue $X_{18}$ is present or absent, and when present is arginine or lysine, and residues $X_{20}$ through $X_{24}$ are present or absent, and when present are the residues naturally present in the M2 protein sequence that are asparagine, glycine or serine, aspartic acid or glycine, serine, serine and aspartic acid respectively, with the proviso that when one subscripted X residue is present, any remaining subscripted X residue with a lower subscript number down to 15 is also present.

In the similar polypeptide of SEQ ID NO:10, $X_1$ through $X_8$ are absent or present, and when present are the residues naturally present in the reported M2 protein sequence; i.e., methionine, serine, leucine, leucine, threonine, glutamic acid or aspartic acid, valine, and glutamic acid, respectively, with the proviso that when one subscripted X is present, any remaining subscripted X residue with a higher subscript number up to 8 is also present. Thus, when $X_1$ is present, each of $X_2$ through $X_8$ is also present. Similarly, when $X_3$ is present, each of $X_4$ through $X_8$ is also present, and the like. On the other hand, $X_8$ can be present without any other of the remaining X residues having a lower valued subscript number being present. The residues $X_{15}$ and $X_{16}$ are present or absent, and when present are tryptophan and glycine or glutamic acid, respectively. Residues $X_{17}$ and $X_{19}$ are present or absent, and when present are independently cysteine, serine, or alanine. It is preferred that at least one of $X_{17}$ and $X_{19}$ be cysteine, particularly when an M2 polypeptide epitope is present at the N-terminus of the chimer molecule. It is more preferred that two cysteines be present when a plurality of M2e sequences are present, and that those two cysteines be present in the M2 sequence nearest to the N-terminal residue of the HBc sequence portion. Residue $X_{18}$ is present or absent, and when present is arginine or lysine. Residues $X_{20}$ through $X_{24}$ are present or absent, and when present are the residues naturally present in the reported M2 protein sequence; i.e., asparagine, glycine or serine, aspartic acid or glycine, serine, serine and aspartic acid respectively, with the proviso that when one subscripted X is present, any remaining X residue with a lower subscript number through 15 is also present. Thus, for example, when $X_{23}$ is present, so are each of residues $X_{15}$ through $X_{22}$.

Domain III contains the sequence of HBc about position 86 through about position 135 peptide-bonded at its N-terminus to about residue 85.

The fourth domain, Domain IV, comprises (i) the residues of positions 136 through 140 plus up to sixteen residues of an HBc amino acid residue sequence from position 141 through position 156, and preferably nine residues through 149 peptide-bonded to the residue of about position 135 of Domain III, (ii) zero to three cysteine residues, and preferably one cysteine residue, (iii) fewer than four arginine or lysine residues, or mixtures thereof adjacent to each other, and (iv) up to about 100 amino acid residues, preferably up to 50 amino acid residues, and more preferably up to about 25 residues, in a sequence heterologous to HBc from position 164, or preferably from position 156, to the C-terminus.

It is preferred that Domain IV contain up to fourteen residues of an HBc sequence from position 136 through position 149 peptide-bonded to residue 135; i.e., an HBc sequence that begins with the residue of position 136 that can continue through position 149. Thus, if the residue of position 148 is present, so is the sequence of residues of positions 136 through 147, or if residue 141 is present, so is the sequence of residues of positions 136 through 140.

Domain IV can also contain zero to three cysteine residues and those Cys residues are present within about 30 residues of the carboxy-terminus (C-terminus) of the chimer molecule. Preferably, one cysteine (Cys) residue is present, and that Cys is preferably present as the carboxy-terminal (C-terminal) residue, unless an influenza T cell epitope is present as part of Domain IV. When such a T cell epitope is present, the preferred Cys is preferably within the C-terminal last five residues of the HBc chimer.

The presence of the above-discussed N-terminal cysteine residue(s) provides an unexpected enhancement of the ability of the chimer molecules to form stable immunogenic particles (discussed hereinafter). Thus, a contemplated HBc chimer immunogen tends to form particles that stay together upon collection and initial purification as measured by analytical size exclusion chromatography, whose details are discussed hereinafter.

The contemplated particles can also be more stable to decomposition at 37° C. after aging than are similar chimer particles lacking that cysteine residue. This latter type of enhanced stability can be measured using 15 percent SDS-PAGE gels with particles dispersed in sample buffer (reducing). Gels are stained using Coomassie Blue, and then analyzed. This type of stability is believed to be exhibited against hydrolysis, whereas the stability determined by size exclusion chromatography is that of initial particle formation.

Particles that additionally contain one or more C-terminal cysteine residues exhibit enhanced stability in formation and also toward decomposition on aging, with some particles containing both N- and C-terminal cysteines usually exhibiting greater stability in either measure than those particles having only an added cysteine at either the N- or C-terminus.

Domain IV contains fewer than four arginine or lysine residues, or mixtures thereof adjacent to each other. Arginine and lysines are present in the C-terminal region of HBc that extends from position 156 through the C-terminus of the native molecule. That region is sometimes referred to as the "protamine" or "arginine-rich" region of the molecule and binds nucleic acids. A contemplated HBc chimer molecule and particle are substantially free of bound nucleic acids.

The substantial freedom of nucleic acid binding can be readily determined by a comparison of the absorbance of the particles in aqueous solution measured at both 280 and 260 nm; i.e., a 280/260 absorbance ratio. The contemplated particles do not bind substantially to nucleic acids that are oligomeric and/or polymeric DNA and RNA species originally present in the cells of the organism used to express the protein. Such nucleic acids exhibit an absorbance at 260 nm and relatively less absorbance at 280 nm, whereas a protein such as a contemplated chimer absorbs relatively less at 260 nm and has a greater absorbance at 280 nm.

Thus, recombinantly expressed HBc particles or chimeric HBc particles that contain the arginine-rich sequence at residue positions 150-183 (or 150-185) exhibit a ratio of absorbance at 280 nm to absorbance at 260 nm (280:260 absorbance ratio) of about 0.8, whereas particles free of the arginine-rich nucleic acid binding region of naturally occurring HBc such as those that contain fewer than four arginine or lysine residues or mixtures thereof adjacent to each other, or those having a native or chimeric sequence that ends at about HBc residue position 140 to position 149, exhibit a 280:260 absorbance ratio of about 1.2 to about 1.6.

Chimeric HBc particles of the present invention are substantially free of nucleic acid binding and exhibit a 280:260 absorbance ratio of about 1.2 to about 1.7, and more typically, about 1.4 to about 1.6. This range is due in large part to the number of aromatic amino acid residues present in Domains II and IV of a given chimeric HBc particle. That range is also in part due to the presence of the Cys in Domain IV of a contemplated chimer, whose presence can diminish the observed ratio by about 0.1 for a reason that is presently unknown.

The contemplated chimer HBc particles are more stable in aqueous buffer at 37° C. over a time period of about two weeks to about one month than are particles formed from a HBc chimer containing the same peptide-linked Domain II, III and IV sequences and an otherwise same Domain I sequence in which the one to three cysteine residues [N-terminal cysteine residue(s)] are absent or a single N-terminal residue present is replaced by another residue such as an alanine residue.

Thus, for example, particles containing an influenza A M2e polypeptide in Domain I [e.g. ICC-1590 particles] that include two cysteine residues are more stable than otherwise identical particles [ICC-1603 particles] assembled from chimer molecules whose N-terminal M2 variant sequence contains serine residues in place of the cysteines. Similarly, particles containing the above serine-containing influenza B cell epitopes in Domain I and a single cysteine at the C-terminus [ICC-1605 particles] are more stable than are otherwise identical particles in which that cysteine is absent, but are less stable than are the particles containing the two N-terminal cysteines, ICC-1590 particles or those particles that contained both N-terminal and C-terminal cysteines [ICC-1604 particles].

It is noted that particles and the chimer molecules of which they are constituted are interchangeably referred to by the prefix "ICC-", or the prefix-"CV-" followed by a four-digit number, or by just a four-digit number without a prefix. Thus, the above ICC-1590 particles could also be referred to as CV-1590 particles or just as 1590 particles. Each designation has the same meaning.

A contemplated particle containing a N-terminal cysteine residue is also typically prepared in greater yield than is a particle assembled from a chimer molecule lacking a N-terminal cysteine.

Although the T cell help afforded by HBc is highly effective in enhancing antibody responses (i.e. B cell-mediated) to 'carried' immunogenic sequences following vaccination, HBc does not activate influenza-specific T cells, except in restricted individuals for whom a B cell epitope containing sequence also contains a T cell epitope. To help ensure universal priming of influenza-specific T helper cells, in addition to B cells, one or more influenza-specific T helper epitopes is preferably incorporated into a contemplated immunogen and is located in Domain IV of the immunogen.

A plurality of the above or another T cell epitopes can be present in Domain IV or another B cell epitope can be present. In preferred practice, Domain IV has up to about 50 residues in a sequence heterologous to HBc. More preferably, that sequence is up to about 25 residues and includes a T cell epitope.

Because M2 is expressed abundantly by infected cells, it has the potential to serve as a target for influenza-specific CTL activity. The extracellular domain is a possible attachment site for antibody, which may function to immobilize the function of M2, in an analogous manner to the therapeutic drug amantadine, or via the activation of antibody-dependent cellular cytotoxicity (ADCC) and/or complement-dependent cytotoxicity (CDC).

Indeed, the extracellular domain of M2 has been shown to contain at least two distinct human CTL epitopes, one at 7-15 [Jameson et al., (1998) *J. Virol.,* 72(11):8682-8689] and another at 3-11 [Gianfrani er al., (2000) *Hum. Immunol.,* 61(5):438-352]. Anti-M2e mediated lysis of influenza-infected cells via ADCC and/or CDC may be the preferred mechanisms of target cell lysis, compared with CTL, because, unlike CTL, they are not subject to MHC restriction. Therefore, an ability to evoke sufficient titers of anti-M2 antibodies displaying a required IgG subclass profile, and M2e specificity, should evoke broad protection across diverse populations.

The capacity of antibodies to the extracellular domain of M2 to have a biological effect was first described by Zebedee and Lamb, who showed that the monoclonal anti-M2 antibody 14C2 slows the growth of the virus in culture [Zebedee et al, (1988) *J Virol,* 62(8):2762-2772]. In 1990, Treanor and colleagues showed that the same monoclonal antibody successfully inhibited influenza A virus replication in mice [Treanor et al., (1990) *J. Virol.,* 64(3):1375-1377]. Palladino et al. determined that 14C2 was not virus neutralizing in vivo, but did bind infected cells and inhibited virus growth in vitro; however, it failed to cure the infection [Palladino et al., (1995) *J. Virol.,* 69(4):2075-2081]. The authors of the latter paper duly noted that 14C2 is an IgG1 subclass antibody, and that IgG2a and IgG2b are most effective at fixing complement; they are also superior to IgG1 for binding to FcγRIII receptors on NK cells. Indeed, as is shown hereinafter, high titers of IgG2a antibodies in the mouse, which are typical of a Th1 immune response, appear to correlate with protection. An immune response that can provide anti-M2e mediated lysis of influenza-infected cells via ADCC and/or CDC is thus a preferred response.

Anamnestic anti-M2 responses have repeatedly been observed following challenge of mice previously immunized with HBc-M2 particles, which is indicative of M2e-HBc particles priming M2-specific T cells. To investigate this, preliminary studies were conducted to investigate whether lymphocytes from immunized mice can be recalled by M2e peptide, in vitro. Significant increases in the number of interferon-gamma secreting cells was observed following recall with peptides derived from M2, HBc p85-100, and recombinant HBcAg, but not p100-120 from HBc. The recall with HBcAg was most prominent, which is expected since this is a potent T cell immunogen containing many functional T cell epitopes for BALB/c mice [Saito et al., (2001) *Vaccine,* 20(1-2):125-133].

Recall with all antigens appeared to be stronger for lymphocytes isolated from mice immunized with ICC-1604 particles versus ICC-1569 particles. This result indicates that ICC-1604 particles may be a superior T cell immunogen compared with to ICC-1569 particles. However, it is important to note that the M2 recall antigen for these studies was M2e (2-24), which contains cysteine residues at 17 and 19, and was therefore only truly homologous for ICC-1604 particles and not ICC-1569 particles, because the latter contains serine residues in place of the two cysteines residues.

The reduced level of restimulation with M2e for ICC-1569 particles versus ICC-1604 particle-immunized mice could be explained if the cysteine residues at positions 17 and/or 19 are components of one or more T cell epitope(s). However, the presence of cysteine residue-containing T cell epitopes does not explain the reduced level of restimulation with HBc-derived antigens.

The observation of an anamnestic response, with regard to anti-M2e titers, following viral challenge of M2e-HBc-immunized mice, appears to indicate the presence of at least one T-helper cell epitope in the M2e domain (positions 2-24).

The epitopes derived from the influenza nucleoprotein (NP 206-229), which is broadly reactive in humans (HLA-DR1, HLA-DR2, HLA-DRw13) [Brett et al., (1991) *J. Immunol.,* 147(3):984-991] and also functional in BALB/c mice are contemplated for use as T cell epitopes herein. Particles with this epitope fused to the C-terminus of HBc particles have been expressed and purified. Additional influenza Th epitopes are also considered, such as NP 341-362, NP 297-318 and NP 182-205 [Brett et al., (1991) *J. Immunol.,* 147(3):984-991]; these sequences can ultimately be linked in series at the C-terminus of the M2e-expressing particle. These illustrative sequences are provided below.

| NP Position | Sequence | SEQ ID NO |
|---|---|---|
| 206-229 | FWRGENGRKTRSAYERMCNILKGK | 39 |
| 341-362 | LRVLSFIRGTKVSPRGKLSTRG | 40 |
| 297-318 | SLVGIDPFKLLQNSQVYSLIRP | 41 |
| 182-205 | AVKGVGTMVMELIRMIKRGINDRN | 42 |

A contemplated recombinant HBc chimer molecule is typically present and is used in an immunogen or vaccine as a self-assembled particle. These particles are comprised of 180 to 240 chimer molecules that separate into protein molecules in the presence of disulfide reducing agents such as 2-mercaptoethanol and denaturing reagents such as SDS. The individual molecules are bound together into the particle by protein-protein interactions, and these interactions are stabilized by the presence of disulfide bonds. These particles are similar to the particles observed in patients infected with HBV, but these particles are non-infectious. Upon expression in various prokaryotic and eukaryotic hosts, the individual recombinant HBc chimer molecules assemble in the host into particles that can be readily harvested from the host cells.

In addition to the before-discussed N- and C-truncations and insertion of influenza M2 polypeptide epitopes, a contemplated chimer molecule can also contain conservative substitutions in the amino acid residues that constitute HBc Domains I, II, III and IV. Conservative substitutions are as defined before.

More rarely, a "nonconservative" change, e.g., replacement of a glycine with a tryptophan is contemplated. Analogous minor variations can also include amino acid deletions or insertions, or both. Guidance in determining which amino acid residues can be substituted, inserted, or deleted without abolishing biological activity can be found using computer programs well known in the art, for example LASERGENE software (DNASTAR Inc., Madison, Wis.)

The HBc portion of a chimer molecule of the present invention [the portion having the HBc sequence that has other than a sequence of an added epitope, or heterologous residue(s) that are a restriction enzyme artifact] most preferably has the amino acid residue sequence at positions 2 through 149 of subtype ayw that is shown in FIG. 1 (SEQ ID NO:1), when present. Somewhat less preferred are the corresponding amino acid residue sequences of subtypes adw, adw2 and adyw that are also shown in FIG. 1 (SEQ ID NOs:2, 3 and 4). Less preferred still are the sequences of woodchuck and ground squirrel at aligned positions 2 through 149 that are the last two sequences of FIG. 1 (SEQ ID NOs:5 and 6). As noted elsewhere, portions of different sequences from different mammalian HBc proteins can be used together in a single chimer.

When the HBc portion of a chimer molecule of the present invention has other than a sequence of a mammalian HBc molecule at positions 2 through 156 or through position 149, when present, because one or more conservative substitutions has been made, it is preferred that no more than 10 percent, and more preferably no more than 5 percent, and most preferably no more than 3 percent of the amino acid residues are substituted as compared to SEQ ID NO:1 from position 2 through 149 or 156. A contemplated chimer of 149 HBc residues can therefore contain up to about 15 or 16 residues that are different from those of SEQ ID NO:1 at positions 2 through 149, and preferably about 7 or 8 residues. More preferably, up to about 5 residues are different from the ayw sequence (SEQ ID NO:1) at residue positions 2-149. Where an HBc sequence is truncated further at one or both termini, the number of substituted residues is proportionally different. Deletions elsewhere in the molecule are considered conservative substitutions for purposes of calculation so that if, for example, Domain I were to have a C-terminus at position 133 instead of 135, two residues (134 and 135) would be presumed to be present for purposes of calculation.

Chimer Preparation

A contemplated chimeric immunogen is prepared using the well-known techniques of recombinant DNA technology. Thus, sequences of nucleic acid that encode particular polypeptide sequences are added and deleted from the precursor sequence that encodes HBV.

A contemplated chimeric immunogen typically utilizes a cysteine residue present in the M2 sequence as the N-terminal cysteine. Primers for the preparation of such chimer molecules by in vitro mutagenesis of a polynucleotide encoding an HBc molecule are discussed hereinafter. When a cysteine-containing M2 polypeptide epitope is not present at the N-terminus, the N-terminal cysteine can be provided by in vitro mutagenesis using a primer that encodes just a cysteine-containing portion of the M2 polypeptide or a simple N-terminal start sequence such as Met-Cys- or Met-Gly-Cys-.

As was noted previously, the HBc immunodominant loop is usually recited as being located at about positions 75 through 85 from the amino-terminus (N-terminus) of the intact protein. The influenza A M2 B cell epitope-containing sequence can be placed into that immunodominant loop sequence of Domain II. That placement substantially eliminates the HBc immunogenicity and antigenicity of the HBc loop sequence, while presenting the influenza A M2 B cell epitope in an extremely immunogenic position in the assembled chimer particles.

One of two well-known strategies is particularly useful for placing the influenza A M2 B cell sequence into the loop sequence at a desired location such as between residues 78 and 79. A first, less successful strategy is referred to as replacement in which DNA that codes for a portion of the loop is excised and replaced with DNA that encodes an influenza A M2 B cell sequence. The second strategy is referred to as insertion in which an influenza A M2 B cell sequence is inserted between adjacent residues in the loop.

Site-directed mutagenesis using the polymerase chain reaction (PCR) is used in one exemplary replacement approach to provide a chimeric HBc DNA sequence that encodes a pair of different restriction sites, e.g. EcoRI and SacI, one near each end of the immunodominant loop-encoding DNA. Exemplary residues replaced are 76 through 81. The loop-encoding section is excised, an influenza A M2 B cell epitope-encoding sequence flanked on each side by appropriate HBc sequence residues is ligated into the restriction sites and the resulting DNA is used to express the HBc chimer. See, for example, Table 2 of Pumpens et al., (1995) *Intervirology,* 38:63-74 for exemplary uses of a similar technique.

Alternatively, a single restriction site or two sites can be encoded into the region, the DNA cut with a restriction enzyme(s) to provide "sticky" or ends, and an appropriate sticky- or blunt-ended heterologous DNA segment ligated into the cut region. Examples of this type of sequence replacement into HBc can be found in the work reported in Schodel et al., (1991) F. Brown et al. eds., *Vaccines* 91, Cold Spring Harbor Laboratory, Cold Spring Harbor, N.Y., pp. 319-325, Schodel et al., *Behring Inst. Mitt.,* 1997(98):114-119 and Schodel et al., *J. Exp. Med.,* (1994) 180(3): p. 1037-4, the latter two papers discussing the preparation of vaccines against malarial pathogens *P. yoelii* and *P. berghei*, respectively. A replacement strategy that results in a net removal of residues from the immunodominant loop is usually not used herein.

Insertion is preferred. In an illustrative example of the insertion strategy, site-directed mutagenesis is used to create two restriction sites adjacent to each other and between codons encoding adjacent amino acid residues, such as those at residue positions 78 and 79. This technique adds twelve base pairs that encode four amino acid residues (two for each restriction site) between formerly adjacent residues in the HBc loop.

Upon cleavage with the restriction enzymes, ligation of the DNA coding for the illustrative influenza A M2 sequence and expression of the DNA to form HBc chimers, the HBc loop amino acid sequence is seen to be interrupted on its N-terminal side by the two residues encoded by the 5' restriction site, followed toward the C-terminus by the influenza A M2 B-cell epitope sequence, followed by two more heterologous, non-loop residues encoded by the 3' restriction site and then the rest of the loop sequence. This same strategy is also preferably used for insertion into Domain IV of a T cell epitope or one or more cysteine residues that are not a part of a T cell epitope. A similar strategy using an insertion between residues 82 and 83 is reported in Schoedel et al., (1990) F. Brown et al. eds., *Vaccines* 90, Cold Spring Harbor Laboratory, Cold Spring Harbor, N.Y., pp. 193-198.

For example, a DNA sequence that encodes a C-terminal truncated HBc sequence (HBc149) is engineered to contain adjacent EcoRI and SacI sites between residues 78 and 79. Cleavage of that DNA with both enzymes provides one fragment that encodes HBc positions 1-78 3'-terminated with an EcoRI sticky end, whereas the other fragment has a 5'-terminal SacI sticky end and encodes residues of positions 79-149. Ligation of a synthetic nucleic acid having a 5' AATT overhang followed by a sequence that encodes a desired influenza A M2 B cell epitope and a AGCT 3'overhang provides a HBc chimer sequence that encodes that B cell epitope flanked on each side by two heterologous residues (GI and EL, respectively) between residues 78 and 79, while destroying the EcoRI site and preserving the SacI site.

A similar strategy can be used for insertion of a C-terminal cysteine-containing sequence. Here, EcoRI and HindIII restriction sites are engineered in to the HBc DNA sequence after amino acid residue position 149. After digestion with EcoRI and HindIII, a synthetic DNA having the above AATT 5'overhang followed by a T cell epitope-encoding sequence, a stop codon and a 3' AGCT overhang were ligated into the digested sequence to form a sequence that encoded HBc residues 1-149 followed by two heterologous residues (GI), the stop codon and the HindIII site.

PCR amplification using a forward primer having a SacI restriction site followed by a sequence encoding HBc beginning at residue position 79, followed by digestion with SacI and HindIII provided a sequence encoding HBc positions 79-149 plus the two added residues and the T cell epitope at the C-terminus. Digestion of that construct with SacI and ligation provides the complete gene encoding a desired recombinant HBc chimer immunogen having the sequence, from the N-terminus, of HBc positions 1-78, two added residues, the influenza A M2-sequence containing B cell epitopes, two added residues, HBc positions 79-149, two added residues, and the T cell epitope.

It is noted that the preferred use of two heterologous residues on either side of (flanking) a heterologous immunogenic sequence containing B cell or T cell epitopes is a matter of convenience. As a consequence, one can also use zero to three or more added residues that are not part of the HBc sequence on either or both sides of an inserted sequence. One or both ends of the insert and HBc nucleic acid can be "chewed back" with an appropriate nuclease (e.g. S1 nuclease) to provide blunt ends that can be ligated together. Added heterologous residues that are neither part of the inserted B cell or T cell epitopes nor a part of the HBc sequence are not counted in the number of residues present in a recited Domain.

It is also noted that one can also synthesize all or a part of a desired recombinant HBc chimer nucleic acid using well-known synthetic methods as is discussed and illustrated in U.S. Pat. No. 5,656,472 for the synthesis of the 177 base pair DNA that encodes the 59 residue ribulose bis-phosphate carboxylase-oxygenase signal peptide of *Nicotiana tabacum*. For example, one can synthesize Domains I and II with a blunt or "sticky" end that can be ligated to Domains III and IV to provide a construct that expresses a contemplated HBc chimer that contains zero added residues to the N-terminal side of the B cell epitope and zero to three added residues on the C-terminal side or at the Domain II/III junction or at some other desired location.

A nucleic acid sequence (segment) that encodes a previously described HBc chimer molecule or a complement of that coding sequence is also contemplated herein. Such a nucleic acid segment is present in isolated and purified form in some preferred embodiments.

In living organisms, the amino acid residue sequence of a protein or polypeptide is directly related via the genetic code to the deoxyribonucleic acid (DNA) sequence of the gene that codes for the protein. Thus, through the well-known degeneracy of the genetic code additional DNAs and corresponding RNA sequences (nucleic acids) can be prepared as desired that encode the same chimer amino acid residue sequences, but are sufficiently different from a before-discussed gene sequence that the two sequences do not hybridize at high stringency, but do hybridize at moderate stringency.

High stringency conditions can be defined as comprising hybridization at a temperature of about 50°-55° C. in 6×SSC and a final wash at a temperature of 68° C. in 1-3×SSC. Moderate stringency conditions comprise hybridization at a temperature of about 50° C. to about 65° C. in 0.2 to 0.3 M NaCl, followed by washing at about 50° C. to about 55° C. in 0.2×SSC, 0.1% SDS (sodium dodecyl sulfate).

A nucleic sequence (DNA sequence or an RNA sequence) that (1) itself encodes, or its complement encodes, a chimer molecule whose HBc portion from residue position 1 through 136, when present, is that of SEQ ID NOs: 1, 2, 3, 4, 5 or 6 and (2) hybridizes with a DNA sequence of SEQ ID NOs:43, 44, 45, 46, 47 or 48 at least at moderate stringency (discussed above); and (3) whose HBc sequence shares at least 80 percent, and more preferably at least 90 percent, and even more preferably at least 95 percent, and most preferably 100 percent identity with a DNA sequence of SEQ ID NOs: 43, 44, 45, 46, 47 and 48, is defined as a DNA variant sequence. As is well-known, a nucleic acid sequence such as a contemplated nucleic acid sequence is expressed when operatively linked to an appropriate promoter in an appropriate expression system as discussed elsewhere herein.

An analog or analogous nucleic acid (DNA or RNA) sequence that encodes a contemplated chimer molecule is also contemplated as part of this invention. A chimer analog nucleic acid sequence or its complementary nucleic acid sequence encodes a HBc amino acid residue sequence that is at least 80 percent, and more preferably at least 90 percent, and most preferably is at least 95 percent identical to the HBc sequence portion from residue position 1 through residue position 136 shown in SEQ ID NOs: 1, 2, 3, 4, 5 and 6. This DNA or RNA is referred to herein as an "analog of" or "analogous to" a sequence of a nucleic acid of SEQ ID NOs: 43, 44, 45, 46, 47 and 48, and hybridizes with the nucleic acid sequence of SEQ ID NOs: 43, 44, 45, 46, 47 and 48 or their complements herein under moderate stringency hybridization conditions. A nucleic acid that encodes an analogous sequence, upon suitable transfection and expression, also produces a contemplated chimer.

Different hosts often have preferences for a particular codon to be used for encoding a particular amino acid residue. Such codon preferences are well known and a DNA sequence encoding a desired chimer sequence can be altered, using in vitro mutagenesis for example, so that host-preferred codons are utilized for a particular host in which the enzyme is to be expressed. In addition, one can also use the degeneracy of the genetic code to encode the HBc portion of a sequence of SEQ ID NOs: 1, 2, 3, 4, 5 or 6 that avoids substantial identity with a DNA of SEQ ID Nos: 43, 44, 45, 46, 47 or 48 or their complements. Thus, a useful analogous DNA sequence need not hybridize with the nucleotide sequences of SEQ ID NOs: 43, 44, 45, 46, 47 or 48 or a complement under conditions of moderate stringency, but can still provide a contemplated chimer molecule.

```
HBcAYW DNA
                                                            SEQ ID NO 43
atggacatcg acccttataa agaatttgga gctactgtgg agttactctc gtttttgcct  60
tctgacttct ttccttcagt acgagatctt ctagataccg cctcagctct gtatcgggaa 120
gccttagagt ctcctgagca ttgttcacct caccatactg cactcaggca agcaattctt 180
tgctgggggg aactaatgac tctagctacc tgggtgggtg ttaatttgga agatccagcg 240
tctagagacc tagtagtcag ttatgtcaac actaatatgg gcctaaagtt caggcaactc 300
ttgtggtttc acatttcttg tctcactttt ggaagagaaa cagttataga gtatttggtg 360
tctttcggag tgtggattcg cactcctcca gcttatagac caccaaatgc ccctatccta 420
tcaacacttc cggagactac tgttgttaga cgacgaggca ggtcccctag aagaagaact 480
ccctcgcctc gcagacgaag gtctcaatcg ccgcgtcgca gaagatctca atctcgggaa 540
tctcaatgt HBcADW DNA
                                                            SEQ ID NO 44
atggacattg acccttataa agaatttgga gctactgtgg agttactctc gtttttgcct  60
tctgacttct ttccttccgt acgagatctc ctagacaccg cctcagctct gtatcgagaa 120
gccttagagt ctcctgagca ttgctcacct caccatactg cactcaggca agccattctc 180
tgctgggggg aattgatgac tctagctacc tgggtgggta ataatttgca agatccagca 240
tccagagatc tagtagtcaa ttatgttaat actaacatgg gtttaaagat caggcaacta 300
ttgtggtttc atatatcttg ccttactttt ggaagagaga ctgtacttga atatttggtc 360
tctttcggag tgtggattcg cactcctcca gcctatagac caccaaatgc ccctatctta 420
tcaacacttc cggaaactac tgttgttaga cgacgggacc gaggcaggtc ccctagaaga 480
agaactccct cgcctcgcag acgcagatct caatcgccgc gtcgcagaag atctcaatct 540
cgggaatctc aatgt HBcADW2 DNA
                                                            SEQ ID NO 45
atggacattg acccttataa agaatttgga gctactgtgg agttactctc gtttttgcct  60
tctgacttct ttccttccgt cagagatctc ctagacaccg cctcagctct gtatcgagaa 120
gccttagagt ctcctgagca ttgctcacct caccatactg cactcaggca agccattctc 180
tgctgggggg aattgatgac tctagctacc tgggtgggta ataatttgga agatccagca 240
tctagggatc ttgtagtaaa ttatgttaat actaacgtgg gtttaaagat caggcaacta 300
ttgtggtttc atatatcttg ccttactttt ggaagagaga ctgtacttga atatttggtc 360
tctttcggag tgtggattcg cactcctcca gcctatagac caccaaatgc ccctatctta 420
tcaacacttc cggaaactac tgttgttaga cgacgggacc gaggcaggtc ccctagaaga 480
agaactccct cgcctcgcag acgcagatct ccatcgccgc gtcgcagaag atctcaatct 540
cgggaatctc aatgt HBcADYW DNA
                                                            SEQ ID NO 46
atggacattg acccttataa agaatttgga gctactgtgg agttactctc gtttttgcct  60
tctgacttct ttccttccgt acgagatctt ctagataccg ccgcagctct gtatcgggat 120
gccttagagt ctcctgagca ttgttcacct caccatactg cactcaggca agcaattctt 180
tgctggggag acttaatgac tctagctacc tgggtgggta ctaatttaga agatccagca 240
tctagggacc tagtagtcag ttatgtcaac actaatgtgg gcctaaagtt cagacaatta 300
ttgtggtttc acatttcttg tctcactttt ggaagagaaa cggttctaga gtatttggtg 360
tcttttggag tgtggattcg cactcctcca gcttatagac caccaaatgc ccctatccta 420
tcaacgcttc cggagactac tgttgttaga cgacgaggca ggtcccctag aagaagaact 480
ccctcgcctc gcagacgaag atctcaatcg ccgcgtcgca gaagatctca atctcgggaa 540
tctcaatgt Woodchuck DNA
                                                            SEQ ID NO 47
atggctttgg ggcatggaca tagatcctta taaagaattt ggttcatctt atcagttgtt  60
gaattttctt cctttggact tctttcctga tcttaatgct ttggtggaca ctgctactgc 120
cttgtatgaa gaagaactaa caggtaggga acattgctct ccgcaccata cagctattag 180
acaagcttta gtatgctggg atgaattaac taaattgata gcttggatga gctctaacat 240
aacttctgaa caagtaagaa caatcattgt aaatcatgtc aatgatacct ggggacttaa 300
ggtgagacaa agtttatggt ttcatttgtc atgtctcact ttcggacaac atacagttca 360
agaattttta gtaagttttg gagtatggat caggactcca gctccatata gacctcctaa 420
tgcacccatt ctctcgactc ttccggaaca tacagtcatt aggagaagag gaggtgcaag 480
agcttctagg tcccccagaa gacgcactcc ctctcctcgc aggagaagat ctcaatcacc 540
gcgtcgcag Ground Squirrel DNA
atgtatcttt ttcacctgtg ccttgttttt gcctgtgttc catgtcctac tgttcaagcc  60
tccaagctgt gccttggatg gctttgggac atggacatag atccctataa agaatttggt 120
tcttcttatc agttgttgaa ttttcttcct ttggactttt ttcctgatct caatgcattg 180
```

-continued

```
gtggacactg ctgctgctct ttatgaagaa gaattaacag gtagggagca ttgttctcct 240
catcatactg ctattagaca ggccttagtg tgttgggaag aattaactag attaattaca 300
tggatgagtg aaaatacaac agaagaagtt agaagaatta ttgttgatca tgtcaataat 360
acttggggac ttaaagtaag acagacttta tggtttcatt tatcatgtct tacttttgga 420
caacacacag ttcaagaatt tttggttagt tttggagtat ggattagaac tccagctcct 480
tatagaccac ctaatgcacc cattttatca actcttccgg aacatacagt cattaggaga 540
agaggaggtt caagagctgc taggtccccc cgaagacgca ctccctctcc tcgcaggaga 600
aggtctcaat caccgcgtcg cagacgctct caatctccag cttccaactg c          651
```

A recombinant nucleic acid molecule such as a DNA molecule, comprising a vector operatively linked to an exogenous nucleic acid segment (e.g., a DNA segment or sequence) that defines a gene that encodes a contemplated chimer, as discussed above, and a promoter suitable for driving the expression of the gene in a compatible host organism, is also contemplated in this invention. More particularly, also contemplated is a recombinant DNA molecule that comprises a vector comprising a promoter for driving the expression of the chimer in host organism cells operatively linked to a DNA segment that defines a gene for the HBc portion of a chimer or a DNA variant that has at least 90 percent identity to the chimer gene of SEQ ID NOs: 43, 44, 45, 46, 47 or 48 and hybridizes with that gene under moderate stringency conditions.

Further contemplated is a recombinant DNA molecule that comprises a vector containing a promoter for driving the expression of a chimer in host organism cells operatively linked to a DNA segment that is an analog nucleic acid sequence that encodes an amino acid residue sequence of a HBc chimer portion that is at least 80 percent identical, more preferably 90 percent identical, and most preferably 95 percent identical to the HBc portion of a sequence of SEQ ID NOs: 1, 2, 3, 4, 5 or 6. That recombinant DNA molecule, upon suitable transfection and expression in a host cell, provides a contemplated chimer molecule.

It is noted that because of the 30 amino acid residue N-terminal sequence of ground squirrel HBc does not align with any of the other HBc sequences, that sequence and its encoding nucleic acid sequences and their complements are not included in the above percentages of identity, nor are the portions of nucleic acid that encode that 30-residue sequence or its complement used in hybridization determinations. Similarly, sequences that are truncated at either or both of the HBc N- and C-termini are not included in identity calculations, nor are those sequences in which residues of the immunodominant loop are removed for insertion of a heterologous epitope. Thus, only those HBc-encoding bases or HBc sequence residues that are present in a chimer molecule are included and compared to an aligned nucleic acid or amino acid residue sequence in the identity percentage calculations.

Inasmuch as the coding sequences for the gene disclosed herein is illustrated in SEQ ID NOs: 43, 44, 45, 46, 47 and 48, isolated nucleic acid segments, preferably DNA sequences, variants and analogs thereof can be prepared by in vitro mutagenesis, as is well known in the art and discussed in *Current Protocols In Molecular Biology*, Ausabel et al. eds., John Wiley & Sons (New York: 1987) p. 8.1.1-8.1.6, that begin at the initial ATG codon for a gene and end at or just downstream of the stop codon for each gene. Thus, a desired restriction site can be engineered at or upstream of the initiation codon, and at or downstream of the stop codon so that other genes can be prepared, excised and isolated.

As is well known in the art, so long as the required nucleic acid, illustratively DNA sequence, is present, (including start and stop signals), additional base pairs can usually be present at either end of the segment and that segment can still be utilized to express the protein. This, of course, presumes the absence in the segment of an operatively linked DNA sequence that represses expression, expresses a further product that consumes the enzyme desired to be expressed, expresses a product that consumes a wanted reaction product produced by that desired enzyme, or otherwise interferes with expression of the gene of the DNA segment.

Thus, so long as the DNA segment is free of such interfering DNA sequences, a DNA segment of the invention can be about 500 to about 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known. Such long DNA segments are not preferred, but can be used.

DNA segments that encode the before-described chimer can be synthesized by chemical techniques, for example, the phosphotriester method of Matteucci et al. (1981) *J. Am. Chem. Soc.,* 103:3185. Of course, by chemically synthesizing the coding sequence, any desired modifications can be made simply by substituting the appropriate bases for those encoding the native amino acid residue sequence. However, DNA segments including sequences discussed previously are preferred.

A contemplated HBc chimer can be produced (expressed) in a number of transformed host systems, typically host cells although expression in acellular, in vitro, systems is also contemplated. These host cellular systems include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g. baculovirus); plant cell systems transformed with virus expression vectors (e.g. cauliflower mosaic virus; tobacco mosaic virus) or with bacterial expression vectors (e.g., Ti plasmid); or appropriately transformed animal cell systems such as CHO or COS cells. The invention is not limited by the host cell employed.

DNA segments containing a gene encoding the HBc chimer are preferably obtained from recombinant DNA molecules (plasmid vectors) containing that gene. Vectors capable of directing the expression of a chimer gene into the protein of a HBc chimer is referred to herein as an "expression vector".

An expression vector contains expression control elements including the promoter. The chimer-coding gene is operatively linked to the expression vector to permit the promoter sequence to direct RNA polymerase binding and expression of the chimer-encoding gene. Useful in expressing the polypeptide coding gene are promoters that are inducible, viral, synthetic, constitutive as described by Poszkowski et al. (1989) *EMBO J.,* 3:2719 and Odell et al. (1985) *Nature,* 313:810, as well as temporally regulated, spatially regulated, and spatiotemporally regulated as given in Chua et al. (1989) *Science,* 244:174-181.

One preferred promoter for use in prokaryotic cells such as *E. coli* is the Rec 7 promoter that is inducible by exogenously supplied nalidixic acid. A more preferred promoter is present in plasmid vector JHEX25 (available from Promega) that is inducible by exogenously supplied isopropyl-β-D-thiogalacto-pyranoside (IPTG). A still more preferred promoter, the tac promoter, is present in plasmid vector pKK223-3 and is also inducible by exogenously supplied IPTG. The pKK223-3 plasmid can be successfully expressed in a number of *E. coli* strains, such as XL-1, TB1, BL21 and BLR, using about 25 to about 100 μM IPTG for induction. Surprisingly, concentrations of about 25 to about 50 μM IPTG have been found to provide optimal results in 2 L shaker flasks and fermentors.

Expression of a contemplated chimer molecule in other microbes such as *Salmonella* like *S. typhi* and *S. typhimurium* and *S. typhimurium-E. coli* hybrids, yeasts such as *S. cerivisiae* or *Pichia pastoris*, in mammalian cells such as Chinese hamster ovary (CHO) cells, in both monocot and dicot plant cells generally and particularly in dicot plant storage organs such as a root, seed or fruit as where an oral vaccine or inoculum is desired, and in insect cells such as those of *S. Frugiperda* cells or *Trichoplusia* by use of *Autographa californica* nuclear polyhedrosis virus (AcNPV) or baculovirus are discussed in detail in the before-noted parental application as well as in published WO 02/14478 A2. These modes of expression, although contemplated, will therefore not be discussed further herein.

A variety of methods have been developed to operatively link DNA to vectors via complementary cohesive termini or blunt ends. For instance, complementary homopolymer tracts can be added to the DNA segment to be inserted into the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector, as noted before. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase.

Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass. A desired DNA segment can also be obtained using PCR technology in which the forward and reverse primers contain desired restriction sites that can be cut after amplification so that the gene can be inserted into the vector. Alternatively PCR products can be directly cloned into vectors containing T-overhangs (Promega Corp., A3600, Madison, Wis.) as is well known in the art.

The expressed chimeric protein self-assembles into particles within the host cells, whether in single cells or in cells within a multicelled host. The particle-containing cells are harvested using standard procedures, and the cells are lysed using a French pressure cell, lysozyme, sonicator, bead beater or a microfluidizer (Microfluidics International Corp., Newton Mass.). After clarification of the lysate, particles are precipitated with 45% ammonium sulfate, resuspended in 20 mM sodium phosphate, pH 6.8 and dialyzed against the same buffer. The dialyzed material is clarified by brief centrifugation and the supernatant subjected to gel filtration chromatography using Sepharose® CL-4B. Particle-containing fractions are identified, subjected to hydroxyapatite chromatography, and reprecipitated with ammonium sulfate prior to resuspension, dialysis and sterile filtration and storage at −70° C.

Inocula and Vaccines

A before-described recombinant HBc chimer immunogen preferably in particulate form is dissolved or dispersed in an immunogenic effective amount in a pharmaceutically acceptable vehicle composition that is preferably aqueous to form an inoculum or vaccine. When administered to a host animal in need of immunization or in which antibodies are desired to be induced such as a mammal (e.g., a mouse, dog, goat, sheep, horse, bovine, monkey, ape, or human) or bird (e.g., a chicken, turkey, duck or goose), an inoculum induces antibodies that immunoreact with an influenza A M2 B cell epitope present in the immunogen. In a vaccine, those induced antibodies also believed to immunoreact in vivo with (bind to) the virus or virally-infected cells and protect the host from a pathogenic influenza infection. A composition that is a vaccine in one animal can be an inoculum for another host, as where the antibodies are induced in a second host that is not infected by influenza A.

The amount of recombinant HBc chimer immunogen utilized in each immunization is referred to as an immunogenic effective amount and can vary widely, depending inter alia, upon the recombinant HBc chimer immunogen, animal host immunized, and the presence of an adjuvant in the vaccine, as discussed below. Immunogenic effective amounts for a vaccine and an inoculum provide the protection or antibody activity, respectively, discussed hereinbefore.

Vaccines or inocula typically contain a recombinant HBc chimer immunogen concentration of about 1 microgram to about 1 milligram per inoculation (unit dose), and preferably about 10 micrograms to about 50 micrograms per unit dose. Immunizations in mice typically contain 10 or 20 μg of chimer particles.

The term “unit dose” as it pertains to a vaccine or inoculum of the present invention refers to a physically discrete unit suitable as an unitary dosage for animals, each unit containing a predetermined quantity of active material calculated to individually or collectively produce the desired immunogenic effect in association with the required diluent; i.e., carrier, or vehicle. A single unit dose or a plurality of unit doses can be used to provide an immunogenic effective amount of recombinant HBc chimer immunogen particles.

Vaccines or inocula are typically prepared from a recovered recombinant HBc chimer immunogen particles by dispersing the particles in a physiologically tolerable (acceptable) diluent vehicle such as water, saline phosphate-buffered saline (PBS), acetate-buffered saline (ABS), Ringer’s solution or the like to form an aqueous composition. The diluent vehicle can also include oleaginous materials such as peanut oil, squalane or squalene as is discussed hereinafter.

The immunogenic active ingredient is often mixed with excipients that are pharmaceutically acceptable and compatible with the active ingredient. Suitable excipients are, for example, water, saline, dextrose, glycerol, ethanol, or the like and combinations thereof. In addition, if desired, an inoculum or vaccine can contain minor amounts of auxiliary substances such as wetting or emulsifying agents, pH buffering agents that enhance the immunogenic effectiveness of the composition.

A contemplated vaccine or inoculum advantageously also includes an adjuvant. Suitable adjuvants for vaccines and inocula of the present invention comprise those adjuvants that are capable of enhancing the antibody responses against B cell epitopes of the chimer, as well as adjuvants capable of enhancing cell mediated responses towards T cell epitopes contained in the chimer, if present. Adjuvants are well known in the art (see, for example, *Vaccine Design—The Subunit and Adjuvant Approach,* 1995, Pharmaceutical Biotechnology, Volume 6, Eds. Powell, M. F., and Newman, M. J., Plenum Press, New York and London, ISBN 0-306-44867-X).

Exemplary adjuvants include complete Freund's adjuvant (CFA) that is not used in humans, incomplete Freund's adjuvant (IFA), squalene, squalane and alum [e.g., Alhydrogel™ (Superfos, Denmark)], which are materials well known in the art, and are available commercially from several sources.

Preferred adjuvants for use with immunogens of the present invention include aluminum or calcium salts (for example hydroxide or phosphate salts). A particularly preferred adjuvant for use herein is an aluminum hydroxide gel such as Alhydrogel™. For aluminum hydroxide gels (alum), the chimer protein is admixed with the adjuvant so that about 50 to about 800 micrograms of aluminum are present per dose, and preferably about 400 to about 600 micrograms are present. Calcium phosphate nanoparticles (CAP) is an adjuvant being developed by Biosante, Inc (Lincolnshire, Ill.). The immunogen of interest can be either coated to the outside of particles, or encapsulated inside on the inside [He et al. (November 2000) *Clin. Diagn. Lab. Immunol.,* 7(6):899-903].

Another particularly preferred adjuvant for use with an immunogen of the present invention is an emulsion. A contemplated emulsion can be an oil-in-water emulsion or a water-in-oil emulsion. In addition to the immunogenic chimer protein particles, such emulsions comprise an oil phase of squalene, squalane, peanut oil or the like as are well known, and a dispersing agent. Non-ionic dispersing agents are preferred and such materials include mono- and di-$C_{12}$-$C_{24}$-fatty acid esters of sorbitan and mannide such as sorbitan mono-stearate, sorbitan mono-oleate and mannide mono-oleate. An immunogen-containing emulsion is administered as an emulsion.

Preferably, such emulsions are water-in-oil emulsions that comprise squalene, glycerol and a surfactant such as mannide mono-oleate (Arlacel™ A), optionally with squalane, emulsified with the chimer protein particles in an aqueous phase. The oil phase preferably comprises about 0.1 to about 10 percent of the vaccine, and more preferably about 0.2 to about 1 percent. Alternative components of the oil-phase include alpha-tocopherol, mixed-chain di- and tri-glycerides, and sorbitan esters. Well-known examples of such emulsions include Montanide™ ISA-720, and Montanide™ ISA 703 (Seppic, Castres, France), each of which is understood to contain both squalene and squalane, with squalene predominating in each, but to a lesser extent in Montanide™ ISA 703. Most preferably, Montanide™ ISA-720 is used, and a ratio of oil-to-water of 7:3 (w/w) is used. Other preferred oil-in-water emulsion adjuvants include those disclosed in WO 95/17210 and EP 0 399 843.

The use of small molecule adjuvants is also contemplated herein. One type of small molecule adjuvant useful herein is a 7-substituted-8-oxo- or 8-sulfo-guanosine derivative described in U.S. Pat. Nos. 4,539,205, 4,643,992, 5,011,828 and 5,093,318, whose disclosures are incorporated by reference. Of these materials, 7-allyl-8-oxoguanosine (loxoribine) is particularly preferred. That molecule has been shown to be particularly effective in inducing an antigen- (immunogen-) specific response.

A preferred useful adjuvant includes monophosphoryl lipid A (MPL®), 3-deacyl monophosphoryl lipid A (3D-MPL®), a well-known adjuvant manufactured by Corixa Corp. of Seattle, formerly Ribi Immunochem, Hamilton, Mont. The adjuvant contains three components extracted from bacteria: monophosphoryl lipid (MPL) A, trehalose dimycolate (TDM) and cell wall skeleton (CWS) (MPL+TDM+CWS) in a 2% squalene/Tween® 80 emulsion. This adjuvant can be prepared by the methods taught in GB 2122204B. A preferred form of 3-de-O-acylated monophosphoryl lipid A is in the form of an emulsion having a small particle size less than 0.2 μm in diameter (EP 0 689 454 B1).

Most preferred are a compound structurally related to MPL® adjuvant called aminoalkyl glucosamide phosphates (AGPs) such as those available from Corixa Corp under the designation RC-529™ adjuvant {2-[(R)-3-tetra-decanoyloxytetradecanoylamino]-ethyl-2-deoxy -4-O-phosphono-3-O-[(R)-3-tetradecanoyloxytetra-decanoyl]-2-[(R)-3-tetra-decanoyloxytetradecanoyl-amino]-p-D-glucopyranoside triethylammonium salt}. An RC-529 adjuvant is available in a squalene emulsion sold as RC-529SE and in an aqueous formulation as RC-529AF available from Corixa Corp. (see, U.S. Pat. Nos. 6,355,257 and 6,303,347; 6,113,918; and U.S. Publication No. 03-0092643).

Further contemplated adjuvants include synthetic oligonucleotide adjuvants containing the CpG nucleotide motif one or more times (plus flanking sequences) available from Coley Pharmaceutical Group. The adjuvant designated QS21, available from Aquila Biopharmaceuticals, Inc., is an immunologically active saponin fractions having adjuvant activity derived from the bark of the South American tree *Quillaja Saponaria Molina* (e.g. Quil™ A), and the method of its production is disclosed in U.S. Pat. No. 5,057,540. Derivatives of Quil™ A, for example QS21 (an HPLC purified fraction derivative of Quil™ A also known as QA21), and other fractions such as QA17 are also disclosed. Semi-syntheic and synthetic derivatives of *Quillaja Saponaria Molina* saponins are also useful, such as those described in U.S. Pat. Nos. 5,977,081 and 6,080,725. The adjuvant denominated MF59 available from Chiron Corp. is described in U.S. Pat. Nos. 5,709,879 and 6,086,901.

Muramyl dipeptide adjuvants are also contemplated and include N-acetyl-muramyl-L-threonyl-D-isoglutamine (thur-MDP), N-acetyl-nor-muramyl-L-alanyl-D-isoglutamine [CGP 11637, referred to as nor-MDP], and N-acetylmuramyl-L-alanyl-D-isoglutaminyl-L-alanine -2-(1'-2'-dipalmityol-sn-glycero-3-hydroxyphosphoryloxy) ethylamine [(CGP) 1983A, referred to as MTP-PE]. The so-called muramyl dipeptide analogues are described in U.S. Pat. No. 4,767,842.

Preferred adjuvant mixtures include combinations of 3D-MPL and QS21 (EP 0 671 948 B1), oil-in-water emulsions comprising 3D-MPL and QS21 (WO 95/17210, PCT/EP98/05714), 3D-MPL formulated with other carriers (EP 0 689 454 B1), QS21 formulated in cholesterol-containing liposomes (WO 96/33739), or immunostimulatory oligonucleotides (WO 96/02555). Adjuvant SBAS2 (now ASO2) available from SKB (now Glaxo-SmithKline) contains QS21 and MPL in an oil-in-water emulsion is also useful. Alternative adjuvants include those described in WO 99/52549 and non-particulate suspensions of polyoxyethylene ether (UK Patent Application No. 9807805.8).

The use of an adjuvant that contains one or more agonists for toll-like receptor-4 (TLR-4) such as an MPL® adjuvant or a structurally related compound such as an RC-529™ adjuvant or a Lipid A mimetic, alone or along with an agonist for TLR-9 such as a non-methylated oligo deoxynucleotide-containing the CpG motif is particularly preferred. Such adjuvants enhance the production of gamma-producing CD 8+, CD 4+ T cells and cytotoxic lymphocytes when admixed with a contemplated immunogenic HBc-containing particles or chemically linked to such an immunogen. Alum also can be present in such an adjuvant mixture. Initial results indicate that alum tends to enhance the Th2 immune response that favors production of IgG1-type antibodies, whereas the RC-529-type adjuvant favors a Th1 immune response that favors production of IgG2a and IgG2b antibodies and a T cell response when a T cell immunogen is present as is the case when HBc particles comprise the immunogen.

A most preferred adjuvant mixture comprises a stable water-in-oil emulsion further containing aminoalkyl glucosamine phosphates such as described in U.S. Pat. No. 6,113,918. Of the aminoalkyl glucosamine phosphates the molecule known as RC-529 {(2-[(R)-3-tetradecanoyloxytetradecanoylamino]ethyl 2-deoxy-4-O-phosphono-3-O-[(R)-3-tetradecanoyloxy-tetradecanoyl]-2-[(R)-3-tetradecanoyloxytetra-decanoylamino]-p-D-glucopyranoside triethylammonium salt.)} is the most preferred. A preferred water-in-oil emulsion is described in WO 9956776.

Adjuvants are utilized in an adjuvant amount, which can vary with the adjuvant, host animal and recombinant HBc chimer immunogen. Typical amounts can vary from about 1 μg to about 1 mg per immunization. Those skilled in the art know that appropriate concentrations or amounts can be readily determined.

Inocula and vaccines are conventionally administered parenterally, by injection, for example, either subcutaneously or intramuscularly. Additional formulations that are suitable for other modes of administration include suppositories and, in some cases, oral formulation or by nasal spray. For suppositories, traditional binders and carriers can include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like.

An inoculum or vaccine composition takes the form of a solution, suspension, tablet, pill, capsule, sustained release formulation or powder, and contains an immunogenic effective amount of HBc chimer, preferably as particles, as active ingredient. In a typical composition, an immunogenic effective amount of preferred HBc chimer particles is about 1 μg to about 1 mg of active ingredient per dose, and more preferably about 5 μg to about 50 μg per dose, as noted before.

A vaccine or inoculum is typically formulated for internasal (IN) or parenteral administration. Exemplary immunizations are carried out sub-cutaneously (SC) intra-muscularly (IM), intravenusly (IV), intraperitoneally (IP) or intra-dermally (ID).

The HBc chimer particles and HBc chimer particle conjugates can be formulated into the vaccine as neutral or salt forms. Pharmaceutically acceptable salts, include the acid addition salts (formed with the free amino groups of the protein or hapten) and are formed with inorganic acids such as, for example, hydrochloric or phosphoric acids, or such organic acids as acetic, oxalic, tartaric, mandelic, and the like. Salts formed with the free carboxyl groups can also be derived form inorganic bases such as, for example, sodium, potassium, ammonium, calcium, or ferric hydroxides, and such organic bases as isopropylamine, trimethylamine, 2-ethylamino ethanol, histidine, procaine, and the like.

The inocula or vaccines are administered in a manner compatible with the dosage formulation, and in such amount as are therapeutically effective and immunogenic (an antibody-inducing amount or protective amount, as is desired). The quantity to be administered depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in intervals (weeks or months) by a subsequent injection or other administration.

Once immunized, the host animal is maintained for a period of time sufficient for the recombinant HBc chimer immunogen to induce the production of a sufficient titer of antibodies that bind to the M2 protein. The maintenance time for the production of anti-M2 antibodies typically lasts for a period of about three to about twelve weeks, and can include a booster, second immunizing administration of the vaccine. A third immunization is also contemplated, if desired, at a time several weeks to five years after the first immunization. It is particularly contemplated that once a protective level titer of antibodies is attained, the vaccinated host animal is preferably maintained at or near that antibody titer by periodic booster immunizations administered at intervals of about 1 to about 5 years.

The production of antibodies is readily ascertained by obtaining a plasma or serum sample from the immunized host and assaying the antibodies therein for their ability to bind to a synthetic M2 polypeptide antigen in an ELISA assay as described hereinafter or by another immunoassay such as a Western blot as is well known in the art.

It is noted that the before-described antibodies so induced can be isolated from the blood of the host using well-known techniques, and then reconstituted into a second vaccine for passive immunization as is also well known. Similar techniques are used for gamma-globulin immunizations of humans. For example, antiserum from one or a number of immunized hosts can be precipitated in aqueous ammonium sulfate (typically at 40-50 percent of saturation), and the precipitated antibodies purified chromatographically as by use of affinity chromatography in which an M2 polypeptide is utilized as the antigen immobilized on the chromatographic column.

Inocula are preparations that are substantially identical to vaccines, but are used in a host animal in which antibodies to influenza are desired to be induced, but in which protection from influenza is not desired.

Without further elaboration, it is believed that one skilled in the art can, using the preceding description and the detailed examples below, utilize the present invention to its fullest extent. The following preferred specific embodiments are, therefore, to be construed as merely illustrative, and not limiting of the remainder of the disclosure in any way whatsoever.

EXAMPLE 1

B Cell Epitope-Containing Chimer Preparation

A. Preparation of Plasmid Vector pKK223-3N, a Modified Form of pKK223-3

Plasmid vector pKK223-3 (Pharmacia) was modified by the establishment of a unique NcoI restriction site to enable insertion of HBc genes as NcoI-HindIII restriction fragments and subsequent expression in *E. coli* host cells. To modify the pKK223-3 plasmid vector, a new SphI-HindIII fragment was prepared using the PCR primers pKK223-3/433-452-F and pKK223-NcoI-mod-R, and pKK223-3 as the template.

This PCR fragment was cut with the restriction enzymes SphI and HindIII to provide a 467 bp fragment that was then ligated with a 4106 bp fragment of the pKK223-3 vector, effectively replacing the original 480 bp SphI-HindIII fragment. The resultant plasmid (pKK223-3N; 4573 bp) is therefore 13 bp shorter than the parent plasmid and contains modified nucleotide sequence upstream of the introduced NcoI site (see FIG. 2, in which the dashes indicate the absent bases). Restriction sites in plasmid pKK223-3N are indicated in FIG. 2 and nucleotide changes made to the pKK223-3 parent plasmid are indicated by an underline as shown below.

```
pKK223-3/433-452-F
                                            SEQ ID NO: 49
GGTGCATGCAAGGAGATG

pKK223-NcoI-mod-R
                                            SEQ ID NO: 50
GCGAAGCTTCGGATCccatggTTTTTTCCTCCTTATGTGAAATTGTTATC

CGCTC
```

using two PCR primer pairs, one of which amplifies the amino terminus, the other amplifies the carboxyl terminus. For V2, the products of the PCR reactions are a 249 bp (N-terminus) and a 243 bp fragment (C-terminus); for V16, the products are a 249 bp (N-terminus) and a 246 bp fragment (C-terminus; for V8, the products are a 249 bp (N-terminus) and a 349 bp fragment (C-terminus).

The N-terminal fragments prepared were digested with NcoI and EcoRI, and the C-terminal fragments were digested with EcoRI and HindIII. The V2, V16, and V8 fragment pairs were then ligated together at the common EcoRI overhangs. The resultant NcoI-HindIII fragments were then ligated into the pKK223-3N vector, which had been prepared by digestion with NcoI and HindIII.

To insert B cell epitopes into the V2, V16, and V8 plasmids, the appropriate plasmid was digested with EcoRI and SacI restriction enzymes. Synthetic dsDNA fragments containing 5' EcoRI and 3' SacI overhangs were then inserted. In all cases, V2, V16, and V8, glycine-isoleucine (EcoRI) and glutamic acid-leucine (SacI) amino acid pairs, flank the inserted B cell epitopes. The inserted restriction sites are underlined in the primers below.

```
V2
HBc149/NcoI-F
5'-TTGGGCCATGGACATCGACCCTTA                        SEQ ID NO: 51

HBc-D78/EcoRI-R
5'-GCGGAATTCCATCTTCCAAATTAACACCCAC                 SEQ ID NO: 52

HBc-P79/EcoRI-SacI-F
5'-CGCGAATTCAAAAAGAGCTCCCAGCGTCTAGAGACCTAG         SEQ ID NO: 53

HBc149/HindIII-R
5'-CGCAAGCTTAAACAACAGTAGTCTCCGGAAG                 SEQ ID NO: 54

V16
HBc149/NcoI-F
5'-TTGGGCCATGGACATCGACCCTTA                        SEQ ID NO: 51

HBc-D78/EcoRI-R
5'-GCGGAATTCCATCTTCCAAATTAACACCCAC                 SEQ ID NO: 52

HBc-P79/EcoRI-SacI-F
5'-CGCGAATTCAAAAAGAGCTCCCAGCGTCTAGAGACCTAG         SEQ ID NO: 53

HBc149+C/HindIII-R
5'-CGCAAGCTTACTAGCAAACAACAGTAGTCTCCGGAAG           SEQ ID NO: 55

V8
HBC149/NcoI-F
5'-GGGCCATGGACATCGACCCTTA                          SEQ ID NO: 51

HBc-D78/EcoRI-R
5'-GCGGAATTCCATCTTCCAAATTAACACCCAC                 SEQ ID NO: 52

HBc-P79/EcoRI-SacI-F
5'-CGCGAATTCAAAAAGAGCTCCCAGCGTCTAGAGACCTAG         SEQ ID NO: 53

HBc183/HindIII-R
5'-GGAAAGCTTACTAACATTGAGATTCCCG                    SEQ ID NO: 56
```

B. Preparation of V2, V16 and V8 Cloning Vectors

Modified HBc149 (V2 and V16) or HBc183 (V8) genes, able to accept the directional insertion of synthetic dsDNA fragments into the immunodominant loop region, were constructed using PCR. (The plasmid accepting inserts between D78 and P79 and truncated to V149 was named V2, the same plasmid with an additional cysteine following V149 was named V16, and the plasmid accepting inserts between D78 and P79 and terminating at C183, was called V8). The HBc149 and HBc183 genes were amplified in two halves C. Preparation of V34 and V55 Cloning Vectors Modified HBc149 genes, able to accept the directional insertion of synthetic dsDNA fragments into the N-terminal region, 5' to the pre-core sequence LGWLWG, were constructed using PCR. (The plasmid that encoded an HBc sequence terminating at V149 was named V34, whereas the plasmid that encoded an HBc sequence harboring an additional cysteine, C-terminal to V149, was named V55.) The HBc149 gene was amplified in two halves using two PCR primer pairs, one of which amplifies the amino terminus, the other amplifies the carboxyl terminus. For V34, the products of the PCR reactions were a 293 bp (N-terminus) fragment and a 484 bp (C-terminus) fragment; for V55, the same N-terminal fragment was used and a 490 bp C-terminal fragment was prepared.

The N-terminal fragment prepared by PCR was digested with NcoI and SacI, and the C-terminal fragments were digested with SacI and HindIII. The V34 and V55 fragment pairs were then ligated together at the common SacI overhangs. The resultant NcoI-HindIII fragments were then ligated into the pKK223-3N vector, which had been prepared by digestion with NcoI and HindIII.

B cell epitope-containing insertion was accomplished by a procedure identical to that outlined above for the V2, V16, and V8 cloning vectors. Restriction sites are underlined in the oligonucleotides primers below.

```
V34/V55
pKK-BamHI-F
5'-GCGGGATCCGGAGCTTATCGA                          SEQ ID NO: 57

HBc-NcoI/EcoRI/SacI-R
5'-GCGGAGCTCTTTTTGAATTCCCATGGTTTTTTCCTCCTTAT      SEQ ID NO: 58

PreC-SacI-HBc-F
5'-GCGGAGCTCCTTGGGTGGCTTTGGGGCATTGACATCGACCCTTATAAAG  SEQ ID NO: 59

V34
HBc149/HindIII-R
5'-CGCAAGCTTAAACAACAGTAGTCTCCGGAAG                SEQ ID NO: 54

V55
HBc149+C/HindIII-R
5'-CGCAAGCTTACTAGCAAACAACAGTAGTCTCCGGAAG          SEQ ID NO: 55
```

D. Preparation of V47, V48 and V54 Cloning Vectors

Modified HBc149 and HBc183 genes, able to accept the directional insertion of synthetic dsDNA fragments into the N-terminal region between amino acid residues 13 and D4 were constructed using PCR. (The plasmid encoding an HBc chimer terminating at V149 was named V47, the plasmid encoding an HBc chimer harboring an additional cysteine, C-terminal to V149, was named V54, and the plasmid encoding an HBc chimer terminating at C183 was named V48). For V47, V48 and V54, a PCR primer pair was used to amplify the amino-terminal fragment from the template HBc149, including a sequence preceding the HBc gene. The resultant PCR fragment has 190 bp. For the C-terminal fragment of V47, the HBc gene was amplified using a PCR primer pair resulting in a 469 bp fragment; for V54, the C-terminal fragment is 475 bp. For the C-terminus of V48, the HBc183 gene was amplified using a PCR primer pair, resulting in a 574 bp fragment.

The cloning procedure used from this point was identical to that outlined before for the cloning vectors V34 and V55.

To insert heterologous sequences into the V47, V48 and V54 plasmids, the plasmids were first digested with NcoI and SacI restriction enzymes. Synthetic dsDNA fragments containing 5' AflIII and 3' SacI overhangs were then inserted (note, restriction enzymes AflIII and NcoI leave compatible overhangs). In all cases, V47, V48, and V54, HBc residues D2 and I3 were deleted so that the heterologous immunogenic sequence directly follows residue M1; the glutamic acid-leucine (EL) amino acid pairs, coded for by the SacI restriction site, follows the inserted epitope. The inserted restriction sites are underlined in the oligonucleotide primers below.

```
V47/V48/V54
pKK(167-150)-F
5'-GCATAATTCGTGTCGCTC                             SEQ ID NO: 60

HBc-I3/EcoRI-R
5'-GCGGAATTCCGATGTCCATGGTTTTTTCCT                 SEQ ID NO: 61

HBc-EcoRI/SacI/D4-F
5'-GCGGAATTCAAAAAGAGCTCGACCCTTATAAAGAATTTGGA      SEQ ID NO: 62

V47
HBc149/HindIII-R
5'-CGCAAGCTTAAACAACAGTAGTCTCCGGAAG                SEQ ID NO: 54

V54
HBc149+C/HindIII-R
5'-CGCAAGCTTACTAGCAAACAACAGTAGTCTCCGGAAG          SEQ ID NO: 55

V48
HBc183/HindIII-R
5'-GGAAAGCTTACTAACATTGAGATTCCCG                   SEQ ID NO: 56
```

E. Preparation of V7 Cloning Vector

To enable the fusion of T cell epitopes to the C terminus of a HBc chimer, a new vector, V7, was constructed. Unique EcoRI and SacI restriction sites were inserted between valine-149 and the HindIII site to facilitate directional insertion of synthetic dsDNAs into EcoRI-HindIII (or EcoRI-SacI) restriction sites. The pair of PCR primers below was used to amplify the HBc 149 gene with a NcoI restriction site at the amino-terminus and EcoRI, SacI and HindIII sites at the carboxyl-terminus. The product of the PCR reaction (479 bp) was digested with NcoI/HindIII and cloned into pKK223-3N to form V7.

To insert T cell epitopes, the plasmid (V7) was digested EcoRI/HindIII (or EcoRI-SacI) and synthetic dsDNA fragments having EcoRI/HindIII (or EcoRI/SacI) overhangs, were ligated into V7. For all V7 constructs, the final amino acid of native HBc (valine-149) and the first amino acid of the inserted T cell epitope are separated by a glycine-isoleucine dipeptide sequence coded for by the nucleotides that form the EcoRI restriction site. For epitopes inserted at EcoRI/SacI, there are additional glutamic acid-leucine residues after the T cell epitope, prior to the termination codon, contributed by the SacI site. Restriction sites are again underlined in the primers shown.

```
HBc149/NcoI-F
5'-TTGGGCCATGGACATCGACCCTTA                      SEQ ID NO: 51

HBc149/SacI-EcoRI-H3-R
5'-CGCAAGCTTAGAGCTCTTGAATTCCAACAACAGTAGTCTCCG  SEQ ID NO: 63
```

F. Synthesis of Expression Vectors for Expressing Partially Truncated Particles

To generate expression plasmids for truncated HBc particles, a single amino terminal oligonucleotides PCR primer (HBc149/NcoI-F) was used in combination with a unique C-terminal primer. For example, to generate the HBc156 (E.cR) expression plasmid, the primers HBc149/NcoI-F and HBc156(E.cR)-H3-R were used. To generate the HBc156 (E.cR)+C expression plasmids, the primers HBc149/NcoI-F and HBc156C(E.cR)-H3-R were used. In addition to truncating the particles—and in some cases incorporating a C-terminal cysteine residue—codons that are optimal for expression in *E. coli* were also used. To enable sequential replacement of the rare arginine codons found in native HBc sequence, the HBc156 gene was synthesized first, then used as a template for the HBc163 constructs; the HBc163 construct was then used as a template for the HBc171 constructs. The sequences of all primers used are displayed below. All PCR products were cleaved with the restriction enzymes NcoI and HindIII and cloned into the expression vector pKK223-3N, which had been cut with the same enzymes.

```
HBc149/NcoI-F
5'-TTGGGCCATGGACATCGACCCTTA                                       SEQ ID NO: 51

HBc156(E.cR)-H3-R
5'-GCGAAGCTTACTAAGGGGAGCGGCCTCGTCGACGAACAACAGTAGTCTCCGG       SEQ ID NO: 64

HBc156C(E.cR)-H3-R
5'-GCGAAGCTTACTAACAAGGGGAGCGGCCTCGTCGACGAACAACAGTAGTCTCCGG    SEQ ID NO: 65

HBc163(E.cR)-H3-R
5'-GCGAAGCTTACTAAGGCGAGGGAGTGCGCCGACGAGGGGAGCGGCCTCG            SEQ ID NO: 66

HBc163C(E.cR)-H3-R
5'-GCGAAGCTTACTAACAAGGCGAGGGAGTGCGCCGACGAGGGGAGCGGCCTCG         SEQ ID NO: 67

HBc171(E.cR)-H3-R
5'-GCGAAGCTTACTACGGCGATTGAGAGCGTCGACGGCGAGGCGAGGGAGT            SEQ ID NO: 68

HBc171C(E.cR)-H3-R
5'-GCGAAGCTTACTAACACGGCGATTGAGAGCGTCGACGGCGAGGCGAGGGAGT         SEQ ID NO: 69
```

| Clone Number | Clone Name |
|---|---|
| CV-1600 | HBc156(E.cR) |
| CV-1601 | HBc156(E.cR) + C |
| CV-1632 | HBc163(E.cR) + C |
| CV-1634 | HBc163(E.cR) |
| CV-1642 | HBc171(E.cR) |
| CV-1643 | HBc171(E.cR) + C |

EXAMPLE 2

Preparation of Chimers Containing Influenza A M2 Polypeptide Sequences

A. Insertion of Influenza A M2 N-Terminal Domain into V2, V7, V8, V16, V34, V47, V48, V54, and V55 Cloning Vectors For V2, V7, V8, V16, V34 and V55 constructs, synthetic dsDNA fragments coding for a M2e-sequence (residues 2-24 of the influenza A M2 protein; SEQ ID NO:9) were inserted into EcoRI/SacI restriction sites, whereas for V47, V48, and V54 constructs, residues 1-24 of the same were inserted into NcoI/SacI restriction sites. Synthetic dsDNA fragments were prepared by mixing complementary single stranded DNA oligonucleotides at equimolar concentrations, heating to 95° C. for 5 minutes, and then cooling to room temperature at a rate of −1° C. per minute. This annealing reaction was performed in TE buffer. The double-stranded DNAs are shown below with the encoded epitope sequence shown above.

```
V2/V7/VB/V16/V34/V55
M2(2-24)
  I  S  L  L  T  E  V  E  T  P  I  R  N  E  W  G  C  R
AATTAGCCTGTTAACCGAAGTGGAGACGCCGATCCGTAACGAATGGGGCTGCCG
    TCGGACAATTGGCTTCACCTCTGCGGCTAGGCATTGCTTACCCCGACGGC

          C  N  D  S  S  D  E  L                 SEQ ID NO: 70
          CTGTAATGATTCTTCCGACGAGCT               SEQ ID NO: 71
          GACATTACTAAGAAGGCTGC                   SEQ ID NO: 72

V47/V48/V54
M2(1-24)
  M  S  L  L  T  E  V  E  T  P  I  R  N  E  W  G  C  R
CATGTCTCTGCTGACCGAAGTTGAAACCCCTATCAGAAACGAATGGGGGTGCAGA
    AGAGACGACTGGCTTCAACTTTGGGGATAGTCTTTGCTTACCCCCACGTCT

          C  N  D  S  S  D  E  L                 SEQ ID NO: 73
          TGTAACGATTCAAGTGATGAGCT                SEQ ID NO: 74
          ACATTGCTAAGTTCACTAC                    SEQ ID NO: 75
```

B. Insertion of Individual Cysteine-Mutated Influenza A M2 N-Terminal Domains [M2(1-24/C17S), M2(1-24/C19S)] into V47 Expression Vector Annealed DNA fragments encoding residues 1-24 of the M2 protein with the cysteine at either position 17 or 19 mutated to serine are shown below. They were inserted into the NcoI/SacI restriction sites of V47 as described in part A above.

```
V47
M2(1-24/C17S)
  M  S  L  L  T  E  V  E  T  P  I  R  N  E  W  G  S  R
CATGTCTCTGCTGACCGAAGTTGAAACCCCTATCAGAAACGAATGGGGGTCTAGA
    AGAGACGACTGGCTTCAACTTTGGGGATAGTCTTTGCTTACCCCCAGATCT

          C  N  D  S  S  D  E  L                 SEQ ID NO: 76
          TGTAACGATTCAAGTGATGAGCT                SEQ ID NO: 77
          ACATTGCTAAGTTCACTAC                    SEQ ID NO: 78

M2(1-24/C19S)
  M  S  L  L  T  E  V  E  T  P  I  R  N  E  W  G  C  R
CATGTCTCTGCTGACCGAAGTTGAAACCCCTATCAGAAACGAATGGGGGTGCAGA
    AGAGACGACTGGCTTCAACTTTGGGGATAGTCTTTGCTTACCCCCACGTCT

          S  N  D  S  S  D  E  L                 SEQ ID NO: 79
          TCGAACGATTCAAGTGATGAGCT                SEQ ID NO: 80
          AGCTTGCTAAGTTCACTAC                    SEQ ID NO: 81
```

C. Insertion of Cysteine-Mutated Influenza A M2 N-Terminal Domain [M2(2-24/C17S,C19S)] into Expression Vectors V8, V16, V47, V48, and V54

For V8 and V16 constructs, synthetic dsDNA fragments harboring two cysteine to serine mutations and coding for the M2e immunogenic sequence (residues 2-24 of the influenza A M2 protein) were inserted into EcoRI/SacI restriction sites, whereas for V47, V48, and V54 constructs, residues 1-24 of the same were inserted into NcoI/SacI restriction sites. Synthetic dsDNA fragments were prepared as described in part A above.

```
V8,V16
M2(2-24/C17S,C19S)
  I  S  L  L  T  E  V  E  T  P  I  R  N  E  W  G  S  R
AATTTCTCTGTTAACCGAAGTGGAGACGCCGATTCGTAACGAATGGGGTAGCCGC
    AGAGACAATTGGCTTCACCTCTGCGGCTAAGCATTGCTTACCCCATCGGCG

 S  N  D  S  S  D  E  L                             SEQ ID NO: 82
TCTAATGATAGCTCTGACGAGCT                             SEQ ID NO: 83
AGATTACTATCGAGACTGC                                 SEQ ID NO: 84

M2(1-24/C17S,C19S)
  M  S  L  L  T  E  V  E  T  P  I  R  N  E  W  G  S  R
CATGTCTCTGCTGACCGAAGTTGAAACCCCTATCAGAAACGAATGGGGGTCTAGA
    AGAGACGACTGGCTTCAACTTTGGGGATAGTCTTTGCTTACCCCCAGATCT

            S  N  D  S  S  D  E  L                  SEQ ID NO: 85
           TCGAACGATTCAAGTGATGAGCT                  SEQ ID NO: 86
           AGCTTGCTAAGTTCACTAC                      SEQ ID NO: 87
```

D. Insertion of Additional Copies Domain of the Influenza A M2 N-Terminal onto the N-Terminus of the Expression Vector V54.M2(1-24)

One additional copy of either native M2 sequence [M2(1-24)] or mutated M2 sequence [M2(1-24/C17S, C19S) was cloned N-terminally to the existing M2(1-24) sequence. In constructing these clones, the original methionine is removed, such that the added copy supplies only one initiator methionine. PCR was used to make the constructs in two fragments. To make the clone containing two native M2 copies [M2(1-24)/V54.M2(2-24)], the template V54.M2(1-24) was used to amplify first the N-terminal fragment, which inserts an XhoI site (and, therefore, amino acids leucine, followed by glutamic acid) after D24 of the M2 sequence (resultant fragment is 353 bp), then the C-terminal fragment, which inserts an XhoI site N-terminal to S2 of the M2 sequence, thereby removing the methionine (resultant fragment is 538 bp). To make the clone containing a mutant, followed by a native copy of M2 [M2(1-24/C17S,C19S/V54.M2(2-24)]), the template V54.M2(1-24/C17S,C19S) was used to generate the N-terminal fragment, while the C-terminal fragment is identical to that above (resultant fragment sizes are also identical).

The N-terminal fragments prepared were digested with BamHI and XhoI, and the C-terminal fragment was digested with XhoI and HindIII. Fragment pairs were then ligated together at the common XhoI overhangs. The resultant BamHI-HindIII fragments were then ligated into the pKK223-3N vector, which had been prepared by digestion with BamHI and HindIII.

Two additional copies of mutated M2 sequence were cloned N-terminally to existing M2(2-24) sequence. Again, only one initiator methionine was preserved at position one of the gene to yield the construct M2(1-24/C17S,C19S/M2(2-24/C17S,C19S/V54.M2(2-24). Again, the clone was produced in two PCR fragments. The template V54.M2(1-24/C17S,C19S) was used to generate the N-terminal fragment, which inserts a PstI site (and, therefore, amino acids leucine, followed by glutamine) after residue D24 of the mutant M2 sequence (resultant fragment is 353 bp). The template M2(1-24/C17S,C19S/V54.M2(2-24) from above was used to generate the C-terminal fragment, which inserts a PstI site N-terminal to S2 of the mutant M2 sequence, thereby removing the methionine (resultant fragment is 613 bp).

The N-terminal fragment prepared was digested with BamHI and PstI, and the C-terminal fragment was digested with PstI and HindIII. Fragment pairs were then ligated together at the common PstI overhangs. The resultant BamHI-HindIII fragment was then ligated into the pKK223-3N vector, which had been prepared by digestion with BamHI and HindIII.

```
M2(1-24)/V54.M2(2-24); M2(1-24/C17S,C19S/V54.M2
(2-24)
pKK-BamHI-F
                                           SEQ ID NO: 88
5'-CGTAGAGGATCCGGAGCTTATCGACTGCACGG

M2-D24/XhoI-R
                                           SEQ ID NO: 89
5'-GCGCTCGAGATCACTTGAATCGTT

M2-XhoI/S2-F
                                           SEQ ID NO: 90
5'-GCGCTCGAGAGCTTATTGACCGAAGTTGAAACC

HBc149+C/HindIII-R
                                           SEQ ID NO: 55
5'-CGCAAGCTTACTAGCAAACAACAGTAGTCTCCGGAAG

M2(1-24/C17S,C19S)/M2(2-24/C17S,C19S)/V54.M2(2-24)
pKK-BamHI-F
                                           SEQ ID NO: 57
5'-CGTAGAGGATCCGGAGCTTATCGACTGCACGG

M2-D24/PstI-R
                                           SEQ ID NO: 91
5'-GCGCTGCAGATCACTTGAATCGTT

M2-PstI/S2-F
                                           SEQ ID NO: 92
5'-GCGCTGCAGTCTCTGCTGACCGAAG

HBc149+C/HindIII-R
                                           SEQ ID NO: 55
5'-CGCAAGCTTACTAGCAAACAACAGTAGTCTCCGGAAG
```

E. Construction of Truncated Version of Native M2-HBc

The original M2-HBc construct [Neirynck et al., (October 1999) *Nature Med.,* 5(10):1157-1163: WO 99/07839] that contained the 183-residue, full length HBc sequence was truncated to V149, and the entire gene was moved into the pKK223-3 expression vector. To achieve this, the plasmid 3453, which was provided by the University of Gent, was used as a template for a PCR reaction that yielded a product of 523 bp. This product was digested with restriction enzymes AflIII and HindIII, and then ligated into the pKK223-3N vector, which had been prepared by digestion with NcoI and HindIII.

```
AflIII-M2-F
5'-CGCGACATGTCTCTGCTGACCG          SEQ ID NO: 93

HBc149-HindIII-R
5'-CGCAAGCTTAAACAACAGTAGTCTCCGGAAG  SEQ ID NO: 54
```

| Clone Number | Clone Name |
|---|---|
| CV-1438 | V34.M2(2-24) |
| CV-1440 | V2.M2(2-24) |
| CV-1475 | V16.M2(2-24) |
| CV-1492 | V52.M2(2-24) |
| CV-1560 | 3453/149 |
| CV-1569 | V16.M2(1-24/C17S, C19S) |
| CV-1586 | V8.M2(2-24) |
| CV-1587 | V8.M2(1-24/C17S, C19S) |
| CV-1588 | V7.M2(2-24) |
| CV-1590 | V47.M2(1-24) |
| CV-1603 | V47.M2(1-24/C17S, C19S) |
| CV-1604 | V54.M2(1-24) |
| CV-1605 | V54.M2(1-24/C17S, C19S) |
| CV-1606 | V48.M2(1-24) |
| CV-1607 | V48.M2(1-24/C17S, C19S) |
| CV-1671 | V47.M2(1-24/C17S) |
| CV-1672 | V47.M2(1-24/C19S) |
| CV-1816 | M2(1-24)/V54.M2(2-24) |
| CV-1817 | M2(1-24/C17S, C19S/V54.M2(2-24) |
| CV-1818 | M2(1-24/C17S, C19S)/M2(2-24/C17S, C19S)/V54.M2(2-24) |

EXAMPLE 3

Assay Procedures

A. Antigenicity

1. Particle ELISA

Purified particles were diluted to a concentration of 10 μg/mL in coating buffer (50 mM sodium bicarbonate, pH 9.6) and coated onto the wells of ELISA strips or plates (50 μL/well). The ELISA strips were incubated at room temperature overnight (about 18 hours). Next morning, the wells were washed with ELISA wash buffer [phosphate buffered saline (PBS), pH 7.4, 0.05% Tween®-20] and blocked with 3% BSA in PBS for 1 hour (75 μL/well). ELISA strips were stored, dry, at −20° C. until needed.

To determine the antigenicity of particles, antisera were diluted using 1% BSA in PBS and 50 μL/well added to antigen-coated ELISA wells. Sera were incubated for 1 hour, washed with ELISA wash buffer (above) and probed using an anti-mouse (IgG)-HRP (The Binding Site, San Diego, Calif.; HRP=horseradish peroxidase) conjugate (50 μL/well) or other appropriate secondary antibody for 30 minutes. After washing with ELISA wash buffer the reaction was visualized by the addition of TM blue substrate (50 μL/well). After 10 minutes, the reaction was stopped by the addition of 1N $H_2SO_4$ (100 μL/well) and read on an ELISA plate reader set at 450 nm.

2. Synthetic Peptide ELISA

A 24 amino acid residue synthetic peptide M2 is diluted to a concentration of 2 μg/mL in coating buffer (50 mM sodium bicarbonate, pH 9.6) and coated onto the wells of ELISA strips (50 μL/well). Peptides are dried onto the wells by incubating overnight (about 18 hours), in a hood with the exhaust on. Next morning, the wells are washed with ELISA wash buffer (phosphate buffered saline, pH 7.4, 0.05% Tween®-20) and blocked with 3% BSA in PBS (75 μL/well) for 1 hour. ELISA strips are stored, dry, at −20° C. until needed.

To determine antibody binding of particles, antisera (monoclonal or polyclonal) are diluted using 1% BSA in PBS, and 50 μL/well added to antigen-coated ELISA wells. Sera are incubated for 1 hour, washed with ELISA wash buffer, and probed using an anti-mouse (IgG)-HRP conjugate or other secondary antibody (as above at 50 μL/well) for 30 minutes, washed again with ELISA wash buffer, and then visualized by the addition of TM blue (50 μL/well) or other appropriate substrate. After 10 minutes, the reaction is stopped by the addition of 1N $H_2SO_4$ (100 μL/well) and read on an ELISA plate reader set at 450 nm.

B. Immunogenicity of Particles

To assay the immunogenicity of particles, mice are immunized, IP, with 10 μg of particles in adjuvant of choice, and then boosted once or twice at 3 weeks intervals with 10 μg in the same adjuvant. Mice were bled before and at 2, 4, 6, and 8 weeks after each immunization.

EXAMPLE 4

Determination of 280:260 Absorbance Ratios

To determine the 280:260 absorbance ratio of purified particles, the particles were diluted to a concentration of approximately 0.2 mg/mL in 20 mM sodium phosphate buffer, pH 6.8, and absorbance values determined at wavelengths of 260 and 280 nm. The absorbance measured at 280 nm was divided by the value at 260 nm to determine the 280:260 ratio. The ratios were obtained for several samples, including native particles (HBc183), HBc particles truncated after residue position 149 (HBc149), and several HBc chimers that are identified elsewhere herein, are shown below in Table 1. Full length particles ICC-1559 are a preparation of the particles first reported in Neirynck et al., (October 1999) *Nature Med.,* 5(10):1157-1163 and patent application WO9907839, whereas full length particles ICC-1607 are similar particles in which the M2 polypeptide cysteines at polypeptide positions 17 and 19, ($X_{17}$ and $X_{19}$ of SEQ ID NO:9) were mutated to serine residues.

TABLE 1

| Particle Number | Full Length, (F) or C-Terminal Truncated, (T) | 280:260 Absorbance Ratio |
|---|---|---|
| HBc183 | F | 0.84 |
| CV-1532 | | |
| HBc149 | T | 1.59 |
| CV-1438 | T | 1.57 |
| CV-1440 | T | NT |
| CV-1475 | T | 1.04 |
| CV-1492 | T | 1.33 |
| *CV-1559* | F | 0.68 |
| CV-1560 | T | 1.36 |
| CV-1569 | T | 1.38 |
| CV-1588 | T | 1.16 |
| CV-1590 | T | 1.51 |
| CV-1603 | T | 1.68 |
| CV-1604 | T | 1.40 |
| CV-1605 | T | 1.26 |

TABLE 1-continued

| Particle Number | Full Length, (F) or C-Terminal Truncated, (T) | 280:260 Absorbance Ratio |
|---|---|---|
| CV-1607 | F | 0.73 |
| CV-1600 | T | 1.23 |
| CV-1601 | T | 1.12 |
| CV-1634 | T | 0.92 |
| CV-1632 | T | 0.96 |
| CV-1642 | T | 0.79 |
| CV-1643 | T | 0.77 |
| CV-1671 | T | NT |
| CV-1672 | T | 1.27 |

NT, not tested.
*CV-1159 is identical to IM2-HBc described by Neirynck, 1999.

EXAMPLE 5

Thermal Stability Protocol

Purified particles were diluted to a concentration of 1 mg/mL using 50 mM $NaPO_4$, pH 6.8 and sodium azide was added to a final concentration of 0.02% to prevent bacterial growth. Samples were mixed with SDS-PAGE sample buffer (reducing) and run on 15% SDS-PAGE gels. Gels were stained using Coomassie Blue, and then analyzed.

EXAMPLE 6

Analytical Gel Filtration

Analysis of Hybrid Particles

Analytical gel filtration analysis of purified hybrid HBc particles was performed using a 25 mL Superose® 6 HR 10/30 chromatographic column (Amersham Pharmacia # 17-0537-01) and a BioCAD™ SPRINT Perfusion Chromatography System. The UV detector was set to monitor a wavelength of 280 nm. The column was equilibrated with 3 column volumes (CV; about 75 mL) of buffer (50 mM $NaPO_4$, pH 6.8) at a flow rate of 0.75 mL/minute.

The particles to be analyzed were diluted to a concentration of 1 mg/mL using 50 mM $NaPO_4$, pH 6.8. 200 Microliters (μL) of the sample were then loaded onto a 200 μL loop and injected onto the column. The sample was eluted from the column with 50 mM $NaPO_4$, pH 6.8 at a flow rate of 0.75 mL/minute.

Particles containing N-terminal cysteine residues or similar particles free of such cysteines were analyzed using the above procedure. Integration of the 280 nm trace was carried out using BioCAD™ software (PerSeptive™) to provide the results in

EXAMPLE 7

Influenza M2 Constructs

Recently, Neirynck et al., (October 1999) *Nature Med.*, 5(10):1157-1163 and WO 99/07839 reported the fusion of the 24 amino acid extracellular domain of M2 to the N-terminus of full-length HBc particles (HBc183), lacking amino acid residues 1-4. A schematic representation of that construct referred to herein as IM2HBc is shown below in which the 24-mer is linked to the N-terminus of HBc.

```
IM2HBc
MSLLTEVETPIRNEWGCRCNDSSD-HBc(5-183)  SEQ ID NO: 94
```

In one illustrative preparation, the M2 epitope was inserted into the immunodominant loop of hepatitis B core and particles referred to as ICC-1475 were successfully expressed and purified using techniques discussed previously for such insertions and purifications. A mutated version of the M2 epitope, in which two cysteine residues at M2 native positions 17 and 19 were substituted by alanine residues, was also expressed in the immunodominant loop (ICC-1473 particles) and the resulting particles purified. These two particles are illustrated schematically below.

```
ICC-1475
                                      SEQ ID NO: 95
HBc(1-78)-GI-SLLTEVETPIRNEWGCRCNDSSD-EL-HBc

(79-149)

ICC-1473
                                      SEQ ID NO: 96
HBc(1-78)-GI-SLLTEVETPIRNEWGARANDSSD-EL-HBc

(79-149)-C
```

The ICC-1473 particle construct yielded approximately 7-fold more purified particles when compared with the native sequence (ICC-1475). It remains to be determined if the mutation of the cysteine residues alters protective potential of the particles. However, epitopes delivered on the immunodominant loops of HBc are usually significantly more immunogenic as compared to when they are fused to other regions (including the N-terminus), and resulting particles exhibit reduced anti-HBc immunogenicity.

Particles have also been prepared in which the M2 N-terminal 24-mer sequence was fused to the N-terminus of C-terminal truncated hepatitis B core particles. That construct (ICC-1438) also contained the N-terminal pre-core sequence (SEQ ID NO:66). A similar construct was prepared that contained a single cysteine residue at the end of the hybrid protein (ICC-1492), in this case immediately after Val-149 of the HBc gene. These constructs are shown schematically below.

```
ICC-1438
                                      SEQ ID NO: 97
MGISLLTEVETPIRNEWGCRCNDSSDELLGWLWGI-HBc(2-149)

ICC-1492
                                      SEQ ID NO: 98
MGISLLTEVETPIRNEWGCRCNDSSDELLGWLWGI-HBc(2-149)-C
```

It should be noted that to guard against translation initiation from the natural HBc initiator methionine, the codon for that residue was mutated to code for an isoleucine residue. Residues contributed by EcoRI (GI) and SacI (EL) restriction sites are underlined. The pre-core sequence is recited between the underlined EL residues and "–HBc(2-149)".

Figure 10:
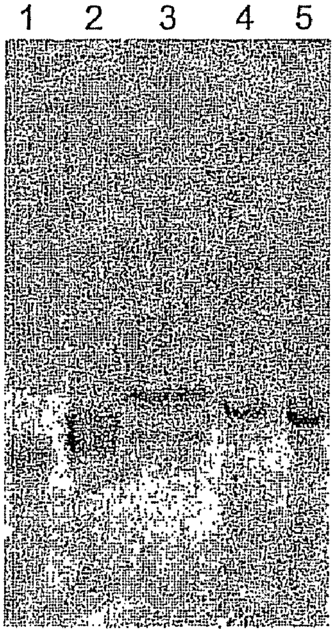
FIG. 10 is a photograph of an SDS-PAGE analysis under reducing conditions following particle preparation that shows the ICC-1438 monomer construct was unstable after aging (Lane 2) as compared to the ICC-1492 construct (Lane 3), with HBc-149 (Lane 1), ICC-1475 (Lane 4) and ICC-1473 (Lane 5) serving as additional molecular weight controls.

Analysis by SDS-PAGE as discussed elsewhere herein, showed that upon preparation, the ICC-1438 monomer construct was unstable (Lane 2) as compared to the ICC-1492 (Lane 3), with HBc-149 (Lane 1), ICC-1475 (Lane 4) and ICC-1473 (Lane 5) serving as additional molecular weight controls on the SDS-PAGE gel in FIG. 10. The instability of the ICC-1438 monomers was not evident using analytical gel filtration of particles.

Both ICC-1475 (FIG. 10, lane 4) and ICC-1473 (FIG. 10, lane 5) were expected to have slightly lower molecular weights than ICC-1438 and ICC-1492, because the former two contain the M2 sequence inserted directly into the immunodominant loop and therefore lack the pre-core sequence (SEQ ID NO:66) present in ICC-1438 and ICC-1498. As expected, ICC-1492 was larger than ICC-1475 and ICC-1473; however, ICC-1438, which is identical to ICC-1492 save the C-terminal cysteine residue, is clearly not larger than ICC-1475 and ICC-1473 due to an apparent cleavage.

A construct containing a M2 N-terminal extracellular sequence as discussed before linked to the HBc N-terminus (Domain I) or loop (Domain II) and also containing a cysteine residue at the C-terminus (Domain IV) of HBc is also contemplated.

To modify the amino-terminus of hybrid HBc particles containing immunodominant loop fusions to incorporate a cysteine residue, and minimal M2-derived sequence, a series of synthetic oligonucleotides are synthesized. To make V2.Pf1 (N-M2(17-24/C17S), the oligonucleotides M2(17-24/C17S)-NcoI-F and HBc149/HindIII-R are used to amplify the hybrid HBc gene from vector V2.Pf1. The resultant 546 bp fragment is cleaved with NcoI and HindIII and inserted into pKK-223-3N, which has been cleaved with the same two enzymes.

To make V2.Pf1 (N-M2(17-24/C19S), the oligonucleotides M2(17-24/C19S)-NcoI-F and HBc149/HindIII-R are used to amplify the hybrid HBc gene in vector V2.Pf1. The resultant 540 bp fragment is cleaved with NcoI and HindIII and inserted into pKK-223-3N, which had been cleaved with the same two enzymes.

Figure 5:
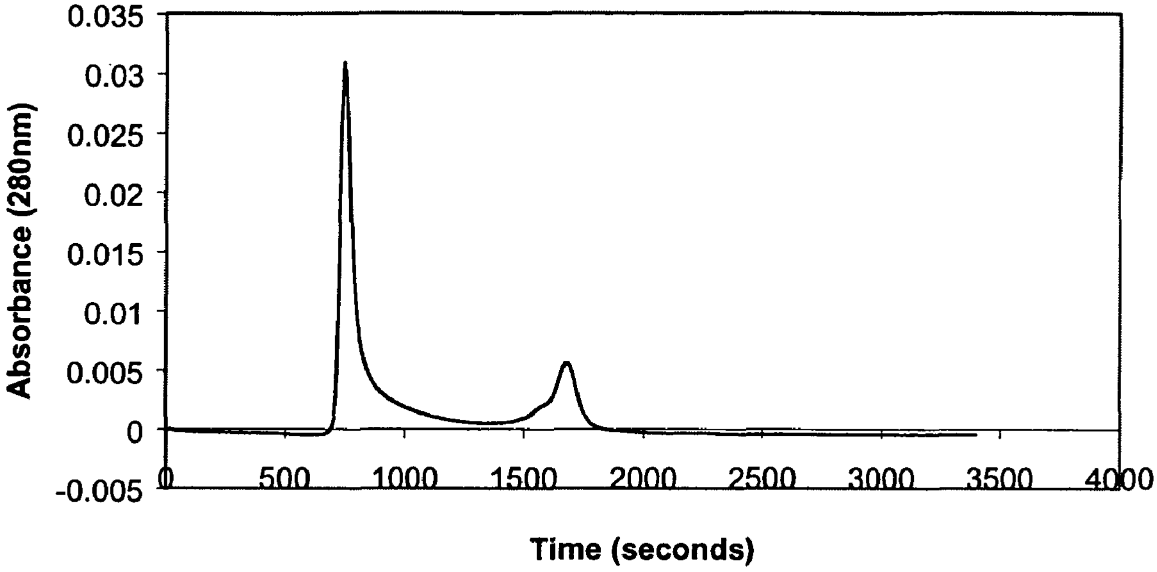
FIG. 5 is an analytical size exclusion chromatography elution profile for ICC-1560 particles as discussed for FIG. 3.

Analysis of ICC-1560 particles, whose chimer protein also has two N-terminal cysteine residues, revealed that it too was particulate following purification, although it did exhibit some degree of disassembly (FIG. 5), suggesting that the stabilization was not quite as robust as it was for ICC-1590 particles. Comparison of the N-terminal configurations of ICC-1590 and ICC-1560 particles (Table 2, hereinafter), shows that the relative position of the two cysteine residues in ICC-1560 particles is shifted by 3 amino acid residues relative to ICC-1590 particles via the deletion of three amino acid residues (DEL), indicating that the cysteine residues may be required to be a minimal distance from the start of the core gene to enable optimal cross-linking.

EXAMPLE 9

Figure 6:
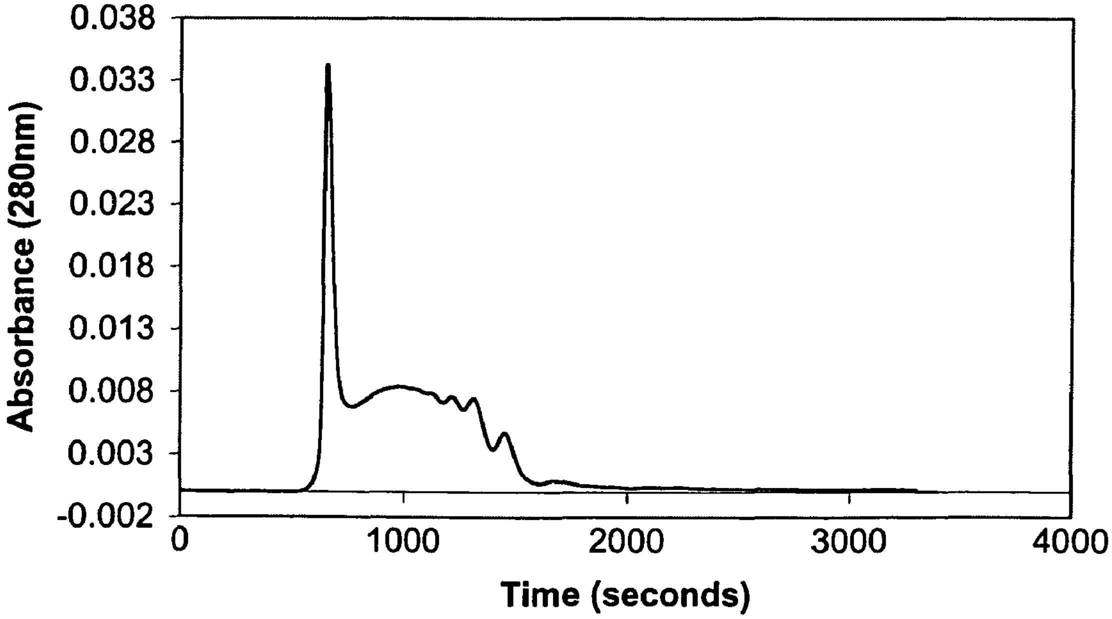
FIG. 6 is an analytical size exclusion chromatography elution profile for ICC-1605 particles as discussed for FIG. 3.

Particles with an M2 or M2 Variant Sequence and a C-Terminal Cysteine Residue ICC-1603 particles were shown in FIG. 3 to rapidly disassemble following purification. The HBc chimer molecules that comprise ICC-1605 particles are similar to those of ICC-1603 particles, except that the ICC-1605 component chimer molecules have a single C-terminal stabilizing cysteine. A plasmid was made to direct the expression of ICC-1605 particles to investigate if the addition of a C-terminal cysteine residue to ICC-1603 particles could impart greater stability on the particle. Following purification, ICC-1605 particles were analyzed using analytical size exclusion chromatography (FIG. 6).

```
M2(17-24/C17S)-NcoI-F
       M   G   S   R   C   N   D   S   S   D   I   D   P   Y   K   E   F   G  SEQ ID NO: 99
.GGCGCCATGGGGTCTAGATGTAACGATTCAAGTGACATCGACCCTTATAAAGAATTTCG  SEQ ID NO: 100

M2(17-24/C19S)-NcoI-F
     M   G   C   N   D   S   S   D   I   D   P   Y   K   E   F   G            SEQ ID NO: 101
GCGCCATGGGGTGTAACGATTCAAGTGACATCGACCCTTATAAAGAATTTGG                          SEQ ID NO: 102
```

EXAMPLE 8

HBc Chimer Molecules with and without Both N- and C-Terminal Cysteine Residues A series of HBc chimer molecule-containing particles was prepared that contained residues 1-24 of the influenza A, M2 protein peptide-bonded at or near the N-terminus of HBc whose C-terminus was truncated at residue 149. The component chimeric protein molecules contained different N-terminal sequences that included an M2 sequence or variant, and some contained a C-terminal cysteine residue.

All purified particles listed in Table 2, below, were analyzed by analytical size exclusion chromatography to assess the retention of particulate structure following purification. Particles designated ICC-1603, which contain no N-terminal cysteine residues, displayed evidence of disassembly back to sub-particulate structures (FIG. 3) because the protein eluted in the 1500 seconds range (correctly formed particles elute at approximately 1000 seconds).

Figure 4:
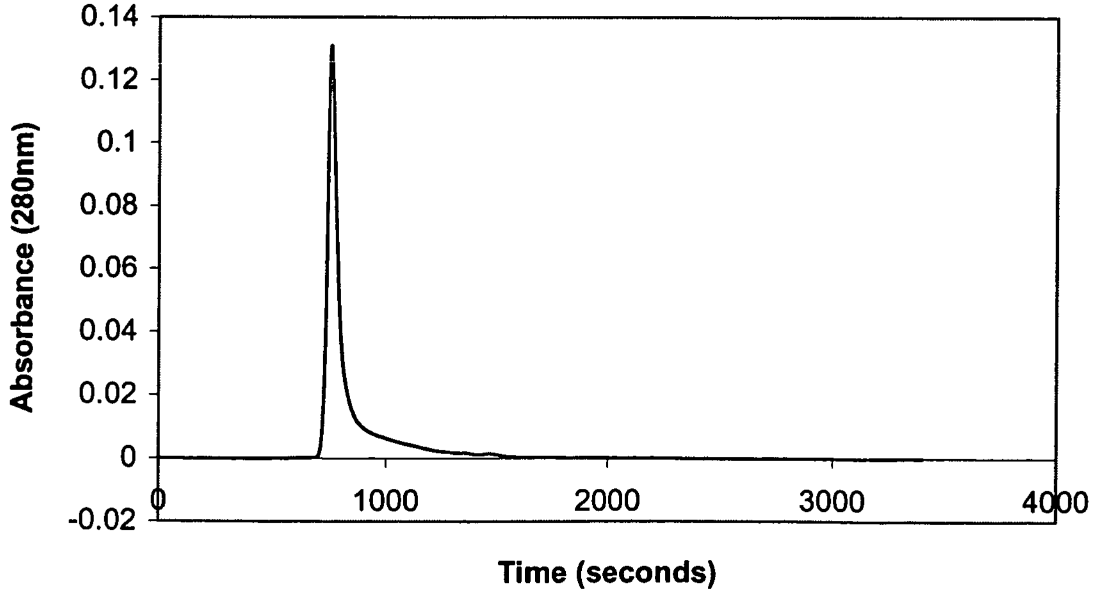
FIG. 4 is an analytical size exclusion chromatography elution profile for ICC-1590 particles as discussed for FIG. 3.

Similar analysis of particles ICC-1590, which are similar to ICC-1603 ICC-particles except for the mutation of two serine residues to cysteine residues in the N-terminal M2 sequence, revealed that that construct remained particulate following purification, with elution occurring at around 1000 seconds, which is typical for a hybrid particle (FIG. 4). There was no evidence of disassembly for ICC-1590 particles.

The results of this study demonstrated that particle stabilization was more complete than for the ICC-1603 particles, but incomplete compared to ICC-1590 particles, which contains two amino-terminal cysteine residues and no C-terminal stabilizing cysteine. Although a significant amount of ICC-1605 remained particulate, there was evidence of a heterogeneous mixture of sub-particulate structures that eluted over a broad range. These observations suggest that for this hybrid particle (ICC-1603), C-terminal stabilization as found in ICC-1605 particles was less complete than for the N-terminal stabilization found in ICC-1590 particles.

Figure 7:
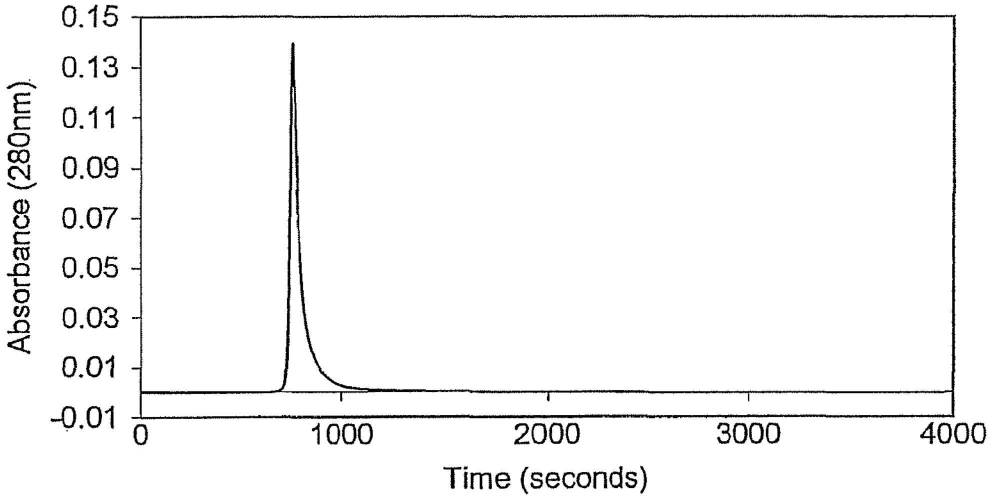
FIG. 7 is an analytical size exclusion chromatography elution profile for ICC-1604 particles as discussed for FIG. 3.

To investigate the compatibility of combined amino and carboxyl-terminal cysteine stabilization of hybrid particles, an expression plasmid was constructed to direct the expression of ICC-1604 particles. The component chimer molecules of ICC-1604 particles contain both the two amino-terminal stabilizing cysteine residues present in a native M2 polypeptide sequence (as in ICC-1590) as well as a C-terminal stabilizing cysteine (as in ICC-1605 particles). Analysis of ICC-1604 particles showed that they retained a homogeneous particulate state following purification (FIG. 7), indicating that the two stabilizing methods are complementary and can be used in concert with each other.

Alternative linker sequences between the N-terminus of HBc and the N-terminal cysteine residues were investigated using particles ICC-1438 and ICC-1492. Both of these particles contain the amino acid sequence ELLGWLWGIDI (SEQ ID NO:103) between the M2 fusion and amino acid D4 of HBc. Amino acid residues LGWLWGIDI are derived from amino acids −6 of pre-core to amino acid I3 of HBc, with the initiator codon of HBc mutated to an isoleucine to prevent translation initiation from this position, which would compromise the study. The HB pre-core sequence includes a cysteine at position −7.

Figure 8:
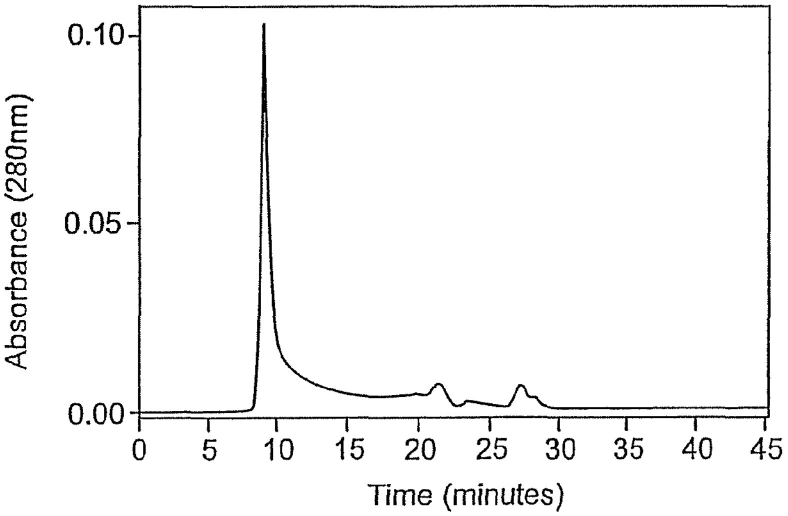
FIG. 8 is an analytical size exclusion chromatography elution profile for ICC-1438 particles as discussed for FIG. 3.
Figure 9:
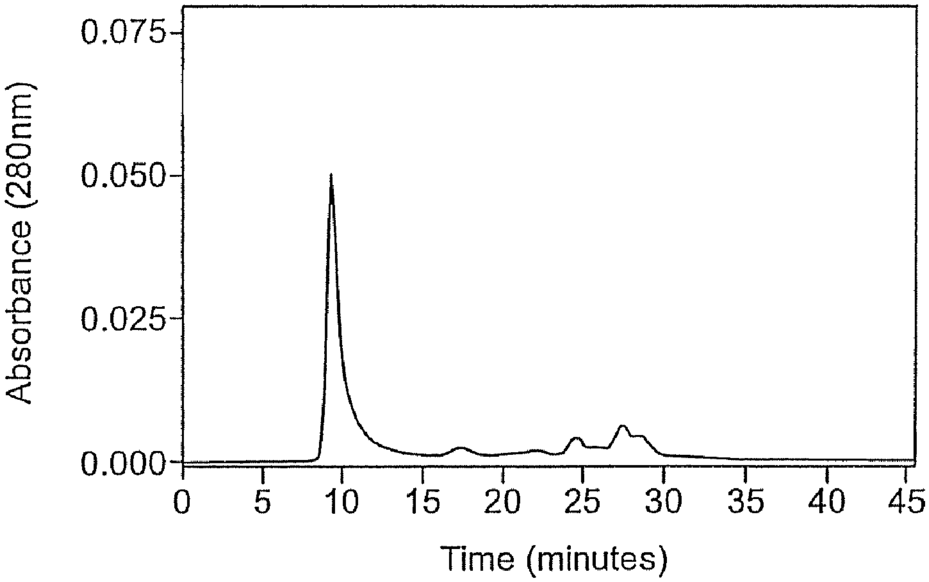
FIG. 9 is an analytical size exclusion chromatography elution profile for ICC-1492 particles as discussed for FIG. 3.

These particles differed only in the fact that the ICC-1438 component chimer molecule terminated at position 149 of HBc, whereas the ICC-1492 component chimer molecule terminated at 149 of HBc and contained a terminal cysteine at position 150 relative to the HBc of SEQ ID NO:1. When analyzed by analytical gel filtration, using an alternative but similar method to that discussed before, whereby particles elute at approximately 10 minutes, both constructs were shown to be particulate following purification (ICC-1438 in FIG. 8 and ICC-1492 in FIG. 10). This study demonstrated the compatibility of amino- and carboxyl-terminal cysteine stabilization of truncated particles, and the tolerance of substantial variability in the amino acid sequence and distance between the N-terminal cysteine residues and start of the HBc gene. The data from several studies are shown in Tables 2A, 2B and 2C below.

TABLE 2A

| Construct Number | N-terminal Fusion | HBc N-term Start | Residues Between M2 and HBc | C-term End | Bound Nucleic Acid | C-term Cysteine Stab |
|---|---|---|---|---|---|---|
| ICC-1438 | M2 (2-24) | D2 | ELLGWLWGI | 149 | No | No |
| ICC-1492 | M2 (2-24) | D2 | ELLGWLWGI | 149 | No | Yes (C150) |
| ICC-1560 | M2 (1-24) | D4 | None | 149 | No | No |
| ICC-1590 | M2 (1-24) | D4 | EL | 149 | No | No |
| ICC-1603 | M2 (1-24) (2C > 2S) | D4 | EL | 149 | No | No |
| ICC-1604 | M2 (1-24) | D4 | EL | 149 | No | Yes (C150) |
| ICC-1605 | M2 (1-24) (2C > 2S) | D4 | EL | 149 | No | Yes (C150) |
| ICC-1606 | M2 (1-24) | D4 | EL | 183 | Yes | Yes (C183) |
| ICC-1607 | M2 (1-24) (2C > 2S) | D4 | EL | 183 | Yes | Yes (C183) |
| ICC-1671 | M2 (1-24) (C17S) | D4 | EL | 149 | No | No |
| ICC-1672 | M2 (1-24) (C19S) | D4 | EL | 149 | No | No |
| ICC-1816 | M2 (1-24)/ LE/M2 (2-24) | D4 | EL | 149 | No | Yes (C150) |
| ICC-1817 | M2 (1-24) (2C > 2S)/ LE/M2 (2-24) | D4 | EL | 149 | No | Yes (C150) |
| ICC-1818 | M2 (1-24) (2C > 2S)/ LQ/M2 (2-24) (2C > 2S)/ LE/M2 (2-24) | D4 | EL | 149 | No | Yes (C150) |

TABLE 2B

| Construct Number | Loop Fusion | 5'/3' Fusion Flanking Sequence | C-term End | Bound Nucleic Acid | C-term Cysteine Stab |
|---|---|---|---|---|---|
| ICC-1440 | M2 (2-24) | GI/EL | 149 | No | No |
| ICC-1475 | M2(2-24) | GI/EL | 149 | No | Yes (C150) |
| ICC-1569 | M2 (2-24) (2C > 2S) | GI/EL | 149 | No | Yes (C150) |
| ICC-1586 | M2 (2-24) | GI/EL | 183 | Yes | Yes (C183) |
| ICC-1587 | M2 (2-24) (2C > 2S) | GI/EL | 183 | Yes | Yes (C183) |

TABLE 2C

| Construct Number | C-terminal Fusion | HBc C-term End | Residues Between M2 and HBc | C-term End | Bound Nucleic Acid | C-term Cys-teine Stab |
|---|---|---|---|---|---|---|
| ICC-1588 | M2 (2-24) | V149 | GI | (M2) EL | No | No |

Table 3, below, shows an alignment that illustrates the configuration of the N-termini of HBeAg, and particles harboring N-terminal fusions. Sequences are aligned according to amino acid residue position 4 from the N-terminus of HBc of SEQ ID NO:1 that is shared by all constructs. N-terminal cysteine residues, when present, are underlined.

TABLE 3

| Construct Name | Sequence | SEQ ID NO |
|---|---|---|
| HBeAg | SKLCLGWLWGMDID | 103 |
| ICC-1438/ ICC-1492 | MGISLLTEVETPIRNEWGCRCNDSSDELLGWLWG IDID | 104 |
| ICC-1560 | MSLLTEVETPIRNEWGCRCNDSSD | 105 |
| ICC-1590/ ICC-1604/ ICC-1606 | MSLLTEVETPIRNEWGCRCNDSSDELD | 106 |
| ICC-1603/ ICC-1605/ ICC-1607 | MSLLTEVETPIRNEWGSRSNDSSDELD | 107 |
| ICC-1671 | MSLLTEVETPIRNEWGSRCNDSSDELD | 108 |
| ICC-1672 | MSLLTEVETPIRNEWGCRSNDSSDELD | 109 |
| ICC-1816 | MSLLTEVETPIRNEWGCRCNDSSDLESLLTEVET PIRNEWGCRCNDSSDELD | 110 |
| ICC-1817 | MSLLTEVETPIRNEWGSRSNDSSDLESLLTEVET PIRNEWGCRCNDSSDELD | 111 |
| ICC-1818 | MSLLTEVETPIRNEWGSRSNDSSDLQSLLTEVET PIRNEWGSRSNDSSDLESLLTEVETPIRNEWGCR CNDSSDELD | 112 |

Table 4, below, provides a tabulation of the results in which stability was assessed for particles containing an N-terminal influenza A M2 sequence or variant contemplated herein. As is seen, stable particles have been prepared from HBc chimer molecules that contain an N-terminal cysteine residue at a position of minus 14 (−14) relative to the N-terminus of the HBc sequence of SEQ ID NO:1 to about the N-terminus itself.

TABLE 4

| Construct | Amino Acids Between HBc D4 and N-terminal Cysteine Residues | | C-terminal Cysteine | Stable Particle |
|---|---|---|---|---|
| Name | Cys 1 | Cys 2 | Stabilization | Formed |
| HBeAg | — | 9 | No | No |
| ICC-1438 | 18 | 16 | No | Yes |
| ICC-1492 | 18 | 16 | Yes | Yes |
| ICC-1560 | 6 | 4 | No | Yes |
| ICC-1590 | 9 | 7 | No | Yes |
| ICC-1603 | — | — | No | No |
| ICC-1604 | 9 | 7 | Yes | Yes |
| ICC-1605 | — | — | Yes | Yes/No |
| ICC-1607 | — | — | Yes | Yes |
| ICC-1671 | — | 7 | No | Yes |
| ICC-1672 | 9 | — | No | Yes |
| ICC-1816 | 34*/9 | 32*/7 | Yes | Not Done |
| ICC-1817 | 9 | 7 | Yes | Yes |
| ICC-1818 | 9 | 7 | Yes | Yes |

*from second N-terminal M2 copy

EXAMPLE 10

Yield and Nucleic Acid Binding of M2-Containing Particles

Yields are expressed as milligrams of purified particles from a 500 mL culture. Presence of bound nucleic acid was determined by measuring the A280:A260 ratio of the purified particle. A ratio of more than 1.0 indicates no bound nucleic acid, and a ratio of less than 1.0 indicates the presence of bound nucleic acid. The original full length IM2HBc described by Fiers and colleagues [Neirynck et al., (1999) *Nat. Med.,* 5(10):1157-1163, and patent application WO9907839], is the same as ICC-1559.

| Particle | M2e sequence | Insertion Site | C-Terminus | Bound Nucleic Acid | Yield (mg/500 mL) |
|---|---|---|---|---|---|
| 1123 (HBc149 + C) | None | NA | Truncated/ Stabilized | No | 16.6 |
| 1559 (IM2HBc) | M2 (1-24) | N-terminus | Full Length | Yes | 3.2 |
| 1604 | M2 (1-24) | N-terminus | Truncated/ Stabilized | No | 16.7 |
| 1569 | M2 (2-24) (C17S, C19S) | Immunodominant loop (Between D78 and P79) | Truncated Stabilized | No | 11.2 |
| 1475 | M2 (2-24) | Immunodominant loop (Between D78 and P79) | Truncated/ Stabilized | No | 1.1 |

EXAMPLE 11

Antigenicity of Various M2-Containing Particles

The antigenicity of the various particles to the monoclonal antibody 14C2 was examined using an ELISA. To ensure retention of particles in their native conformation, ELISA plates were first coated with a polyclonal antibody (rabbit) to capture the particles, which were then probed with various dilutions of either the 14C2 monoclonal antibody, or two anti-HBc monoclonal antibodies with specificity for the immunodominant loop region of HBc particles. The data, presented in the table below, demonstrate that presentation of M2e in the immunodominant loop of HBc does not significantly alter the accessibility of the M2e epitope to the 14C2 monoclonal antibody, relative to presentation at the N-terminus (IM2HBc/ICC-1559 and ICC-1604). These observations were not surprising because it has shown previously been shown that 14C2 binds to an internal region of M2e (amino acids 8, 10, 11, and 14 of M2, as opposed to the N-terminus [Zebedee et al., (1988) *J. Virol.,* 62(8):2762-2772].

In addition, all particles, with the exception of ICC-1569, retained antigenicity to anti-HBc monoclonal antibodies 3120 and 3105. The loss of recognition by 3105 is a previously observed phenomenon for particles with sequences inserted into the immunodominant loop, and this typically translates to reduced anti-HBc responses for these particles following immunization. Monoclonal antibodies 3105 and 3120 were purchased from the Tokyo Institute of Immunology, Japan.

| | Monoclonal Antibody | | |
|---|---|---|---|
| Particle | 14C2 | 3105 | 3120 |
| ICC-1123 | − | + | + |
| IM2HBc/ ICC-1559 | + | + | + |
| ICC-1604 | + | + | + |
| ICC-1569 | + | − | + |

EXAMPLE 12

Immunogenicity of Various M2-Containing Particles

The immunogenicity of ICC-1604 and ICC-1569 particles was investigated in mice. There was little difference in anti-M2e titers between the two particles, whereas a significant difference in the anti-HBc titers was observed between the two particles. ICC-1604 particles, with a native immunodominant loop, elicited anti-HBc titers that, like IM2HBc, were approximately 100-fold higher than those for ICC-1569 particles. These data re-emphasize the fact that disruption of the immunodominant loop of HBc, by epitope insertion, which results in loss of recognition by the HBc monoclonal antibody 3105, dramatically decreases anti-HBc antibody responses. Conversely, both particles elicited anti-M2e antibody responses that were similar, and comparable to those seen previously for IM2HBc/ICC-1559, with end point titers of approximately 1:100,000.

Particles were formulated on Alhydrogel™, and groups of 10 mice were immunized with two 10 μg doses of formulated particles on days 0 (zero) and 28. Pooled sera were analyzed 2 weeks after the second injection for anti-HBc and anti-M2e antibody responses using ELISA assays. Pooled sera from 10 mice at 2 weeks post boost were analyzed in ELISAs, with M2e (2-24) synthetic peptide and recombinant HBc (ICC-1123) serving as the capture antigens.

A direct comparison of ICC-1569 and ICC-1604 particles in the mouse lethal challenge model revealed that both particles, when formulated on Alhydrogel™, afforded complete protection from a lethal challenge dose. These results are therefore consistent with the observation that both particles elicit similar titers of anti-M2e antibodies.

Compilation of data from multiple mouse studies by Fiers and co-workers at the University of Ghent, using an array of different particles and adjuvants, has revealed evidence of a possible correlation between titers of anti-M2e of the IgG2a subclass and protective efficacy. Mice displaying anti-M2e IgG2a titers of more than $10^4$ are reliably protected from a lethal challenge, whereas mice that exhibit anti-M2e IgG2a titers below $10^4$, but IgG1 titers of more than $10^4$, typically show less complete protection. These data have relevance to the potential mechanism of protection in that they suggest that anti-M2e antibodies do not simply block the function of M2, otherwise the protection would be independent of IgG subclass bias. Rather, because mouse IgG2a (and IgG2b) are the most efficient subclass for fixing complement and binding FcγRIII receptors, which are expressed by NK cell [Ravetch et al., (1991) *Annu. Rev. Immunol.,* 9:457-492], the data suggest an immune mechanism involving CDC and/or ADCC.

EXAMPLE 13

Antibody Subclass and Protection

A summary of several studies in which various M2e-Hbc constructs (10 μg/mouse) and various adjuvants were assayed. About one-half were i.p. administration and about one-half i.n. For each group (14 mice) the sera were pooled and the titer of anti-M2e IgG subclass antibodies was determined. The results are from sera taken one week after the second boost. For mice where the IgG2a titer was more than $10^4$, the IgG1 titer was $10^4$ (*).

| IgG2a | Number of Groups | Percent Protection |
|---|---|---|
| $10^4$ | 8 | 100 |
| $<10^4$* | 4 | 70-95 |

Adjuvants are increasingly being investigated for their ability to enhance the magnitude and persistence of immune responses to vaccines, as well as modulate the Th1/Th2 bias of the immune response. Although many experimental adjuvants are under investigation, alum remains the only adjuvant that is a component of FDA-approved vaccines in the US. Typically, alum biases immune responses towards a Th2 type, which is manifested by the production of high levels of IgG1 antibody in mice.

It is found that alum-formulated M2e-HBc particles do elicit a significant IgG1 response; however, IgG2a and IgG2b antibodies, which are Th1 indicators, are also elicited. In an attempt to enhance the production of Th1-type IgG subclasses, the immunogenicity of Alhydrogel™-formulated particles supplemented with RC-529, a compound structurally related to MPL® developed by Corixa Corporation, was tested in mice. These studies revealed that inclusion of RC-529 in the Alhydrogel™ formulation resulted in a dramatic enhancement of anti-M2e IgG2a titers, increasing the anti-M2e IgG2a:IgG1 ratio by approximately 10-fold. All mice in both groups were completely protected from lethal challenge; however, there was an indication of reduced morbidity (temperature decrease and weight loss) in mice immunized with ICC-1569 formulated with Alhydrogel™+RC-529, versus Alhydrogel™ alone.

EXAMPLE 14

Partially Truncated HBc Particles: Synthesis of Expression Vectors for Expressing Partially Truncated Particles To prepare expression plasmids for expressing partially truncated HBc particles, a single amino terminal oligonucleotide PCR primer (HBc149/NcoI-F) was used in combination with a unique C-terminal primer. For example, to prepare the HBc156 (E.Cr; ICC-1600 particles) expression plasmid, the primers HBc149/NcoI-F and HBc156(E.cR)-H3-R are used. Primers HBc149/NcoI-F and HBc156C(E.cR)-H3-R are used to prepare the HBc156(E.cR)+C (ICC-1601 particles) expression plasmids. The sequences of all primers used are displayed below.

In addition to truncating the particles—and in some cases the incorporating a C-terminal cysteine residue—codons that are optimal for expression in *E. coli* were also used. It is known that several arginine codons, particularly AGA and AGG are rarely used by *E. coli* and are believe to be problematic for efficient expression of proteins in *E. coli* by leading to stalling of polypeptide synthesis during translation, resulting in premature termination. Of the 16 arginine codons between 150 and 183 of HBc, 7 are encoded by the rare AGA codon and 2 are encoded by the very rare AGG codon. Therefore, in this study, all AGA and AGG codons were replaced with codons that are more frequently used by *E. coli.*

To enable sequential replacement of the rare arginine codons, HBc156 genes are synthesized first (ICC-1600 and HBc156+C ICC-1601 particles), and then used as a template for the HBc163 constructs (ICC-1634 and HBc163+C ICC-1632 particles); the HBc163 constructs are thereafter used as template for the HBc171 constructs (ICC-1642 and HBC171+C ICC-1643 particles); finally, the HBc 171 constructs are used as a templates for the arginine codon optimized HBc182 and HBc183 constructs. A non-optimized HBc182 construct (ICC-1575) is also prepared for control purposes. All PCR products are cleaved with the restriction enzymes NcoI and HindIII and cloned into the expression vector pKK223-3N, which had been cut with the same enzymes as discussed before.

Amino Terminal Primer Sequence (NcoI restriction site is underlined):

```
HBc149/NcoI-F
5'-TTGGGCCATGGACATCGACCCTTA     SEQ ID NO: 51
```

Carboxyl-Terminal Primer Sequences (HindIII restriction sites are underlined):

```
HBc156(E.cR)-H3-R
5'-GCGAAGCTTACTAAGGGGAGCGGCCTCGTCGAC SEQ ID NO: 64
GAACAACAGTAGTCTCCGG

HBc156C(E.cR)-H3-R
5'-GCGAAGCTTACTAACAAGGGGAGCGGCCTCGTC SEQ ID NO: 65
GACGAACAACAGTAGTCTCCGG

HBc163(E.cR)-H3-R
5'-GCGAAGCTTACTAAGGCGAGGGAGTGCGCCGAC SEQ ID NO: 66
GAGGGGAGCGGCCTCG

HBc163C(E.cR)-H3-R
5'-GCGAAGCTTACTAACAAGGCGAGGGAGTGCGCC SEQ ID NO: 67
GACGAGGGGAGCGGCCTCG

HBc171(E.cR)-H3-R
5'-GCGAAGCTTACTACGGCGATTGAGAGCGTCGAC SEQ ID NO: 68
GGCGAGGCGAGGGAGT

HBc171C(E.cR)-H3-R
5'-GCGAAGCTTACTAACACGGCGATTGAGAGCGTC SEQ ID NO: 69
GACGGCGAGGCGAGGGAGT

HBc183(E.cR)-H3-R
5'-GCGAAGCTTACTAACATTGAGATTCCCGAGATT SEQ ID NO: 113
GAGATCGCCGGCGACGCGGCGATTGAGAGCGTC

HBc182-H3-R
5'-GCGAAGCTTACTATTGAGATTCCCGAGATTGA  SEQ ID NO: 114

HBc183-H3-R
5'-GGAAAGCTTACTAACATTGAGATTCCCG      SEQ ID NO: 115

HBc149/HindIII-R
5'-CGCAAGCTTAAACAACAGTAGTCTCCGGAAG   SEQ ID NO: 54

HBc149+C/HindIII-R
5'-CGCAAGCTTACTAGCAAACAACAGTAGTCTCCG SEQ ID NO: 55
GAAG
```

Table 5, below, shows an alignment that illustrates the configuration of the C-termini of the full-length HBcAg (HBc183), and all particles harboring C-terminal truncations.

Sequences are aligned according to amino acid residue position 149 from the N-terminus of HBc of SEQ ID NO:1 that is shared by all constructs. C-terminal cysteine residues, when present, are underlined.

TABLE 5

| Construct Name | Sequence | SEQ ID NO |
|---|---|---|
| HBc183 | VRRRGRSPRRRTPSPRRRRSQSPRRRRSQSRESQC | 116 |
| HBc182 | VRRRGRSPRRRTPSPRRRRSQSPRRRRSQSRESQ | 117 |
| HBc171 (E.cR)+C | VRRRGRSPRRRTPSPRRRRSQSPC | 118 |
| HBc171 (E.cR) | VRRRGRSPRRRTPSPRRRRSQSP | 119 |
| HBc163 (E.cR)+C | VRRRGRSPRRRTPSPC | 120 |
| HBc163 (E.cR) | VRRRGRSPRRRTPSP | 121 |
| HBc156 (E.cR)+C | VRRRGRSPC | 122 |
| HBc156 (E.cR) | VRRRGRSP | 123 |

EXAMPLE 15

Particle Formation and Stability Using HBc Chimers with and without N-Terminal Cysteines A series of four chimer proteins containing short N-terminal fusions to amino acid D4 of hepatitis B core truncated at position 149 were prepared that contained zero (particle 1891), 1 (particles 1892 and 1893), or 2 (particle 1890) cysteine residues. The chimers were analyzed using analytical size exclusion chromatography (SEC) to assess particle integrity following purification. The sequences of those N-terminal fusions and isolated yields are shown in Table 6, below.

TABLE 6

| Chimer Protein | N-terminal Fusion* | SEQ ID NO | Yield (mg/500 mL cell Culture) |
|---|---|---|---|
| 1890 | MGCRCNDSS | 124 | 6.8 |
| 1891 | MGSRSNDSS | 125 | ZERO |
| 1892 | MGSRCNDSS | 126 | 1.9 |
| 1893 | MGCRSNDSS | 127 | 6.7 |

The three chimer proteins containing one or more cysteines were successfully purified at yields ranging from 1.9 to 6.8 mg/500 mL cell culture. The chimer containing two cysteines (particle 1890) at positions 3 and 5, relative to the initiator methionine, or the single cysteine at position 3 (particle 1893) were purified in higher yields compared to the chimer having a single cysteine at position 5 (particle 1892). Chimer proteins containing neither cysteine 3 or 5 could not be purified as particles, suggesting that the chimer protein molecule does not form stable particles.

When analyzed by analytical SEC, all three proteins exhibited a dominant peak eluting at approximately 5-8 mL, which represents particles. This finding is in contrast to chimer protein molecules particles lacking N-terminal cysteine(s), such as chimer particle ICC-1048, which exist as a mixture of particles and lower order structures (non-particulate material). More detailed analysis of the SEC profiles revealed that chimer protein molecule 1890 formed superior particles, with no detectible lower order structures, whereas chimer 1892 revealed a small amount of non-particulate material, and chimer 1893 revealed still more non-particulate material.

To examine the ability of N-terminal cysteine residues to stabilize particles displaying heterologous epitopes, a chimer protein molecule was constructed that contains the same N-terminal configuration as chimer 1890, with CS-repeats from *P. falciparum* (NANPNVDPNANPNANPNANP; SEQ ID NO:128) inserted in the immunodominant loop between amino acids 78 and 79. Following purification, the integrity of particles from the resulting chimer (1894) was compared to particles of a similar chimer protein that lacked the N-terminal fusion (1045).

SEC analysis of these constructs showed that chimer 1045 exhibited peaks for both particles and lower order structures. A similar analysis of the data for chimer 1894 showed an unexplained lack of particle formation that is being investigated.

EXAMPLE 16

Immunogenicities of Particles with Serially-linked N-Terminal M2 Peptides

The immunogenicities of particles genetically engineered to contain variable copies of M2 [1, 1604 (Example 12); 2, 1817 (Example 9); or 3, 1818 (Example 9)] fused to the N-terminus, were assayed in rabbits. These particles were frozen after their preparation to minimize the effect of a protease believed to be present, as discussed previously and in the next Example. Groups of 4 rabbits were immunized, via the intramuscular route, with 3 doses of particles (25 μg/dose) formulated with Alhydrogel™ (500 μg aluminum per dose)/RC-529-AF (25 μg per dose). Rabbits were immunized on days zero, 28 and 56, and bled on days zero (Prebleed), 14, 28, 56 and 70. Sera were tested for the levels of anti-M2e antibody using ELISA.

The ELISA was performed using microtiter plates coated with M2e(2-24/C17S,C19S) peptide (2 μg/mL, for about 18 hours) and blocked with 3% BSA. Sera were added to the plates, in duplicate, starting at a 1:100 dilution and continuing in 3-fold dilutions, except prebleeds, which were analyzed in triplicate. To detect immobilized antibodies, an anti-rabbit IgG HRP conjugate was added followed by the chromgenic substrate TM blue. Using the prebleed data, ‘cut-offs’ were calculated, for each rabbit, at each serum dilution, by determining the background plus 3 standard deviations of the pre-bleed serum sample Day zero). End point titers were determined by identifying the last serum dilution that gave an absorbance value greater than the cut-off as a given serum dilution. If an individual rabbit was a non-responder (i.e. titer of zero) in a group where other rabbits gave detectible titers (i.e. >0), the non-responder was assigned a titer of 10 to enable the calculation of a geometric mean titer (GMT) for the group.

Surprisingly, the particles with only a single copy of M2e fused to the N-terminus (1604) failed to yield a detectible anti-M2e response (Table 11); however, particles 1817 and 1818 yielded detectible anti-M2e immune responses just 14 days after a primary injection (Table 7). The peak titer for 1817 particles of 14,030 was observed on day 70, whereas the peak titer for 1818 particles of 24,300, was observed on day 56. Anti-M2e titers were not detected in any of the rabbits immunized 1604, after 1, 2, or 3 doses.

TABLE 7

GMTs for rabbits immunized with various M2e-containing particles

| Particle | Day 14 | Day 28 | Day 56 | Day 70 |
|---|---|---|---|---|
| 1604 | 0 | 0 | 0 | 0 |
| 1817 | 0 | 1,559 | 6,155 | 14,030 |
| 1818 | 684 | 14,030 | 24,300 | 8,100 |

EXAMPLE 17

Avoiding Endogenous Protease Activity

Continuing work has shown that M2-containing particles are subject to cleavage by an unknown protease that appears to be a metalloprotease because proteolysis of those particles can be prevented by the inclusion of 10 mM EDTA in a buffer used for isolation and storage of the particles. To determine if lower concentrations of EDTA were also effective, a stability study was performed using the ICC-1818 particles prepared in Example 9 and discussed above. These particles were placed into storage buffer that contained 20 mM sodium phosphate, at pH 7.2, and also contained 0, 1, 2, 5 or 10 mM EDTA. The results, presented in FIG. 11, clearly show that 1 mM EDTA is as effective as 10 mM EDTA at preventing proteolysis. Indeed, concentrations lower than 1 mM may also be effective.

Surprisingly, in the absence of EDTA, proteolysis was reduced at 37° C. compared to room temperature incubation. This observation suggested that the protease may be highly labile and therefore subject to inactivation at relatively low temperatures (40-60° C.). Therefore, a study was initiated to determine if the proteolytic activity could be destroyed by heat treatment, while maintaining the integrity of the particles.

Figure 12A:
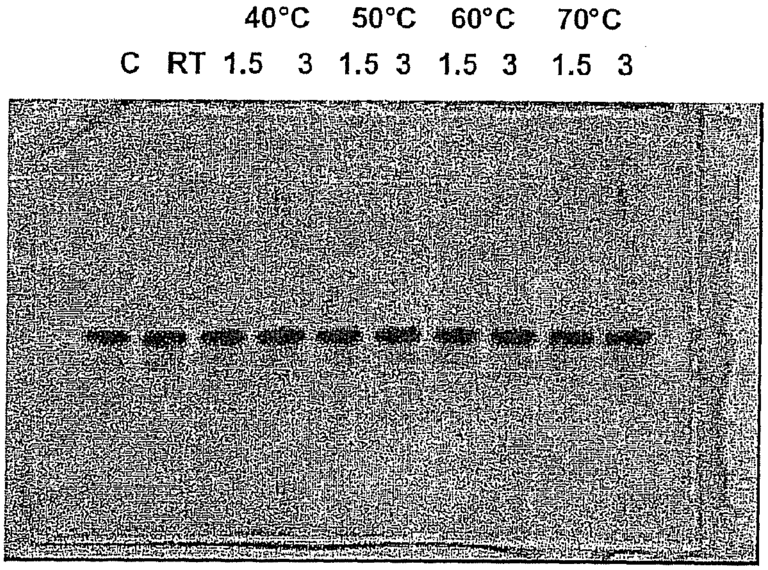
FIG. 12 in two panels shows photographs of SDS-PAGE analysis demonstrating reduced proteolysis of monomers of the CV-1818 particle following storage at room temperature (RT), heat treatment at the temperature shown for 1.5 or 3 hours, as shown, of the control as in FIG. 11 (FIG. 12A) or after one week of storage (FIG. 12B).

To evaluate the possibility of using a heat step to inactivate the protease, particles were heated to 40, 50, 60, or 70° C. for either 1.5 or 3 hours. The integrity of monomers evaluated using SDS-PAGE (FIG. 12A), and the data show that all monomers appear similar after heat treatment. A second gel, presented in FIG. 12B, clearly shows that untreated particles are completely cleaved after 1 week at room temperature (RT), whereas particles that were heat treated at 40° C. show reduced cleavage, those incubated at 50° C. show minimal cleavage, and those incubated at 60 or 70° C. appear indistinguishable from non-incubated controls.

To evaluate the effect of heat treatment on particle integrity, heat treated particles were analyzed using analytical SEC. The data, presented in FIG. 13A, show that heat-treatment at 60° and 70° C. had a minor impact on particle integrity, as evidenced by a slight increase in monomer/dimer peaks, which elute after the main particle peak. Heat-treatment at 50° C. and below had no apparent impact on the SEC elution profile, suggesting that particles withstood the heat step with no adverse effects.

Figure 12B:
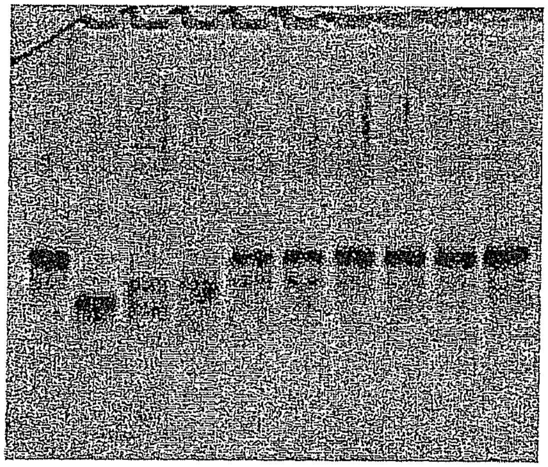

SEC analysis of heat-treated particles following an one-week RT incubation clearly reveals the proteolysis of the non-heat-treated control, as evidenced by the increased elution time of the particle peak (FIG. 13B, RT sample). This was consistent with the proteolysis observed using SDS-PAGE (FIG. 12B) and suggests that cleavage of M2e from the particles results in reduced particle size. The heat-treated samples all exhibit dominant, intact particle peaks, which is again consistent with the lack of cleavage revealed by SDS-PAGE (FIG. 12).

These data suggest that heat-treatment used to inactivate the proteolytic activity responsible for cleaving M2e-containing particles can be a viable option for limiting proteolysis. Preliminary studies suggest that a 3-hour incubation at 55-60° C. may be optimal for achieving proteolysis inactivation, while maintaining particle integrity. Further, in terms of the manufacturing process, it is likely to be preferable for the heat step to be performed prior to Sepharose® CL-4B step so that monomers and dimers that are released as a consequence of the heat step are effectively removed. The use of this method may enable particles to be stored in the absence of EDTA.

EXAMPLE 18

Purification Using EDTA and a Heating Step Results in Stable Particles

Based on the data presented above, a prototype purification process incorporating EDTA and heat inactivation of the protease activity that cleaves M2e was been tested using CV-1906 particles that contain 3 N-terminal copies of M2e as in ICC-1818 particles, linked to a HBc sequence that starts at residue 4 (aspartic acid) and in which cysteines at positions 48 and 107 are replaced with serine residues, the HBc sequence is truncated to remove residues C-terminal to position 149, and a cysteine residue was added at position 150 (HBc149C48S/C107S, C150). Of the six cysteine residues that could be present in the three copies of M2e, only the two cysteines in the M2e sequence closest to the HBc sequence are in fact present, with the other four cysteines being replaced by serine residues.

Figure 14:
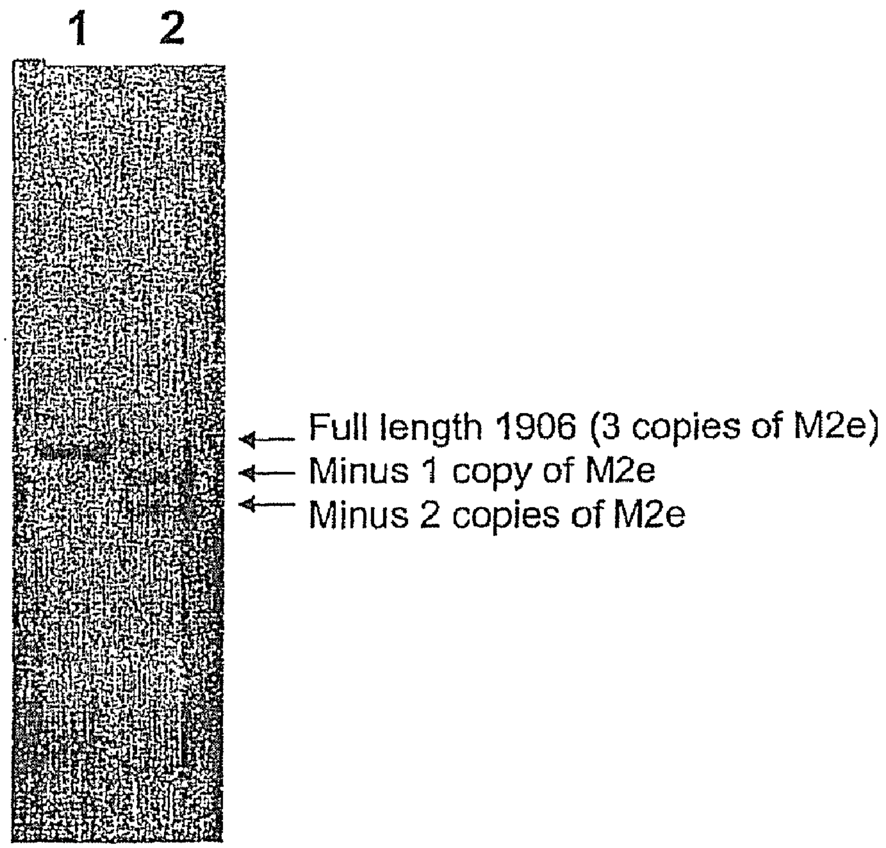
FIG. 14 is a photograph of a reducing SDS-PAGE gel show CV-1906 particle monomers following purification using the process described, including the heat step (Lane 1) and lacking the heat step (Lane 2).

The purification process involved the use of 10 mM EDTA in all buffers until the inactivation of the protease via heat treatment, at which point the EDTA was removed during Sepharose® CL-4B chromatography. A comparison of the process containing or lacking the heat inactivation step was performed. The process used is detailed below:

- Lysis using microfluidizer in Tris/EDTA buffer
- Centrifugation
- 20% ammonium sulfate precipitation
- Centrifugation
- Resuspension of pellet in 1M NaCl/10 mM EDTA
- Phenyl HIC in presence of EDTA (elution at ~300 mM NaCl)
- +/−Heat inactivation (60° C., 3 hours)
- Sepharose® CL-4B chromatography in absence of EDTA
- Ceramic HA chromatography This comparative study revealed that, as expected, the CV-1906 particles not subject to the heat step began cleaving as soon as the EDTA was removed; i.e., following Sepharose® CL-4B (FIG. 14, Lane 2). In contrast, the CV-1906 particles purified using the process that included the heat step remained intact (FIG. 14, Lane 1).

EXAMPLE 19

Size Studies with Chimers Containing 1, 2 or 3 Tandem M2 Peptides

Figure 15:
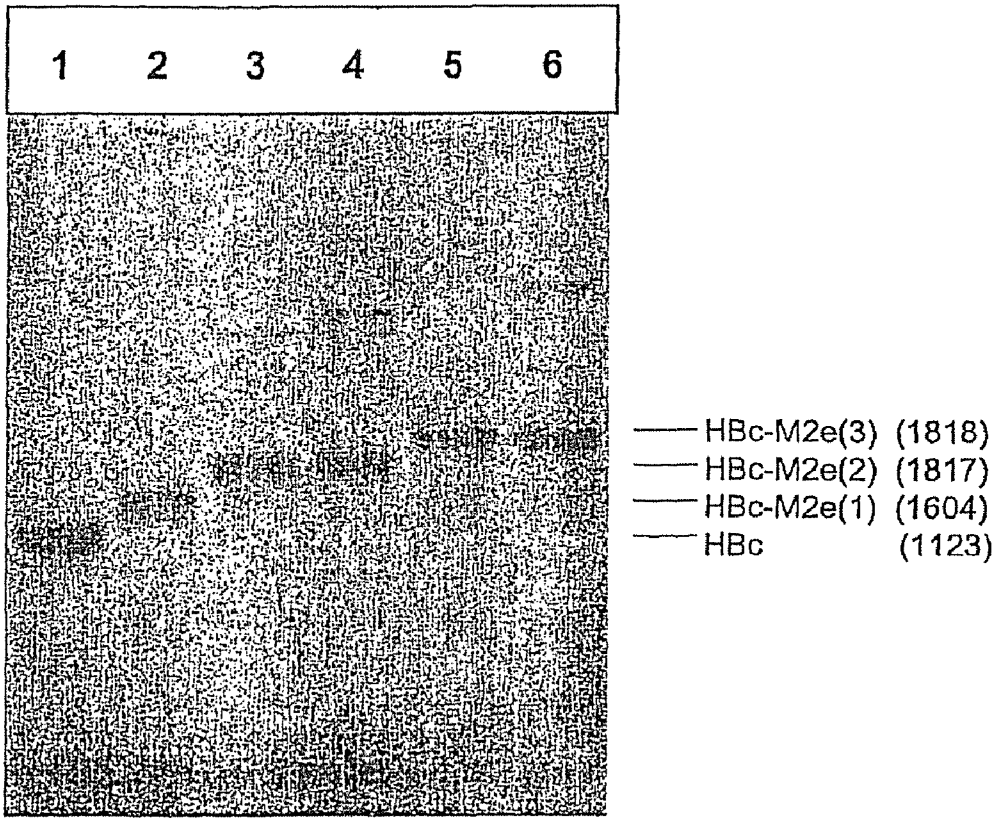
FIG. 15 is a photograph of a reducing SDS-PAGE gel analysis of particles containing 0 (1123, Lane 1), 1 (1604, Lane 2), 2 (1817, Lanes 3 and 4), and 3 (1818, Lanes 5 and 6) copies of M2e expressed fused in tandem to the N-terminus of HBc particles truncated after position 149 and including an added cysteine residue at position 150.

Hybrid HBc-M2e particles with zero, 1, 2, or 3 tandem copies of M2e fused to the N-terminus of HBc were expressed in *E. coli* and purified (Table 8). These particles were also frozen after their preparation and thawed just prior to use, as discussed before. The size of the various monomers was compared using reducing SDS-PAGE (FIG. 15). The relative mobilities of the M2e-HBc hybrids were consistent with their expected molecular weights (Table 8).

TABLE 8

Details of M2e-HBc Hybrid Particles

| | Copies M2e | Total No. Amino Acids | Expected Mwt (kDa) of Monomers |
|---|---|---|---|
| 1123 | 0 | 150 | 16.95 |
| 1604 | 1 | 173 | 19.57 |
| 1817 | 2 | 198 | 22.39 |
| 1818 | 3 | 223 | 25.20 |

EXAMPLE 20

Immunogenicity Studies with Chimers Containing 1, 2 or 3 Tandem M2 Peptides

The immunogenicity and protective efficacy of particles genetically engineered to contain variable copies of M2 [1, 1604; 2, 1817; or 3, 1818] fused to the N-terminus was compared in BALB/c mice using the lethal challenge model. Pathogen-free, female BALB/c mice were obtained from Charles River (Germany) and were used for immunization at 8 weeks of age. The animals were housed in a temperature-controlled environment with 12-hour light/dark cycles, and received food and water ad libitum.

All the mice (14 per group) were vaccinated i.p. with 100 µl vaccine using the following immunization protocol: first vaccination, first and second boost with 10 µM2e-HBc particles, formulated with Alhydrogel™ (100 µg/dose) and RC-539-AF (10 µg/dose) at three week intervals. These particles were also frozen after preparation and thawed just prior to use to minimize the effect of the protease. Before and two weeks after each immunization, blood samples were collected by piercing of the ventral tail vein. The final bleed was performed by cardiac puncture. Blood clotting was permitted for 30 minutes at 37° C. and serum was collected by taking the supernatant from two subsequent centrifugations. The titers of M2e-specific IgG were determined by ELISA.

Figure 16:
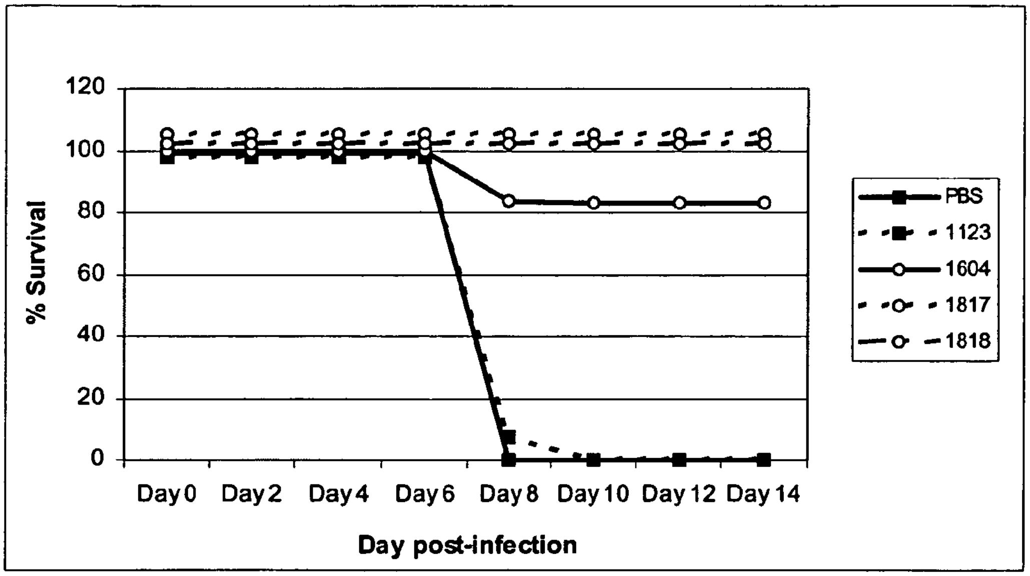
FIG. 16 is a graph showing survival of mice immunized with one or another of the M2e-containing HBc chimers of FIG. 15 or a control as noted in the figure following lethal challenge with influenza A virus.
Figure 17:
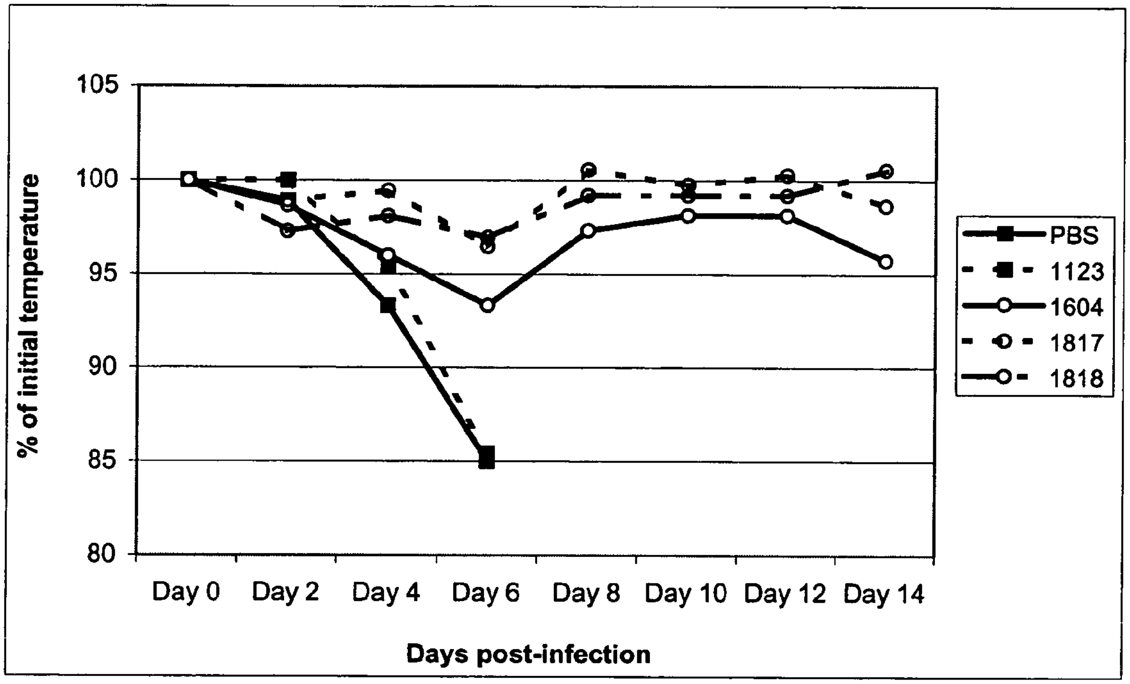
FIG. 17 is a graph showing body temperature of the mice of FIG. 16 and as noted in the figure challenged with influenza A virus.
Figure 18:
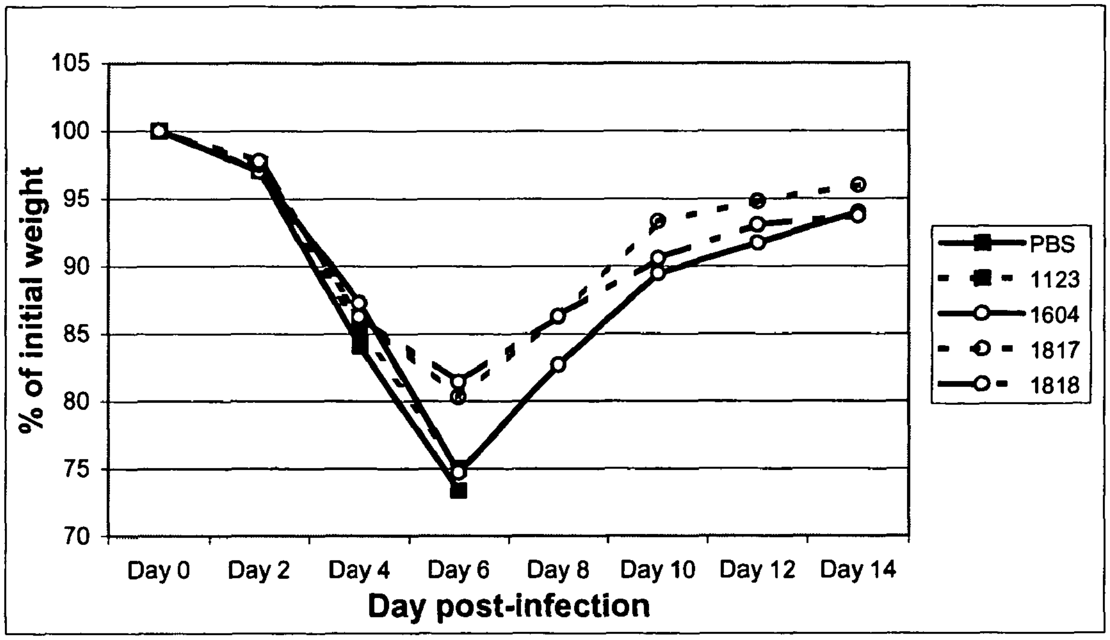
FIG. 18 is a graph showing weight of the above mice challenged with influenza A virus.

Mice immunized with 1817 or 1818 particles exhibited complete survival following a lethal challenge, whereas mice immunized with 1604 particles exhibited some mortality (See, FIG. 16). Mice immunized with non-M2e containing particles (1123), or PBS, exhibited 100 percent mortality (FIG. 16), highlighting the high stringency of the challenge. The enhanced protection in the mice immunized with 1817 and 1818 particles was complemented by reduced morbidity (weight loss and reduction in body temperature) relative to 1604 particles, indicating that the protection was more robust in the mice immunized with particles expressing 2 or 3 copies of M2e (1817 and 1818), compared with just one (1604) (FIG. 17 and FIG. 18).

Anti-M2e titers were determined using ELISA. ELISA plates were coated overnight (about 18 hours) at 37° C. with 50 µl of a 2 µg/ml M2e peptide solution in 50 mM sodium bicarbonate buffer, pH 9.7. Microtiter plates (type II F96 MaxiSorp™) were used. After washing the plates, 200 µl of a PBS+2% BSA solution was used for blocking. After 1 hour of incubation, a series of 1/3 dilutions of the different serum samples, starting with a 1/50 dilution, were loaded on peptide-coated wells. The bound antibodies were detected with a peroxidase-labeled antibody directed against respectively mouse IgG1 and IgG2a (Southern Biotechnology Associates, Inc.), diluted 1/6000 in PBS+1% BSA+0.05% Tween®-20. After washing, the microtiter plates were incubated for 5 minutes with of TMB substrate. The reaction was stopped by addition of 1M $H_3PO_4$ and the absorbance at 450 nm was measured. To obtain the value for the specific binding to M2e, the absorbances obtained for the pre-immune sera were subtracted from the absorbances obtained for the immune sera at the corresponding dilution.

ELISA data revealed that particles 1817 and 1818 elicited anti-M2e IgG1 titers that were 10.4- and 8.4-fold higher, respectively, than those observed for 1604 particles. Similarly, particles 1817 and 1818 elicited anti-M2e IgG2a titers that were 5.5- and 7.6-fold higher, respectively, than those observed for 1604 (Table 9)

TABLE 9

Comparison of Anti-M2e Titers for Particles 1604, 1817 and 1818* (IgG1 and IgG2a subclasses)

| | Anti-M2e | |
|---|---|---|
| Particle | IgG1 | IgG2a |
| 1604 | 149,850 (82,901) | 9,100 (7,386) |
| 1817 | 1,564,546 (605,630) | 50,469 (24,228) |
| 1818 | 1,261,731 (654,156) | 69,161 (48,556) |

*Serum samples from individual mice were assayed.
Standard deviations are shown in parentheses.

For anti-HBc determination, ELISA plate (type II F96 MaxiSorp™) were coated with 100 µL of a 10 µg/ml solution of polyclonal rabbit antibody directed against HBc (DAKO). After washing the plates, a PBS+3% BSA solution was used for blocking. After washing, capturing of HBc antigen (10 µg/ml in bicarbonate buffer) was permitted for 1 hour. After washing, a series of 1/3 dilutions of the different serum samples, starting with a 1/1000 dilution, were loaded on the wells. The bound antibodies were detected with an alkaline phosphatase-labeled antibody directed against mouse IgG (Sigma), diluted 1/10,000 in PBS+1% BSA. After washing further, the microtiter plates were incubated for 30 minutes with substrate. The absorbance at 415 nm was measured.

To obtain the value for the specific reactivity to the hepatitis B core antigen, the absorbances obtained for the pre-immune serum were subtracted from the absorbances obtained for the immune serum at the corresponding dilution. For the determination of the IgG1 anti-HBc-titers for individual samples, the bound antibodies were detected with a peroxidase-labeled antibody directed against mouse IgG1 (Southern Biotechnology Associates, Inc.), diluted 1/6000 in PBS+0.5% BSA+0.05% Tween®-20. After washing, the microtiter plates were incubated for 5 minutes with TMB substrate. The reaction was stopped by addition of 1M $H_3PO_4$ and the absorbance at 450 nm was measured.

ELISA data revealed that particles 1817 and 1818 elicited anti-HBc IgG1 titers that were 2.4- and 10.1-fold lower, respectively, than those observed for 1604 particles (Table 10). These data indicate that increased M2e density at the surface of the HBc particle actively suppresses antibody responses to the HBc carrier. Accordingly, the anti-M2e:anti-HBc ratios (IgG1) were 75-fold higher for 1818 particles, and 23-fold higher for 1817 particles, compared with 1604 particles (Table 10). Thus, the immune response against influenza M2e in the vaccinated host is even higher than that against the HBc carrier particle, known to be highly immunogenic.

TABLE 10

Comparison of Anti-M2e and Anti-HBc Titers* (IgG1 Subclass)

| | Anti-M2e | Anti-HBc | Anti-M2e:Anti-HBc Ratio |
|---|---|---|---|
| 1604 | 149,850<br>(82,901) | 4,264,650<br>(1940769) | 0.04 |
| 1817 | 1,564,546<br>(605,630) | 1,766,423<br>(473443) | 0.89 |
| 1818 | 1,261,731<br>(654,156) | 420,577<br>(218052) | 3.00 |

*Serum samples from individual mice were tested.
*Standard deviations are shown in parentheses.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. In a method for the preparation of recombinant chimeric immunogenic particles that are comprised of a plurality of monomers containing influenza A virus M2e polypeptide fused to hepatitis B virus core (HBc) protein, wherein a host organism is transformed with nucleic acid that encodes said monomers, said transformed host expresses said monomers and said monomers are present in said host as said recombinant chimeric immunogenic particles, the improvement that comprises recovering said recombinant chimeric immunogenic particles (i) after heating a buffer solution of said particles at a temperature of about 50° to about 70° C. for a time period of about 1.5 to about 3 hours, or (ii) after heating a buffer solution of said particles and an effective amount of a protease inhibitor at a temperature of about 50° to about 70° C. for a time period of about 1.5 to about 3 hours.

2. The method of claim 1, wherein the protease inhibitor is a chelating agent.

3. The method of claim 2, wherein the chelating agent is selected from the group consisting of ethylenediaminetetraacetic acid, 2,2'-bipyridyl, dimercaptopropanol, ethyleneglycol-bis-(2-aminoethyl)-N,N,N'N"-tetraacetic acid, nitrilotriacetic acid, ortho-phenanthroline, salicylic acid, triethanolamine, bestatin, and phosphoramidon.

4. The method of claim 2, wherein the chelating agent is ethylenediaminetetraacetic acid.

5. The method of claim 1, wherein the protease inhibitor is phenylmethanesulfonyl fluoride.

6. The method of claim 1, wherein the particles are recovered after heating a buffer solution of said particles at a temperature of about 50° to about 70° C. for a time period of about 1.5 to about 3 hours.

7. A method for the preparation of recombinant chimeric immunogenic particles of influenza A virus M2e polypeptide fused to the hepatitis B virus core (HBc) protein comprising:

expressing the recombinant chimeric immunogenic particles in host cells;

lysing the host cells;

collecting the recombinant chimeric immunogenic particles in a buffer solution and heating said buffer solution of said particles at a temperature of about 50° to about 70° C. for a time period of about 1.5 to about 3 hours; and purifying the recombinant chimeric immunogenic particles.

8. The method of claim 7, wherein the host cells are from an organism that is a member of the group consisting of virus, bacteria, yeast, mammal, plant, insect, and hybrids thereof.

9. The method of claim 7, wherein the host organism is *E. coli.*

10. A method for the preparation of recombinant immunogenic particles having a plurality of chimeric molecules comprising influenza A virus M2e polypeptide fused to the hepatitis B virus core (HBc) protein comprising the steps of:

a) expressing the particles of recombinant HBc chimer protein molecules in host cells, b) lysing the host cells; and c) isolating the particles of recombinant HBc chimer protein molecules in buffer that contains a protease-inhibiting amount of metalloprotease-inhibiting chelating agent;

wherein the chimeric molecules have a sequence length of about 150 to about 375 amino acid residues that contains four peptide-linked amino acid residue sequence domains from the N-terminus that are denominated Domains I, II, III and IV, wherein (a) Domain I comprises (i) about 75 to about 160 amino acid residues whose sequence includes at least the sequence of the residues of position 4 through about position 75 of HBc, (ii) one to three cysteine residues present at a position in the chimer molecule of about one to about −55 relative to the N-terminus of HBc of SEQ ID NO:1 [N-terminal cysteine residue(s)], said one or more N-terminal cysteine residues being present within a sequence other than that of the pre-core sequence of HBc, and (iii) includes two to four sequences of about 6 to about 24 residues of the influenza A M2 polypeptide of SEQ ID NO:9 that is peptide-bonded to or within about 15 residues of the N-terminus of the HBc sequence;

(b) Domain II comprises about zero to about 60 amino acid residues peptide-bonded to about residue 75 of which (i) zero to all of the sequence of HBc is present from position 76 through 85 and (ii) an optional sequence of 6 to about 48 residues that constitute one or more repeats of 6 to about 24 residues of an influenza A M2 polypeptide of SEQ ID NO:9;

(c) Domain III is an HBc sequence from about position 86 through about position 135 peptide-bonded to about residue 85; and (d) Domain IV comprises (i) the residues of about positions 136 through 140 plus up to sixteen residues of an HBc amino acid residue sequence from position 141 through 156 peptide-bonded to the residue of about position 135 of Domain III, (ii) zero to three cysteine residues, and (iii) up to about 100 amino acid residues in a sequence heterologous to HBc from position 164 to the HBc C-terminus;

said chimer molecule (i) containing no more than 10 percent conservatively substituted amino acid residues in the HBc sequence relative to SEQ ID NOs: 1-6, (ii) self-assembling into particles that are substantially free of binding to nucleic acids on expression in a host cell, and said particles being more stable on formation than are particles formed from an otherwise identical HBc chimer that lacks said N-terminal cysteine residue(s) or in which an N-terminal cysteine residue present in the chimer molecule is replaced by another residue.

11. The method of claim 10, wherein said isolated particles are stored in buffer that contains a protease-inhibiting amount of metalloprotease-inhibiting chelating agent.

12. The method of claim 11, wherein said metalloprotease-inhibiting chelating agent is selected from the group consisting of ethylenediaminetetraacetic acid (EDTA), 2,2'-bipyridyl, dimercaptopropanol, ethyleneglycol-bis-(2-aminoethyl)-N,N,N'N''-tetraacetic acid, nitrilotriacetic acid, ortho-phenanthroline, salicylic acid, triethanolamine, bestatin, and phosphoramidon.

13. The method of claim 12, wherein said metalloprotease-inhibiting chelating agent is EDTA.

14. The method of claim 13, wherein said EDTA is present at about 1 to 10 mM.

15. The method of claim 14 including the additional step of heating the buffer solution of chimer particles and metalloprotease-inhibiting chelating agent to a temperature of about 50° C. to about 70° C. for a time period of about 1.5 to about 3 hours.

16. The method of claim 15 including the additional step of separating the chimer particles from the metalloprotease-inhibiting chelating agent.

17. The method of claim 16 including the further step of collecting the separated chimer particles.

18. The method of claim 14, wherein said HBc protein chimer molecules of said particles have a sequence of about 150 to about 235 amino acid residues, wherein (a) Domain I comprises (i) about 95 to about 140 amino acid residues; and d) Domain IV comprises zero or one cysteine residue, and up to about 50 amino acid residues in a sequence heterologous to HBc from position 156 to the HBc C-terminus.

19. The method of claim 18, wherein Domain I of said HBc protein chimer molecules of said particles includes one N-terminal cysteine residue.

20. The method of claim 18, wherein Domain I of said HBc protein chimer molecules of said particles includes one C-terminal cysteine residue.

21. The method of claim 18, wherein Domain I of said HBc protein chimer molecules of said particles includes three of said M2 polypeptide sequences.

22. The method of claim 18, wherein Domain I of said HBc protein chimer molecules of said particles includes two of said M2 polypeptides.

23. The method of claim 18, wherein said M2 polypeptide of SEQ ID NO:9 includes residues $X_6$ through $X_{24}$.

24. The method of claim 18, wherein Domain II of said HBc protein chimer molecules of said particles comprises the amino acid residues of the sequence of HBc from position 76 through 85.

25. The method of claim 18, wherein Domain II of said HBc protein chimer molecules of said particles comprises the amino acid residues of the sequence of HBc from position 76 through 85 and further includes 6 to about 23 residues of the influenza A M2 polypeptide of SEQ ID NO:9.

26. The method of claim 18, wherein one of said residues $X_{17}$ and $X_{19}$ of said M2 polypeptide of SEQ ID NO:9 is cysteine.

27. The method of claim 18, wherein said HBc protein chimer molecules of said particles have a length of about 170 to about 215 residues.

28. The method of claim 18, wherein the residues $X_{17}$ and $X_{19}$ of one of the M2 polypeptides of SEQ ID NO:9 are serine or alanine.

29. The method of claim 18, wherein the M2 polypeptides of SEQ ID NO:9 include residues $X_2$ through $X_{24}$.

30. The method of claim 18, wherein two of the residues $X_{17}$ and $X_{19}$ of one of the M2 polypeptides of SEQ ID NO:9 are cysteine.

31. The method of claim 14, wherein Domain IV of said HBc protein chimer molecules of said particles includes a sequence of about nine amino acid residues of the HBc sequence from residue position 141 through about position 149 peptide-bonded to residue 140.

32. The method of claim 10 including the additional step of separating the chimer particles from the metalloprotease-inhibiting chelating agent.

33. The method of claim 32 including the further step of collecting the separated chimer particles.

34. A method for the preparation of recombinant immunogenic particles having a plurality of chimeric molecules comprising influenza A virus M2e polypeptide fused to the hepatitis B virus core (HBc) protein comprising the steps of:

a) expressing the particles of recombinant HBc chimer protein molecules in host cells, b) lysing the host cells;

c) isolating the particles of recombinant HBc chimer protein molecules in buffer that contains a protease-inhibiting amount of metalloprotease-inhibiting chelating agent;

d) heating the buffer solution of chimer particles and metalloprotease-inhibiting chelating agent to a temperature of about 50° C. to about 70° C. for a time period of about 1.5 to about 3 hours;

e) separating the chimer particles from the metalloprotease-inhibiting chelating agent; and f) collecting the separated chimer particles;

wherein the chimeric molecules have a sequence length of about 150 to about 235 amino acid residues that contains four peptide-linked amino acid residue sequence domains from the N-terminus that are denominated Domains I, II, III and IV, wherein (a) Domain I comprises (i) about 95 to about 140 amino acid residues whose sequence includes at least the sequence of the residues of position 4 through about position 75 of HBc, (ii) one to three cysteine residues present at a position in the chimer molecule of about one to about −55 relative to the N-terminus of HBc of SEQ ID NO:1 [N-terminal cysteine residue(s)], said one or more N-terminal cysteine residues being present within a sequence other than that of the pre-core sequence of HBc, and (iii) includes two to four sequences of about 6 to about 24 residues of the influenza A M2 polypeptide of SEQ ID NO:9 that is peptide-bonded to or within about 15 residues of the N-terminus of the HBc sequence;

(b) Domain II comprises residues 76 through 85 peptide-bonded to residue 75;

(c) Domain III is an HBc sequence from about position 86 through about position 135 peptide-bonded to about residue 85; and (d) Domain IV comprises (i) the residues of about positions 136 through 140 plus up to sixteen residues of an HBc amino acid residue sequence from position 141 through 156 peptide-bonded to the residue of about position 135 of Domain III, (ii) zero or one cysteine residues, and (iii) up to about 50 amino acid residues in a sequence heterologous to HBc from position 156 to the HBc C-terminus;

said chimer molecule (i) containing no more than 10 percent conservatively substituted amino acid residues in the HBc sequence, (ii) self-assembling into particles that are substantially free of binding to nucleic acids on expression in a host cell, and said particles being more stable on formation than are particles formed from an otherwise identical HBc chimer that lacks said N-terminal cysteine residue(s) or in which an N-terminal cysteine residue present in the chimer molecule is replaced by another residue.

35. The method of claim 34, wherein said metalloprotease-inhibiting chelating agent is selected from the group consisting of ethylenediaminetetraacetic acid (EDTA), 2,2'-bipyridyl, dimercaptopropanol, ethyleneglycol-bis -(2-aminoethyl)-N,N,N'N"-tetraacetic acid, nitrilotriacetic acid, ortho-phenanthroline, salicylic acid, triethanolamine, bestatin, and phosphoramidon.

36. The method of claim 35, wherein said metalloprotease-inhibiting chelating agent is EDTA.

37. The method of claim 36, wherein said EDTA is present at about 1 to 10 mM.

* * * * *

SEQUENCE LISTING

```
<160> NUMBER OF SEQ ID NOS: 140

<210> SEQ ID NO 1
<211> LENGTH: 183
<212> TYPE: PRT
<213> ORGANISM: Hepatitis B virus, human ayw subtype

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 2
<211> LENGTH: 185
<212> TYPE: PRT
<213> ORGANISM: Hepatitis B virus, human adw subtype

<400> SEQUENCE: 2
```

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Gln Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185


<210> SEQ ID NO 3
<211> LENGTH: 185
<212> TYPE: PRT
<213> ORGANISM: Hepatitis B virus, human adw2 subtype

<400> SEQUENCE: 3

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Val Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Pro Ser Gln Ser Pro Arg Arg Arg
                165                 170                 175

Arg Ser Gln Ser Arg Glu Ser Gln Cys
            180                 185
```

-continued

<210> SEQ ID NO 4
<211> LENGTH: 183
<212> TYPE: PRT
<213> ORGANISM: Hepatitis B virus, human adyw subtype

<400> SEQUENCE: 4

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Arg Asp Leu Leu Asp
20 25 30

Thr Ala Ala Ala Leu Tyr Arg Asp Ala Leu Glu Ser Pro Glu His Cys
35 40 45

Ser Pro His His Thr Ala Leu Arg Gln Ala Ile Leu Cys Trp Gly Asp
50 55 60

Leu Met Thr Leu Ala Thr Trp Val Gly Thr Asn Leu Glu Asp Pro Ala
65 70 75 80

Ser Arg Asp Leu Val Val Ser Tyr Val Asn Thr Asn Val Gly Leu Lys
85 90 95

Phe Arg Gln Leu Leu Trp Phe His Ile Ser Cys Leu Thr Phe Gly Arg
100 105 110

Glu Thr Val Leu Glu Tyr Leu Val Ser Phe Gly Val Trp Ile Arg Thr
115 120 125

Pro Pro Ala Tyr Arg Pro Pro Asn Ala Pro Ile Leu Ser Thr Leu Pro
130 135 140

Glu Thr Thr Val Val Arg Arg Arg Gly Arg Ser Pro Arg Arg Arg Thr
145 150 155 160

Pro Ser Pro Arg Arg Arg Arg Ser Gln Ser Pro Arg Arg Arg Arg Ser
165 170 175

Gln Ser Arg Glu Ser Gln Cys
180

<210> SEQ ID NO 5
<211> LENGTH: 183
<212> TYPE: PRT
<213> ORGANISM: woodchuck

<400> SEQUENCE: 5

Met Asp Ile Asp Pro Tyr Lys Glu Phe Gly Ser Ser Tyr Gln Leu Leu
1 5 10 15

Asn Phe Leu Pro Leu Asp Phe Phe Pro Asp Leu Asn Ala Leu Val Asp
20 25 30

Thr Ala Thr Ala Leu Tyr Glu Glu Glu Leu Thr Gly Arg Glu His Cys
35 40 45

Ser Pro His His Thr Ala Ile Arg Gln Ala Leu Val Cys Trp Asp Glu
50 55 60

Leu Thr Lys Leu Ile Ala Trp Met Ser Ser Asn Ile Thr Ser Glu Gln
65 70 75 80

Val Arg Thr Ile Ile Val Asn His Val Asn Asp Thr Trp Gly Leu Lys
85 90 95

Val Arg Gln Ser Leu Trp Phe His Leu Ser Cys Leu Thr Phe Gly Gln
100 105 110

His Thr Val Gln Glu Phe Leu Val Ser Phe Gly Val Trp Ile Arg Thr
115 120 125

Pro Ala Pro Tyr Arg Pro Pro Asn Ala Pro Ile Leu Ser Thr Leu Pro
130 135 140

```
Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Cys
            180


<210> SEQ ID NO 6
<211> LENGTH: 217
<212> TYPE: PRT
<213> ORGANISM: ground squirrel

<400> SEQUENCE: 6

Met Tyr Leu Phe His Leu Cys Leu Val Phe Ala Cys Val Pro Cys Pro
1               5                   10                  15

Thr Val Gln Ala Ser Lys Leu Cys Leu Gly Trp Leu Trp Asp Met Asp
            20                  25                  30

Ile Asp Pro Tyr Lys Glu Phe Gly Ser Ser Tyr Gln Leu Leu Asn Phe
        35                  40                  45

Leu Pro Leu Asp Phe Phe Pro Asp Leu Asn Ala Leu Val Asp Thr Ala
    50                  55                  60

Ala Ala Leu Tyr Glu Glu Glu Leu Thr Gly Arg Glu His Cys Ser Pro
65                  70                  75                  80

His His Thr Ala Ile Arg Gln Ala Leu Val Cys Trp Glu Glu Leu Thr
                85                  90                  95

Arg Leu Ile Thr Trp Met Ser Glu Asn Thr Thr Glu Glu Val Arg Arg
            100                 105                 110

Ile Ile Val Asp His Val Asn Asn Thr Trp Gly Leu Lys Val Arg Gln
        115                 120                 125

Thr Leu Trp Phe His Leu Ser Cys Leu Thr Phe Gly Gly His Thr Val
    130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
            180                 185                 190

Arg Thr Pro Ser Pro Arg Arg Arg Arg Ser Gln Ser Pro Arg Arg Arg
        195                 200                 205

Arg Ser Gln Ser Pro Ala Ser Asn Cys
    210                 215


<210> SEQ ID NO 7
<211> LENGTH: 51
<212> TYPE: DNA
<213> ORGANISM: Artificial Sequence
<220> FEATURE:
<223> OTHER INFORMATION: modified plasmid pkk223

<400> SEQUENCE: 7

ttcacacagg aaacagaatt cccggggatc cgtcgacctg cagccaagct t              51


<210> SEQ ID NO 8
<211> LENGTH: 38
<212> TYPE: DNA
<213> ORGANISM: Artificial Sequence
<220> FEATURE:
<223> OTHER INFORMATION: plasmid pkk223

<400> SEQUENCE: 8
```

-continued ttcacataag gaggaaaaaa ccatgggatc cgaagctt 38

<210> SEQ ID NO 9
<211> LENGTH: 24
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: Xaa at position 1 is methionine or absent. If methionine then Xaa in position 2 through 8 are not absent.
<220> FEATURE:
<221> NAME/KEY: MISC_FEATURE
<222> LOCATION: (2)..(2)
<223> OTHER INFORMATION: Xaa at position 2 is serine or absent. If serine then Xaa in position 3 through 8 are not absent.
<220> FEATURE:
<221> NAME/KEY: MISC_FEATURE
<222> LOCATION: (3)..(3)
<223> OTHER INFORMATION: Xaa at position 3 is leucine or absent. If leucine then Xaa in position 4 through 8 are not absent.
<220> FEATURE:
<221> NAME/KEY: MISC_FEATURE
<222> LOCATION: (4)..(4)
<223> OTHER INFORMATION: Xaa at position 4 is leucine or absent. If leucine then Xaa in position 5 through 8 are not absent.
<220> FEATURE:
<221> NAME/KEY: MISC_FEATURE
<222> LOCATION: (5)..(5)
<223> OTHER INFORMATION: Xaa at position 4 is threonine or proline or absent. If threonine or proline then Xaa in position 6 through 8 are not absent.
<220> FEATURE:
<221> NAME/KEY: MISC_FEATURE
<222> LOCATION: (6)..(6)
<223> OTHER INFORMATION: Xaa at position 6 is glutamic acid or absent. If glutamic acid then Xaa in position 7 through 8 are not absent.
<220> FEATURE:
<221> NAME/KEY: MISC_FEATURE
<222> LOCATION: (7)..(7)
<223> OTHER INFORMATION: Xaa at position 7 is valine or absent. If valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or aspartic acid or absent.
<220> FEATURE:
<221> NAME/KEY: MISC_FEATURE
<222> LOCATION: (10)..(10)
<223> OTHER INFORMATION: Xaa at position 10 is proline, leucine or histidine.
<220> FEATURE:
<221> NAME/KEY: MISC_FEATURE
<222> LOCATION: (11)..(11)
<223> OTHER INFORMATION: Xaa at position 11 is isoleucine or threonine.
<220> FEATURE:
<221> NAME/KEY: MISC_FEATURE
<222> LOCATION: (12)..(12)
<223> OTHER INFORMATION: Xaa at position 12 is arginine or lysine.
<220> FEATURE:
<221> NAME/KEY: MISC_FEATURE
<222> LOCATION: (13)..(13)
<223> OTHER INFORMATION: Xaa at position 13 is asparagine or serine.
<220> FEATURE:
<221> NAME/KEY: MISC_FEATURE
<222> LOCATION: (14)..(14)
<223> OTHER INFORMATION: Xaa at position 14 is glutamic acid or glycine.
<220> FEATURE:
<221> NAME/KEY: MISC_FEATURE
<222> LOCATION: (15)..(15)
<223> OTHER INFORMATION: Xaa at position 15 is tryptophan or absent.
<220> FEATURE:
<221> NAME/KEY: MISC_FEATURE
<222> LOCATION: (16)..(16)
<223> OTHER INFORMATION: Xaa at position 16 is glycine, glutamic acid or absent. If glycine or glutamic acid then Xaa in position 16 is not absent.

<220> FEATURE:
<221> NAME/KEY: MISC_FEATURE
<222> LOCATION: (17)..(17)
<223> OTHER INFORMATION: Xaa at position 17 is absent or present, if present Xaa in position 17 is cysteine, serine or alanine. If Xaa in position 17 is present then positions 15 through 16 are not absent.
<220> FEATURE:
<221> NAME/KEY: MISC_FEATURE
<222> LOCATION: (18)..(18)
<223> OTHER INFORMATION: Xaa at position 18 arginine, lysine or absent. If arginine or lysine then Xaa in positions 15 through 17 are not absent.
<220> FEATURE:
<221> NAME/KEY: MISC_FEATURE
<222> LOCATION: (19)..(19)
<223> OTHER INFORMATION: Xaa at position 19 is absent or present, if present Xaa in position 19 is cysteine, serine or alanine. If Xaa is position 19 is present then positions 15 through 18 are not absent.
<220> FEATURE:
<221> NAME/KEY: MISC_FEATURE
<222> LOCATION: (20)..(20)
<223> OTHER INFORMATION: Xaa at position 20 is asparagine, serine, glycine or absent. If asparagine or serine or glycine then Xaa is positions 15 through 19 are not absent.
<220> FEATURE:
<221> NAME/KEY: MISC_FEATURE
<222> LOCATION: (21)..(21)
<223> OTHER INFORMATION: Xaa at position 21 is aspartic acid, glycine or absent. If aspartic acid or glycine then Xaa is positions 15 through 20 are not absent.
<220> FEATURE:
<221> NAME/KEY: MISC_FEATURE
<222> LOCATION: (22)..(22)
<223> OTHER INFORMATION: Xaa at position 22 is serine or absent. If serine then Xaa is positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent. If serine then Xaa is positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent. If aspartic acid then Xaa is positions 15 through 23 are not absent.

<400> SEQUENCE: 9

```
Xaa Xaa Xaa Xaa Xaa Xaa Xaa Xaa Thr Xaa Xaa Xaa Xaa Xaa Xaa Xaa
1               5                   10                  15

Xaa Xaa Xaa Xaa Xaa Xaa Xaa Xaa
            20
```

<210> SEQ ID NO 10
<211> LENGTH: 24
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: Xaa at position 1 is methionine or absent. If methionine then Xaa in positions 2 through 8 are not absent
<220> FEATURE:
<221> NAME/KEY: MISC_FEATURE
<222> LOCATION: (2)..(2)
<223> OTHER INFORMATION: Xaa at position 2 is serine or absent. If serine then Xaa in positions 3 through 8 are not absent.
<220> FEATURE:
<221> NAME/KEY: MISC_FEATURE
<222> LOCATION: (3)..(3)
<223> OTHER INFORMATION: Xaa at position 3 is leucine or absent. If leucine then Xaa in positions 4 through 8 are not absent.
<220> FEATURE:
<221> NAME/KEY: MISC_FEATURE
<222> LOCATION: (4)..(4)

```
<223> OTHER INFORMATION: Xaa at position 4 is leucine or absent.  If
      leucine then Xaa in positions 5 through 8 are not absent.
<220> FEATURE:
<221> NAME/KEY: MISC_FEATURE
<222> LOCATION: (5)..(5)
<223> OTHER INFORMATION: Xaa at position 5 is threonine or absent.  If
      threonine than Xaa in positions 6 through 8 are not absent.
<220> FEATURE:
<221> NAME/KEY: MISC_FEATURE
<222> LOCATION: (6)..(6)
<223> OTHER INFORMATION: Xaa at position 6 is glutamic acid or absent.
      If glutamic acid then Xaa in positions 7 through 8 are not absent.
<220> FEATURE:
<221> NAME/KEY: MISC_FEATURE
<222> LOCATION: (7)..(7)
<223> OTHER INFORMATION: Xaa at position 7 is valine or absent.  If
      valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or absent.
<220> FEATURE:
<221> NAME/KEY: MISC_FEATURE
<222> LOCATION: (15)..(15)
<223> OTHER INFORMATION: Xaa at position 15 is tryptophan or absent.
<220> FEATURE:
<221> NAME/KEY: MISC_FEATURE
<222> LOCATION: (16)..(16)
<223> OTHER INFORMATION: Xaa at position 16 is glycine or absent.  If
      glycine then Xaa in position 15 is not absent.
<220> FEATURE:
<221> NAME/KEY: MISC_FEATURE
<222> LOCATION: (17)..(17)
<223> OTHER INFORMATION: Xaa at position 17 is absent or present, if
      present Xaa in position 17 is cysteine, serine or alanine.  If Xaa
      in position 17 is present then positions 15 through 16 are not
      absent.
<220> FEATURE:
<221> NAME/KEY: MISC_FEATURE
<222> LOCATION: (18)..(18)
<223> OTHER INFORMATION: Xaa at position 18 is arginine or absent.  If
      arginine then Xaa in positions 15 through 17 are not absent.
<220> FEATURE:
<221> NAME/KEY: MISC_FEATURE
<222> LOCATION: (19)..(19)
<223> OTHER INFORMATION: Xaa at position 19 is absent or present, if
      present Xaa in position 19 is cysteine, serine or alanine.  If Xaa
      in position 19 is present then positions 15 through 18 are not
      absent.
<220> FEATURE:
<221> NAME/KEY: MISC_FEATURE
<222> LOCATION: (20)..(20)
<223> OTHER INFORMATION: Xaa at position 20 is asparagine or absent.  If
      asparagine then Xaa in positions 15 through 19 are not absent.
<220> FEATURE:
<221> NAME/KEY: MISC_FEATURE
<222> LOCATION: (21)..(21)
<223> OTHER INFORMATION: Xaa at position 21 is aspartic acid or absent.
      If aspartic acid then Xaa in positions 15 through 20 are not
      absent.
<220> FEATURE:
<221> NAME/KEY: MISC_FEATURE
<222> LOCATION: (22)..(22)
<223> OTHER INFORMATION: Xaa at position 22 is serine or absent.  If
      serine then Xaa in positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent.  If
      serine then Xaa in positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent.
      If aspartic acid then Xaa in positions 15 through 23 are not
      absent.

<400> SEQUENCE: 10

Xaa Xaa Xaa Xaa Xaa Xaa Xaa Xaa Thr Pro Ile Arg Asn Glu Xaa Xaa
```

1 5 10 15

Xaa Xaa Xaa Xaa Xaa Xaa Xaa Xaa
20

<210> SEQ ID NO 11
<211> LENGTH: 23
<212> TYPE: PRT
<213> ORGANISM: Influenza A virus

<400> SEQUENCE: 11

Ser Leu Leu Thr Glu Val Glu Thr Pro Ile Arg Asn Glu Trp Gly Cys
1 5 10 15

Arg Cys Asn Gly Ser Ser Asp
20

<210> SEQ ID NO 12
<211> LENGTH: 23
<212> TYPE: PRT
<213> ORGANISM: Influenza A virus

<400> SEQUENCE: 12

Ser Leu Leu Thr Glu Val Glu Thr Pro Ile Arg Asn Glu Trp Gly Cys
1 5 10 15

Arg Cys Asn Asp Ser Ser Asp
20

<210> SEQ ID NO 13
<211> LENGTH: 23
<212> TYPE: PRT
<213> ORGANISM: Influenza A virus

<400> SEQUENCE: 13

Ser Leu Leu Thr Glu Val Glu Thr Pro Ile Arg Asn Glu Trp Gly Ala
1 5 10 15

Arg Ala Asn Asp Ser Ser Asp
20

<210> SEQ ID NO 14
<211> LENGTH: 23
<212> TYPE: PRT
<213> ORGANISM: Influenza A virus

<400> SEQUENCE: 14

Ser Leu Leu Thr Glu Val Glu Thr Pro Ile Arg Asn Glu Trp Gly Ser
1 5 10 15

Arg Ser Asn Asp Ser Ser Asp
20

<210> SEQ ID NO 15
<211> LENGTH: 23
<212> TYPE: PRT
<213> ORGANISM: Influenza A virus

<400> SEQUENCE: 15

Ser Leu Leu Thr Glu Val Glu Thr Pro Ile Arg Asn Glu Trp Gly Ser
1 5 10 15

Arg Cys Asn Asp Ser Ser Asp
20

<210> SEQ ID NO 16
<211> LENGTH: 23
<212> TYPE: PRT
<213> ORGANISM: Influenza A virus

<400> SEQUENCE: 16

Ser Leu Leu Thr Glu Val Glu Thr Pro Ile Arg Asn Glu Trp Gly Cys
1 5 10 15

Arg Ser Asn Asp Ser Ser Asp
20

<210> SEQ ID NO 17
<211> LENGTH: 23
<212> TYPE: PRT
<213> ORGANISM: Influenza A virus

<400> SEQUENCE: 17

Ser Leu Leu Thr Glu Val Glu Thr Pro Ile Arg Asn Glu Trp Gly Cys
1 5 10 15

Arg Ala Asn Asp Ser Ser Asp
20

<210> SEQ ID NO 18
<211> LENGTH: 23
<212> TYPE: PRT
<213> ORGANISM: Influenza A virus

<400> SEQUENCE: 18

Ser Leu Leu Thr Glu Val Glu Thr Pro Ile Arg Asn Glu Trp Gly Ala
1 5 10 15

Arg Cys Asn Asp Ser Ser Asp
20

<210> SEQ ID NO 19
<211> LENGTH: 24
<212> TYPE: PRT
<213> ORGANISM: Influenza A virus

<400> SEQUENCE: 19

Met Ser Leu Leu Thr Glu Val Glu Thr Pro Ile Arg Asn Glu Trp Gly
1 5 10 15

Cys Arg Cys Asn Asp Ser Ser Asp
20

<210> SEQ ID NO 20
<211> LENGTH: 24
<212> TYPE: PRT
<213> ORGANISM: Influenza A virus

<400> SEQUENCE: 20

Met Ser Leu Leu Thr Glu Val Glu Thr Pro Ile Arg Asn Glu Trp Gly
1 5 10 15

Ser Arg Ser Asn Asp Ser Ser Asp
20

<210> SEQ ID NO 21
<211> LENGTH: 35
<212> TYPE: PRT
<213> ORGANISM: Influenza A virus

<400> SEQUENCE: 21

Met Gly Ile Ser Leu Leu Thr Glu Val Glu Thr Pro Ile Arg Asn Glu
1 5 10 15

Trp Gly Cys Arg Cys Asn Asp Ser Ser Asp Glu Leu Leu Gly Trp Leu
20 25 30

Trp Gly Ile

-continued

35

<210> SEQ ID NO 22
<211> LENGTH: 24
<212> TYPE: PRT
<213> ORGANISM: Influenza A virus

<400> SEQUENCE: 22

Met Ser Leu Leu Thr Glu Val Glu Thr Pro Ile Arg Asn Glu Trp Gly
1 5 10 15

Ala Arg Ala Asn Asp Ser Ser Asp
20

<210> SEQ ID NO 23
<211> LENGTH: 24
<212> TYPE: PRT
<213> ORGANISM: Influenza A virus

<400> SEQUENCE: 23

Met Ser Leu Leu Thr Glu Val Glu Thr Pro Ile Arg Asn Glu Trp Gly
1 5 10 15

Cys Arg Ala Asn Asp Ser Ser Asp
20

<210> SEQ ID NO 24
<211> LENGTH: 24
<212> TYPE: PRT
<213> ORGANISM: Influenza A virus

<400> SEQUENCE: 24

Met Ser Leu Leu Thr Glu Val Glu Thr Pro Ile Arg Asn Glu Trp Gly
1 5 10 15

Ala Arg Cys Asn Asp Ser Ser Asp
20

<210> SEQ ID NO 25
<211> LENGTH: 24
<212> TYPE: PRT
<213> ORGANISM: Influenza A virus

<400> SEQUENCE: 25

Met Ser Leu Leu Thr Glu Val Glu Thr Pro Ile Arg Asn Glu Trp Gly
1 5 10 15

Cys Arg Ser Asn Asp Ser Ser Asp
20

<210> SEQ ID NO 26
<211> LENGTH: 24
<212> TYPE: PRT
<213> ORGANISM: Influenza A virus

<400> SEQUENCE: 26

Met Ser Leu Leu Thr Glu Val Glu Thr Pro Ile Arg Asn Glu Trp Gly
1 5 10 15

Ser Arg Cys Asn Asp Ser Ser Asp
20

<210> SEQ ID NO 27
<211> LENGTH: 46
<212> TYPE: PRT
<213> ORGANISM: Influenza A virus

<400> SEQUENCE: 27

Ser Leu Leu Thr Glu Val Glu Thr Pro Ile Arg Asn Glu Trp Gly Ser
1 5 10 15

Arg Ser Asn Asp Ser Ser Asp Ser Leu Leu Thr Glu Val Glu Thr Pro
20 25 30

Ile Arg Asn Glu Trp Gly Ser Arg Ser Asn Asp Ser Ser Asp
35 40 45

<210> SEQ ID NO 28
<211> LENGTH: 69
<212> TYPE: PRT
<213> ORGANISM: Influenza A virus

<400> SEQUENCE: 28

Ser Leu Leu Thr Glu Val Glu Thr Pro Ile Arg Asn Glu Trp Gly Ser
1 5 10 15

Arg Ser Asn Asp Ser Ser Asp Ser Leu Leu Thr Glu Val Glu Thr Pro
20 25 30

Ile Arg Asn Glu Trp Gly Ser Arg Ser Asn Asp Ser Ser Asp Ser Leu
35 40 45

Leu Thr Glu Val Glu Thr Pro Ile Arg Asn Glu Trp Gly Cys Arg Cys
50 55 60

Asn Asp Ser Ser Asp
65

<210> SEQ ID NO 29
<211> LENGTH: 46
<212> TYPE: PRT
<213> ORGANISM: Influenza A virus

<400> SEQUENCE: 29

Ser Leu Leu Thr Glu Val Glu Thr Pro Ile Arg Asn Glu Trp Gly Ala
1 5 10 15

Arg Ala Asn Asp Ser Ser Asp Ser Leu Leu Thr Glu Val Glu Thr Pro
20 25 30

Ile Arg Asn Glu Trp Gly Cys Arg Cys Asn Asp Ser Ser Asp
35 40 45

<210> SEQ ID NO 30
<211> LENGTH: 69
<212> TYPE: PRT
<213> ORGANISM: Influenza A virus

<400> SEQUENCE: 30

Ser Leu Leu Thr Glu Val Glu Thr Pro Ile Arg Asn Glu Trp Gly Ala
1 5 10 15

Arg Ala Asn Asp Ser Ser Asp Ser Leu Leu Thr Glu Val Glu Thr Pro
20 25 30

Ile Arg Asn Glu Trp Gly Ala Arg Ala Asn Asp Ser Ser Asp Ser Leu
35 40 45

Leu Thr Glu Val Glu Thr Pro Ile Arg Asn Glu Trp Gly Cys Arg Cys
50 55 60

Asn Asp Ser Ser Asp
65

<210> SEQ ID NO 31
<211> LENGTH: 19
<212> TYPE: PRT
<213> ORGANISM: Influenza A virus

<400> SEQUENCE: 31

```
Glu Val Glu Thr Pro Ile Arg Asn Glu Trp Gly Ser Arg Cys Asn Asp
1               5                   10                  15

Ser Ser Asp


<210> SEQ ID NO 32
<211> LENGTH: 38
<212> TYPE: PRT
<213> ORGANISM: Influenza A virus

<400> SEQUENCE: 32

Glu Val Glu Thr Pro Ile Arg Asn Glu Trp Gly Ser Arg Cys Asn Asp
1               5                   10                  15

Ser Ser Asp Glu Val Glu Thr Pro Ile Arg Asn Glu Trp Gly Ser Arg
            20                  25                  30

Cys Asn Asp Ser Ser Asp
        35


<210> SEQ ID NO 33
<211> LENGTH: 57
<212> TYPE: PRT
<213> ORGANISM: Influenza A virus

<400> SEQUENCE: 33

Glu Val Glu Thr Pro Ile Arg Asn Glu Trp Gly Ser Arg Cys Asn Asp
1               5                   10                  15

Ser Ser Asp Glu Val Glu Thr Pro Ile Arg Asn Glu Trp Gly Ser Arg
            20                  25                  30

Cys Asn Asp Ser Ser Asp Glu Val Glu Thr Pro Ile Arg Asn Glu Trp
        35                  40                  45

Gly Cys Arg Cys Asn Asp Ser Ser Asp
    50                  55


<210> SEQ ID NO 34
<211> LENGTH: 47
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: Xaa at position 1 is methionine or absent.  If
      methionine then Xaa in positions 2 through 8 are not absent
<220> FEATURE:
<221> NAME/KEY: MISC_FEATURE
<222> LOCATION: (2)..(2)
<223> OTHER INFORMATION: Xaa at position 2 is serine or absent.  If
      serine then Xaa in positions 3 through 8 are not absent.
<220> FEATURE:
<221> NAME/KEY: MISC_FEATURE
<222> LOCATION: (3)..(3)
<223> OTHER INFORMATION: Xaa at position 3 is leucine or absent.  If
      leucine then Xaa in positions 4 through 8 are not absent.
<220> FEATURE:
<221> NAME/KEY: MISC_FEATURE
<222> LOCATION: (4)..(4)
<223> OTHER INFORMATION: Xaa at position 4 is leucine or absent.  If
      leucine then Xaa in positions 5 through 8 are not absent.
<220> FEATURE:
<221> NAME/KEY: MISC_FEATURE
<222> LOCATION: (5)..(5)
<223> OTHER INFORMATION: Xaa at position 5 is threonine or absent.  If
      threonine than Xaa in positions 6 through 8 are not absent.
<220> FEATURE:
<221> NAME/KEY: MISC_FEATURE
<222> LOCATION: (6)..(6)
<223> OTHER INFORMATION: Xaa at position 6 is glutamic acid or absent.
      If glutamic acid then Xaa in positions 7 through 8 are not absent.
<220> FEATURE:
<221> NAME/KEY: MISC_FEATURE
<222> LOCATION: (7)..(7)
```

```
<223> OTHER INFORMATION: Xaa at position 7 is valine or absent.  If
      valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or absent.
<220> FEATURE:
<221> NAME/KEY: MISC_FEATURE
<222> LOCATION: (15)..(15)
<223> OTHER INFORMATION: Xaa at position 15 is tryptophan or absent.
<220> FEATURE:
<221> NAME/KEY: MISC_FEATURE
<222> LOCATION: (16)..(16)
<223> OTHER INFORMATION: Xaa at position 16 is glycine or absent.  If
      glycine then Xaa in position 15 is not absent.
<220> FEATURE:
<221> NAME/KEY: MISC_FEATURE
<222> LOCATION: (17)..(17)
<223> OTHER INFORMATION: Xaa at position 17 is absent or present, if
      present Xaa in position 17 is cysteine, serine or alanine.  If Xaa
      in position 17 is present then positions 15 through 16 are not
      absent.
<220> FEATURE:
<221> NAME/KEY: MISC_FEATURE
<222> LOCATION: (18)..(18)
<223> OTHER INFORMATION: Xaa at position 18 is arginine or absent.  If
      arginine then Xaa in positions 15 through 17 are not absent.
<220> FEATURE:
<221> NAME/KEY: MISC_FEATURE
<222> LOCATION: (19)..(19)
<223> OTHER INFORMATION: Xaa at position 19 is absent or present, if
      present Xaa in position 19 is cysteine, serine or alanine.  If Xaa
      in position 19 is present then positions 15 through 18 are not
      absent.
<220> FEATURE:
<221> NAME/KEY: MISC_FEATURE
<222> LOCATION: (20)..(20)
<223> OTHER INFORMATION: Xaa at position 20 is asparagine or absent.  If
      asparagine then Xaa in positions 15 through 19 are not absent.
<220> FEATURE:
<221> NAME/KEY: MISC_FEATURE
<222> LOCATION: (21)..(21)
<223> OTHER INFORMATION: Xaa at position 21 is aspartic acid or absent.
      If aspartic acid then Xaa in positions 15 through 20 are not
      absent.
<220> FEATURE:
<221> NAME/KEY: MISC_FEATURE
<222> LOCATION: (22)..(22)
<223> OTHER INFORMATION: Xaa at position 22 is serine or absent.  If
      serine then Xaa in positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent.  If
      serine then Xaa in positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent.
      If aspartic acid then Xaa in positions 15 through 23 are not
      absent.
<220> FEATURE:
<221> NAME/KEY: MISC_FEATURE
<222> LOCATION: (25)..(25)
<223> OTHER INFORMATION: -- Xaa at position 25 is serine or absent.  If
      serine then Xaa in positions 26 through 31 are not absent.
<220> FEATURE:
<221> NAME/KEY: MISC_FEATURE
<222> LOCATION: (26)..(26)
<223> OTHER INFORMATION: Xaa at position 26 is leucine or absent.  If
      leucine then Xaa in positions 27 through 31 are not absent.
<220> FEATURE:
<221> NAME/KEY: MISC_FEATURE
<222> LOCATION: (27)..(27)
<223> OTHER INFORMATION: Xaa in position 27 is leucine or absent.  If
      leucine then Xaa in positions 28 through 31 are not absent.
<220> FEATURE:
<221> NAME/KEY: MISC_FEATURE
<222> LOCATION: (28)..(28)
<223> OTHER INFORMATION: Xaa in position 28 is threoninie or absent.  If
```

```
      threonine then Xaa in positions 29 through 31 are not absent.
<220> FEATURE:
<221> NAME/KEY: MISC_FEATURE
<222> LOCATION: (29)..(29)
<223> OTHER INFORMATION: Xaa at position 29 is glutamic acid or absent.
      If glutamic acid then Xaa in positions 30 through 31 are not
      absent.
<220> FEATURE:
<221> NAME/KEY: MISC_FEATURE
<222> LOCATION: (30)..(30)
<223> OTHER INFORMATION: Xaa at position 30 is valine or absent.  If
      valine then Xaa in position 31 is not absent.
<220> FEATURE:
<221> NAME/KEY: MISC_FEATURE
<222> LOCATION: (31)..(31)
<223> OTHER INFORMATION: Xaa at position 31 is glutamic acid or absent.
<220> FEATURE:
<221> NAME/KEY: MISC_FEATURE
<222> LOCATION: (38)..(38)
<223> OTHER INFORMATION: Xaa at position 38 is tryptophan or absent
<220> FEATURE:
<221> NAME/KEY: MISC_FEATURE
<222> LOCATION: (39)..(39)
<223> OTHER INFORMATION: Xaa at position 39 is glycine or absent.  If
      glycine then Xaa in position 38 is not absent.
<220> FEATURE:
<221> NAME/KEY: MISC_FEATURE
<222> LOCATION: (40)..(40)
<223> OTHER INFORMATION: Xaa at position 40 is absent or present, if
      present Xaa in position 40 is cysteine, serine or alanine.  If Xaa
      in position 17 is present then positions 38 through 39 are not
      absent.
<220> FEATURE:
<221> NAME/KEY: MISC_FEATURE
<222> LOCATION: (41)..(41)
<223> OTHER INFORMATION: Xaa at position 40 is arginine or absent.  If
      arginine then Xaa in positions 38 through 40 are not absent.
<220> FEATURE:
<221> NAME/KEY: MISC_FEATURE
<222> LOCATION: (42)..(42)
<223> OTHER INFORMATION: Xaa at position 42 is absent or present, if
      present Xaa in position 42 is cysteine, serine or alanine.  If Xaa
      in position 42 is present then positions 38 through 41 are not
      absent.
<220> FEATURE:
<221> NAME/KEY: MISC_FEATURE
<222> LOCATION: (43)..(43)
<223> OTHER INFORMATION: Xaa at position 43 is asparagine or absent.  If
      asparagine then Xaa in positions 38 through 42 are not absent.
<220> FEATURE:
<221> NAME/KEY: MISC_FEATURE
<222> LOCATION: (44)..(44)
<223> OTHER INFORMATION: Xaa at position 44 is aspartic acid or absent.
      If aspartic acid then Xaa in positions 38 through 43 are not
      absent.
<220> FEATURE:
<221> NAME/KEY: MISC_FEATURE
<222> LOCATION: (45)..(45)
<223> OTHER INFORMATION: Xaa at position 45 is serine or absent.  If
      serine then Xaa in positions 38 through 44 are not absent.
<220> FEATURE:
<221> NAME/KEY: MISC_FEATURE
<222> LOCATION: (46)..(46)
<223> OTHER INFORMATION: Xaa at position 46 is serine or absent.  If
      serine then Xaa in positions 38 through 45 are not absent.
<220> FEATURE:
<221> NAME/KEY: MISC_FEATURE
<222> LOCATION: (47)..(47)
<223> OTHER INFORMATION: Xaa at position 47 is aspartic acid or absent.
      If aspartic acid then Xaa in positions 38 through 46 are not
      absent.

<400> SEQUENCE: 34

Xaa Xaa Xaa Xaa Xaa Xaa Xaa Xaa Thr Pro Ile Arg Asn Glu Xaa Xaa
1               5                   10                  15

Xaa Xaa Xaa Xaa Xaa Xaa Xaa Xaa Xaa Xaa Xaa Xaa Xaa Xaa Xaa Thr
            20                  25                  30
```

```
Pro Ile Arg Asn Glu Xaa Xaa Xaa Xaa Xaa Xaa Xaa Xaa Xaa Xaa
        35                  40                  45


<210> SEQ ID NO 35
<211> LENGTH: 70
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: Xaa at position 1 is methionine or absent.  If
      methionine then Xaa in positions 2 through 8 are not absent
<220> FEATURE:
<221> NAME/KEY: MISC_FEATURE
<222> LOCATION: (2)..(2)
<223> OTHER INFORMATION: Xaa at position 2 is serine or absent.  If
      serine then Xaa in positions 3 through 8 are not absent.
<220> FEATURE:
<221> NAME/KEY: MISC_FEATURE
<222> LOCATION: (3)..(3)
<223> OTHER INFORMATION: Xaa at position 3 is leucine or absent.  If
      leucine then Xaa in positions 4 through 8 are not absent.
<220> FEATURE:
<221> NAME/KEY: MISC_FEATURE
<222> LOCATION: (4)..(4)
<223> OTHER INFORMATION: Xaa at position 4 is leucine or absent.  If
      leucine then Xaa in positions 5 through 8 are not absent.
<220> FEATURE:
<221> NAME/KEY: MISC_FEATURE
<222> LOCATION: (5)..(5)
<223> OTHER INFORMATION: Xaa at position 5 is threonine or absent.  If
      threonine than Xaa in positions 6 through 8 are not absent.
<220> FEATURE:
<221> NAME/KEY: MISC_FEATURE
<222> LOCATION: (6)..(6)
<223> OTHER INFORMATION: Xaa at position 6 is glutamic acid or absent.
      If glutamic acid then Xaa in positions 7 through 8 are not absent.
<220> FEATURE:
<221> NAME/KEY: MISC_FEATURE
<222> LOCATION: (7)..(7)
<223> OTHER INFORMATION: Xaa at position 7 is valine or absent.  If
      valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or absent.
<220> FEATURE:
<221> NAME/KEY: MISC_FEATURE
<222> LOCATION: (15)..(15)
<223> OTHER INFORMATION: Xaa at position 15 is tryptophan or absent.
<220> FEATURE:
<221> NAME/KEY: MISC_FEATURE
<222> LOCATION: (16)..(16)
<223> OTHER INFORMATION: Xaa at position 16 is glycine or absent.  If
      glycine then Xaa in position 15 is not absent.
<220> FEATURE:
<221> NAME/KEY: MISC_FEATURE
<222> LOCATION: (17)..(17)
<223> OTHER INFORMATION: Xaa at position 17 is absent or present, if
      present Xaa in position 17 is cysteine, serine or alanine.  If Xaa
      in position 17 is present then positions 15 through 16 are not
      absent.
<220> FEATURE:
<221> NAME/KEY: MISC_FEATURE
<222> LOCATION: (18)..(18)
<223> OTHER INFORMATION: Xaa at position 18 is arginine or absent.  If
      arginine then Xaa in positions 15 through 17 are not absent.
<220> FEATURE:
<221> NAME/KEY: MISC_FEATURE
<222> LOCATION: (19)..(19)
<223> OTHER INFORMATION: Xaa at position 19 is absent or present, if
      present Xaa in position 19 is cysteine, serine or alanine.  If Xaa
      in position 19 is present then positions 15 through 18 are not
      absent.
<220> FEATURE:
<221> NAME/KEY: MISC_FEATURE
<222> LOCATION: (20)..(20)
<223> OTHER INFORMATION: Xaa at position 20 is asparagine or absent.  If
      asparagine then Xaa in positions 15 through 19 are not absent.
```

<220> FEATURE:
<221> NAME/KEY: MISC_FEATURE
<222> LOCATION: (21)..(21)
<223> OTHER INFORMATION: Xaa at position 21 is aspartic acid or absent. If aspartic acid then Xaa in positions 15 through 20 are not absent.
<220> FEATURE:
<221> NAME/KEY: MISC_FEATURE
<222> LOCATION: (22)..(22)
<223> OTHER INFORMATION: Xaa at position 22 is serine or absent. If serine then Xaa in positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent. If serine then Xaa in positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent. If aspartic acid then Xaa in positions 15 through 23 are not absent.
<220> FEATURE:
<221> NAME/KEY: MISC_FEATURE
<222> LOCATION: (25)..(25)
<223> OTHER INFORMATION: Xaa at position 25 is serine or absent. If serine then Xaa in positions 26 through 31 are not absent
<220> FEATURE:
<221> NAME/KEY: MISC_FEATURE
<222> LOCATION: (26)..(26)
<223> OTHER INFORMATION: Xaa at position 26 is leucine or absent. If leucine then Xaa in positions 27 through 31 are not absent.
<220> FEATURE:
<221> NAME/KEY: MISC_FEATURE
<222> LOCATION: (27)..(27)
<223> OTHER INFORMATION: Xaa at position 27 is leucine or absent. If leucine then Xaa in positions 28 through 31 are not absent.
<220> FEATURE:
<221> NAME/KEY: MISC_FEATURE
<222> LOCATION: (28)..(28)
<223> OTHER INFORMATION: Xaa at position 28 is threonine or absent. If threonine than Xaa in positions 29 through 31 are not absent.
<220> FEATURE:
<221> NAME/KEY: MISC_FEATURE
<222> LOCATION: (29)..(29)
<223> OTHER INFORMATION: Xaa at position 29 is glutamic acid or absent. If glutamic acid then Xaa in positions 30 through 31 are not absent.
<220> FEATURE:
<221> NAME/KEY: MISC_FEATURE
<222> LOCATION: (30)..(30)
<223> OTHER INFORMATION: Xaa at position 30 is valine or absent. If valine then Xaa in position 31 is not absent.
<220> FEATURE:
<221> NAME/KEY: MISC_FEATURE
<222> LOCATION: (31)..(31)
<223> OTHER INFORMATION: Xaa at position 31 is glutamic acid or absent.
<220> FEATURE:
<221> NAME/KEY: MISC_FEATURE
<222> LOCATION: (38)..(38)
<223> OTHER INFORMATION: Xaa at position 38 is tryptophan or absent.
<220> FEATURE:
<221> NAME/KEY: MISC_FEATURE
<222> LOCATION: (39)..(39)
<223> OTHER INFORMATION: Xaa at position 39 is glycine or absent. If glycine then Xaa in position 38 is not absent.
<220> FEATURE:
<221> NAME/KEY: MISC_FEATURE
<222> LOCATION: (40)..(40)
<223> OTHER INFORMATION: Xaa at position 40 is absent or present, if present Xaa in position 40 is cysteine, serine or alanine. If Xaa in position 40 is present then positions 38 through 39 are not absent.
<220> FEATURE:
<221> NAME/KEY: MISC_FEATURE
<222> LOCATION: (41)..(41)
<223> OTHER INFORMATION: Xaa at position 41 is arginine or absent. If arginine then Xaa in positions 38 through 40 are not absent.
<220> FEATURE:
<221> NAME/KEY: MISC_FEATURE

```
<222> LOCATION: (42)..(42)
<223> OTHER INFORMATION: Xaa at position 42 is absent or present, if
      present Xaa in position 42 is cysteine, serine or alanine.  If Xaa
      in position 42 is present then positions 38 through 41 are not
      absent.
<220> FEATURE:
<221> NAME/KEY: MISC_FEATURE
<222> LOCATION: (43)..(43)
<223> OTHER INFORMATION: Xaa at position 43 is asparagine or absent.  If
      asparagine then Xaa in positions 38 through 42 are not absent.
<220> FEATURE:
<221> NAME/KEY: MISC_FEATURE
<222> LOCATION: (44)..(44)
<223> OTHER INFORMATION: Xaa at position 44 is aspartic acid or absent.
      If aspartic acid then Xaa in positions 38 through 43 are not
      absent.
<220> FEATURE:
<221> NAME/KEY: MISC_FEATURE
<222> LOCATION: (45)..(45)
<223> OTHER INFORMATION: Xaa at position 45 is serine or absent.  If
      serine then Xaa in positions 38 through 44 are not absent.
<220> FEATURE:
<221> NAME/KEY: MISC_FEATURE
<222> LOCATION: (46)..(46)
<223> OTHER INFORMATION: Xaa at position 46 is serine or absent.  If
      serine then Xaa in positions 38 through 45 are not absent.
<220> FEATURE:
<221> NAME/KEY: MISC_FEATURE
<222> LOCATION: (47)..(47)
<223> OTHER INFORMATION: Xaa at position 47 is aspartic acid or absent.
      If aspartic acid then Xaa in positions 38 through 46 are not
      absent.
<220> FEATURE:
<221> NAME/KEY: MISC_FEATURE
<222> LOCATION: (48)..(48)
<223> OTHER INFORMATION: Xaa at position 48 is serine or absent.  If
      serine then Xaa in positions 49 through 54 are not absent.
<220> FEATURE:
<221> NAME/KEY: MISC_FEATURE
<222> LOCATION: (49)..(49)
<223> OTHER INFORMATION: Xaa at position 49 is leucine or absent.  If
      leucine then Xaa in positions 50 through 54 are not absent.
<220> FEATURE:
<221> NAME/KEY: MISC_FEATURE
<222> LOCATION: (50)..(50)
<223> OTHER INFORMATION: Xaa at position 50 is leucine or absent.  If
      leucine then Xaa in positions 51 through 54 are not absent.
<220> FEATURE:
<221> NAME/KEY: MISC_FEATURE
<222> LOCATION: (51)..(51)
<223> OTHER INFORMATION: Xaa at position 51 is threonine or absent.  If
      threonine than Xaa in positions 52 through 54 are not absent.
<220> FEATURE:
<221> NAME/KEY: MISC_FEATURE
<222> LOCATION: (52)..(52)
<223> OTHER INFORMATION: Xaa at position 52 is glutamic acid or absent.
      If glutamic acid then Xaa in positions 53 through 54 are not
      absent.
<220> FEATURE:
<221> NAME/KEY: MISC_FEATURE
<222> LOCATION: (53)..(53)
<223> OTHER INFORMATION: Xaa at position 53 is valine or absent.  If
      valine then Xaa in position 54 is not absent.
<220> FEATURE:
<221> NAME/KEY: MISC_FEATURE
<222> LOCATION: (54)..(54)
<223> OTHER INFORMATION: Xaa at position 54 is glutamic acid or absent
<220> FEATURE:
<221> NAME/KEY: MISC_FEATURE
<222> LOCATION: (61)..(61)
<223> OTHER INFORMATION: Xaa at position 61 is tryptophan or absent.
<220> FEATURE:
<221> NAME/KEY: MISC_FEATURE
<222> LOCATION: (62)..(62)
<223> OTHER INFORMATION: Xaa at position 62 is glycine or absent.  If
      glycine then Xaa in position 61 is not absent.
<220> FEATURE:
<221> NAME/KEY: MISC_FEATURE
<222> LOCATION: (63)..(63)
<223> OTHER INFORMATION: Xaa at position 63 is absent or present, if
```

```
      present Xaa in position 63 is cysteine, serine or alanine.  If Xaa
      in position 63 is present then positions 61 through 62 are not
      absent.
<220> FEATURE:
<221> NAME/KEY: MISC_FEATURE
<222> LOCATION: (64)..(64)
<223> OTHER INFORMATION: Xaa at position 64 is arginine or absent.  If
      arginine then Xaa in positions 61 through 63 are not absent
<220> FEATURE:
<221> NAME/KEY: MISC_FEATURE
<222> LOCATION: (65)..(65)
<223> OTHER INFORMATION: Xaa at position 65 is absent or present, if
      present Xaa in position 65 is cysteine, serine or alanine.  If Xaa
      in position 65 is present then positions 61 through 64 are not
      absent.
<220> FEATURE:
<221> NAME/KEY: MISC_FEATURE
<222> LOCATION: (66)..(66)
<223> OTHER INFORMATION: Xaa at position 66 is asparagine or absent.  If
      asparagine then Xaa in positions 61 through 65 are not absent.
<220> FEATURE:
<221> NAME/KEY: MISC_FEATURE
<222> LOCATION: (67)..(67)
<223> OTHER INFORMATION: Xaa at position 67 is aspartic acid or absent.
      If aspartic acid then Xaa in positions 61 through 66 are not
      absent.
<220> FEATURE:
<221> NAME/KEY: MISC_FEATURE
<222> LOCATION: (68)..(68)
<223> OTHER INFORMATION: Xaa at position 68 is serine or absent.  If
      serine then Xaa in positions 61 through 67 are not absent.
<220> FEATURE:
<221> NAME/KEY: MISC_FEATURE
<222> LOCATION: (69)..(69)
<223> OTHER INFORMATION: Xaa at position 69 is serine or absent.  If
      serine then Xaa in positions 61 through 68 are not absent.
<220> FEATURE:
<221> NAME/KEY: MISC_FEATURE
<222> LOCATION: (70)..(70)
<223> OTHER INFORMATION: Xaa at position 70 is aspartic acid or absent.
      If aspartic acid then Xaa in positions 61 through 69 are not
      absent.

<400> SEQUENCE: 35

Xaa Xaa Xaa Xaa Xaa Xaa Xaa Xaa Thr Pro Ile Arg Asn Glu Xaa Xaa
1               5                   10                  15

Xaa Xaa Xaa Xaa Xaa Xaa Xaa Xaa Xaa Xaa Xaa Xaa Xaa Xaa Xaa Thr
            20                  25                  30

Pro Ile Arg Asn Glu Xaa Xaa Xaa Xaa Xaa Xaa Xaa Xaa Xaa Xaa Xaa
        35                  40                  45

Xaa Xaa Xaa Xaa Xaa Xaa Thr Pro Ile Arg Asn Glu Xaa Xaa Xaa Xaa
    50                  55                  60

Xaa Xaa Xaa Xaa Xaa Xaa
65                  70


<210> SEQ ID NO 36
<211> LENGTH: 47
<212> TYPE: PRT
<213> ORGANISM: Influenza A virus
<220> FEATURE:
<221> NAME/KEY: MISC_FEATURE
<222> LOCATION: (1)..(1)
<223> OTHER INFORMATION: Xaa at position 1 is methionine or absent.  If
      methionine then Xaa in position 2 through 8 are not absent.
<220> FEATURE:
<221> NAME/KEY: MISC_FEATURE
<222> LOCATION: (2)..(2)
<223> OTHER INFORMATION: Xaa at position 2 is serine or absent.  If
      serine then Xaa in position 3 through 8 are not absent.
<220> FEATURE:
<221> NAME/KEY: MISC_FEATURE
<222> LOCATION: (3)..(3)
<223> OTHER INFORMATION: Xaa at position 3 is leucine or absent.  If
      leucine then Xaa in position 4 through 8 are not absent.
```

```
<220> FEATURE:
<221> NAME/KEY: MISC_FEATURE
<222> LOCATION: (4)..(4)
<223> OTHER INFORMATION: Xaa at position 4 is leucine or absent.  If
      leucine then Xaa in position 5 through 8 are not absent.
<220> FEATURE:
<221> NAME/KEY: MISC_FEATURE
<222> LOCATION: (5)..(5)
<223> OTHER INFORMATION: Xaa at position 4 is threonine or absent.  If
      threonine then Xaa in position 6 through 8 are not absent.
<220> FEATURE:
<221> NAME/KEY: MISC_FEATURE
<222> LOCATION: (6)..(6)
<223> OTHER INFORMATION: Xaa at position 6 is glutamic acid or absent.
      If glutamic acid then Xaa in position 7 through 8 are not absent.
<220> FEATURE:
<221> NAME/KEY: MISC_FEATURE
<222> LOCATION: (7)..(7)
<223> OTHER INFORMATION: Xaa at position 7 is valine or absent.  If
      valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or aspartic
      acid or absent.
<220> FEATURE:
<221> NAME/KEY: MISC_FEATURE
<222> LOCATION: (10)..(10)
<223> OTHER INFORMATION: Xaa at position 10 is proline, leucine or
      histidine.
<220> FEATURE:
<221> NAME/KEY: MISC_FEATURE
<222> LOCATION: (11)..(11)
<223> OTHER INFORMATION: Xaa at position 11 is isoleucine or threonine.
<220> FEATURE:
<221> NAME/KEY: MISC_FEATURE
<222> LOCATION: (12)..(12)
<223> OTHER INFORMATION: Xaa at position 12 is arginine or lysine.
<220> FEATURE:
<221> NAME/KEY: MISC_FEATURE
<222> LOCATION: (13)..(13)
<223> OTHER INFORMATION: Xaa at position 13 is asparagine or serine.
<220> FEATURE:
<221> NAME/KEY: MISC_FEATURE
<222> LOCATION: (14)..(14)
<223> OTHER INFORMATION: Xaa at position 14 is glutamic acid or glycine.
<220> FEATURE:
<221> NAME/KEY: MISC_FEATURE
<222> LOCATION: (15)..(15)
<223> OTHER INFORMATION: Xaa at position 15 is tryptophan or absent.
<220> FEATURE:
<221> NAME/KEY: MISC_FEATURE
<222> LOCATION: (16)..(16)
<223> OTHER INFORMATION: Xaa at position 16 is glycine, glutamic acid or
      absent.  If glycine or glutamic acid then Xaa in position 16 is
      not absent.
<220> FEATURE:
<221> NAME/KEY: MISC_FEATURE
<222> LOCATION: (17)..(17)
<223> OTHER INFORMATION: Xaa at position 17 is absent or present, if
      present Xaa in position 17 is cysteine, serine or alanine.  If Xaa
      in position 17 is present then positions 15 through 16 are not
      absent.
<220> FEATURE:
<221> NAME/KEY: MISC_FEATURE
<222> LOCATION: (18)..(18)
<223> OTHER INFORMATION: Xaa at position 18 arginine, lysine or absent.
      If arginine or lysine then Xaa in positions 15 through 17 are not
      absent.
<220> FEATURE:
<221> NAME/KEY: MISC_FEATURE
<222> LOCATION: (19)..(19)
<223> OTHER INFORMATION: Xaa at position 19 is absent or present, if
      present Xaa in position 19 is cysteine, serine or alanine.  If Xaa
      is position 19 is present then positions 15 through 18 are not
      absent.
<220> FEATURE:
<221> NAME/KEY: MISC_FEATURE
<222> LOCATION: (20)..(20)
<223> OTHER INFORMATION: Xaa at position 20 is asparagine, serine or
```

glycine or absent. If asparagine or serine then Xaa is positions 15 through 19 are not absent.
<220> FEATURE:
<221> NAME/KEY: MISC_FEATURE
<222> LOCATION: (21)..(21)
<223> OTHER INFORMATION: Xaa at position 21 is aspartic acid, glycine or absent. If aspartic acid or glycine then Xaa is positions 15 through 20 are not absent.
<220> FEATURE:
<221> NAME/KEY: MISC_FEATURE
<222> LOCATION: (22)..(22)
<223> OTHER INFORMATION: Xaa at position 22 is serine or absent. If serine then Xaa is positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent. If serine then Xaa is positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent. If aspartic acid then Xaa is positions 15 through 23 are not absent.
<220> FEATURE:
<221> NAME/KEY: MISC_FEATURE
<222> LOCATION: (25)..(25)
<223> OTHER INFORMATION: Xaa at position 25 is serine or absent. If serine then Xaa in positions 26 through 31 are not absent.
<220> FEATURE:
<221> NAME/KEY: MISC_FEATURE
<222> LOCATION: (26)..(26)
<223> OTHER INFORMATION: Xaa at position 26 is leucine or absent. If leucine then Xaa in positions 27 through 31 are not absent.
<220> FEATURE:
<221> NAME/KEY: MISC_FEATURE
<222> LOCATION: (27)..(27)
<223> OTHER INFORMATION: Xaa at position 27 is leucine or absent. If leucine then Xaa in positions 28 through 31 are not absent.
<220> FEATURE:
<221> NAME/KEY: MISC_FEATURE
<222> LOCATION: (28)..(28)
<223> OTHER INFORMATION: Xaa at position 28 is threonine, proline or absent. If threonine or proline then Xaa in positions 29 through 31 are not absent.
<220> FEATURE:
<221> NAME/KEY: MISC_FEATURE
<222> LOCATION: (29)..(29)
<223> OTHER INFORMATION: Xaa at position 29 is glutamic acid or absent. If glutamic acid then Xaa in positions 30 through 31 are not absent.
<220> FEATURE:
<221> NAME/KEY: MISC_FEATURE
<222> LOCATION: (30)..(30)
<223> OTHER INFORMATION: Xaa at position 30 is valine or absent. If valine then Xaa in position 31 is not absent.
<220> FEATURE:
<221> NAME/KEY: MISC_FEATURE
<222> LOCATION: (31)..(31)
<223> OTHER INFORMATION: Xaa at position 31 is glutamic acid or aspartic acid or absent.
<220> FEATURE:
<221> NAME/KEY: MISC_FEATURE
<222> LOCATION: (33)..(33)
<223> OTHER INFORMATION: Xaa at position 33 is proline, leucine or histidine.
<220> FEATURE:
<221> NAME/KEY: MISC_FEATURE
<222> LOCATION: (34)..(34)
<223> OTHER INFORMATION: Xaa at position 34 is isoleucine or threonine
<220> FEATURE:
<221> NAME/KEY: MISC_FEATURE
<222> LOCATION: (35)..(35)
<223> OTHER INFORMATION: Xaa at position 35 is arginine or lysine.
<220> FEATURE:
<221> NAME/KEY: MISC_FEATURE
<222> LOCATION: (36)..(36)
<223> OTHER INFORMATION: Xaa at position 36 is asparagine or serine.
<220> FEATURE:
<221> NAME/KEY: MISC_FEATURE
<222> LOCATION: (37)..(37)
<223> OTHER INFORMATION: Xaa at position 37 is glumatic acid or glycine.
<220> FEATURE:
<221> NAME/KEY: MISC_FEATURE
<222> LOCATION: (38)..(38)
<223> OTHER INFORMATION: Xaa at position 38 is tryptophan or absent.
<220> FEATURE:
<221> NAME/KEY: MISC_FEATURE
<222> LOCATION: (39)..(39)
<223> OTHER INFORMATION: Xaa at position 39 is glycine, glutamic acid or absent. If glycine or glutamic acid then Xaa in position 38 is not absent.
<220> FEATURE:
<221> NAME/KEY: MISC_FEATURE
<222> LOCATION: (40)..(40)
<223> OTHER INFORMATION: Xaa at position 40 is absent of present, if present Xaa in position 40 is cysteine, serine or alanine. If Xaa in position 40 is present then positions 38 through 39 are not absent.
<220> FEATURE:
<221> NAME/KEY: MISC_FEATURE
<222> LOCATION: (41)..(41)
<223> OTHER INFORMATION: Xaa at position 41 is arginine, lysine or absent. If arginine or lysine than Xaa in positions 38 through 40 are not absent.
<220> FEATURE:
<221> NAME/KEY: MISC_FEATURE
<222> LOCATION: (42)..(42)
<223> OTHER INFORMATION: Xaa at position 42 is absent or present, if present Xaa in position 42 is cysteine, serine or alanine. If Xaa in position 42 is present then positions 38 through 41 are not absent.
<220> FEATURE:
<221> NAME/KEY: MISC_FEATURE
<222> LOCATION: (43)..(43)
<223> OTHER INFORMATION: Xaa at position 43 is asparagine, serine or absent. If asparagine or serine then Xaa in positions 38 through 42 are not absent.
<220> FEATURE:
<221> NAME/KEY: MISC_FEATURE
<222> LOCATION: (44)..(44)
<223> OTHER INFORMATION: Xaa at position 44 is aspartic acid, glycine or absent. If aspartic acid or glycine then Xaa in positions 38 through 43 are not absent.
<220> FEATURE:
<221> NAME/KEY: MISC_FEATURE
<222> LOCATION: (45)..(45)
<223> OTHER INFORMATION: Xaa at position 45 is serine or absent. If serine then Xaa in positions 38 through 44 are not absent.
<220> FEATURE:
<221> NAME/KEY: MISC_FEATURE
<222> LOCATION: (46)..(46)
<223> OTHER INFORMATION: Xaa at position 46 is serine or absent. If serine then Xaa in positions 38 through 45 are not absent.
<220> FEATURE:
<221> NAME/KEY: MISC_FEATURE
<222> LOCATION: (47)..(47)
<223> OTHER INFORMATION: Xaa at position 47 is aspartic acid or absent. If aspartic acid then Xaa in positions 38 through 46 are not absent.

<400> SEQUENCE: 36

```
Xaa Xaa Xaa Xaa Xaa Xaa Xaa Xaa Thr Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Thr
            20                  25                  30

Xaa Xaa Xaa Xaa Xaa Xaa Xaa Xaa Xaa Xaa Xaa Xaa Xaa Xaa Xaa
        35                  40                  45
```

<210> SEQ ID NO 37
<211> LENGTH: 70
<212> TYPE: PRT
<213> ORGANISM: Influenza A virus
<220> FEATURE:
<221> NAME/KEY: MISC_FEATURE
<222> LOCATION: (1)..(1)

-continued

<223> OTHER INFORMATION: Xaa at position 1 is methionine or absent. If methionine then Xaa in position 2 through 8 are not absent.
<220> FEATURE:
<221> NAME/KEY: MISC_FEATURE
<222> LOCATION: (2)..(2)
<223> OTHER INFORMATION: Xaa at position 2 is serine or absent. If serine then Xaa in position 3 through 8 are not absent.
<220> FEATURE:
<221> NAME/KEY: MISC_FEATURE
<222> LOCATION: (3)..(3)
<223> OTHER INFORMATION: Xaa at position 3 is leucine or absent. If leucine then Xaa in position 4 through 8 are not absent.
<220> FEATURE:
<221> NAME/KEY: MISC_FEATURE
<222> LOCATION: (4)..(4)
<223> OTHER INFORMATION: Xaa at position 4 is leucine or absent. If leucine then Xaa in position 5 through 8 are not absent.
<220> FEATURE:
<221> NAME/KEY: MISC_FEATURE
<222> LOCATION: (5)..(5)
<223> OTHER INFORMATION: Xaa at position 5 is threonine or absent. If threonine then Xaa in position 6 through 8 are not absent.
<220> FEATURE:
<221> NAME/KEY: MISC_FEATURE
<222> LOCATION: (6)..(6)
<223> OTHER INFORMATION: Xaa at position 6 is glutamic acid or absent. If glutamic acid then Xaa in position 7 through 8 are not absent.
<220> FEATURE:
<221> NAME/KEY: MISC_FEATURE
<222> LOCATION: (7)..(7)
<223> OTHER INFORMATION: Xaa at position 7 is valine or absent. If valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or absent.
<220> FEATURE:
<221> NAME/KEY: MISC_FEATURE
<222> LOCATION: (10)..(10)
<223> OTHER INFORMATION: Xaa at position 10 is proline, leucine or histidine.
<220> FEATURE:
<221> NAME/KEY: MISC_FEATURE
<222> LOCATION: (11)..(11)
<223> OTHER INFORMATION: Xaa at position 11 is isoleucine or threonine.
<220> FEATURE:
<221> NAME/KEY: MISC_FEATURE
<222> LOCATION: (12)..(12)
<223> OTHER INFORMATION: Xaa at position 12 is arginine or lysine.
<220> FEATURE:
<221> NAME/KEY: MISC_FEATURE
<222> LOCATION: (13)..(13)
<223> OTHER INFORMATION: Xaa at position 13 is asparagine or serine.
<220> FEATURE:
<221> NAME/KEY: MISC_FEATURE
<222> LOCATION: (14)..(14)
<223> OTHER INFORMATION: Xaa at position 14 is glutamic acid or glycine.
<220> FEATURE:
<221> NAME/KEY: MISC_FEATURE
<222> LOCATION: (15)..(15)
<223> OTHER INFORMATION: Xaa at position 15 is tryptophan or absent.
<220> FEATURE:
<221> NAME/KEY: MISC_FEATURE
<222> LOCATION: (16)..(16)
<223> OTHER INFORMATION: Xaa at position 16 is glycine, glutamic acid or absent. If glycine or glutamic acid then Xaa in position 16 is not absent.
<220> FEATURE:
<221> NAME/KEY: MISC_FEATURE
<222> LOCATION: (17)..(17)
<223> OTHER INFORMATION: Xaa at position 17 is absent or present, if present Xaa in position 17 is cysteine, serine or alanine. If Xaa in position 17 is present then positions 15 through 16 are not absent.
<220> FEATURE:
<221> NAME/KEY: MISC_FEATURE
<222> LOCATION: (18)..(18)
<223> OTHER INFORMATION: Xaa at position 18 arginine, lysine or absent. If arginine or lysine then Xaa in positions 15 through 17 are not absent.

-continued

<220> FEATURE:
<221> NAME/KEY: MISC_FEATURE
<222> LOCATION: (19)..(19)
<223> OTHER INFORMATION: Xaa at position 19 is absent or present, if present Xaa in position 19 is cysteine, serine or alanine. If Xaa is position 19 is present then positions 15 through 18 are not absent.
<220> FEATURE:
<221> NAME/KEY: MISC_FEATURE
<222> LOCATION: (20)..(20)
<223> OTHER INFORMATION: Xaa at position 20 is asparagine, serine, glycine or absent. If asparagine or serine then Xaa is positions 15 through 19 are not absent.
<220> FEATURE:
<221> NAME/KEY: MISC_FEATURE
<222> LOCATION: (21)..(21)
<223> OTHER INFORMATION: Xaa at position 21 is aspartic acid, glycine or absent. If aspartic acid or glycine then Xaa is positions 15 through 20 are not absent.
<220> FEATURE:
<221> NAME/KEY: MISC_FEATURE
<222> LOCATION: (22)..(22)
<223> OTHER INFORMATION: Xaa at position 22 is serine or absent. If serine then Xaa is positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent. If serine then Xaa is positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent. If aspartic acid then Xaa is positions 15 through 23 are not absent.
<220> FEATURE:
<221> NAME/KEY: MISC_FEATURE
<222> LOCATION: (25)..(25)
<223> OTHER INFORMATION: Xaa at position 25 is serine or absent. If serine then Xaa in positions 26 through 31 are not absent.
<220> FEATURE:
<221> NAME/KEY: MISC_FEATURE
<222> LOCATION: (26)..(26)
<223> OTHER INFORMATION: Xaa at position 26 is leucine or absent. If leucine then Xaa in positions 27 through 31 are not absent.
<220> FEATURE:
<221> NAME/KEY: MISC_FEATURE
<222> LOCATION: (27)..(27)
<223> OTHER INFORMATION: Xaa at position 27 is leucine or absent. If leucine then Xaa in positions 28 through 31 are not absent.
<220> FEATURE:
<221> NAME/KEY: MISC_FEATURE
<222> LOCATION: (28)..(28)
<223> OTHER INFORMATION: Xaa at position 28 is threonine, proline or absent. If threonine or proline then Xaa in positions 29 through 31 are not absent.
<220> FEATURE:
<221> NAME/KEY: MISC_FEATURE
<222> LOCATION: (29)..(29)
<223> OTHER INFORMATION: Xaa at position 29 is glutamic acid or absent. If glutamic acid then Xaa in positions 30 through 31 are not absent.
<220> FEATURE:
<221> NAME/KEY: MISC_FEATURE
<222> LOCATION: (30)..(30)
<223> OTHER INFORMATION: Xaa at position 30 is valine or absent. If valine then Xaa in position 31 is not absent.
<220> FEATURE:
<221> NAME/KEY: MISC_FEATURE
<222> LOCATION: (31)..(31)
<223> OTHER INFORMATION: Xaa at position 31 is glutamic acid or aspartic acid or absent.
<220> FEATURE:
<221> NAME/KEY: MISC_FEATURE
<222> LOCATION: (33)..(33)
<223> OTHER INFORMATION: Xaa at position 33 is proline, leucine or histidine.
<220> FEATURE:
<221> NAME/KEY: MISC_FEATURE
<222> LOCATION: (34)..(34)

```
<223> OTHER INFORMATION: Xaa at position 34 is isoleucine or threonine
<220> FEATURE:
<221> NAME/KEY: MISC_FEATURE
<222> LOCATION: (35)..(35)
<223> OTHER INFORMATION: Xaa at position 35 is arginine or lysine.
<220> FEATURE:
<221> NAME/KEY: MISC_FEATURE
<222> LOCATION: (36)..(36)
<223> OTHER INFORMATION: Xaa at position 36 is asparagine or serine.
<220> FEATURE:
<221> NAME/KEY: MISC_FEATURE
<222> LOCATION: (37)..(37)
<223> OTHER INFORMATION: Xaa at position 37 is glumatic acid or glycine.
<220> FEATURE:
<221> NAME/KEY: MISC_FEATURE
<222> LOCATION: (38)..(38)
<223> OTHER INFORMATION: Xaa at position 38 is tryptophan or absent.
<220> FEATURE:
<221> NAME/KEY: MISC_FEATURE
<222> LOCATION: (39)..(39)
<223> OTHER INFORMATION: Xaa at position 39 is glycine, glutamic acid or
      absent.  If glycine or glutamic acid then Xaa in position 38 is
      not absent.
<220> FEATURE:
<221> NAME/KEY: MISC_FEATURE
<222> LOCATION: (40)..(40)
<223> OTHER INFORMATION: Xaa at position 40 is absent of present, if
      present Xaa in position 40 is cysteine, serine or alanine.  If Xaa
      in position 40 is present then positions 38 through 39 are not
      absent.
<220> FEATURE:
<221> NAME/KEY: MISC_FEATURE
<222> LOCATION: (41)..(41)
<223> OTHER INFORMATION: Xaa at position 41 is arginine, lysine or
      absent.  If arginine or lysine than Xaa in positions 38 through 40
      are not absent.
<220> FEATURE:
<221> NAME/KEY: MISC_FEATURE
<222> LOCATION: (42)..(42)
<223> OTHER INFORMATION: Xaa at position 42 is absent or present, if
      present Xaa in position 42 is cysteine, serine or alanine.  If Xaa
      in position 42 is present then positions 38 through 41 are not
      absent.
<220> FEATURE:
<221> NAME/KEY: MISC_FEATURE
<222> LOCATION: (43)..(43)
<223> OTHER INFORMATION: Xaa at position 43 is asparagine, serine,
      glycine or absent.  If asparagine or serine or glycine then Xaa in
      positions 38 through 42 are not absent.
<220> FEATURE:
<221> NAME/KEY: MISC_FEATURE
<222> LOCATION: (44)..(44)
<223> OTHER INFORMATION: Xaa at position 44 is aspartic acid, glycine or
      absent.  If aspartic acid or glycine then Xaa in positions 38
      through 43 are not absent.
<220> FEATURE:
<221> NAME/KEY: MISC_FEATURE
<222> LOCATION: (45)..(45)
<223> OTHER INFORMATION: Xaa at position 45 is serine or absent.  If
      serine then Xaa in positions 38 through 44 are not absent.
<220> FEATURE:
<221> NAME/KEY: MISC_FEATURE
<222> LOCATION: (46)..(46)
<223> OTHER INFORMATION: Xaa at position 46 is serine or absent.  If
      serine then Xaa in positions 38 through 45 are not absent.
<220> FEATURE:
<221> NAME/KEY: MISC_FEATURE
<222> LOCATION: (47)..(47)
<223> OTHER INFORMATION: Xaa at position 47 is aspartic acid or absent.
      If aspartic acid then Xaa in positions 38 through 46 are not
      absent.
<220> FEATURE:
<221> NAME/KEY: MISC_FEATURE
<222> LOCATION: (48)..(48)
<223> OTHER INFORMATION: Xaa at position 48 is serine or absent.  If
      serine then Xaa in positions 49 through 54 are not absent.
<220> FEATURE:
<221> NAME/KEY: MISC_FEATURE
<222> LOCATION: (49)..(49)
<223> OTHER INFORMATION: Xaa at position 49 is leucine or absent.  If
```

```
      leucine then Xaa in positions 50 through 54 are not absent.
<220> FEATURE:
<221> NAME/KEY: MISC_FEATURE
<222> LOCATION: (50)..(50)
<223> OTHER INFORMATION: Xaa at position 50 is leucine or absent.  If
      leucine then Xaa in positions 51 through 54 are not absent.
<220> FEATURE:
<221> NAME/KEY: MISC_FEATURE
<222> LOCATION: (51)..(51)
<223> OTHER INFORMATION: Xaa at position 51 is threonine, proline or
      absent.  If threonine or proline then Xaa in positions 52 through
      54 are not absent.
<220> FEATURE:
<221> NAME/KEY: MISC_FEATURE
<222> LOCATION: (52)..(52)
<223> OTHER INFORMATION: Xaa at position 52 is glutamic acid or absent.
      If glutamic acid then Xaa in positions 53 through 54 are not
      absent.
<220> FEATURE:
<221> NAME/KEY: MISC_FEATURE
<222> LOCATION: (53)..(53)
<223> OTHER INFORMATION: Xaa at position 53 is valine or absent.  If
      valine then Xaa in position 54 is not absent.
<220> FEATURE:
<221> NAME/KEY: MISC_FEATURE
<222> LOCATION: (54)..(54)
<223> OTHER INFORMATION: Xaa at position 54 is glutamic acid or aspartic
      acid or absent
<220> FEATURE:
<221> NAME/KEY: MISC_FEATURE
<222> LOCATION: (56)..(56)
<223> OTHER INFORMATION: Xaa at position 56 is proline, leucine or
      histidine.
<220> FEATURE:
<221> NAME/KEY: MISC_FEATURE
<222> LOCATION: (57)..(57)
<223> OTHER INFORMATION: Xaa at position 57 is isoleucine or threonine.
<220> FEATURE:
<221> NAME/KEY: MISC_FEATURE
<222> LOCATION: (58)..(58)
<223> OTHER INFORMATION: Xaa at position 58 is arginine or lysine.
<220> FEATURE:
<221> NAME/KEY: MISC_FEATURE
<222> LOCATION: (59)..(59)
<223> OTHER INFORMATION: Xaa at position 59 is asparagine or serine.
<220> FEATURE:
<221> NAME/KEY: MISC_FEATURE
<222> LOCATION: (60)..(60)
<223> OTHER INFORMATION: Xaa at position 60 is glumatic acid or glycine.
<220> FEATURE:
<221> NAME/KEY: MISC_FEATURE
<222> LOCATION: (61)..(61)
<223> OTHER INFORMATION: Xaa at position 61 is tryptophan or absent.
<220> FEATURE:
<221> NAME/KEY: MISC_FEATURE
<222> LOCATION: (62)..(62)
<223> OTHER INFORMATION: Xaa at position 62 is glycine, glutamic acid or
      absent.  If glycine or glutamic acid then Xaa in position 61 is
      not absent.
<220> FEATURE:
<221> NAME/KEY: MISC_FEATURE
<222> LOCATION: (63)..(63)
<223> OTHER INFORMATION: Xaa at position 63 is absent of present, if
      present Xaa in position 63 is cysteine, serine or alanine.  If Xaa
      in position 63 is present then positions 61 through 62 are not
      absent.
<220> FEATURE:
<221> NAME/KEY: MISC_FEATURE
<222> LOCATION: (64)..(64)
<223> OTHER INFORMATION: Xaa at position 64 is arginine, lysine or
      absent.  If arginine or lysine than Xaa in positions 61 through 63
      are not absent.
<220> FEATURE:
<221> NAME/KEY: MISC_FEATURE
<222> LOCATION: (65)..(65)
<223> OTHER INFORMATION: Xaa at position 65 is absent or present, if
      present Xaa in position 65 is cysteine, serine or alanine.  If Xaa
      in position 65 is present then positions 61 through 64 are not
      absent.
<220> FEATURE:
```

<221> NAME/KEY: MISC_FEATURE
<222> LOCATION: (66)..(66)
<223> OTHER INFORMATION: Xaa at position 66 is asparagine, serine, glycine or absent. If asparagine or serine or glycine then Xaa in positions 61 through 65 are not absent.
<220> FEATURE:
<221> NAME/KEY: MISC_FEATURE
<222> LOCATION: (67)..(67)
<223> OTHER INFORMATION: Xaa at position 67 is aspartic acid, glycine or absent. If aspartic acid or glycine then Xaa in positions 61 through 66 are not absent.
<220> FEATURE:
<221> NAME/KEY: MISC_FEATURE
<222> LOCATION: (68)..(68)
<223> OTHER INFORMATION: Xaa at position 68 is serine or absent. If serine then Xaa in positions 61 through 67 are not absent.
<220> FEATURE:
<221> NAME/KEY: MISC_FEATURE
<222> LOCATION: (69)..(69)
<223> OTHER INFORMATION: Xaa at position 69 is serine or absent. If serine then Xaa in positions 61 through 68 are not absent.
<220> FEATURE:
<221> NAME/KEY: MISC_FEATURE
<222> LOCATION: (70)..(70)
<223> OTHER INFORMATION: Xaa at position 70 is aspartic acid or absent. If aspartic acid then Xaa in positions 61 through 69 are not absent.

<400> SEQUENCE: 37

```
Xaa Xaa Xaa Xaa Xaa Xaa Xaa Xaa Thr Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Thr
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Thr Xaa Xaa Xaa Xaa Xaa Xaa Xaa Xaa Xaa
    50                  55                  60

Xaa Xaa Xaa Xaa Xaa Xaa
65                  70
```

<210> SEQ ID NO 38
<211> LENGTH: 17
<212> TYPE: PRT
<213> ORGANISM: Influenza B virus

<400> SEQUENCE: 38

```
Asn Asn Ala Thr Phe Asn Tyr Thr Asn Val Asn Pro Ile Ser His Ile
1               5                   10                  15

Arg
```

<210> SEQ ID NO 39
<211> LENGTH: 24
<212> TYPE: PRT
<213> ORGANISM: Influenza A virus

<400> SEQUENCE: 39

```
Phe Trp Arg Gly Glu Asn Gly Arg Lys Thr Arg Ser Ala Tyr Glu Arg
1               5                   10                  15

Met Cys Asn Ile Leu Lys Gly Lys
            20
```

<210> SEQ ID NO 40
<211> LENGTH: 22
<212> TYPE: PRT
<213> ORGANISM: Influenza A virus

<400> SEQUENCE: 40

Leu Arg Val Leu Ser Phe Ile Arg Gly Thr Lys Val Ser Pro Arg Gly
1 5 10 15

Lys Leu Ser Thr Arg Gly
20

<210> SEQ ID NO 41
<211> LENGTH: 22
<212> TYPE: PRT
<213> ORGANISM: Influenza A virus

<400> SEQUENCE: 41

Ser Leu Val Gly Ile Asp Pro Phe Lys Leu Leu Gln Asn Ser Gln Val
1 5 10 15

Tyr Ser Leu Ile Arg Pro
20

<210> SEQ ID NO 42
<211> LENGTH: 24
<212> TYPE: PRT
<213> ORGANISM: Influenza A virus

<400> SEQUENCE: 42

Ala Val Lys Gly Val Gly Thr Met Val Met Glu Leu Ile Arg Met Ile
1 5 10 15

Lys Arg Gly Ile Asn Asp Arg Asn
20

<210> SEQ ID NO 43
<211> LENGTH: 549
<212> TYPE: DNA
<213> ORGANISM: Hepatitis B virus

<400> SEQUENCE: 43
atggacatcg acccttataa agaatttgga gctactgtgg agttactctc gtttttgcct 60
tctgacttct ttccttcagt acgagatctt ctagataccg cctcagctct gtatcgggaa 120
gccttagagt ctcctgagca ttgttcacct caccatactg cactcaggca agcaattctt 180
tgctgggggg aactaatgac tctagctacc tgggtgggtg ttaatttgga agatccagcg 240
tctagagacc tagtagtcag ttatgtcaac actaatatgg gcctaaagtt caggcaactc 300
ttgtggtttc acatttcttg tctcactttt ggaagagaaa cagttataga gtatttggtg 360
tctttcggag tgtggattcg cactcctcca gcttatagac caccaaatgc ccctatccta 420
tcaacacttc cggagactac tgttgttaga cgacgaggca ggtcccctag aagaagaact 480
ccctcgcctc gcagacgaag gtctcaatcg ccgcgtcgca gaagatctca atctcgggaa 540
tctcaatgt 549

<210> SEQ ID NO 44
<211> LENGTH: 555
<212> TYPE: DNA
<213> ORGANISM: Hepatitis B virus

<400> SEQUENCE: 44
atggacattg acccttataa agaatttgga gctactgtgg agttactctc gtttttgcct 60
tctgacttct ttccttccgt acgagatctc ctagacaccg cctcagctct gtatcgagaa 120
gccttagagt ctcctgagca ttgctcacct caccatactg cactcaggca agccattctc 180
tgctgggggg aattgatgac tctagctacc tgggtgggta ataatttgca agatccagca 240
tccagagatc tagtagtcaa ttatgttaat actaacatgg gtttaaagat caggcaacta 300

-continued

```
ttgtggtttc atatatcttg ccttactttt ggaagagaga ctgtacttga atatttggtc    360

tctttcggag tgtggattcg cactcctcca gcctatagac caccaaatgc ccctatctta    420

tcaacacttc cggaaactac tgttgttaga cgacgggacc gaggcaggtc ccctagaaga    480

agaactccct cgcctcgcag acgcagatct caatcgccgc gtcgcagaag atctcaatct    540

cgggaatctc aatgt                                                     555
```

<210> SEQ ID NO 45
<211> LENGTH: 555
<212> TYPE: DNA
<213> ORGANISM: Hepatitis B virus

<400> SEQUENCE: 45

```
atggacattg acccttataa agaatttgga gctactgtgg agttactctc gtttttgcct     60

tctgacttct ttccttccgt cagagatctc ctagacaccg cctcagctct gtatcgagaa    120

gccttagagt ctcctgagca ttgctcacct caccatactg cactcaggca agccattctc    180

tgctgggggg aattgatgac tctagctacc tgggtgggta ataatttgga agatccagca    240

tctagggatc ttgtagtaaa ttatgttaat actaacgtgg gtttaaagat caggcaacta    300

ttgtggtttc atatatcttg ccttactttt ggaagagaga ctgtacttga atatttggtc    360

tctttcggag tgtggattcg cactcctcca gcctatagac caccaaatgc ccctatctta    420

tcaacacttc cggaaactac tgttgttaga cgacgggacc gaggcaggtc ccctagaaga    480

agaactccct cgcctcgcag acgcagatct ccatcgccgc gtcgcagaag atctcaatct    540

cgggaatctc aatgt                                                     555
```

<210> SEQ ID NO 46
<211> LENGTH: 549
<212> TYPE: DNA
<213> ORGANISM: Hepatitis B virus

<400> SEQUENCE: 46

```
atggacattg acccttataa agaatttgga gctactgtgg agttactctc gtttttgcct     60

tctgacttct ttccttccgt acgagatctt ctagataccg ccgcagctct gtatcgggat    120

gccttagagt ctcctgagca ttgttcacct caccatactg cactcaggca agcaattctt    180

tgctggggag acttaatgac tctagctacc tgggtgggta ctaatttaga agatccagca    240

tctagggacc tagtagtcag ttatgtcaac actaatgtgg gcctaaagtt cagacaatta    300

ttgtggtttc acatttcttg tctcactttt ggaagagaaa cggttctaga gtatttggtg    360

tcttttggag tgtggattcg cactcctcca gcttatagac caccaaatgc ccctatccta    420

tcaacgcttc cggagactac tgttgttaga cgacgaggca ggtcccctag aagaagaact    480

ccctcgcctc gcagacgaag atctcaatcg ccgcgtcgca gaagatctca atctcgggaa    540

tctcaatgt                                                            549
```

<210> SEQ ID NO 47
<211> LENGTH: 549
<212> TYPE: DNA
<213> ORGANISM: woodchuck

<400> SEQUENCE: 47

```
atggctttgg ggcatggaca tagatcctta taaagaattt ggttcatctt atcagttgtt     60

gaattttctt cctttggact tctttcctga tcttaatgct ttggtggaca ctgctactgc    120

cttgtatgaa gaagaactaa caggtaggga acattgctct ccgcaccata cagctattag    180
```

acaagcttta gtatgctggg atgaattaac taaattgata gcttggatga gctctaacat 240
aacttctgaa caagtaagaa caatcattgt aaatcatgtc aatgatacct ggggacttaa 300
ggtgagacaa agtttatggt ttcatttgtc atgtctcact ttcggacaac atacagttca 360
agaattttta gtaagttttg gagtatggat caggactcca gctccatata gacctcctaa 420
tgcacccatt ctctcgactc ttccggaaca tacagtcatt aggagaagag gaggtgcaag 480
agcttctagg tcccccagaa gacgcactcc ctctcctcgc aggagaagat ctcaatcacc 540
gcgtcgcag 549

<210> SEQ ID NO 48
<211> LENGTH: 651
<212> TYPE: DNA
<213> ORGANISM: ground squirrel

<400> SEQUENCE: 48
atgtatcttt ttcacctgtg ccttgttttt gcctgtgttc catgtcctac tgttcaagcc 60
tccaagctgt gccttggatg gctttgggac atggacatag atccctataa agaatttggt 120
tcttcttatc agttgttgaa ttttcttcct ttggactttt ttcctgatct caatgcattg 180
gtggacactg ctgctgctct ttatgaagaa gaattaacag gtagggagca ttgttctcct 240
catcatactg ctattagaca ggccttagtg tgttgggaag aattaactag attaattaca 300
tggatgagtg aaaatacaac agaagaagtt agaagaatta ttgttgatca tgtcaataat 360
acttggggac ttaaagtaag acagacttta tggtttcatt tatcatgtct tacttttgga 420
caacacacag ttcaagaatt tttggttagt tttggagtat ggattagaac tccagctcct 480
tatagaccac ctaatgcacc cattttatca actcttccgg aacatacagt cattaggaga 540
agaggaggtt caagagctgc taggtccccc cgaagacgca ctccctctcc tcgcaggaga 600
aggtctcaat caccgcgtcg cagacgctct caatctccag cttccaactg c 651

<210> SEQ ID NO 49
<211> LENGTH: 18
<212> TYPE: DNA
<213> ORGANISM: Artificial Sequence
<220> FEATURE:
<223> OTHER INFORMATION: Amplification primer containing a restriction endonuclease site

<400> SEQUENCE: 49
ggtgcatgca aggagatg 18

<210> SEQ ID NO 50
<211> LENGTH: 55
<212> TYPE: DNA
<213> ORGANISM: Artificial Sequence
<220> FEATURE:
<223> OTHER INFORMATION: plasmid pkk223

<400> SEQUENCE: 50
gcgaagcttc ggatcccatg gtttttttcct ccttatgtga aattgttatc cgctc 55

<210> SEQ ID NO 51
<211> LENGTH: 24
<212> TYPE: DNA
<213> ORGANISM: Artificial sequence
<220> FEATURE:
<223> OTHER INFORMATION: primer

<400> SEQUENCE: 51
ttgggccatg gacatcgacc ctta 24

<210> SEQ ID NO 52
<211> LENGTH: 31
<212> TYPE: DNA
<213> ORGANISM: Artificial sequence
<220> FEATURE:
<223> OTHER INFORMATION: primer

<400> SEQUENCE: 52
gcggaattcc atcttccaaa ttaacaccca c 31

<210> SEQ ID NO 53
<211> LENGTH: 39
<212> TYPE: DNA
<213> ORGANISM: Artificial sequence
<220> FEATURE:
<223> OTHER INFORMATION: primer

<400> SEQUENCE: 53
cgcgaattca aaaagagctc ccagcgtcta gagacctag 39

<210> SEQ ID NO 54
<211> LENGTH: 31
<212> TYPE: DNA
<213> ORGANISM: Artificial sequence
<220> FEATURE:
<223> OTHER INFORMATION: primer

<400> SEQUENCE: 54
cgcaagctta aacaacagta gtctccggaa g 31

<210> SEQ ID NO 55
<211> LENGTH: 37
<212> TYPE: DNA
<213> ORGANISM: Artificial Sequence
<220> FEATURE:
<223> OTHER INFORMATION: Amplification primer containing a restriction endonuclease site

<400> SEQUENCE: 55
cgcaagctta ctagcaaaca acagtagtct ccggaag 37

<210> SEQ ID NO 56
<211> LENGTH: 28
<212> TYPE: DNA
<213> ORGANISM: Artificial Sequence
<220> FEATURE:
<223> OTHER INFORMATION: Amplification primer containing a restriction endonuclease site

<400> SEQUENCE: 56
ggaaagctta ctaacattga gattcccg 28

<210> SEQ ID NO 57
<211> LENGTH: 21
<212> TYPE: DNA
<213> ORGANISM: Artificial Sequence
<220> FEATURE:
<223> OTHER INFORMATION: Amplification primer containing a restriction endonuclease site

<400> SEQUENCE: 57
gcgggatccg gagcttatcg a 21

<210> SEQ ID NO 58
<211> LENGTH: 41
<212> TYPE: DNA

<213> ORGANISM: Artificial Sequence
<220> FEATURE:
<223> OTHER INFORMATION: Amplification primer containing a restriction endonuclease site

<400> SEQUENCE: 58
gcggagctct ttttgaattc ccatggtttt ttcctcctta t 41

<210> SEQ ID NO 59
<211> LENGTH: 49
<212> TYPE: DNA
<213> ORGANISM: Artificial Sequence
<220> FEATURE:
<223> OTHER INFORMATION: Amplification primer containing a restriction endonuclease site

<400> SEQUENCE: 59
gcggagctcc ttgggtggct ttggggcatt gacatcgacc cttataaag 49

<210> SEQ ID NO 60
<211> LENGTH: 18
<212> TYPE: DNA
<213> ORGANISM: Artificial Sequence
<220> FEATURE:
<223> OTHER INFORMATION: Amplification primer containing a restriction endonuclease site.

<400> SEQUENCE: 60
gcataattcg tgtcgctc 18

<210> SEQ ID NO 61
<211> LENGTH: 30
<212> TYPE: DNA
<213> ORGANISM: Artificial Sequence
<220> FEATURE:
<223> OTHER INFORMATION: Amplification primer containing a restriction endonuclease site.

<400> SEQUENCE: 61
gcggaattcc gatgtccatg gtttttttcct 30

<210> SEQ ID NO 62
<211> LENGTH: 41
<212> TYPE: DNA
<213> ORGANISM: Artificial Sequence
<220> FEATURE:
<223> OTHER INFORMATION: Amplification primer containing a restriction endonuclease site.

<400> SEQUENCE: 62
gcggaattca aaaagagctc gacccttata aagaatttgg a 41

<210> SEQ ID NO 63
<211> LENGTH: 42
<212> TYPE: DNA
<213> ORGANISM: Artificial Sequence
<220> FEATURE:
<223> OTHER INFORMATION: Amplification primer containing a restriction endonuclease site

<400> SEQUENCE: 63
cgcaagctta gagctcttga attccaacaa cagtagtctc cg 42

<210> SEQ ID NO 64
<211> LENGTH: 52
<212> TYPE: DNA
<213> ORGANISM: Artificial Sequence
<220> FEATURE:

-continued

<223> OTHER INFORMATION: Amplification primer containing a restriction endonuclease site

<400> SEQUENCE: 64
gcgaagctta ctaaggggag cggcctcgtc gacgaacaac agtagtctcc gg 52

<210> SEQ ID NO 65
<211> LENGTH: 55
<212> TYPE: DNA
<213> ORGANISM: Artificial Sequence
<220> FEATURE:
<223> OTHER INFORMATION: Amplification primer containing a restriction endonuclease site

<400> SEQUENCE: 65
gcgaagctta ctaacaaggg gagcggcctc gtcgacgaac aacagtagtc tccgg 55

<210> SEQ ID NO 66
<211> LENGTH: 49
<212> TYPE: DNA
<213> ORGANISM: Artificial Sequence
<220> FEATURE:
<223> OTHER INFORMATION: Amplification primer containing a restriction endonuclease site

<400> SEQUENCE: 66
gcgaagctta ctaaggcgag ggagtgcgcc gacgagggga gcggcctcg 49

<210> SEQ ID NO 67
<211> LENGTH: 52
<212> TYPE: DNA
<213> ORGANISM: Artificial Sequence
<220> FEATURE:
<223> OTHER INFORMATION: Amplification primer containing a restriction endonuclease site

<400> SEQUENCE: 67
gcgaagctta ctaacaaggc gagggagtgc gccgacgagg ggagcggcct cg 52

<210> SEQ ID NO 68
<211> LENGTH: 49
<212> TYPE: DNA
<213> ORGANISM: Artificial Sequence
<220> FEATURE:
<223> OTHER INFORMATION: Amplification primer containing a restriction endonuclease site

<400> SEQUENCE: 68
gcgaagctta ctacggcgat tgagagcgtc gacggcgagg cgagggagt 49

<210> SEQ ID NO 69
<211> LENGTH: 52
<212> TYPE: DNA
<213> ORGANISM: Artificial Sequence
<220> FEATURE:
<223> OTHER INFORMATION: Amplification primer containing a restriction endonuclease site

<400> SEQUENCE: 69
gcgaagctta ctaacacggc gattgagagc gtcgacggcg aggcgaggga gt 52

<210> SEQ ID NO 70
<211> LENGTH: 26
<212> TYPE: PRT
<213> ORGANISM: Influenza A

<400> SEQUENCE: 70

```
Ile Ser Leu Leu Thr Glu Val Glu Thr Pro Ile Arg Asn Glu Trp Gly
1               5                   10                  15

Cys Arg Cys Asn Asp Ser Ser Asp Glu Leu
            20                  25


<210> SEQ ID NO 71
<211> LENGTH: 78
<212> TYPE: DNA
<213> ORGANISM: Influenza A

<400> SEQUENCE: 71

aattagcctg ttaaccgaag tggagacgcc gatccgtaac gaatggggct gccgctgtaa     60

tgattcttcc gacgagct                                                   78


<210> SEQ ID NO 72
<211> LENGTH: 70
<212> TYPE: DNA
<213> ORGANISM: Influenza A

<400> SEQUENCE: 72

cgtcggaaga atcattacag cggcagcccc attcgttacg gatcggcgtc tccacttcgg     60

ttaacaggct                                                            70


<210> SEQ ID NO 73
<211> LENGTH: 26
<212> TYPE: PRT
<213> ORGANISM: Influenza A

<400> SEQUENCE: 73

Met Ser Leu Leu Thr Glu Val Glu Thr Pro Ile Arg Asn Glu Trp Gly
1               5                   10                  15

Cys Arg Cys Asn Asp Ser Ser Asp Glu Leu
            20                  25


<210> SEQ ID NO 74
<211> LENGTH: 78
<212> TYPE: DNA
<213> ORGANISM: Influenza A

<400> SEQUENCE: 74

catgtctctg ctgaccgaag ttgaaacccc tatcagaaac gaatgggggt gcagatgtaa     60

cgattcaagt gatgagct                                                   78


<210> SEQ ID NO 75
<211> LENGTH: 70
<212> TYPE: DNA
<213> ORGANISM: Influenza A

<400> SEQUENCE: 75

catcacttga atcgttacat ctgcaccccc attcgtttct gataggggtt tcaacttcgg     60

tcagcagaga                                                            70


<210> SEQ ID NO 76
<211> LENGTH: 26
<212> TYPE: PRT
<213> ORGANISM: Artificial Sequence
<220> FEATURE:
<223> OTHER INFORMATION: Influenza A mutant

<400> SEQUENCE: 76

Met Ser Leu Leu Thr Glu Val Glu Thr Pro Ile Arg Asn Glu Trp Gly
1               5                   10                  15
```

Ser Arg Cys Asn Asp Ser Ser Asp Glu Leu
20 25

<210> SEQ ID NO 77
<211> LENGTH: 78
<212> TYPE: DNA
<213> ORGANISM: Artificial Sequence
<220> FEATURE:
<223> OTHER INFORMATION: Amplification primer containing a restriction endonuclease site

<400> SEQUENCE: 77
catgtctctg ctgaccgaag ttgaaacccc tatcagaaac gaatgggggt ctagatgtaa 60
cgattcaagt gatgagct 78

<210> SEQ ID NO 78
<211> LENGTH: 70
<212> TYPE: DNA
<213> ORGANISM: Artificial Sequence
<220> FEATURE:
<223> OTHER INFORMATION: Amplification primer containing a restriction endonuclease site

<400> SEQUENCE: 78
catcacttga atcgttacat ctagaccccc attcgtttct gataggggtt tcaacttcgg 60
tcagcagaga 70

<210> SEQ ID NO 79
<211> LENGTH: 26
<212> TYPE: PRT
<213> ORGANISM: Artificial Sequence
<220> FEATURE:
<223> OTHER INFORMATION: Influenza A mutant

<400> SEQUENCE: 79

Met Ser Leu Leu Thr Glu Val Glu Thr Pro Ile Arg Asn Glu Trp Gly
1 5 10 15

Cys Arg Ser Asn Asp Ser Ser Asp Glu Leu
20 25

<210> SEQ ID NO 80
<211> LENGTH: 78
<212> TYPE: DNA
<213> ORGANISM: Artificial Sequence
<220> FEATURE:
<223> OTHER INFORMATION: Amplification primer containing a restriction endonuclease site

<400> SEQUENCE: 80
catgtctctg ctgaccgaag ttgaaacccc tatcagaaac gaatgggggt gcagatcgaa 60
cgattcaagt gatgagct 78

<210> SEQ ID NO 81
<211> LENGTH: 70
<212> TYPE: DNA
<213> ORGANISM: Artificial Sequence
<220> FEATURE:
<223> OTHER INFORMATION: Amplification primer containing a restriction endonuclease site

<400> SEQUENCE: 81
catcacttga atcgttcgat ctgcaccccc attcgtttct gataggggtt tcaacttcgg 60
tcagcagaga 70

<210> SEQ ID NO 82
<211> LENGTH: 26
<212> TYPE: PRT
<213> ORGANISM: Artificial Sequence
<220> FEATURE:
<223> OTHER INFORMATION: Influenza A mutant

<400> SEQUENCE: 82

Ile Ser Leu Leu Thr Glu Val Glu Thr Pro Ile Arg Asn Glu Trp Gly
1 5 10 15

Ser Arg Ser Asn Asp Ser Ser Asp Glu Leu
20 25

<210> SEQ ID NO 83
<211> LENGTH: 78
<212> TYPE: DNA
<213> ORGANISM: Artificial Sequence
<220> FEATURE:
<223> OTHER INFORMATION: Amplification primer containing a restriction endonuclease site

<400> SEQUENCE: 83
aatttctctg ttaaccgaag tggagacgcc gattcgtaac gaatggggta gccgctctaa 60
tgatagctct gacgagct 78

<210> SEQ ID NO 84
<211> LENGTH: 70
<212> TYPE: DNA
<213> ORGANISM: Artificial Sequence
<220> FEATURE:
<223> OTHER INFORMATION: Amplification primer containing a restriction endonuclease site

<400> SEQUENCE: 84
cgtcagagct atcattagag cggctacccc attcgttacg aatcggcgtc tccacttcgg 60
ttaacagaga 70

<210> SEQ ID NO 85
<211> LENGTH: 26
<212> TYPE: PRT
<213> ORGANISM: Artificial Sequence
<220> FEATURE:
<223> OTHER INFORMATION: Influenza A mutant

<400> SEQUENCE: 85

Met Ser Leu Leu Thr Glu Val Glu Thr Pro Ile Arg Asn Glu Trp Gly
1 5 10 15

Ser Arg Ser Asn Asp Ser Ser Asp Glu Leu
20 25

<210> SEQ ID NO 86
<211> LENGTH: 78
<212> TYPE: DNA
<213> ORGANISM: Artificial Sequence
<220> FEATURE:
<223> OTHER INFORMATION: Amplification primer containing a restriction endonuclease site

<400> SEQUENCE: 86
catgtctctg ctgaccgaag ttgaaacccc tatcagaaac gaatgggggt ctagatcgaa 60
cgattcaagt gatgagct 78

<210> SEQ ID NO 87
<211> LENGTH: 70

<212> TYPE: DNA
<213> ORGANISM: Artificial Sequence
<220> FEATURE:
<223> OTHER INFORMATION: Amplification primer containing a restriction
      endonuclease site.

<400> SEQUENCE: 87
catcacttga atcgttcgat ctagaccccc attcgtttct gataggggtt tcaacttcgg     60
tcagcagaga                                                            70

<210> SEQ ID NO 88
<211> LENGTH: 32
<212> TYPE: DNA
<213> ORGANISM: Artificial sequence
<220> FEATURE:
<223> OTHER INFORMATION: pkk-BamHI-F-2

<400> SEQUENCE: 88
cgtagaggat ccggagctta tcgactgcac gg                                   32

<210> SEQ ID NO 89
<211> LENGTH: 24
<212> TYPE: DNA
<213> ORGANISM: Artificial Sequence
<220> FEATURE:
<223> OTHER INFORMATION: Amplification primer containing a restriction
      endonuclease site

<400> SEQUENCE: 89
gcgctcgaga tcacttgaat cgtt                                            24

<210> SEQ ID NO 90
<211> LENGTH: 33
<212> TYPE: DNA
<213> ORGANISM: Artificial Sequence
<220> FEATURE:
<223> OTHER INFORMATION: Amplification primer containing a restriction
      endonuclease site

<400> SEQUENCE: 90
gcgctcgaga gcttattgac cgaagttgaa acc                                  33

<210> SEQ ID NO 91
<211> LENGTH: 24
<212> TYPE: DNA
<213> ORGANISM: Artificial Sequence
<220> FEATURE:
<223> OTHER INFORMATION: Amplification primer containing a restriction
      endonuclease site

<400> SEQUENCE: 91
gcgctgcaga tcacttgaat cgtt                                            24

<210> SEQ ID NO 92
<211> LENGTH: 25
<212> TYPE: DNA
<213> ORGANISM: Artificial Sequence
<220> FEATURE:
<223> OTHER INFORMATION: Amplification primer containing a restriction
      endonuclease site

<400> SEQUENCE: 92
gcgctgcagt ctctgctgac cgaag                                           25

<210> SEQ ID NO 93
<211> LENGTH: 22
<212> TYPE: DNA

<213> ORGANISM: Artificial Sequence
<220> FEATURE:
<223> OTHER INFORMATION: Amplification primer containing a restriction
endonuclease site

<400> SEQUENCE: 93
cgcgacatgt ctctgctgac cg 22

<210> SEQ ID NO 94
<211> LENGTH: 203
<212> TYPE: PRT
<213> ORGANISM: Hepatitis B virus

<400> SEQUENCE: 94

```
Met Ser Leu Leu Thr Glu Val Glu Thr Pro Ile Arg Asn Glu Trp Gly
1               5                   10                  15

Cys Arg Cys Asn Asp Ser Ser Asp Pro Tyr Lys Glu Phe Gly Ala Thr
            20                  25                  30

Val Glu Leu Leu Ser Phe Leu Pro Ser Asp Phe Phe Pro Ser Val Arg
        35                  40                  45

Asp Leu Leu Asp Thr Ala Ser Ala Leu Tyr Arg Glu Ala Leu Glu Ser
    50                  55                  60

Pro Glu His Cys Ser Pro His His Thr Ala Leu Arg Gln Ala Ile Leu
65                  70                  75                  80

Cys Trp Gly Glu Leu Met Thr Leu Ala Thr Trp Val Gly Val Asn Leu
                85                  90                  95

Glu Asp Pro Ala Ser Arg Asp Leu Val Val Ser Tyr Val Asn Thr Asn
            100                 105                 110

Met Gly Leu Lys Phe Arg Gln Leu Leu Trp Phe His Ile Ser Cys Leu
        115                 120                 125

Thr Phe Gly Arg Glu Thr Val Ile Glu Tyr Leu Val Ser Phe Gly Val
    130                 135                 140

Trp Ile Arg Thr Pro Pro Ala Tyr Arg Pro Pro Asn Ala Pro Ile Leu
145                 150                 155                 160

Ser Thr Leu Pro Glu Thr Thr Val Val Arg Arg Arg Gly Arg Ser Pro
                165                 170                 175

Arg Arg Arg Thr Pro Ser Pro Arg Arg Arg Arg Ser Gln Ser Pro Arg
            180                 185                 190

Arg Arg Arg Ser Gln Ser Arg Glu Ser Gln Cys
        195                 200
```

<210> SEQ ID NO 95
<211> LENGTH: 176
<212> TYPE: PRT
<213> ORGANISM: Hepatitis B virus

<400> SEQUENCE: 95

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Gly Ile
65                  70                  75                  80

Ser Leu Leu Thr Glu Val Glu Thr Pro Ile Arg Asn Glu Trp Gly Cys
```

```
                85                  90                  95

Arg Cys Asn Asp Ser Ser Asp Glu Leu Pro Ala Ser Arg Asp Leu Val
            100                 105                 110

Val Ser Tyr Val Asn Thr Asn Met Gly Leu Lys Phe Arg Gln Leu Leu
        115                 120                 125

Trp Phe His Ile Ser Cys Leu Thr Phe Gly Arg Glu Thr Val Ile Glu
    130                 135                 140

Tyr Leu Val Ser Phe Gly Val Trp Ile Arg Thr Pro Pro Ala Tyr Arg
145                 150                 155                 160

Pro Pro Asn Ala Pro Ile Leu Ser Thr Leu Pro Glu Thr Thr Val Val
                165                 170                 175


<210> SEQ ID NO 96
<211> LENGTH: 177
<212> TYPE: PRT
<213> ORGANISM: Hepatitis B virus

<400> SEQUENCE: 96

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Gly Ile
65                  70                  75                  80

Ser Leu Leu Thr Glu Val Glu Thr Pro Ile Arg Asn Glu Trp Gly Ala
                85                  90                  95

Arg Ala Asn Asp Ser Ser Asp Glu Leu Pro Ala Ser Arg Asp Leu Val
            100                 105                 110

Val Ser Tyr Val Asn Thr Asn Met Gly Leu Lys Phe Arg Gln Leu Leu
        115                 120                 125

Trp Phe His Ile Ser Cys Leu Thr Phe Gly Arg Glu Thr Val Ile Glu
    130                 135                 140

Tyr Leu Val Ser Phe Gly Val Trp Ile Arg Thr Pro Pro Ala Tyr Arg
145                 150                 155                 160

Pro Pro Asn Ala Pro Ile Leu Ser Thr Leu Pro Glu Thr Thr Val Val
                165                 170                 175

Cys


<210> SEQ ID NO 97
<211> LENGTH: 183
<212> TYPE: PRT
<213> ORGANISM: Hepatitis B virus

<400> SEQUENCE: 97

Met Gly Ile Ser Leu Leu Thr Glu Val Glu Thr Pro Ile Arg Asn Glu
1               5                   10                  15

Trp Gly Cys Arg Cys Asn Asp Ser Ser Asp Glu Leu Leu Gly Trp Leu
            20                  25                  30

Trp Gly Ile Asp Ile Asp Pro Tyr Lys Glu Phe Gly Ala Thr Val Glu
        35                  40                  45

Leu Leu Ser Phe Leu Pro Ser Asp Phe Phe Pro Ser Val Arg Asp Leu
    50                  55                  60
```

Leu Asp Thr Ala Ser Ala Leu Tyr Arg Glu Ala Leu Glu Ser Pro Glu
65 70 75 80

His Cys Ser Pro His His Thr Ala Leu Arg Gln Ala Ile Leu Cys Trp
85 90 95

Gly Glu Leu Met Thr Leu Ala Thr Trp Val Gly Val Asn Leu Glu Asp
100 105 110

Pro Ala Ser Arg Asp Leu Val Val Ser Tyr Val Asn Thr Asn Met Gly
115 120 125

Leu Lys Phe Arg Gln Leu Leu Trp Phe His Ile Ser Cys Leu Thr Phe
130 135 140

Gly Arg Glu Thr Val Ile Glu Tyr Leu Val Ser Phe Gly Val Trp Ile
145 150 155 160

Arg Thr Pro Pro Ala Tyr Arg Pro Pro Asn Ala Pro Ile Leu Ser Thr
165 170 175

Leu Pro Glu Thr Thr Val Val
180

<210> SEQ ID NO 98
<211> LENGTH: 184
<212> TYPE: PRT
<213> ORGANISM: Hepatitis B virus

<400> SEQUENCE: 98

Met Gly Ile Ser Leu Leu Thr Glu Val Glu Thr Pro Ile Arg Asn Glu
1 5 10 15

Trp Gly Cys Arg Cys Asn Asp Ser Ser Asp Glu Leu Leu Gly Trp Leu
20 25 30

Trp Gly Ile Asp Ile Asp Pro Tyr Lys Glu Phe Gly Ala Thr Val Glu
35 40 45

Leu Leu Ser Phe Leu Pro Ser Asp Phe Phe Pro Ser Val Arg Asp Leu
50 55 60

Leu Asp Thr Ala Ser Ala Leu Tyr Arg Glu Ala Leu Glu Ser Pro Glu
65 70 75 80

His Cys Ser Pro His His Thr Ala Leu Arg Gln Ala Ile Leu Cys Trp
85 90 95

Gly Glu Leu Met Thr Leu Ala Thr Trp Val Gly Val Asn Leu Glu Asp
100 105 110

Pro Ala Ser Arg Asp Leu Val Val Ser Tyr Val Asn Thr Asn Met Gly
115 120 125

Leu Lys Phe Arg Gln Leu Leu Trp Phe His Ile Ser Cys Leu Thr Phe
130 135 140

Gly Arg Glu Thr Val Ile Glu Tyr Leu Val Ser Phe Gly Val Trp Ile
145 150 155 160

Arg Thr Pro Pro Ala Tyr Arg Pro Pro Asn Ala Pro Ile Leu Ser Thr
165 170 175

Leu Pro Glu Thr Thr Val Val Cys
180

<210> SEQ ID NO 99
<211> LENGTH: 18
<212> TYPE: PRT
<213> ORGANISM: Influenza A virus

<400> SEQUENCE: 99

Met Gly Ser Arg Cys Asn Asp Ser Ser Asp Ile Asp Pro Tyr Lys Glu
1 5 10 15

Phe Gly

<210> SEQ ID NO 100
<211> LENGTH: 59
<212> TYPE: DNA
<213> ORGANISM: Influenza A virus

<400> SEQUENCE: 100
ggcgccatgg ggtctagatg taacgattca agtgacatcg acccttataa agaatttcg 59

<210> SEQ ID NO 101
<211> LENGTH: 16
<212> TYPE: PRT
<213> ORGANISM: Influenza A virus

<400> SEQUENCE: 101

Met Gly Cys Asn Asp Ser Ser Asp Ile Asp Pro Tyr Lys Glu Phe Gly
1 5 10 15

<210> SEQ ID NO 102
<211> LENGTH: 52
<212> TYPE: DNA
<213> ORGANISM: Influenza A virus

<400> SEQUENCE: 102
gcgccatggg gtgtaacgat tcaagtgaca tcgaccctta taaagaattt gg 52

<210> SEQ ID NO 103
<211> LENGTH: 11
<212> TYPE: PRT
<213> ORGANISM: Artificial Sequence
<220> FEATURE:
<223> OTHER INFORMATION: xxx

<400> SEQUENCE: 103

Glu Leu Leu Gly Trp Leu Trp Gly Ile Asp Ile
1 5 10

<210> SEQ ID NO 104
<211> LENGTH: 14
<212> TYPE: PRT
<213> ORGANISM: Hepatitis B virus

<400> SEQUENCE: 104

Ser Lys Leu Cys Leu Gly Trp Leu Trp Gly Met Asp Ile Asp
1 5 10

<210> SEQ ID NO 105
<211> LENGTH: 38
<212> TYPE: PRT
<213> ORGANISM: Artificial sequence
<220> FEATURE:
<223> OTHER INFORMATION: chimera of influenza A and hepatitis B

<400> SEQUENCE: 105

Met Gly Ile Ser Leu Leu Thr Glu Val Glu Thr Pro Ile Arg Asn Glu
1 5 10 15

Trp Gly Cys Arg Cys Asn Asp Ser Ser Asp Glu Leu Leu Gly Trp Leu
20 25 30

Trp Gly Ile Asp Ile Asp
35

<210> SEQ ID NO 106
<211> LENGTH: 24
<212> TYPE: PRT
<213> ORGANISM: Artificial sequence
<220> FEATURE:
<223> OTHER INFORMATION: chimera of influenza A and hepatitis B

<400> SEQUENCE: 106

Met Ser Leu Leu Thr Glu Val Glu Thr Pro Ile Arg Asn Glu Trp Gly
1 5 10 15

Cys Arg Cys Asn Asp Ser Ser Asp
20

<210> SEQ ID NO 107
<211> LENGTH: 27
<212> TYPE: PRT
<213> ORGANISM: Artificial sequence
<220> FEATURE:
<223> OTHER INFORMATION: chimera of influenza A and hepatitis B

<400> SEQUENCE: 107

Met Ser Leu Leu Thr Glu Val Glu Thr Pro Ile Arg Asn Glu Trp Gly
1 5 10 15

Cys Arg Cys Asn Asp Ser Ser Asp Glu Leu Asp
20 25

<210> SEQ ID NO 108
<211> LENGTH: 27
<212> TYPE: PRT
<213> ORGANISM: Artificial sequence
<220> FEATURE:
<223> OTHER INFORMATION: chimera of hepatitis B and influenza A

<400> SEQUENCE: 108

Met Ser Leu Leu Thr Glu Val Glu Thr Pro Ile Arg Asn Glu Trp Gly
1 5 10 15

Ser Arg Ser Asn Asp Ser Ser Asp Glu Leu Asp
20 25

<210> SEQ ID NO 109
<211> LENGTH: 27
<212> TYPE: PRT
<213> ORGANISM: Artificial sequence
<220> FEATURE:
<223> OTHER INFORMATION: chimera of influenza A and hepatitis B

<400> SEQUENCE: 109

Met Ser Leu Leu Thr Glu Val Glu Thr Pro Ile Arg Asn Glu Trp Gly
1 5 10 15

Ser Arg Cys Asn Asp Ser Ser Asp Glu Leu Asp
20 25

<210> SEQ ID NO 110
<211> LENGTH: 27
<212> TYPE: PRT
<213> ORGANISM: Artificial sequence
<220> FEATURE:
<223> OTHER INFORMATION: chimera of hepatitis B and influenza A

<400> SEQUENCE: 110

Met Ser Leu Leu Thr Glu Val Glu Thr Pro Ile Arg Asn Glu Trp Gly
1 5 10 15

Cys Arg Ser Asn Asp Ser Ser Asp Glu Leu Asp
20 25

<210> SEQ ID NO 111
<211> LENGTH: 52
<212> TYPE: PRT
<213> ORGANISM: Artificial sequence
<220> FEATURE:
<223> OTHER INFORMATION: chimera of hepatitis B and influenza A

<400> SEQUENCE: 111

Met Ser Leu Leu Thr Glu Val Glu Thr Pro Ile Arg Asn Glu Trp Gly
1 5 10 15

Cys Arg Cys Asn Asp Ser Ser Asp Leu Glu Ser Leu Leu Thr Glu Val
20 25 30

Glu Thr Pro Ile Arg Asn Glu Trp Gly Cys Arg Cys Asn Asp Ser Ser
35 40 45

Asp Glu Leu Asp
50

<210> SEQ ID NO 112
<211> LENGTH: 52
<212> TYPE: PRT
<213> ORGANISM: Artificial sequence
<220> FEATURE:
<223> OTHER INFORMATION: chimera of influenza A and hepatitis B

<400> SEQUENCE: 112

Met Ser Leu Leu Thr Glu Val Glu Thr Pro Ile Arg Asn Glu Trp Gly
1 5 10 15

Ser Arg Ser Asn Asp Ser Ser Asp Leu Glu Ser Leu Leu Thr Glu Val
20 25 30

Glu Thr Pro Ile Arg Asn Glu Trp Gly Cys Arg Cys Asn Asp Ser Ser
35 40 45

Asp Glu Leu Asp
50

<210> SEQ ID NO 113
<211> LENGTH: 77
<212> TYPE: PRT
<213> ORGANISM: Artificial sequence
<220> FEATURE:
<223> OTHER INFORMATION: chimera of hepatitis B and influenza A

<400> SEQUENCE: 113

Met Ser Leu Leu Thr Glu Val Glu Thr Pro Ile Arg Asn Glu Trp Gly
1 5 10 15

Ser Arg Ser Asn Asp Ser Ser Asp Leu Gln Ser Leu Leu Thr Glu Val
20 25 30

Glu Thr Pro Ile Arg Asn Glu Trp Gly Ser Arg Ser Asn Asp Ser Ser
35 40 45

Asp Leu Glu Ser Leu Leu Thr Glu Val Glu Thr Pro Ile Arg Asn Glu
50 55 60

Trp Gly Cys Arg Cys Asn Asp Ser Ser Asp Glu Leu Asp
65 70 75

<210> SEQ ID NO 114
<211> LENGTH: 66
<212> TYPE: DNA
<213> ORGANISM: Artificial Sequence
<220> FEATURE:
<223> OTHER INFORMATION: Amplification primer containing a restriction
endonuclease site

<400> SEQUENCE: 114
gcgaagctta ctaacattga gattcccgag attgagatcg ccggcgacgc ggcgattgag 60
agcgtc 66

<210> SEQ ID NO 115
<211> LENGTH: 32
<212> TYPE: DNA
<213> ORGANISM: Artificial Sequence
<220> FEATURE:
<223> OTHER INFORMATION: Amplification primer containing a restriction
endonuclease site

<400> SEQUENCE: 115
gcgaagctta ctattgagat tcccgagatt ga 32

<210> SEQ ID NO 116
<211> LENGTH: 28
<212> TYPE: DNA
<213> ORGANISM: Artificial Sequence
<220> FEATURE:
<223> OTHER INFORMATION: Amplification primer containing a restriction
endonuclease site

<400> SEQUENCE: 116
ggaaagctta ctaacattga gattcccg 28

<210> SEQ ID NO 117
<211> LENGTH: 35
<212> TYPE: PRT
<213> ORGANISM: Hepatitis B virus

<400> SEQUENCE: 117

Val Arg Arg Arg Gly Arg Ser Pro Arg Arg Arg Thr Pro Ser Pro Arg
1 5 10 15

Arg Arg Arg Ser Gln Ser Pro Arg Arg Arg Arg Ser Gln Ser Arg Glu
20 25 30

Ser Gln Cys
35

<210> SEQ ID NO 118
<211> LENGTH: 34
<212> TYPE: PRT
<213> ORGANISM: Hepatitis B virus

<400> SEQUENCE: 118

Val Arg Arg Arg Gly Arg Ser Pro Arg Arg Arg Thr Pro Ser Pro Arg
1 5 10 15

Arg Arg Arg Ser Gln Ser Pro Arg Arg Arg Arg Ser Gln Ser Arg Glu
20 25 30

Ser Gln

<210> SEQ ID NO 119
<211> LENGTH: 24
<212> TYPE: PRT
<213> ORGANISM: Artificial Sequence
<220> FEATURE:
<223> OTHER INFORMATION: mutant of hepatitis B

<400> SEQUENCE: 119

Val Arg Arg Arg Gly Arg Ser Pro Arg Arg Arg Thr Pro Ser Pro Arg
1 5 10 15

Arg Arg Arg Ser Gln Ser Pro Cys
20

<210> SEQ ID NO 120
<211> LENGTH: 23
<212> TYPE: PRT
<213> ORGANISM: Artificial Sequence
<220> FEATURE:

<223> OTHER INFORMATION: hepatitis B mutant

<400> SEQUENCE: 120

Val Arg Arg Arg Gly Arg Ser Pro Arg Arg Arg Thr Pro Ser Pro Arg
1 5 10 15

Arg Arg Arg Ser Gln Ser Pro
20

<210> SEQ ID NO 121
<211> LENGTH: 16
<212> TYPE: PRT
<213> ORGANISM: Artificial Sequence
<220> FEATURE:
<223> OTHER INFORMATION: hepatitis B mutant

<400> SEQUENCE: 121

Val Arg Arg Arg Gly Arg Ser Pro Arg Arg Arg Thr Pro Ser Pro Cys
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: hepatitis B mutant

<400> SEQUENCE: 122

Val Arg Arg Arg Gly Arg Ser Pro Arg Arg Arg Thr Pro Ser Pro
1 5 10 15

<210> SEQ ID NO 123
<211> LENGTH: 9
<212> TYPE: PRT
<213> ORGANISM: Artificial Sequence
<220> FEATURE:
<223> OTHER INFORMATION: hepatitis B mutant

<400> SEQUENCE: 123

Val Arg Arg Arg Gly Arg Ser Pro Cys
1 5

<210> SEQ ID NO 124
<211> LENGTH: 8
<212> TYPE: PRT
<213> ORGANISM: Artificial sequence
<220> FEATURE:
<223> OTHER INFORMATION: hepatitis B mutant

<400> SEQUENCE: 124

Val Arg Arg Arg Gly Arg Ser Pro
1 5

<210> SEQ ID NO 125
<211> LENGTH: 9
<212> TYPE: PRT
<213> ORGANISM: Artificial sequence
<220> FEATURE:
<223> OTHER INFORMATION: chimer protein N-terminal fusion

<400> SEQUENCE: 125

Met Gly Cys Arg Cys Asn Asp Ser Ser
1 5

<210> SEQ ID NO 126
<211> LENGTH: 9
<212> TYPE: PRT
<213> ORGANISM: Artificial sequence
<220> FEATURE:
<223> OTHER INFORMATION: N-terminal fusion protein

<400> SEQUENCE: 126

Met Gly Ser Arg Ser Asn Asp Ser Ser
1 5

<210> SEQ ID NO 127
<211> LENGTH: 9
<212> TYPE: PRT
<213> ORGANISM: Artificial sequence
<220> FEATURE:
<223> OTHER INFORMATION: N-terminal fusion protein

<400> SEQUENCE: 127

Met Gly Ser Arg Cys Asn Asp Ser Ser
1 5

<210> SEQ ID NO 128
<211> LENGTH: 9
<212> TYPE: PRT
<213> ORGANISM: Artificial sequence
<220> FEATURE:
<223> OTHER INFORMATION: N-terminal fusion protein

<400> SEQUENCE: 128

Met Gly Cys Arg Ser Asn Asp Ser Ser
1 5

<210> SEQ ID NO 129
<211> LENGTH: 20
<212> TYPE: PRT
<213> ORGANISM: P. falciparum

<400> SEQUENCE: 129

Asn Ala Asn Pro Asn Val Asp Pro Asn Ala Asn Pro Asn Ala Asn Pro
1 5 10 15

Asn Ala Asn Pro
20

<210> SEQ ID NO 130
<211> LENGTH: 92
<212> TYPE: PRT
<213> ORGANISM: Influenza

<400> SEQUENCE: 130

Ser Leu Leu Thr Glu Val Glu Thr Pro Ile Arg Asn Glu Trp Gly Ser
1 5 10 15

Arg Ser Asn Asp Ser Ser Asp Ser Leu Leu Thr Glu Val Glu Thr Pro
20 25 30

Ile Arg Asn Glu Trp Gly Ser Arg Ser Asn Asp Ser Ser Asp Ser Leu
35 40 45

Leu Thr Glu Val Glu Thr Pro Ile Arg Asn Glu Trp Gly Ser Arg Ser
50 55 60

Asn Asp Ser Ser Asp Ser Leu Leu Thr Glu Val Glu Thr Pro Ile Arg
65 70 75 80

Asn Glu Trp Gly Cys Arg Cys Asn Asp Ser Ser Asp
85 90

<210> SEQ ID NO 131
<211> LENGTH: 115
<212> TYPE: PRT
<213> ORGANISM: Influenza

<400> SEQUENCE: 131

```
Ser Leu Leu Thr Glu Val Glu Thr Pro Ile Arg Asn Glu Trp Gly Ser
1               5                   10                  15

Arg Ser Asn Asp Ser Ser Asp Ser Leu Leu Thr Glu Val Glu Thr Pro
            20                  25                  30

Ile Arg Asn Glu Trp Gly Ser Arg Ser Asn Asp Ser Ser Asp Ser Leu
        35                  40                  45

Leu Thr Glu Val Glu Thr Pro Ile Arg Asn Glu Trp Gly Ser Arg Ser
    50                  55                  60

Asn Asp Ser Ser Asp Ser Leu Leu Thr Glu Val Glu Thr Pro Ile Arg
65                  70                  75                  80

Asn Glu Trp Gly Ser Arg Ser Asn Asp Ser Ser Asp Ser Leu Leu Thr
                85                  90                  95

Glu Val Glu Thr Pro Ile Arg Asn Glu Trp Gly Cys Arg Cys Asn Asp
            100                 105                 110

Ser Ser Asp
        115
```

```
<210> SEQ ID NO 132
<211> LENGTH: 93
<212> TYPE: PRT
<213> ORGANISM: Influenza
<220> FEATURE:
<221> NAME/KEY: MISC_FEATURE
<222> LOCATION: (1)..(1)
<223> OTHER INFORMATION: Xaa at position 1 is methionine or absent.  If
      methionine then Xaa in position 2 through 8 are not absent
<220> FEATURE:
<221> NAME/KEY: MISC_FEATURE
<222> LOCATION: (2)..(2)
<223> OTHER INFORMATION: Xaa at position 2 is serine or absent.  If
      serine then Xaa in position 3 through 8 are not absent.
<220> FEATURE:
<221> NAME/KEY: MISC_FEATURE
<222> LOCATION: (3)..(3)
<223> OTHER INFORMATION: Xaa at position 3 is leucine or absent.  If
      leucine then Xaa in position 4 through 8 are not absent.
<220> FEATURE:
<221> NAME/KEY: MISC_FEATURE
<222> LOCATION: (4)..(4)
<223> OTHER INFORMATION: Xaa at position 4 is leucine or absent.  If
      leucine then Xaa in position 5 through 8 are not absent.
<220> FEATURE:
<221> NAME/KEY: MISC_FEATURE
<222> LOCATION: (5)..(5)
<223> OTHER INFORMATION: Xaa at position 5 is threonine or proline or
      absent.  If threonine then Xaa in position 6 through 8 are not
      absent.
<220> FEATURE:
<221> NAME/KEY: MISC_FEATURE
<222> LOCATION: (6)..(6)
<223> OTHER INFORMATION: Xaa at position 6 is glutamic acid or absent.
      If glutamic acid then Xaa in position 7 through 8 are not absent.
<220> FEATURE:
<221> NAME/KEY: MISC_FEATURE
<222> LOCATION: (7)..(7)
<223> OTHER INFORMATION: Xaa at position 7 is valine or absent.  If
      valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or aspartic
      acid or absent.
<220> FEATURE:
<221> NAME/KEY: MISC_FEATURE
<222> LOCATION: (9)..(9)
<223> OTHER INFORMATION: Xaa at position 8 is glutamic acid or absent.
<220> FEATURE:
<221> NAME/KEY: MISC_FEATURE
<222> LOCATION: (10)..(10)
<223> OTHER INFORMATION: Xaa at position 10 is proline, leucine or
```

histidine.
<220> FEATURE:
<221> NAME/KEY: MISC_FEATURE
<222> LOCATION: (11)..(11)
<223> OTHER INFORMATION: Xaa at position 11 is isoleucine or threonine.
<220> FEATURE:
<221> NAME/KEY: MISC_FEATURE
<222> LOCATION: (12)..(12)
<223> OTHER INFORMATION: Xaa at position 12 is arginine or lysine.
<220> FEATURE:
<221> NAME/KEY: MISC_FEATURE
<222> LOCATION: (13)..(13)
<223> OTHER INFORMATION: Xaa at position 13 is asparagine or serine.
<220> FEATURE:
<221> NAME/KEY: MISC_FEATURE
<222> LOCATION: (14)..(14)
<223> OTHER INFORMATION: Xaa at position 14 is glutamic acid or glycine.
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa at position 16 is glycine, glutamic acid or absent. If glycine or glutamic acid then Xaa in position 16 is not absent.
<220> FEATURE:
<221> NAME/KEY: MISC_FEATURE
<222> LOCATION: (17)..(17)
<223> OTHER INFORMATION: Xaa at position 17 is absent or present, if present Xaa in position 17 is cysteine, serine or alanine. If Xaa in position 17 is present then positions 15 through 16 are not absent.
<220> FEATURE:
<221> NAME/KEY: MISC_FEATURE
<222> LOCATION: (18)..(18)
<223> OTHER INFORMATION: Xaa at position 18 arginine, lysine or absent. If arginine or lysine then Xaa in positions 15 through 17 are not absent.
<220> FEATURE:
<221> NAME/KEY: MISC_FEATURE
<222> LOCATION: (19)..(19)
<223> OTHER INFORMATION: Xaa at position 19 is absent or present, if present Xaa in position 19 is cysteine, serine or alanine. If Xaa is position 19 is present then positions 15 through 18 are not absent.
<220> FEATURE:
<221> NAME/KEY: MISC_FEATURE
<222> LOCATION: (20)..(20)
<223> OTHER INFORMATION: Xaa at position 20 is asparagine, serine, glycine or absent. If asparagine or serine or glycine then Xaa is positions 15 through 19 are not absent.
<220> FEATURE:
<221> NAME/KEY: MISC_FEATURE
<222> LOCATION: (21)..(21)
<223> OTHER INFORMATION: Xaa at position 21 is aspartic acid, glycine or absent. If aspartic acid or glycine then Xaa is positions 15 through 20 are not absent.
<220> FEATURE:
<221> NAME/KEY: MISC_FEATURE
<222> LOCATION: (22)..(22)
<223> OTHER INFORMATION: Xaa at position 22 is serine or absent. If serine then Xaa is positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent. If serine then Xaa is positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent. If aspartic acid then Xaa is positions 15 through 23 are not absent.
<220> FEATURE:
<221> NAME/KEY: MISC_FEATURE
<222> LOCATION: (25)..(25)
<223> OTHER INFORMATION: Xaa at position 25 is serine or absent. If serine then Xaa in positions 26 through 31 are not absent.

-continued

<220> FEATURE:
<221> NAME/KEY: MISC_FEATURE
<222> LOCATION: (26)..(26)
<223> OTHER INFORMATION: Xaa at position 26 is leucine or absent. If leucine then Xaa in positions 27 through 31 are not absent.
<220> FEATURE:
<221> NAME/KEY: MISC_FEATURE
<222> LOCATION: (27)..(27)
<223> OTHER INFORMATION: Xaa at position 27 is leucine or absent. If leucine then Xaa in positions 28 through 31 are not absent.
<220> FEATURE:
<221> NAME/KEY: MISC_FEATURE
<222> LOCATION: (28)..(28)
<223> OTHER INFORMATION: Xaa at position 28 is threonine, proline or absent. If threonine or proline then Xaa in positions 29 through 31 are not absent.
<220> FEATURE:
<221> NAME/KEY: MISC_FEATURE
<222> LOCATION: (29)..(29)
<223> OTHER INFORMATION: Xaa at position 29 is glutamic acid or absent. If glutamic acid then Xaa in positions 30 through 31 are not absent.
<220> FEATURE:
<221> NAME/KEY: MISC_FEATURE
<222> LOCATION: (30)..(30)
<223> OTHER INFORMATION: Xaa at position 30 is valine or absent. If valine then Xaa in position 31 is not absent.
<220> FEATURE:
<221> NAME/KEY: MISC_FEATURE
<222> LOCATION: (31)..(31)
<223> OTHER INFORMATION: Xaa at position 31 is glutamic acid or aspartic acid or absent.
<220> FEATURE:
<221> NAME/KEY: MISC_FEATURE
<222> LOCATION: (33)..(33)
<223> OTHER INFORMATION: Xaa at position 33 is proline, leucine or histidine.
<220> FEATURE:
<221> NAME/KEY: MISC_FEATURE
<222> LOCATION: (34)..(34)
<223> OTHER INFORMATION: Xaa at position 34 is isoleucine or threonine
<220> FEATURE:
<221> NAME/KEY: MISC_FEATURE
<222> LOCATION: (35)..(35)
<223> OTHER INFORMATION: Xaa at position 35 is arginine or lysine.
<220> FEATURE:
<221> NAME/KEY: MISC_FEATURE
<222> LOCATION: (36)..(36)
<223> OTHER INFORMATION: Xaa at position 36 is asparagine or serine.
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: MISC_FEATURE
<222> LOCATION: (38)..(38)
<223> OTHER INFORMATION: Xaa at position 38 is tryptophan or absent.
<220> FEATURE:
<221> NAME/KEY: MISC_FEATURE
<222> LOCATION: (39)..(39)
<223> OTHER INFORMATION: Xaa at position 39 is glycine, glutamic acid or absent. If glycine or glutamic acid then Xaa in position 38 is not absent.
<220> FEATURE:
<221> NAME/KEY: MISC_FEATURE
<222> LOCATION: (40)..(40)
<223> OTHER INFORMATION: Xaa at position 40 is absent of present, if present Xaa in position 40 is cysteine, serine or alanine. If Xaa in position 40 is present then positions 38 through 39 are not absent.
<220> FEATURE:
<221> NAME/KEY: MISC_FEATURE
<222> LOCATION: (41)..(41)
<223> OTHER INFORMATION: Xaa at position 41 is arginine, lysine or absent. If arginine or lysine than Xaa in positions 38 through 40 are not absent.
<220> FEATURE:
<221> NAME/KEY: MISC_FEATURE
<222> LOCATION: (42)..(42)
<223> OTHER INFORMATION: Xaa at position 42 is absent or present, if present Xaa in position 42 is cysteine, serine or alanine. If Xaa in position 42 is present then positions 38 through 41 are not absent.
<220> FEATURE:
<221> NAME/KEY: MISC_FEATURE
<222> LOCATION: (43)..(43)
<223> OTHER INFORMATION: Xaa at position 43 is asparagine, serine, glycine or absent. If asparagine or serine or glycine then Xaa in positions 38 through 42 are not absent.
<220> FEATURE:
<221> NAME/KEY: MISC_FEATURE
<222> LOCATION: (44)..(44)
<223> OTHER INFORMATION: Xaa at position 44 is aspartic acid, glycine or absent. If aspartic acid or glycine then Xaa in positions 38 through 43 are not absent.
<220> FEATURE:
<221> NAME/KEY: MISC_FEATURE
<222> LOCATION: (45)..(45)
<223> OTHER INFORMATION: Xaa at position 45 is serine or absent. If serine then Xaa in positions 38 through 44 are not absent.
<220> FEATURE:
<221> NAME/KEY: MISC_FEATURE
<222> LOCATION: (46)..(46)
<223> OTHER INFORMATION: Xaa at position 46 is serine or absent. If serine then Xaa in positions 38 through 45 are not absent.
<220> FEATURE:
<221> NAME/KEY: MISC_FEATURE
<222> LOCATION: (47)..(47)
<223> OTHER INFORMATION: Xaa at position 47 is aspartic acid or absent. If aspartic acid then Xaa in positions 38 through 46 are not absent.
<220> FEATURE:
<221> NAME/KEY: MISC_FEATURE
<222> LOCATION: (48)..(48)
<223> OTHER INFORMATION: Xaa at position 48 is serine or absent. If serine then Xaa in positions 49 through 54 are not absent.
<220> FEATURE:
<221> NAME/KEY: MISC_FEATURE
<222> LOCATION: (49)..(49)
<223> OTHER INFORMATION: Xaa at position 49 is leucine or absent. If leucine then Xaa in positions 50 through 54 are not absent.
<220> FEATURE:
<221> NAME/KEY: MISC_FEATURE
<222> LOCATION: (50)..(50)
<223> OTHER INFORMATION: Xaa at position 50 is leucine or absent. If leucine then Xaa in positions 51 through 54 are not absent.
<220> FEATURE:
<221> NAME/KEY: MISC_FEATURE
<222> LOCATION: (51)..(51)
<223> OTHER INFORMATION: Xaa at position 51 is threonine, proline or absent. If threonine or proline then Xaa in positions 52 through 54 are not absent.
<220> FEATURE:
<221> NAME/KEY: MISC_FEATURE
<222> LOCATION: (52)..(52)
<223> OTHER INFORMATION: Xaa at position 52 is glutamic acid or absent. If glutamic acid then Xaa in positions 53 through 54 are not absent.
<220> FEATURE:
<221> NAME/KEY: MISC_FEATURE
<222> LOCATION: (53)..(53)
<223> OTHER INFORMATION: Xaa at position 53 is valine or absent. If valine then Xaa in position 54 is not absent.
<220> FEATURE:
<221> NAME/KEY: MISC_FEATURE
<222> LOCATION: (54)..(54)
<223> OTHER INFORMATION: Xaa at position 54 is glutamic acid or aspartic acid or absent
<220> FEATURE:
<221> NAME/KEY: MISC_FEATURE
<222> LOCATION: (56)..(56)
<223> OTHER INFORMATION: Xaa at position 56 is proline, leucine or histidine.
<220> FEATURE:
<221> NAME/KEY: MISC_FEATURE
<222> LOCATION: (57)..(57)
<223> OTHER INFORMATION: Xaa at position 57 is isoleucine or threonine.
<220> FEATURE:
<221> NAME/KEY: MISC_FEATURE
<222> LOCATION: (58)..(58)

<223> OTHER INFORMATION: Xaa at position 58 is arginine or lysine.
<220> FEATURE:
<221> NAME/KEY: MISC_FEATURE
<222> LOCATION: (59)..(59)
<223> OTHER INFORMATION: Xaa at position 59 is asparagine or serine.
<220> FEATURE:
<221> NAME/KEY: MISC_FEATURE
<222> LOCATION: (60)..(60)
<223> OTHER INFORMATION: Xaa at position 60 is glumatic acid or glycine.
<220> FEATURE:
<221> NAME/KEY: MISC_FEATURE
<222> LOCATION: (61)..(61)
<223> OTHER INFORMATION: Xaa at position 61 is tryptophan or absent.
<220> FEATURE:
<221> NAME/KEY: MISC_FEATURE
<222> LOCATION: (62)..(62)
<223> OTHER INFORMATION: Xaa at position 62 is glycine, glutamic acid or absent. If glycine or glutamic acid then Xaa in position 61 is not absent.
<220> FEATURE:
<221> NAME/KEY: MISC_FEATURE
<222> LOCATION: (63)..(63)
<223> OTHER INFORMATION: Xaa at position 63 is absent of present, if present Xaa in position 63 is cysteine, serine or alanine. If Xaa in position 63 is present then positions 61 through 62 are not absent.
<220> FEATURE:
<221> NAME/KEY: MISC_FEATURE
<222> LOCATION: (64)..(64)
<223> OTHER INFORMATION: Xaa at position 64 is arginine, lysine or absent. If arginine or lysine than Xaa in positions 61 through 63 are not absent.
<220> FEATURE:
<221> NAME/KEY: MISC_FEATURE
<222> LOCATION: (65)..(65)
<223> OTHER INFORMATION: Xaa at position 65 is absent or present, if present Xaa in position 65 is cysteine, serine or alanine. If Xaa in position 65 is present then positions 61 through 64 are not absent.
<220> FEATURE:
<221> NAME/KEY: MISC_FEATURE
<222> LOCATION: (66)..(66)
<223> OTHER INFORMATION: Xaa at position 66 is asparagine, serine, glycine or absent. If asparagine or serine or glycine then Xaa in positions 61 through 65 are not absent.
<220> FEATURE:
<221> NAME/KEY: MISC_FEATURE
<222> LOCATION: (67)..(67)
<223> OTHER INFORMATION: Xaa at position 67 is aspartic acid, glycine or absent. If aspartic acid or glycine then Xaa in positions 61 through 66 are not absent.
<220> FEATURE:
<221> NAME/KEY: MISC_FEATURE
<222> LOCATION: (68)..(68)
<223> OTHER INFORMATION: Xaa at position 68 is serine or absent. If serine then Xaa in positions 61 through 67 are not absent.
<220> FEATURE:
<221> NAME/KEY: MISC_FEATURE
<222> LOCATION: (69)..(69)
<223> OTHER INFORMATION: Xaa at position 69 is serine or absent. If serine then Xaa in positions 61 through 68 are not absent.
<220> FEATURE:
<221> NAME/KEY: MISC_FEATURE
<222> LOCATION: (70)..(70)
<223> OTHER INFORMATION: Xaa at position 70 is aspartic acid or absent. If aspartic acid then Xaa in positions 61 through 69 are not absent.
<220> FEATURE:
<221> NAME/KEY: MISC_FEATURE
<222> LOCATION: (71)..(71)
<223> OTHER INFORMATION: Xaa at position 71 is serine or absent. If serine then Xaa in positions 72 through 77 are not absent.
<220> FEATURE:
<221> NAME/KEY: MISC_FEATURE
<222> LOCATION: (72)..(72)
<223> OTHER INFORMATION: Xaa at position 72 is leucine or absent. If leucine then Xaa in positions 73 through 77 are not absent.
<220> FEATURE:
<221> NAME/KEY: MISC_FEATURE
<222> LOCATION: (73)..(73)

```
<223> OTHER INFORMATION: Xaa at position 73 is leucine or absent.  If
      leucine then Xaa in positions 74 through 77 are not absent.
<220> FEATURE:
<221> NAME/KEY: MISC_FEATURE
<222> LOCATION: (74)..(74)
<223> OTHER INFORMATION: Xaa at position 74 is threonine, proline or
      absent.  If threonine or proline then Xaa in positions 75 through
      77 are not absent.
<220> FEATURE:
<221> NAME/KEY: MISC_FEATURE
<222> LOCATION: (75)..(75)
<223> OTHER INFORMATION: Xaa at position 75 is glutamic acid or absent.
      If glutamic acid then Xaa in positions 76 through 77 are not
      absent.
<220> FEATURE:
<221> NAME/KEY: MISC_FEATURE
<222> LOCATION: (76)..(76)
<223> OTHER INFORMATION: Xaa at position 76 is valine or absent.  If
      valine then Xaa in position 77 is not absent.
<220> FEATURE:
<221> NAME/KEY: MISC_FEATURE
<222> LOCATION: (77)..(77)
<223> OTHER INFORMATION: Xaa at position 77 is glutamic acid or aspartic
      acid or absent
<220> FEATURE:
<221> NAME/KEY: MISC_FEATURE
<222> LOCATION: (79)..(79)
<223> OTHER INFORMATION: Xaa at position 79 is proline, leucine or
      histidine.
<220> FEATURE:
<221> NAME/KEY: MISC_FEATURE
<222> LOCATION: (80)..(80)
<223> OTHER INFORMATION: Xaa at position 80 is isoleucine or threonine.
<220> FEATURE:
<221> NAME/KEY: MISC_FEATURE
<222> LOCATION: (81)..(81)
<223> OTHER INFORMATION: Xaa at position 81 is arginine or lysine.
<220> FEATURE:
<221> NAME/KEY: MISC_FEATURE
<222> LOCATION: (82)..(82)
<223> OTHER INFORMATION: Xaa at position 82 is asparagine or serine.
<220> FEATURE:
<221> NAME/KEY: MISC_FEATURE
<222> LOCATION: (83)..(83)
<223> OTHER INFORMATION: Xaa at position 83 is glumatic acid or glycine.
<220> FEATURE:
<221> NAME/KEY: MISC_FEATURE
<222> LOCATION: (84)..(84)
<223> OTHER INFORMATION: Xaa at position 84 is tryptophan or absent.
<220> FEATURE:
<221> NAME/KEY: MISC_FEATURE
<222> LOCATION: (85)..(85)
<223> OTHER INFORMATION: Xaa at position 85 is glycine, glutamic acid or
      absent.  If glycine or glutamic acid then Xaa in position 84 is
      not absent.
<220> FEATURE:
<221> NAME/KEY: MISC_FEATURE
<222> LOCATION: (86)..(86)
<223> OTHER INFORMATION: Xaa at position 86 is absent of present, if
      present Xaa in position 86 is cysteine, serine or alanine.  If Xaa
      in position 86 is present then positions 84 through 85 are not
      absent.
<220> FEATURE:
<221> NAME/KEY: MISC_FEATURE
<222> LOCATION: (87)..(87)
<223> OTHER INFORMATION: Xaa at position 87 is arginine, lysine or
      absent.  If arginine or lysine than Xaa in positions 84 through 86
      are not absent.
<220> FEATURE:
<221> NAME/KEY: MISC_FEATURE
<222> LOCATION: (88)..(88)
<223> OTHER INFORMATION: Xaa at position 88 is absent or present, if
      present Xaa in position 88 is cysteine, serine or alanine.  If Xaa
      in position 88 is present then positions 84 through 87 are not
      absent.
<220> FEATURE:
<221> NAME/KEY: MISC_FEATURE
<222> LOCATION: (89)..(89)
<223> OTHER INFORMATION: Xaa at position 89 is asparagine, serine,
      glycine or absent.  If asparagine or serine or glycine then Xaa in
```

```
      positions 84 through 88 are not absent.
<220> FEATURE:
<221> NAME/KEY: MISC_FEATURE
<222> LOCATION: (90)..(90)
<223> OTHER INFORMATION: Xaa at position 90 is aspartic acid, glycine or
      absent.  If aspartic acid or glycine then Xaa in positions 84
      through 89 are not absent.
<220> FEATURE:
<221> NAME/KEY: MISC_FEATURE
<222> LOCATION: (91)..(91)
<223> OTHER INFORMATION: Xaa at position 91 is serine or absent.  If
      serine then Xaa in positions 84 through 90 are not absent.
<220> FEATURE:
<221> NAME/KEY: MISC_FEATURE
<222> LOCATION: (92)..(92)
<223> OTHER INFORMATION: Xaa at position 92 is serine or absent.  If
      serine then Xaa in positions 84 through 91 are not absent.
<220> FEATURE:
<221> NAME/KEY: MISC_FEATURE
<222> LOCATION: (93)..(93)
<223> OTHER INFORMATION: Xaa at position 93 is aspartic acid or absent.
      If aspartic acid then Xaa in positions 84 through 92 are not
      absent.

<400> SEQUENCE: 132

Xaa Xaa Xaa Xaa Xaa Xaa Xaa Xaa Thr Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Thr
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Thr Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Thr Xaa Xaa
65                  70                  75                  80

Xaa Xaa Xaa Xaa Xaa Xaa Xaa Xaa Xaa Xaa Xaa Xaa Xaa
                85                  90


<210> SEQ ID NO 133
<211> LENGTH: 93
<212> TYPE: PRT
<213> ORGANISM: Influenza
<220> FEATURE:
<221> NAME/KEY: MISC_FEATURE
<222> LOCATION: (1)..(1)
<223> OTHER INFORMATION: Xaa at position 1 is methionine or absent.  If
      methionine then Xaa in positions 2 through 8 are not absent
<220> FEATURE:
<221> NAME/KEY: MISC_FEATURE
<222> LOCATION: (2)..(2)
<223> OTHER INFORMATION: Xaa at position 2 is serine or absent.  If
      serine then Xaa in positions 3 through 8 are not absent
<220> FEATURE:
<221> NAME/KEY: MISC_FEATURE
<222> LOCATION: (3)..(3)
<223> OTHER INFORMATION: Xaa at position 3 is leucine or absent.  If
      leucine then Xaa in positions 4 through 8 are not absent.
<220> FEATURE:
<221> NAME/KEY: MISC_FEATURE
<222> LOCATION: (4)..(4)
<223> OTHER INFORMATION: Xaa at position 4 is leucine or absent.  If
      leucine then Xaa in positions 5 through 8 are not absent.
<220> FEATURE:
<221> NAME/KEY: MISC_FEATURE
<222> LOCATION: (5)..(5)
<223> OTHER INFORMATION: Xaa at position 5 is threonine or absent.  If
      threonine than Xaa in positions 6 through 8 are not absent.
<220> FEATURE:
<221> NAME/KEY: MISC_FEATURE
<222> LOCATION: (6)..(6)
<223> OTHER INFORMATION: Xaa at position 6 is glutamic acid or absent.
      If glutamic acid then Xaa in positions 7 through 8 are not absent.
<220> FEATURE:
```

<221> NAME/KEY: MISC_FEATURE
<222> LOCATION: (7)..(7)
<223> OTHER INFORMATION: Xaa at position 7 is valine or absent. If valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or absent.
<220> FEATURE:
<221> NAME/KEY: MISC_FEATURE
<222> LOCATION: (15)..(15)
<223> OTHER INFORMATION: Xaa at position 15 is tryptophan or absent.
<220> FEATURE:
<221> NAME/KEY: MISC_FEATURE
<222> LOCATION: (16)..(16)
<223> OTHER INFORMATION: Xaa at position 16 is glycine or absent. If glycine then Xaa in position 15 is not absent.
<220> FEATURE:
<221> NAME/KEY: MISC_FEATURE
<222> LOCATION: (17)..(17)
<223> OTHER INFORMATION: Xaa at position 17 is absent or present, if present Xaa in position 17 is cysteine, serine, or alanine. If Xaa in position 17 is present then positions 15 through 16 are not absent.
<220> FEATURE:
<221> NAME/KEY: MISC_FEATURE
<222> LOCATION: (18)..(18)
<223> OTHER INFORMATION: Xaa at position 18 is arginine or absent. If arginine then Xaa in positions 15 through 17 are not absent.
<220> FEATURE:
<221> NAME/KEY: MISC_FEATURE
<222> LOCATION: (19)..(19)
<223> OTHER INFORMATION: Xaa at position 19 is absent or present, if present Xaa in position 19 is cysteine, serine or alanine. If Xaa in position 19 is present then positions 15 through 18 are not absent.
<220> FEATURE:
<221> NAME/KEY: MISC_FEATURE
<222> LOCATION: (20)..(20)
<223> OTHER INFORMATION: Xaa at position 20 is asparagine or absent. If asparagine then Xaa in positions 15 through 19 are not absent.
<220> FEATURE:
<221> NAME/KEY: MISC_FEATURE
<222> LOCATION: (21)..(21)
<223> OTHER INFORMATION: Xaa at position 21 is aspartic acid or absent. If aspartic acid then Xaa in positions 15 through 20 are not absent.
<220> FEATURE:
<221> NAME/KEY: MISC_FEATURE
<222> LOCATION: (22)..(22)
<223> OTHER INFORMATION: Xaa at position 22 is serine or absent. If serine then Xaa in positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent. If serine then Xaa in positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent. If aspartic acid then Xaa in positions 15 through 23 are not absent.
<220> FEATURE:
<221> NAME/KEY: MISC_FEATURE
<222> LOCATION: (25)..(25)
<223> OTHER INFORMATION: Xaa at position 25 is serine or absent. If serine then Xaa in positions 26 through 31 are not absent
<220> FEATURE:
<221> NAME/KEY: MISC_FEATURE
<222> LOCATION: (26)..(26)
<223> OTHER INFORMATION: Xaa at position 26 is leucine or absent. If serine then Xaa in positions 27 through 31 are not absent
<220> FEATURE:
<221> NAME/KEY: MISC_FEATURE
<222> LOCATION: (27)..(27)
<223> OTHER INFORMATION: Xaa at position 27 is leucine or absent. If leucine then Xaa in positions 28 through 31 are not absent.
<220> FEATURE:
<221> NAME/KEY: MISC_FEATURE
<222> LOCATION: (28)..(28)
<223> OTHER INFORMATION: Xaa at position 28 is threonine or absent. If
      threonine than Xaa in positions 29 through 31 are not absent.
<220> FEATURE:
<221> NAME/KEY: MISC_FEATURE
<222> LOCATION: (29)..(29)
<223> OTHER INFORMATION: Xaa at position 29 is glutamic acid or absent.
      If glutamic acid then Xaa in positions 30 through 31 are not
      absent.
<220> FEATURE:
<221> NAME/KEY: MISC_FEATURE
<222> LOCATION: (30)..(30)
<223> OTHER INFORMATION: Xaa at position 30 is valine or absent. If
      valine then Xaa in position 31 is not absent.
<220> FEATURE:
<221> NAME/KEY: MISC_FEATURE
<222> LOCATION: (31)..(31)
<223> OTHER INFORMATION: Xaa at position 31 is glutamic acid or absent.
<220> FEATURE:
<221> NAME/KEY: MISC_FEATURE
<222> LOCATION: (32)..(32)
<223> OTHER INFORMATION: Xaa at position 38 is tryptophan or absent.
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: MISC_FEATURE
<222> LOCATION: (39)..(39)
<223> OTHER INFORMATION: Xaa at position 39 is glycine or absent. If
      glycine then Xaa in position 38 is not absent.
<220> FEATURE:
<221> NAME/KEY: MISC_FEATURE
<222> LOCATION: (40)..(40)
<223> OTHER INFORMATION: Xaa at position 40 is absent or present, if
      present Xaa in position 40 is cysteine, serine or alanine. If Xaa
      in position 40 is present then positions 38 through 39 are not
      absent.
<220> FEATURE:
<221> NAME/KEY: MISC_FEATURE
<222> LOCATION: (41)..(41)
<223> OTHER INFORMATION: Xaa at position 41 is arginine or absent. If
      arginine then Xaa in positions 38 through 40 are not absent
<220> FEATURE:
<221> NAME/KEY: MISC_FEATURE
<222> LOCATION: (42)..(42)
<223> OTHER INFORMATION: Xaa at position 42 is absent or present, if
      present Xaa in position 42 is cysteine, serine or alanine. If Xaa
      in position 42 is present then positions 38 through 41 are not
      absent.
<220> FEATURE:
<221> NAME/KEY: MISC_FEATURE
<222> LOCATION: (43)..(43)
<223> OTHER INFORMATION: Xaa at position 43 is asparagine or absent. If
      asparagine then Xaa in positions 38 through 42 are not absent.
<220> FEATURE:
<221> NAME/KEY: MISC_FEATURE
<222> LOCATION: (44)..(44)
<223> OTHER INFORMATION: Xaa at position 44 is aspartic acid or absent.
      If aspartic acid then Xaa in positions 38 through 43 are not
      absent.
<220> FEATURE:
<221> NAME/KEY: MISC_FEATURE
<222> LOCATION: (45)..(45)
<223> OTHER INFORMATION: Xaa at position 45 is serine or absent. If
      serine then Xaa in positions 38 through 44 are not absent.
<220> FEATURE:
<221> NAME/KEY: MISC_FEATURE
<222> LOCATION: (46)..(46)
<223> OTHER INFORMATION: Xaa at position 46 is serine or absent. If
      serine then Xaa in positions 38 through 45 are not absent.
<220> FEATURE:
<221> NAME/KEY: MISC_FEATURE
<222> LOCATION: (47)..(47)
<223> OTHER INFORMATION: Xaa at position 47 is aspartic acid or absent.
      If aspartic acid then Xaa in positions 38 through 46 are not
      absent.
<220> FEATURE:
<221> NAME/KEY: MISC_FEATURE
<222> LOCATION: (48)..(48)

```
<223> OTHER INFORMATION: Xaa at position 48 is serine or absent.  If
      serine then Xaa in positions 49 through 54 are not absent.
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: MISC_FEATURE
<222> LOCATION: (50)..(50)
<223> OTHER INFORMATION: Xaa at position 50 is leucine or absent.  If
      leucine then Xaa in positions 51 through 54 are not absent.
<220> FEATURE:
<221> NAME/KEY: MISC_FEATURE
<222> LOCATION: (51)..(51)
<223> OTHER INFORMATION: Xaa at position 51 is threonine or absent.  If
      threonine than Xaa in positions 52 through 54 are not absent.
<220> FEATURE:
<221> NAME/KEY: MISC_FEATURE
<222> LOCATION: (52)..(52)
<223> OTHER INFORMATION: Xaa at position 52 is glutamic acid or absent.
      If glutamic acid then Xaa in positions 53 through 54 are not
      absent.
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: MISC_FEATURE
<222> LOCATION: (54)..(54)
<223> OTHER INFORMATION: Xaa at position 54 is glutamic acid or absent
<220> FEATURE:
<221> NAME/KEY: MISC_FEATURE
<222> LOCATION: (61)..(61)
<223> OTHER INFORMATION: Xaa at position 61 is tryptophan or absent.
<220> FEATURE:
<221> NAME/KEY: MISC_FEATURE
<222> LOCATION: (62)..(62)
<223> OTHER INFORMATION: Xaa at position 62 is glycine or absent.  If
      glycine then Xaa in position 61 is not absent.
<220> FEATURE:
<221> NAME/KEY: MISC_FEATURE
<222> LOCATION: (63)..(63)
<223> OTHER INFORMATION: Xaa at position 63 is absent or present, if
      present Xaa in position 63 is cysteine, serine or alanine.  If Xaa
      in position 63 is present then positions 61 through 62 are not
      absent.
<220> FEATURE:
<221> NAME/KEY: MISC_FEATURE
<222> LOCATION: (64)..(64)
<223> OTHER INFORMATION: Xaa at position 64 is arginine or absent.  If
      arginine then Xaa in positions 61 through 63 are not absent
<220> FEATURE:
<221> NAME/KEY: MISC_FEATURE
<222> LOCATION: (65)..(65)
<223> OTHER INFORMATION: Xaa at position 65 is absent or present, if
      present Xaa in position 65 is cysteine, serine or alanine.  If Xaa
      in position 65 is present then positions 61 through 64 are not
      absent.
<220> FEATURE:
<221> NAME/KEY: MISC_FEATURE
<222> LOCATION: (66)..(66)
<223> OTHER INFORMATION: Xaa at position 66 is asparagine or absent.  If
      asparagine then Xaa in positions 61 through 65 are not absent.
<220> FEATURE:
<221> NAME/KEY: MISC_FEATURE
<222> LOCATION: (67)..(67)
<223> OTHER INFORMATION: Xaa at position 67 is aspartic acid or absent.
      If aspartic acid then Xaa in positions 61 through 66 are not
      absent.
<220> FEATURE:
<221> NAME/KEY: MISC_FEATURE
<222> LOCATION: (68)..(68)
<223> OTHER INFORMATION: Xaa at position 68 is serine or absent.  If
      serine then Xaa in positions 61 through 67 are not absent.
<220> FEATURE:
<221> NAME/KEY: MISC_FEATURE
<222> LOCATION: (69)..(69)
<223> OTHER INFORMATION: Xaa at position 69 is serine or absent.  If
      serine then Xaa in positions 61 through 68 are not absent.
<220> FEATURE:
```

```
<221> NAME/KEY: MISC_FEATURE
<222> LOCATION: (70)..(70)
<223> OTHER INFORMATION: Xaa at position 70 is aspartic acid or absent.
      If aspartic acid then Xaa in positions 61 through 69 are not
      absent.
<220> FEATURE:
<221> NAME/KEY: MISC_FEATURE
<222> LOCATION: (71)..(71)
<223> OTHER INFORMATION: Xaa at position 71 is serine or absent.  If
      serine then Xaa in positions 72 through 77 are not absent
<220> FEATURE:
<221> NAME/KEY: MISC_FEATURE
<222> LOCATION: (72)..(72)
<223> OTHER INFORMATION: Xaa at position 72 is leucine or absent.  If
      serine then Xaa in positions 73 through 77 are not absent
<220> FEATURE:
<221> NAME/KEY: MISC_FEATURE
<222> LOCATION: (73)..(73)
<223> OTHER INFORMATION: Xaa at position 73 is leucine or absent.  If
      leucine then Xaa in positions 74 through 77 are not absent.
<220> FEATURE:
<221> NAME/KEY: MISC_FEATURE
<222> LOCATION: (74)..(74)
<223> OTHER INFORMATION: Xaa at position 74 is threonine or absent.  If
      threonine than Xaa in positions 75 through 77 are not absent.
<220> FEATURE:
<221> NAME/KEY: MISC_FEATURE
<222> LOCATION: (75)..(75)
<223> OTHER INFORMATION: Xaa at position 75 is glutamic acid or absent.
      If glutamic acid than Xaa in positions 76 through 77 are not
      absent.
<220> FEATURE:
<221> NAME/KEY: MISC_FEATURE
<222> LOCATION: (76)..(76)
<223> OTHER INFORMATION: Xaa at position 76 is valine or absent.  If
      valine then Xaa in position 77 is not absent.
<220> FEATURE:
<221> NAME/KEY: MISC_FEATURE
<222> LOCATION: (77)..(77)
<223> OTHER INFORMATION: Xaa at position 77 is glutamic acid or absent.
<220> FEATURE:
<221> NAME/KEY: MISC_FEATURE
<222> LOCATION: (84)..(84)
<223> OTHER INFORMATION: Xaa at position 84 is tryptophan or absent.
<220> FEATURE:
<221> NAME/KEY: MISC_FEATURE
<222> LOCATION: (85)..(85)
<223> OTHER INFORMATION: Xaa at position 85 is glycine or absent.  If
      glycine then Xaa in position 84 is not absent.
<220> FEATURE:
<221> NAME/KEY: MISC_FEATURE
<222> LOCATION: (86)..(86)
<223> OTHER INFORMATION: Xaa at position 86 is absent or present, if
      present Xaa in position 86 is cysteine, serine or alanine.  If Xaa
      in position 86 is present then positions 84 through 85 are not
      absent.
<220> FEATURE:
<221> NAME/KEY: MISC_FEATURE
<222> LOCATION: (87)..(87)
<223> OTHER INFORMATION: Xaa at position 87 is arginine or absent.  If
      arginine then Xaa in positions 84 through 86 are not absent
<220> FEATURE:
<221> NAME/KEY: MISC_FEATURE
<222> LOCATION: (88)..(88)
<223> OTHER INFORMATION: Xaa at position 88 is absent or present, if
      present Xaa in position 88 is cysteine, serine or alanine.  If Xaa
      in position 88 is present then positions 84 through 87 are not
      absent.
<220> FEATURE:
<221> NAME/KEY: MISC_FEATURE
<222> LOCATION: (89)..(89)
<223> OTHER INFORMATION: Xaa at position 89 is asparagine or absent.  If
      asparagine then Xaa in positions 84 through 88 are not absent.
<220> FEATURE:
<221> NAME/KEY: MISC_FEATURE
<222> LOCATION: (90)..(90)
<223> OTHER INFORMATION: Xaa at position 90 is aspartic acid or absent.
      If aspartic acid then Xaa in positions 84 through 89 are not
      absent.
<220> FEATURE:
```

<221> NAME/KEY: MISC_FEATURE
<222> LOCATION: (91)..(91)
<223> OTHER INFORMATION: Xaa at position 91 is serine or absent. If serine then Xaa in positions 84 through 90are not absent.
<220> FEATURE:
<221> NAME/KEY: MISC_FEATURE
<222> LOCATION: (92)..(92)
<223> OTHER INFORMATION: Xaa at position 92 is serine or absent. If serine then Xaa in positions 84 through 91 are not absent.
<220> FEATURE:
<221> NAME/KEY: MISC_FEATURE
<222> LOCATION: (93)..(93)
<223> OTHER INFORMATION: Xaa at position 93 is aspartic acid or absent. If aspartic acid then Xaa in positions 84 through 92 are not absent.

<400> SEQUENCE: 133

```
Xaa Xaa Xaa Xaa Xaa Xaa Xaa Xaa Thr Pro Ile Arg Asn Glu Xaa Xaa
1               5                   10                  15

Xaa Xaa Xaa Xaa Xaa Xaa Xaa Xaa Xaa Xaa Xaa Xaa Xaa Xaa Xaa Thr
            20                  25                  30

Pro Ile Arg Asn Glu Xaa Xaa Xaa Xaa Xaa Xaa Xaa Xaa Xaa Xaa Xaa
        35                  40                  45

Xaa Xaa Xaa Xaa Xaa Xaa Thr Pro Ile Arg Asn Glu Xaa Xaa Xaa Xaa
    50                  55                  60

Xaa Xaa Xaa Xaa Xaa Xaa Xaa Xaa Xaa Xaa Xaa Xaa Xaa Thr Pro Ile
65                  70                  75                  80

Arg Asn Glu Xaa Xaa Xaa Xaa Xaa Xaa Xaa Xaa Xaa Xaa
                85                  90
```

<210> SEQ ID NO 134
<211> LENGTH: 23
<212> TYPE: PRT
<213> ORGANISM: Influenza

<400> SEQUENCE: 134

```
Ser Leu Leu Thr Glu Val Glu Thr Pro Thr Arg Asn Glu Trp Gly Cys
1               5                   10                  15

Arg Cys Asn Asp Ser Ser Asp
            20
```

<210> SEQ ID NO 135
<211> LENGTH: 23
<212> TYPE: PRT
<213> ORGANISM: Influenza

<400> SEQUENCE: 135

```
Ser Leu Leu Thr Glu Val Glu Thr Pro Thr Arg Asn Gly Trp Gly Cys
1               5                   10                  15

Arg Cys Asn Asp Ser Ser Asp
            20
```

<210> SEQ ID NO 136
<211> LENGTH: 23
<212> TYPE: PRT
<213> ORGANISM: Influenza

<400> SEQUENCE: 136

```
Ser Leu Leu Thr Glu Val Glu Thr Pro Ile Arg Asn Glu Trp Glu Cys
1               5                   10                  15

Arg Cys Asn Gly Ser Ser Asp
            20
```

<210> SEQ ID NO 137

-continued

```
<211> LENGTH: 23
<212> TYPE: PRT
<213> ORGANISM: Influenza

<400> SEQUENCE: 137

Ser Leu Leu Thr Glu Val Glu Thr Pro Thr Lys Asn Glu Trp Glu Cys
1               5                   10                  15

Arg Cys Asn Asp Ser Ser Asp
            20


<210> SEQ ID NO 138
<211> LENGTH: 23
<212> TYPE: PRT
<213> ORGANISM: Influenza

<400> SEQUENCE: 138

Ser Leu Leu Thr Glu Val Glu Thr Pro Thr Arg Asn Gly Trp Glu Cys
1               5                   10                  15

Lys Cys Ser Asp Ser Ser Asp
            20


<210> SEQ ID NO 139
<211> LENGTH: 23
<212> TYPE: PRT
<213> ORGANISM: Influenza

<400> SEQUENCE: 139

Ser Leu Leu Thr Glu Val Asp Thr Leu Thr Arg Asn Gly Trp Gly Cys
1               5                   10                  15

Arg Cys Ser Asp Ser Ser Asp
            20


<210> SEQ ID NO 140
<211> LENGTH: 23
<212> TYPE: PRT
<213> ORGANISM: Influenza

<400> SEQUENCE: 140

Ser Leu Leu Thr Glu Val Glu Thr Leu Thr Arg Asn Gly Trp Glu Cys
1               5                   10                  15

Lys Cys Arg Asp Ser Ser Asp
            20
```